United States Patent [19]
Caldwell et al.

[11] Patent Number: 5,750,549
[45] Date of Patent: May 12, 1998

[54] CYCLOALKYL TACHYKININ RECEPTOR ANTAGONISTS

[75] Inventors: Charles G. Caldwell, Scotch Plains; Ping Chen, Old Bridge; Philippe L. Durette, New Providence; Paul Finke, Milltown; Jeffrey Hale, Westfield, all of N.J.; Edward Holson, New York, N.Y.; Ihor Kopka, Millburn, N.J.; Malcolm MacCoss, Freehold, N.J.; Laura Meurer, Scotch Plains, N.J.; Sander G. Mills, Woodbridge, N.J.; Albert Robichaud, Stirling, N.J.

[73] Assignee: Merck & Co., Inc., Rahway, N.J.

[21] Appl. No.: 730,277

[22] Filed: Oct. 15, 1996

[51] Int. Cl.$^6$ .......... A61K 31/41; C07D 257/04; C07D 271/10
[52] U.S. Cl. .......... 514/364; 514/381; 514/529; 514/530; 514/532; 514/619; 514/620; 514/716; 514/717; 514/730; 514/731; 548/143; 548/250; 548/251; 548/252; 548/253; 548/254; 560/38; 560/39; 560/43; 564/164; 564/163; 564/168
[58] Field of Search ............... 548/143, 250, 548/251, 252, 253, 254; 560/38, 39, 43; 564/163, 164, 168; 568/647, 661; 514/364, 381, 529, 530, 532, 619, 620, 716, 717, 730, 731

[56] References Cited

U.S. PATENT DOCUMENTS

| | | | |
|---|---|---|---|
| 3,574,165 | 4/1971 | Braus et al. | 260/45.95 |
| 4,755,617 | 7/1988 | Miura et al. | 560/59 |
| 5,387,595 | 2/1995 | Mills et al. | 514/357 |
| 5,444,074 | 8/1995 | Baker et al. | 514/326 |
| 5,459,270 | 10/1995 | Williams et al. | 546/152 |
| 5,496,833 | 3/1996 | Baker et al. | 514/326 |
| 5,512,570 | 4/1996 | Dorn et al. | 514/236.2 |
| 5,561,130 | 10/1996 | Seward et al. | 514/235.5 |

FOREIGN PATENT DOCUMENTS

| | | |
|---|---|---|
| 0 142 322 | 5/1985 | European Pat. Off. . |
| 0 436 334 A2 | 7/1991 | European Pat. Off. . |
| WO 93/00331 | 1/1993 | WIPO . |
| WO 94/00440 | 1/1994 | WIPO . |
| WO 95/15311 | 6/1995 | WIPO . |
| WO 95/16679 | 6/1995 | WIPO . |

OTHER PUBLICATIONS

*Chemical Abstracts*, vol. 64, No. 8, Apr. 11, 1966, Abstract pp. 12732–12733.

*Primary Examiner*—Joseph McKane
*Attorney, Agent, or Firm*—J. Eric Thies; David L. Rose

[57] ABSTRACT

The present invention is directed to certain novel compounds represented by structural formula I:

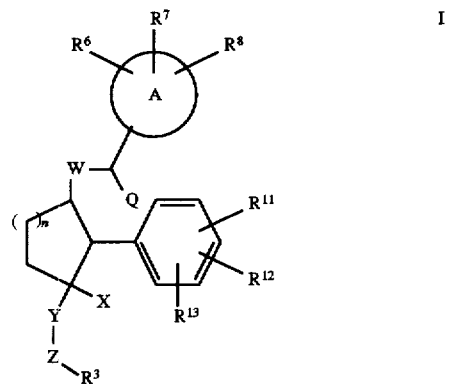

or a pharmaceutically acceptable salt thereof, wherein $R^3$, $R^6$, $R^7$, $R^8$, $R^{11}$, $R^{12}$, $R^{13}$, A, Q, W, X, Y, Z and n are defined herein. The invention is also concerned with pharmaceutical formulations comprising these novel compounds as active ingredients and the use of the novel compounds and their formulations in the treatment of certain disorders. The compounds of this invention are tachykinin receptor antagonists and are useful in the treatment of inflammatory diseases, pain or migraine, asthma and emesis.

30 Claims, No Drawings

CYCLOALKYL TACHYKININ RECEPTOR ANTAGONISTS

CROSS REFERENCE TO RELATED APPLICATIONS

This application claims priority under 35 U.S.C. § 119(e) from U.S. Ser. No. 60/005,558, filed Oct. 18, 1995.

BACKGROUND OF THE INVENTION

Analgesia has historically been achieved in the central nervous system by opiates and analogs which are addictive, and peripherally by cyclooxygenase inhibitors that have gastric side effects. Substance P antagonists may induce analgesia both centrally and peripherally. In addition, substance P antagonists are inhibitory of neurogenic inflammation.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, Pharmacol. Rev., 1983, 35, 85–141). The NK-1 and NK-2 receptor subtypes are implicated in synaptic transmission (Laneuville et al., Life Sci., 42: 1295–1305 (1988)).

The receptor for substance P is a member of the superfamily of G protein-coupled receptors. This superfamily is an extremely diverse group of receptors in terms of activating ligands and biological functions. In addition to the tachykinin receptors, this receptor superfamily includes the opsins, the adrenergic receptors, the muscarinic receptors, the dopamine receptors, the serotonin receptors, a thyroid-stimulating hormone receptor, a luteinizing hormone-choriogonadotropic hormone receptor, the product of the oncogene ras, the yeast mating factor receptors, a Dictyostelium cAMP receptor, and receptors for other hormones and neurotransmitters (A. D. Hershey, et al., J. Biol. Chem., 1991, 226, 4366–4373).

Substance P (also called "SP" herein) is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence Phe-X-Gly-Leu-Met-NH$_2$. In addition to SP the known mammalian tachykinins include neurokinin A and neurokinin B. The current nonmenclature designates the receptors for SP, neurokinin A, and neurokinin B as NK-1, NK-2, and NK-3, respectively. More specifically, substance P is a neuropeptide that is produced in mammals and possesses a characteristic amino acid sequence (Chang et al., Nature New Biol. 232, 86 (1971); D. F. Veber et al., U.S. Pat. No. 4,680,283).

Substance P is a pharmacologically-active neuropeptide that is produced in mammals and acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., Science, 199, 1359 (1978); P. Oehme et al., Science, 208, 305 (1980)) and plays a role in sensory transmission and pain perception (T. M. Jessell, Advan. Biochem. Psychopharmacol. 28, 189 (1981)). For example, substance P is believed to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS, 8 506–510 (December 1987)], specifically in the transmission of pain in migraine (see B. E. B. Sandberg et al., Journal of Medicinal Chemistry, 25, 1009 (1982); M. A. Moskowitz, Trends Pharmacol. Sci., 13, 307–311 (1992)), and in arthritis (Levine, et al. Science, 226 547–549 (1984); M. Lotz, et al., Science, 235, 893–895 (1987)). Tachykinins have also been implicated in gastrointestinal (GI) disorders and diseases of the GI tract, such as inflammatory bowel disease [Neuroscience, 25 (3), 817–37 (1988) and D. Regoli in "Trends in Cluster Headache" Ed. F. Sicuteri et al., Elsevier Scientific Publishers, Amsterdam, pp. 85–95 (1987)], and emesis [Trends Pharmacol. Sci., 9, 334–341 (1988), Eur. J. Pharmacol., 249, R3–R4 (1993), Brit. J. Pharmacol., 115, 84–94 (1995)].

It is also hypothesized that there is a neurogenic mechanism for arthritis in which substance P may play a role [Kidd et al., "A Neurogenic Mechanism for Symmetric Arthritis" in The Lancet, 11 Nov. 1989 and Gronblad et al., "Neuropeptides in Synovium of Patients with Rheumatoid Arthritis and Osteoarthritis" in J. Rheumatol. 15(12) 1807–10 (1988)]. Therefore, substance P is believed to be involved in the inflammatory response in diseases such as rheumatoid arthritis and osteoarthritis [O'Byrne et al., Arthritis and Rheumatism, 33 1023–8 (1990)].

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists," C. A. Maggi, R. Patacchini, P. Rovero and A. Giachetti, J. Auton. Pharmacol, 13, 23–93 (1993); see also R. M. Snider, et al., Chem. Ind., 11, 792–794 (1991). Neurokinin-1 receptor antagonists alone or in combination with bradykinin receptor antagonists may also be useful in the prevention and treatment of inflammatory conditions in the lower urinary tract, especially cystitis [Giuliani, et al., J. Urology, 150, 1014–1017 (1993)]. Other disease areas where tachykinin antagonists are believed to be useful are allergic conditions [Hamelet et al., Can. J. Pharmacol. Physiol., 66, 1361–7 (1988)], immunoregulation [Lotz, et al., Science, 241 1218–21 (1988), Kimball, et al., J. Immunol., 141 (10) 3564–9 (1988); A. Perianin, et al., Biochem. Biophys. Res Commun. 161, 520 (1989)], post-operative pain and nausea [C. Bountra, et al., Eur. J. Pharmacol., 249, R3–R4 (1993), F. D. Tattersall, et al., Neuropharmacology, 33, 259–260 (1994)], vasodilation, bronchospasm, reflex or neuronal control of the viscera [Mantyh et al., PNAS, 85, 3235–9 (1988)] and, possibly by arresting or slowing β-amyloid-mediated neurodegenerative changes [Yankner et al., Science, 250, 279–82 (1990)] in senile dementia of the Alzheimer type, Alzheimer's disease and Downs Syndrome. Substance P may also play a role in demyelinating diseases such as multiple sclerosis and amyotrophic lateral sclerosis [J. Luber-Narod, et. al., poster C.I.N.P. XVIIIth Congress, 28th Jun.–2nd Jul., 1992], and in disorders of bladder function such as bladder detrusor hyperreflexia [*Lancet*, 16th May 1992, 1239]. Antagonists selective for the neurokinin-1 (NK-1) and/or the neurokinin-2 (NK-2) receptor may be useful in the treatment of asthmatic disease (Frossard et al., *Life Sci.*, 49, 1941–1953 (1991); Advenier, et al., *Biochem. Biophys. Res. Comm.*, 184(3), 1418–1424 (1992); P. Barnes, et al., *Trends Pharmacol. Sci.*, 11, 185–189 (1993)). Tachykinin antagonists may also be useful in the treatment of small cell carcinomas, in particular small cell lung cancer (SCLC) [Langdon et al., *Cancer Research*, 52, 4554–7 (1992)].

It has furthermore been suggested that tachykinin receptor antagonists have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus (EPO Publication No. 0,436,334), ophthalmic diseases such as conjunctivitis, vernal conjunctivitis, and the like, and cutaneous diseases such as contact dermatitis, atopic dermatitis, urticaria, and other eczematoid dermatitis (EPO Publication No. 0,394,989).

Substance P antagonists may be useful in mediating neurogenic mucus secretion in mammalian airways and hence provide treatment and symptomatic relief in diseases characterized by mucus secretion, in particular, cystic fibrosis [S. Ramnarine, et al., abstract presented at 1993 ALA/ATS Int'l Conference, 16–19 May, 1993, published in *Am. Rev. of Respiratory Dis.*, May 1993].

In the recent past, some attempts have been made to provide peptide-like substances that are antagonists for the receptors of substance P and other tachykinin peptides in order to more effectively treat the various disorders and diseases mentioned above. For example Lowe, *Drugs of the Future*, 17 (12) 1115–1121 (1992) and EPO Publication Nos. 0,347,802, 0,401,177 and 0,412,452 disclose various peptides as neurokinin A antagonists. Also, PCT Patent Publication WO 93/14113 discloses certain peptides as tachykinin antagonists. In addition, EPO Publication No. 0,336,230 discloses heptapeptides which are substance P antagonists useful in the treatment of asthma. U.S. Pat. No. 4,680,283 also discloses peptidal analogs of substance P. Certain inhibitors of tachykinins have been described in U.S. Pat. No. 4,501,733, by replacing residues in substance P sequence by Trp residues. A further class of tachykinin receptor antagonists, comprising a monomeric or dimeric hexa- or heptapeptide unit in linear or cyclic form, is described in GB-A-2216529. The peptide-like nature of such substances make them too labile from a metabolic point of view to serve as practical therapeutic agents in the treatment of disease. The non-peptidic antagonists of the present invention, on the other hand, do not possess this drawback, as they are expected to be more stable from a metabolic point of view than the previously-discussed agents.

It is known that in the central nervous system baclofen [β-(aminoethyl)-4-chlorobenzenepropanoic acid] effectively blocks the excitatory activity of substance P. WIPO patent applications (PCT Publication Nos. WO 90/05525, WO 90/05729, WO 91/18899, WO 92/12151 and WO 92/12152) and publications (*Science*, 251, 435–437 (1991); *Science*, 251, 437–439 (1991); *J. Med. Chem.*, 35, 2591–2600 (1992)) disclose 2-arylmethyl-3-substituted aminoquinuclidine derivatives which are disclosed as being useful as substance P antagonists for treating gastrointestinal disorders, central nervous system disorders, inflammatory diseases and pain or migraine. A European patent application (EPO Publication No. 0,360,390) discloses various spirolactam-substituted amino acids and peptides which are antagonists or agonists of substance P. A WIPO patent application (PCT Publication No. WO 92/06079) discloses fused-ring analogs of nitrogen-containing nonaromatic heterocycles as useful for the treatment of diseases mediated by an excess of substance P. A WIPO patent application (PCT Publication No. WO 92/15585 discloses 1-azabicyclo[3.2.2] nonan-3-amine derivatives as substance P antagonists. A WIPO patent application (PCT Publication No. WO 93/10073) discloses ethylenediamine derivatives as substance P antagonists. PCT Publication No. WO 93/01169 discloses certain aromatic compounds as tachykinin receptor antagonists. A publication (*Life Sci.*, 50, PL101–PL106 (1992)) discloses a 4-phenyl piperidine derivative as an antagonist of the neurokinin A (NK2) receptor.

Howson et al. (*Biorg. & Med. Chem. Lett.*, 2 (6), 559–564 (1992)) disclose certain 3-amino and 3-oxy quinuclidine compounds and their binding to substance P receptors. EPO Publication 0,499,313 discloses certain 3-oxy and 3-thio azabicyclic compounds as tachykinin antagonists. U.S. Pat. No. 3,506,673 discloses certain 3-hydroxy quinuclidine compounds as central nervous system stimulants. EPO Publication 0,436,334 discloses certain 3-aminopiperidine compounds as substance P antagonists. U.S. Pat. No. 5,064,838 discloses certain 1,4-disubstituted piperidinyl compounds as analgesics. PCT Publication No. WO 92/12128 discloses certain piperidine and pyrrolidine compounds as analgesics. Peyronel, et al.(*Biorg & Med. Chem. Lett.*, 2 (1), 37–40 (1992)) disclose a fused ring pyrrolidine compound as a substance P antagonist. EPO Publication No. 0,360,390 discloses certain spirolactam derivatives as substance P antagonists. U.S. Pat. No. 4,804,661 discloses certain piperazine compounds as analgesics. U.S. Pat. No. 4,943,578 discloses certain piperazine compounds useful in the treatment of pain. PCT Publication No. WO 92/01679 discloses certain 1,4-disubstituted piperazines useful in the treatment of mental disorders in which a dopaminergic deficit is implicated. PCT Publication No. WO 94/00440, EPO Publication No. 0,577,394 and PCT Publication No. WO 95/16679 disclose certain morpholine and thiomorpholine compounds as substance P antagonists. U.S. Pat. No. 5,387, 595 and *Bioorg. & Med. Chem. Lett.*, 1345 (1995) disclose certain alicyclic compounds as tachykinin receptor antagonist. PCT Publications WO 95/06645 and WO 95/08549 discloses certain 3-amino-piperidines as tachykinin antagonists.

SUMMARY OF THE INVENTION

This invention is concerned with novel compounds represented by structural formula I:

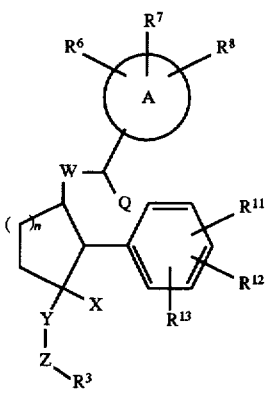

or a pharmaceutically acceptable salt thereof, wherein $R^3$, $R^6$, $R^7$, $R^8$, $R^{11}$, $R^{12}$, $R^{13}$, A, Q, W, X, Y, Z and n are hereinafter defined. The invention is also concerned with pharmaceutical formulations comprising these novel compounds as active ingredients and the use of the novel compounds and their formulations in the treatment of certain disorders. The compounds of this invention are tachykinin receptor antagonists and are useful in the treatment of inflammatory diseases, pain or migraine, asthma and emesis.

DETAILED DESCRIPTION OF THE INVENTION

The present invention is directed to the novel compound of the structural formula I:

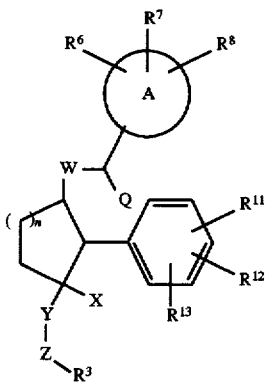

I or a pharmaceutically acceptable salt thereof, wherein: the circle A:

is selected from the group consisting of:
 (A) phenyl,
 (B) benzofuranyl,
 (C) benzothiophenyl,
 (D) benzothiazoyl,
 (E) indolyl,
 (F) imidazolyl,
 (G) oxadiazolyl,
 (H) pyridyl,
 (I) pyrimidyl,
 (J) quinolinyl,
 (K) thiazolyl,
 (L) thienyl,
 (M) thiophenyl, and
 (N) dihydrobenzofuranyl;

Q is selected from the group consisting of:
 (1) hydrogen, and
 (2) $C_{1-6}$ alkyl;

W is selected from the group consisting of:
 (1) —O—,
 (2) —NH—,
 (3) —N($C_{1-6}$ alkyl)—,
 (4) —NH—CO—, and
 (3) —N($C_{1-6}$ alkyl)—CO—, wherein if W is —NHCO— or —N($C_{1-6}$ alkyl)—CO—, then optionally Q and the carbon atom to which it is attached are absent;

X is selected from the group consisting of:
 (1) hydrogen, and
 (2) $C_{1-6}$ alkyl;

Y is selected from the group consisting of:
 (1) a single bond,
 (2) $C_{1-6}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo, wherein halo is fluoro, chloro, bromo or iodo,
  (h) —$NR^9R^{10}$, wherein $R^9$ and $R^{10}$ are independently selected from:
   (I) hydrogen,
   (II) $C_{1-6}$ alkyl,
   (III) phenyl,
   (IV) ($C_{1-6}$ alkyl)-phenyl,
   (V) ($C_{1-6}$ alkyl)-hydroxy, and
   (VI) ($C_{1-6}$ alkyl)-($C_{1-4}$ alkoxy),
  (i) —$NR^9$—$COR^{10}$, wherein $R^9$ and $R^{10}$ are as defined above,
  (j) —$NR^9$—$CO_2R^{10}$, wherein $R^9$ and $R^{10}$ are as defined above,
  (k) —CO—$NR^9R^{10}$, wherein $R^9$ and $R^{10}$ are as defined above,
  (l) —$COR^9$, wherein $R^9$ is as defined above, and
  (m) —$CO_2R^9$, wherein $R^9$ is as defined above;

Z is selected from the group consisting of:
 (1) —$NR^{15}$—, wherein $R^{15}$ is selected from the group consisting of:
  (a) hydrogen;
  (b) $C_{1-6}$ alkyl, unsubstituted or substituted with one or more of the substituents selected from:
   (i) hydroxy,
   (ii) oxo,
   (iii) $C_{1-6}$ alkoxy,
   (iv) phenyl-$C_{1-3}$ alkoxy,
   (v) phenyl,
   (vi) —CN,
   (vii) halo,
   (viii) —$NR^9R^{10}$,
   (ix) —$NR^9$—$COR^{10}$,
   (x) —$NR^9$—$CO_2R^{10}$,
   (xi) —CO—$NR^9R^{10}$,
   (xii) —$COR^9$,
   (xiii) —$CO_2R^9$;
  (c) phenyl, unsubstituted or substituted with one or more of the substituents selected from:

(i) hydroxy,
(ii) $C_{1-6}$ alkoxy,
(iii) $C_{1-6}$ alkyl,
(iv) $C_{2-5}$ alkenyl,
(v) halo,
(vi) —CN,
(vii) —NO$_2$,
(viii) —CF$_3$,
(ix) —(CH$_2$)$_m$—NR$^9$R$^{10}$, wherein m is 0, 1 or 2,
(x) —NR$^9$—COR$^{10}$,
(xi) —NR$^9$—CO$_2$R$^{10}$,
(xii) —CO—NR$^9$R$^{10}$,
(xiii) —CO$_2$—NR$^9$R$^{10}$,
(xiv) —COR$^9$,
(xv) —CO$_2$R$^9$, (2) —CO—NR$^{15}$—,
(3) —NR$^{15}$—CO—,
(4) —SO$_2$—NR$^{15}$—,
(5) —NR$^{15}$—SO$_2$—,
(6) —SO$_2$—,
(7) —CO—O—R$^{15}$,
(8) —O—CO—R$^{15}$,
(9) —CO—R$^{15}$,
(10) —CH$_2$—OR$^{15}$;

or if R$^3$ is other than hydrogen, then Z is optionally absent;

or if X is other than hydrogen, then R$^{15}$ and X may be joined together to form a 3- to 7-membered heterocyclic ring containing a group selected from: —NR$^3$—, —CO—NR$^3$—, —NR$^3$—CO—, —SO$_2$—NR$^3$—, —NR$^3$—SO$_2$—, —SO$_2$—, —CO—O—, —O—CO—, —O—, and —CO—, and wherein the heterocyclic ring is optionally substituted with one or more of the substitutents selected from:
(i) hydroxy,
(ii) oxo,
(iii) $C_{1-6}$ alkoxy,
(iv) phenyl-$C_{1-3}$ alkoxy,
(v) phenyl,
(vi) —CN,
(vii) halo,
(viii) —NR$^9$R$^{10}$,
(ix) —NR$^9$—COR$^{10}$,
(x) —NR$^9$—CO$_2$R$^{10}$,
(xi) —CO—NR$^9$R$^{10}$,
(xii) —COR$^9$,
(xiii) —CO$_2$R$^9$;

R$^3$ is selected from the group consisting of:
(1) hydrogen,
(2) —R$^5$, and
(3) $C_{1-6}$ alkyl substituted with —R$^5$, and if Z is —CO—O—R$^{15}$, —O—CO—R$^{15}$, —CO—R$^{15}$, or —CH$_2$—OR$^{15}$, then R$^3$ is absent;

R$^5$ is selected from the group consisting of:
(1) hydroxy,
(2) $C_{1-6}$ alkoxy,
(3) phenyl-$C_{1-3}$ alkoxy,
(4) phenyl,
(5) —CN,
(6) halo,
(7) —NR$^9$R$^{10}$,
(8) —NR$^9$—COR$^{10}$,
(9) —NR$^9$—CO$_2$R$^{10}$,
(10) —CO—NR$^9$R$^{10}$,
(11) —COR$^9$,
(12) —CO$_2$R$^9$;
(13) heterocycle, wherein the heterocycle is selected from the group consisting of:
(A) benzimidazolyl,
(B) benzofuranyl,
(C) benzothiophenyl,
(D) benzoxazolyl,
(E) furanyl,
(F) imidazolyl,
(G) indolyl,
(H) isooxazolyl,
(I) isothiazolyl,
(J) oxadiazolyl,
(K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl,
(U) thienyl,
(V) triazolyl,
(W) azetidinyl,
(X) 1,4-dioxanyl,
(Y) hexahydroazepinyl,
(Z) piperazinyl,
(AA) piperidinyl,
(AB) pyrrolidinyl,
(AC) morpholinyl,
(AC) thiomorpholinyl,
(AD) dihydrobenzimidazolyl,
(AE) dihydrobenzofuranyl,
(AF) dihydrobenzothiophenyl,
(AG) dihydrobenzoxazolyl,
(AH) dihydrofuranyl
(AI) dihydroimidazolyl,
(AJ) dihydroindolyl,
(AK) dihydroisooxazolyl,
(AL) dihydroisothiazolyl,
(AM) dihydrooxadiazolyl,
(AN) dihydrooxazolyl,
(AO) dihydropyrazinyl,
(AP) dihydropyrazolyl,
(AQ) dihydropyridinyl,
(AR) dihydropyrimidinyl,
(AS) dihydropyrrolyl,
(AT) dihydroquinolinyl,
(AU) dihydrotetrazolyl,
(AV) dihydrothiadiazolyl,
(AW) dihydrothiazolyl,
(AX) dihydrothienyl,
(AY) dihydrotriazolyl,
(AZ) dihydroazetidinyl,
(BA) dihydro-1,4-dioxanyl,
(BB) tetrahydrofuranyl, and
(BC) tetrahydrothienyl, and wherein the heterocycle is unsubstituted or substituted with one or more substituent(s) selected from:
(i) $C_{1-6}$ alkyl, unsubstituted or substituted with halo, —CF$_3$, —OCH$_3$, or phenyl,
(ii) $C_{1-6}$ alkoxy,
(iii) oxo, (iv) hydroxy,
(v) thioxo,
(vi) —$SR^9$,
(vii) halo,
(viii) cyano,
(ix) phenyl,
(x) trifluoromethyl,
(xi) —$(CH_2)_m$—$NR^9R^{10}$,
(xii) —$NR^9COR^{10}$,
(xiii) —$CONR^9R^{10}$,
(xiv) —$CO_2R^9$, and
(xv) —$(CH_2)_m$—$OR^9$,

(14) —CO-heterocycle, wherein heterocycle is as defined above;

$R^6$, $R^7$ and $R^8$ are independently selected from the group consisting of:

(1) hydrogen,
(2) $C_{1-6}$ alkoxy,
(3) halo,
(4) $C_{1-6}$ alkyl, unsubstituted or substituted with one or more of the substituents selected from:
 (a) hydroxy,
 (b) oxo,
 (c) $C_{1-6}$ alkoxy,
 (d) phenyl-$C_{1-3}$ alkoxy,
 (e) phenyl,
 (f) —CN,
 (g) halo,
 (h) —$NR^9R^{10}$,
 (i) —$NR^9$—$COR^{10}$,
 (j) —$NR^9$—$CO_2R^{10}$,
 (k) —CO—$NR^9R^{10}$,
 (l) —$COR^9$,
 (m) —$CO_2R^9$,
 (n) heterocycle, wherein heterocycle is as defined above,
(5) hydroxy,
(6) —CN,
(7) —$CF_3$,
(8) —$NO_2$,
(9) —$SR^{14}$, wherein $R^{14}$ is hydrogen or $C_{1-6}$ alkyl,
(10) —$SOR^{14}$,
(11) —$SO_2R^{14}$,
(12) —$NR^9$—$COR^{10}$,
(13) —CO—$NR^9$—$COR^{10}$,
(14) —$NR^9R^{10}$,
(15) —$NR^9$—$CO_2R^{10}$,
(16) —$COR^9$,
(17) —$CO_2R^9$,
(18) heterocycle, wherein heterocycle is as defined above,
(19) —($C_{1-6}$ alkyl)-heterocycle, wherein heterocycle is as defined above,
(20) —N(heterocycle)—$SO_2R^{14}$, wherein heterocycle is as defined above;

$R^{11}$, $R^{12}$ and $R^{13}$ are independently selected from:

(1) hydrogen,
(2) $C_{1-6}$ alkyl, unsubstituted or substituted with one or more of the substituents selected from:
 (a) hydroxy,
 (b) oxo,
 (c) $C_{1-6}$ alkoxy,
 (d) phenyl-$C_{1-3}$ alkoxy,
 (e) phenyl,
 (f) —CN,
 (g) halo,
 (h) —$NR^9R^{10}$,
 (i) —$NR^9$—$COR^{10}$,
 (j) —$NR^9$—$CO_2R^{10}$,
 (k) —CO—$NR^9R^{10}$,
 (l) —$COR^9$,
 (m) —$CO_2R^9$;
(3) halo,
(4) —CN,
(5) —$CF_3$,
(6) —$NO_2$,
(7) hydroxy,
(8) $C_{1-6}$ alkoxy,
(9) —$COR^9$,
(10) —$CO_2R^9$; and n is an integer selected from 1, 2 or 3.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention.

In addition compounds with carbon-carbon double bonds may occur in Z- and E- forms with all isomeric forms of the compounds being included in the present invention.

When any variable (e.g., alkyl, aryl, Q, W, X, Y, Z, $R^5$, $R^6$, $R^7$, $R^8$, $R^9$, $R^{10}$, $R^{11}$, $R^{12}$, $R^{13}$, $R^{14}$, $R^{15}$, etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentyl, and the like, and includes E and Z forms, where applicable. "Halogen" or "halo", as used herein, means fluoro, chloro, bromo and iodo.

The term "aryl" means phenyl or naphthyl either unsubstituted or substituted with one or more substituents selected from the group consisting of halo, $C_{1-4}$-alkyl, $C_{1-4}$-alkoxy, —$NO_2$, —$CF_3$, $C_{1-4}$-alkylthio, OH, —N($R^9R^{10}$), —$CO_2R^9$, $C_{1-4}$-perfluoroalkyl, $C_{3-6}$-perfluorocycloalkyl, and tetrazol-5-yl.

The term "heteroaryl" means an unsubstituted, monosubstituted or disubstituted five or six membered aromatic heterocycle comprising from 1 to 3 heteroatoms selected from the group consisting of O, N and S and wherein the substituents are members selected from the group consisting of —OH, —SH, —$C_{1-4}$-alkyl, —$C_{1-4}$-alkoxy, —$CF_3$, halo, —$NO_2$, —$CO_2R^9$, —N($R^9R^{10}$) and a fused benzo group.

In the compounds of the present invention, if Y is a single bond, then Z is attached directly to the cyclopentyl ring. Similarly, if $R^3$ is other than hydrogen and Z is absent, then $R^3$ is attached directly to Y. Moreover, if Y is a single bond and Z is absent, then $R^3$ is attached directly to the cyclopentyl ring.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate, 2-hydroxyethylsulfonate, pamoate, salicylate and stearate. Similarly, pharmaceutically acceptable cations include, but are not limited to sodium, potassium, calcium, aluminum, lithium and ammonium.

In the compounds of the present invention, it is preferred that if W is —O—, —NH— or —N($C_{1-6}$ alkyl)—, then at least one of the following four conditions must be met:

(1) Q is other than hydrogen,
(2) Y is a single bond,
(3) X is other than hydrogen, and/or
(4) at least one of $R^6$, $R^7$ and $R^8$ is heterocycle, —($C_{1-6}$ alkyl)-heterocycle, or —N(heterocycle)—$SO_2R^{14}$, wherein heterocycle and $R^{14}$ are as defined above.

In the compounds of the present invention it is preferred that A is selected from the group consisting of:

(A) phenyl,
(B) benzofuranyl,
(C) benzothiazoyl,
(D) indolyl,
(E) imidazolyl,
(F) oxadiazolyl,
(G) pyridyl,
(H) quinolinyl,
(I) thiazolyl,
(J) thienyl, and
(K) dihydrobenzofuranyl.

In the compounds of the present invention it is preferred that n is 1 or 2.

One embodiment of the present invention is directed to the compounds of structural formula I, or a pharmaceutically acceptable salt thereof, in which A is phenyl and W is —O— of the formula:

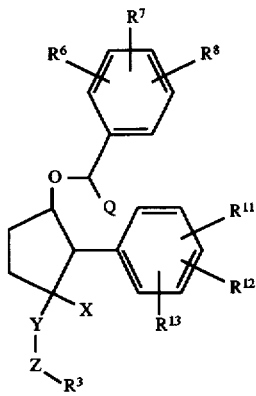

wherein $R^3$, $R^6$, $R^7$, $R^8$, $R^{11}$, $R^{12}$, $R^{13}$, Q, X, Y and Z are as defined above.

One group within the embodiment of the compounds of the invention where W is —O— is that wherein Q is other than hydrogen.

Another group within the embodiment of the compounds of the invention where W is —O— is that wherein Y is a single bond.

Another group within the embodiment of the compounds of the invention where W is —O— is that wherein X is other than hydrogen.

Another group within the embodiment of the compounds of the invention where W is —O— is that wherein at least one of $R^6$, $R^7$ and $R^8$ is heterocycle, —($C_{1-6}$ alkyl)-heterocycle, or —N(heterocycle)—$SO_2R^{14}$, wherein heterocycle and $R^{14}$ are as defined above.

Another embodiment of the present invention is directed to the compounds of structural formula I, or a pharmaceutically acceptable salt thereof, in which A is phenyl and W is —NH— or —N($C_{1-6}$ alkyl)- of the formula:

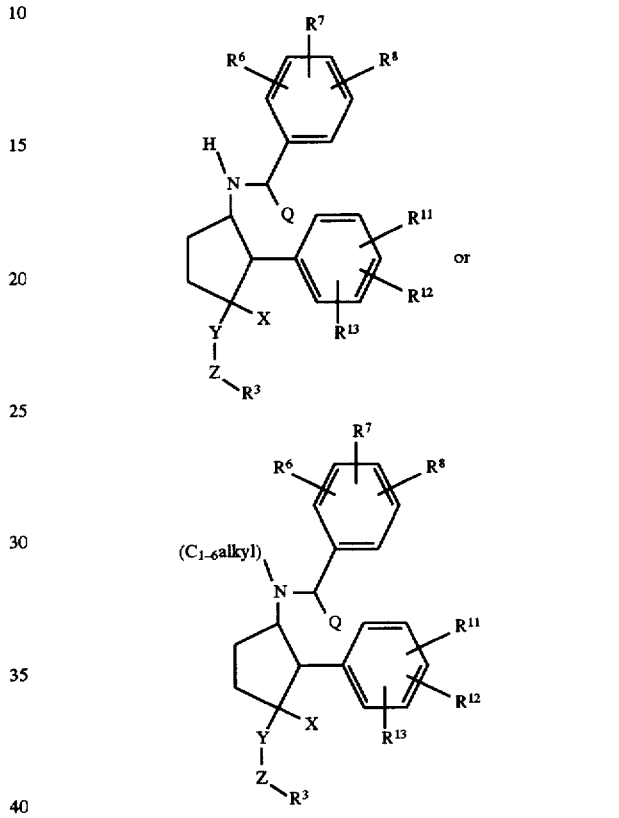

wherein $R^3$, $R^6$, $R^7$, $R^8$, $R^{11}$, $R^{12}$, $R^{13}$, Q, X, Y and Z are as defined above.

One group within the embodiment of the compounds of the invention where W is —NH— or —N($C_{1-6}$ alkyl)- is that wherein Q is other than hydrogen.

Another group within the embodiment of the compounds of the invention where W is —NH— or —N($C_{1-6}$ alkyl)- is that wherein Y is a single bond.

Another group within the embodiment of the compounds of the invention where W is —NH— or —N($C_{1-6}$ alkyl)- is that wherein X is other than hydrogen.

Another group within the embodiment of the compounds of the invention where W is —NH— or —N($C_{1-6}$ alkyl)- is that wherein at least one of $R^6$, $R^7$ and $R^8$ is heterocycle, —($C_{1-6}$ alkyl)-heterocycle, or —N(heterocycle)—$SO_2R^{14}$, wherein heterocycle and $R^{14}$ are as defined above.

In the compounds of the present invention where W is —NH— or —N($C_{1-6}$ alkyl)-, it is preferred that Q is hydrogen, X is hydrogen, Y is a single bond, and one of $R^6$, $R^7$ and $R^8$ is heterocycle, —($C_{1-6}$ alkyl)-heterocycle, or —N(heterocycle)—$SO_2R^{14}$, wherein heterocycle and $R^{14}$ are as defined above, and another of $R^6$, $R^7$ and $R^8$ is —$OCH_3$.

A third embodiment of the present invention is directed to the compounds of structural formula I, or a pharmaceutically acceptable salt thereof, in which A is phenyl and W is —NHCO— or —N(C$_{1-6}$ alkyl)—CO— of the formula:

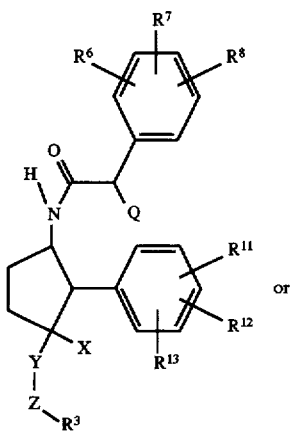

or

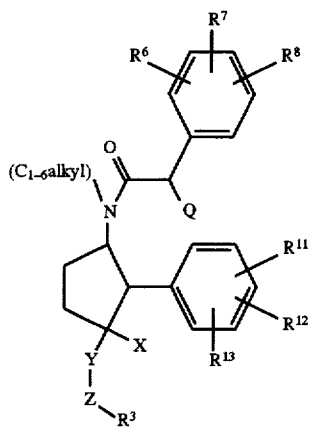

wherein R$^3$, R$^6$, R$^7$, R$^8$, R$^{11}$, R$^{12}$, R$^{13}$, Q, X, Y and Z are as defined above.

A fourth embodiment of the present invention is directed to the compounds of structural formula I, or a pharmaceutically acceptable salt thereof, in which A is phenyl and W is —NH— or —N(C$_{1-6}$ alkyl)—CO— and Q and the carbon atom to which it is attached are absent of the formula:

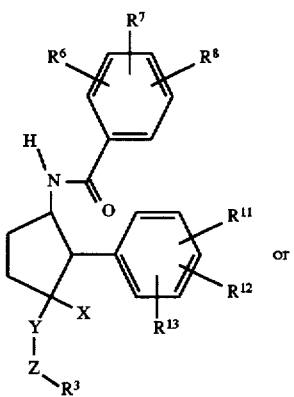

or

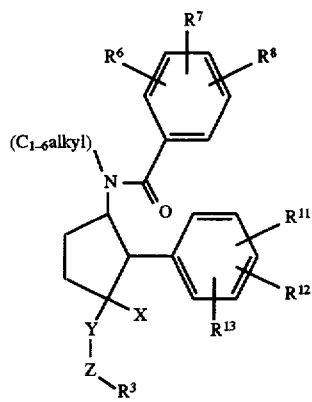

wherein R$^3$, R$^6$, R$^7$, R$^8$, R$^{11}$, R$^{12}$, R$^{13}$, Q, X, Y and Z are as defined above.

As noted above, in the compounds of structural formula I if X is other than hydrogen, then R$^{15}$ and X may be joined together to form bicyclic compounds, for example, of the formula:

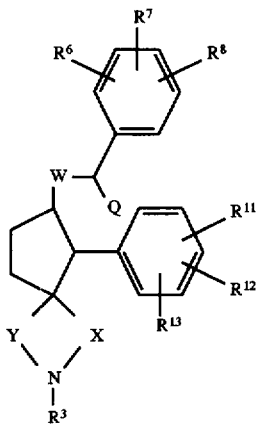

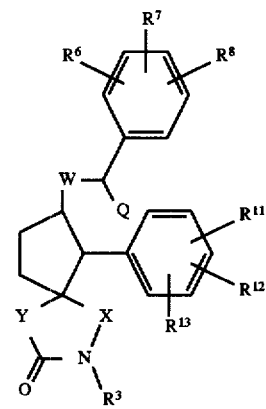

15

-continued

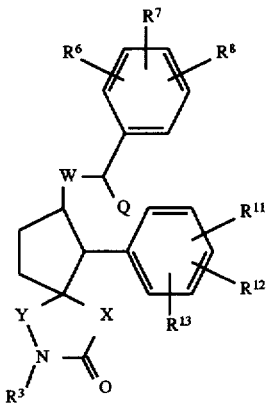

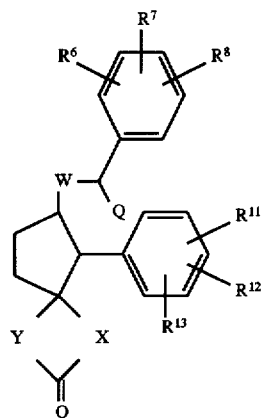

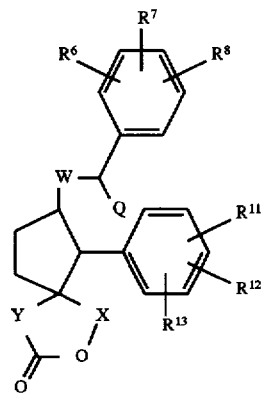

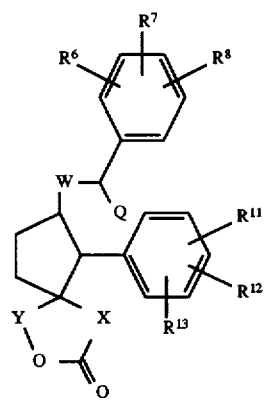

16

-continued

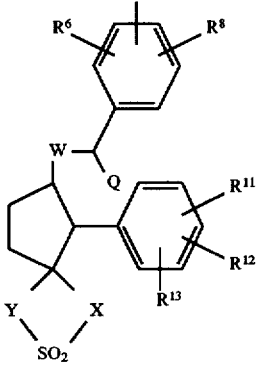

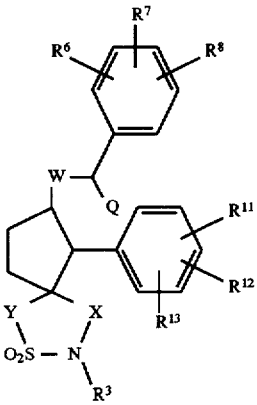

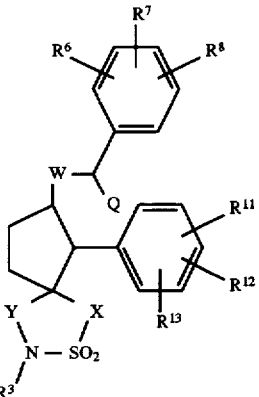

wherein $R^3$, $R^6$, $R^7$, $R^8$, $R^{11}$, $R^{12}$, $R^{13}$, Q, W, X, Y are as defined above.

A preferred embodiment of the present invention includes those compounds of structural formula I, or a pharmaceutically acceptable salt thereof, wherein:

A is selected from the group consisting of:
(A) phenyl,
(B) benzofuranyl,
(C) benzothiazoyl,
(D) indolyl,
(E) imidazolyl,
(F) oxadiazolyl,
(G) pyridyl,
(H) quinolinyl,
(I) thiazolyl,
(J) thienyl, and
(K) dihydrobenzofuranyl;

Q is selected from the group consisting of:
(1) hydrogen, and (2) —CH$_3$;

W is selected from the group consisting of:
(1) —O—,
(2) —NH—, and
(3) —N(CH$_3$)—;

X is hydrogen;

Y is selected from the group consisting of:
(1) a single bond, and
(2) —CH$_2$;

Z is selected from the group consisting of:
(1) —NR$^{15}$—, wherein R$^{15}$ is selected from the group consisting of: hydrogen, —CH$_3$, and —CH$_2$CH$_2$OCH$_3$,
(2) —CO—NR$^{15}$—,
(3) —NR$^{15}$—CO—,
(4) —SO$_2$—NR$^{15}$—, and
(5) —NR$^{15}$—SO$_2$—,
or if R$^3$ is other than hydrogen, then Z is optionally absent;

R$^3$ is selected from the group consisting of:
(1) —R$^5$, and
(2) C$_{1-6}$ alkyl substituted with —R$^5$;

R$^5$ is selected from the group consisting of:
(1) —NR$^9$R$^{10}$, wherein R$^9$ and R$^{10}$ are independently selected from:
(a) hydrogen,
(b) C$_{1-6}$ alkyl,
(c) (C$_{1-6}$ alkyl)-hydroxy, and
(d) (C$_{1-6}$ alkyl)-(C$_{1-4}$ alkoxy),
(2) —CO—NR$^9$R$^{10}$,
(3) —NR$^9$—COR$^{10}$,
(4) heterocycle, wherein the heterocycle is selected from the group consisting of:
(A) imidazolyl,
(B) triazolyl,
(C) tetrazolyl,
(D) pyridyl,
(E) piperazinyl,
(F) piperidinyl,
(G) pyrrolidinyl,
(H) morpholinyl,
and wherein the heterocycle is unsubstituted or substituted with one or more substituent(s) selected from:
(i) C$_{1-6}$ alkyl, unsubstituted or substituted with halo, —CF$_3$, —OCH$_3$, or phenyl,
(ii) C$_{1-6}$ alkoxy,
(iii) oxo, and
(iv) hydroxy,
(5) —CO-heterocycle, wherein heterocycle is as defined above;

R$^6$, R$^7$ and R$^8$ are independently selected from the group consisting of:
(1) hydrogen,
(2) —CF$_3$,
(3) C$_{1-6}$ alkoxy, and
(4) 1-, 2- or 5-tetrazolyl, wherein the tetrazolyl is unsubstituted or substituted with a substitutent selected from the group consisting of:
(a) C$_{1-6}$ alkyl,
(b) -cyclopropyl,
(c) CH$_2$-cyclopropyl,
(d) —S—C$_{1-4}$ alkyl,
(e) —SO—C$_{1-4}$ alkyl,
(f) —SO$_2$—C$_{1-4}$ alkyl,
(g) phenyl,
(h) —NR$^9$R$^{10}$,
(i) —CH$_2$—CO—CF$_3$, and
(j) —CF$_3$;

R$^{11}$, R$^{12}$ and R$^{13}$ are independently selected from:
(1) hydrogen, and
(2) fluoro;

n is 1 or 2;

with the proviso that if W is —O—, —NH— or —N(CH$_3$)—, then at least one of the following conditions must be met:
(1) Q is —CH$_3$,
(2) Y is a single bond, and/or
(3) at least one of R$^6$, R$^7$ and R$^8$ is heterocycle, —(C$_{1-6}$ alkyl)-heterocycle, or —N(heterocycle)—SO$_2$R$^{14}$, wherein heterocycle and R$^{14}$ are as defined above.

In the present invention it is preferred that Q is selected from the group consisting of:
(1) hydrogen, and
(2) methyl.

In the present invention it is preferred that if W is —O— and Y is other than a single bond, then Q is other than hydrogen.

In the present invention it is preferred that Y is selected from the group consisting of:
(1) a single bond, and
(2) —CH$_2$—.

In the present invention it is preferred that Z is selected from the group consisting of:
(1) —NR$^{15}$—, wherein R$^{15}$ is selected from the group consisting of: hydrogen, —CH$_3$, and —CH$_2$CH$_2$OCH$_3$,
(2) —CO—NR$^{15}$—,
(3) —NR$^{15}$—CO—,
(4) —SO$_2$—NR$^{15}$—, and
(5) —NR$^{15}$—SO$_2$—,
or if R$^3$ is other than hydrogen, then Z is optionally absent.

In the present invention it is preferred that R$^3$ is selected from the group consisting of:
(1) —R$^5$, and
(2) C$_{1-6}$ alkyl substituted with —R$^5$,
or if Z is —CO—O—R$^{15}$, —O—CO—R$^{15}$, —CO—R$^{15}$, or —CH$_2$—OR$^{15}$, then R$^3$ is absent.

In the compounds of the present invention wherein R$^3$ is —R$^5$ or C$_{1-6}$ alkyl substituted with —R$^5$, it is preferred that R$^5$ is selected from the group consisting of:
(1) —NR$^9$R$^{10}$, wherein R$^9$ and R$^{10}$ are independently selected from:
(a) hydrogen,
(b) C$_{1-6}$ alkyl,
(c) (C$_{1-6}$ alkyl)-hydroxy, and
(d) (C$_{1-6}$ alkyl)—(C$_{1-4}$ alkoxy),
(2) —CO—NR$^9$R$^{10}$, wherein R$^9$ and R$^{10}$ are as defined immediately above,
(3) —NR$^9$—COR$^{10}$, wherein R$^9$ and R$^{10}$ are as defined immediately above,
(4) heterocycle, wherein the heterocycle is selected from the group consisting of:
(A) imidazolyl,
(B) triazolyl,
(C) tetrazolyl,
(D) pyridyl,
(E) piperazinyl,
(F) piperidinyl, (G) pyrrolidinyl,
(H) morpholinyl,
and wherein the heterocycle is unsubstituted or substituted with one or more substituent(s) selected from:
(i) $C_{1-6}$ alkyl, unsubstituted or substituted with halo, $-CF_3$, $-OCH_3$, or phenyl,
(ii) $C_{1-6}$ alkoxy,
(iii) oxo, and
(iv) hydroxy, (5) —CO-heterocycle, wherein heterocycle is as defined above.

In the present invention a preferred embodiment is directed to those compounds in which $R^6$, $R^7$ and $R^8$ are independently selected from the group consisting of:
(1) hydrogen,
(2) $-CF_3$,
(3) $C_{1-4}$ alkoxy, and
(4) heterocycle, wherein the heterocycle is selected from the group consisting of:
(A) tetrazolyl,
(B) imidazolyl,
(C) triazolyl,
(D) pyridyl,
and wherein the heterocycle is unsubstituted or substituted with one or more substituent(s) selected from:
(i) $C_{1-4}$ alkyl,
(ii) -cyclopropyl, and
(iii) $-CF_3$;

In the present invention a particularly preferred embodiment is directed to those compounds in which the phenyl ring bearing $R^6$, $R^7$ and $R^8$ is selected from:

3,5-bis(trifluormethyl)phenyl,
2-methoxy-5-tetrazol-1-yl-phenyl,
2-methoxy-5-(5-methyl-tetrazol-1-yl)-phenyl,
2-methoxy-5-(5-ethyl-tetrazol-1-yl)-phenyl,
2-methoxy-5-(5-propyl-tetrazol-1-yl)-phenyl,
2-methoxy-5-(5-trifluoromethyl-tetrazol-1-yl)-phenyl,
2-methoxy-5-(5-cyclopropyl-tetrazol-1-yl)-phenyl, and
2-methoxy-5-(5-methylsulfanyl-tetrazol-1-yl)-phenyl.

In the present invention a preferred embodiment is directed to those compounds in which $R^{11}$, $R^{12}$ and $R^{13}$ are independently selected from: (1) hydrogen, and (2) fluoro.

In the present invention a particularly preferred embodiment is directed to those compounds in which the phenyl ring bearing $R^1$, $R^{12}$ and $R^{13}$ is unsubstituted phenyl or is para-fluorophenyl.

Specific compounds within the present invention include:
methyl 3-(SR)-(3,5-bis(trifluoromethyl)phenyl)methoxy)-2-(RS)-phenylcyclopentane-1-(RS)-carboxylate;
methyl 3-(SR)-(3,5-bis(trifluoromethyl)phenyl)methoxy)-2-(RS)-phenylcyclopentane-1-(SR)-carboxylate;
1-(SR)-(3,5-bis(trifluoromethyl)phenyl)methoxy-2-(SR)-phenyl-3-(RS)-(aminocarbonylamino)cyclopentane;
1-(SR)-(3,5-bis(trifluoromethyl)phenyl)methoxy-2-(SR)-phenyl-3-(RS)-(methoxycarbonylamino)cyclopentane;
1-(SR)-(3,5-bis(trifluoromethyl)phenyl)methoxy-2-(SR)-phenyl-3-(RS)-(benzyloxycarbonylamino)cyclopentane;
1-(SR)-(3,5-bis(trifluoromethyl)phenyl)methoxy-2-(SR)-phenyl-3-(RS)-aminocyclopentane;
1-(SR)-(3,5-bis(trifluoromethyl)phenyl)methoxy-2-(SR)-phenyl-3-(RS)-(aminocarbonylmethylamino) cyclopentane;
1-(SR)-(3,5-bis(trifluoromethyl)phenyl)methoxy-2-(SR)-phenyl-3-(RS)-(methylamino)cyclopentane;
1-(SR)-(3,5-bis(trifluoromethyl)phenyl)methoxy-2-(SR)-phenyl-3-(RS)-(N-(aminocarbonylmethyl)-N-methylamino)cyclopentane;
1-(SR)-(3,5-bis(trifluoromethyl)phenyl)methoxy-2-(SR)-phenyl-3-(RS)-(N-acetyl-N-methylamino)cyclopentane;
1-(SR)-(3,5-bis(trifluoromethyl)phenyl)methoxy-2-(SR)-phenyl-3-(RS)-(N-(methoxycarbonyl)-N-methylamino) cyclopentane;
1-(SR)-(3,5-bis(trifluoromethyl)phenyl)methoxy-2-(SR)-phenyl-3-(RS)-(N-(dimethylaminocarbonyl)-N-methylamino)cyclopentane;
1-(SR)-(3,5-bis(trifluoromethyl)phenyl)methoxy-2-(SR)-phenyl-3-(RS)-(methylaminocarbonylamino) cyclopentane;
1-(SR)-(3,5-bis(trifluoromethyl)phenyl)methoxy-2-(SR)-phenyl-3-(RS)-(dimethylaminocarbonylamino) cyclopentane;
1-(SR)-(3,5-bis(trifluoromethyl)phenyl)methoxy-2-(SR)-phenyl-3-(RS)-(N-((2-oxo-1H,3H-1,3-imidazol-4-yl)methyl)-N-methylamino) cyclopentane;
1-(SR)-(3,5-bis(trifluoromethyl)phenyl)methoxy-2-(SR)-phenyl-3-(RS)-(N-((5-oxo-1H,4H-1,2,4-triazol-3-yl)methyl)-N-methylamino) cyclopentane;
1-(SR)-(3,5-bis(trifluoromethyl)phenyl)methoxy-2-(SR)-phenyl-3-(RS)-(N-((1,2,4-triazol-3-yl)methyl)-N-methylamino)cyclopentane;
1-(SR)-(3,5-bis(trifluoromethyl)phenyl)methoxy-2-(RS)-phenyl-3-(SR)-(aminocarbonylamino)cyclopentane;
1-(SR)-(3,5-bis(trifluoromethyl)phenyl)methoxy-2-(RS)-phenyl-3-(SR)-(methoxycarbonylamino)cyclopentane;
1-(SR)-(3,5-bis(trifluoromethyl)phenyl)methoxy-2-(RS)-phenyl-3-(SR)-(benzyloxycarbonylamino)cyclopentane;
1-(SR)-(3,5-bis(trifluoromethyl)phenyl)methoxy-2-(RS)-phenyl-3-(SR)-aminocyclopentane;
1-(SR)-(3,5-bis(trifluoromethyl)phenyl)methoxy-2-(RS)-phenyl-3-(SR)-(methylamino)cyclopentane;
1-(SR)-(3,5-bis(trifluoromethyl)phenyl)methoxy-2-(RS)-phenyl-3-(SR)-(N-(aminocarbonylmethyl)-N-methylamino)cyclopentane;
1-(SR)-(3,5-bis(trifluoromethyl)phenyl)methoxy-2-(RS)-phenyl-3-(SR)-(N-((5-oxo-1H,4H-1,2,4-triazol-3-yl)methyl)-N-methylamino) cyclopentane;
methyl 3-(SR)-(1-(SR)-(3,5-bis(trifluoromethyl)phenyl)ethoxy)-2-(RS)-phenylcyclopentane-1-(RS)-carboxylate;
methyl 3-(SR)-(1-(RS)-(3,5-bis(trifluoromethyl)phenyl)ethoxy)-2-(RS)-phenylcyclopentane-1-(RS)-carboxylate;
methyl 3-(SR)-(1-(SR)-(3,5-bis(trifluoromethyl)phenyl)ethoxy)-2-(SR)-phenylcyclopentane-1-(SR)-carboxylate
ethyl 3-(SR)-(1-(RS)-(3,5-bis(trifluoromethyl)phenyl)ethoxy)-2-(SR)-phenylcyclopentane-1-(SR)-carboxylate;
1-(R)-(1-(S)-(3,5-bis(trifluoromethyl)phenyl)ethoxy)-2-(R)-phenyl-3-(S)-aminocyclopentane;
1-(S)-(1-(R)-(3,5-bis(trifluoromethyl)phenyl)ethoxy)-2-(S)-phenyl-3-(R)-aminocyclopentane;
1-(R)-(1-(S)-(3,5-bis(trifluoromethyl)phenyl)ethoxy)-2-(R)-phenyl-3-(S)-(aminocarbonylmethyl-amino) cyclopentane;

21

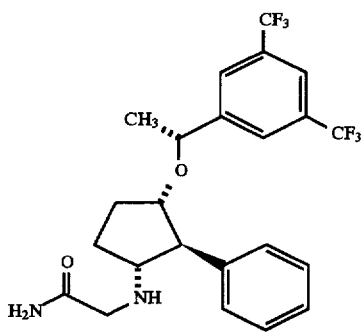

1-(S)-(1-(R)-(3,5-bis(trifluoromethyl)phenyl)ethoxy)-2-(S)-
phenyl-3-(R)-(aminocarbonylmethylamino)
cyclopentane;

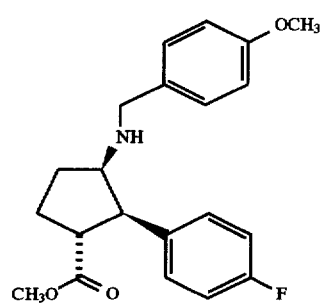

methyl 3-(R)-((4-methoxyphenyl)methylamino)-2-(R)-(4-
fluorophenyl)cyclopentane-1-(R)-carboxylate;

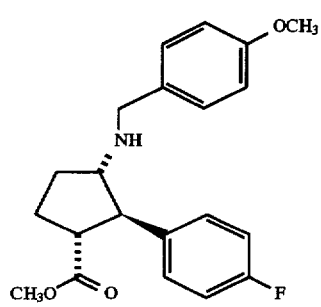

methyl 3-(S)-((4-methoxyphenyl)methylamino)-2-(R)-(4-
fluorophenyl)cyclopentane-1-(R)-carboxylate;

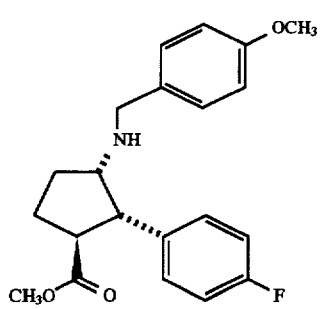

methyl 3-(S)-((4-methoxyphenyl)methylamino)-2-(S)-(4-
fluorophenyl)cyclopentane-1-(S)-carboxylate;

22

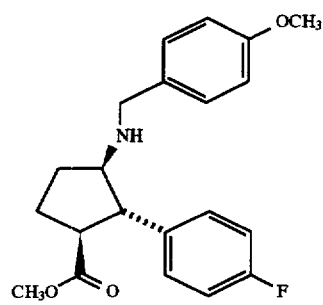

methyl 3-(R)-((4-methoxyphenyl)methylamino)-2-(S)-(4-
fluorophenyl)cyclopentane-1-(S)-carboxylate;

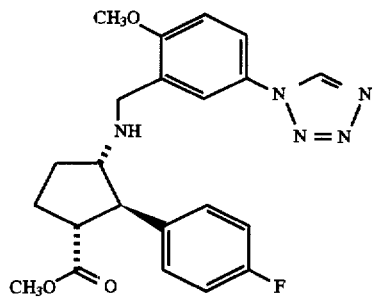

methyl 3-(S)-((2-methoxy-5-(1-tetrazolyl)phenyl)
methylamino)-2-(R)-(4-fluorophenyl)cyclopentane-1-(R)
-carboxylate;

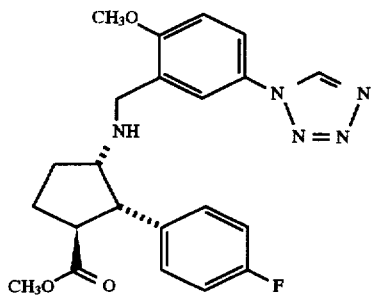

methyl 3-(S)-((2-methoxy-5-(1-tetrazolyl)phenyl)
methylamino)-2-(S)-(4-fluorophenyl)cyclopentane-1-(S)-
carboxylate;

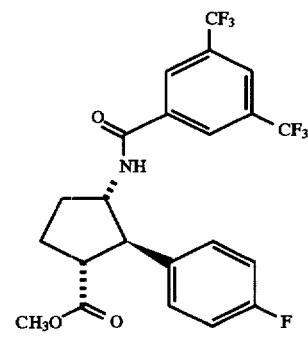

methyl 3-(S)-((3,5-bis(trifluoromethyl)phenyl)
carbonylamino)-2-(R)-(4-fluorophenyl)cyclopentane-1-
(R)-carboxylate;

23

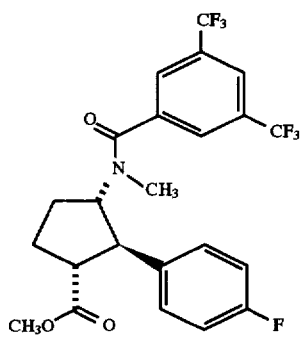

methyl 3-(S)-(N-((3,5-bis(trifluoromethyl)phenyl)carbonyl)
-N-methylamino)-2-(R)-(4-fluorophenyl)cyclopentane-1-
(R)-carboxylate;

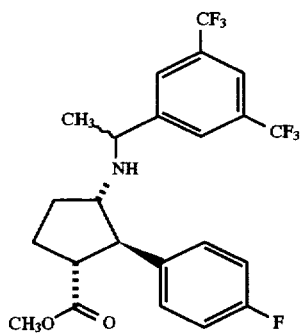

methyl 3-(S)-(1-(RS)-(3,5-bis(trifluoromethyl)phenyl)
ethylamino)-2-(R)-(4-fluorophenyl)cyclopentane-1-(R)-
carboxylate;

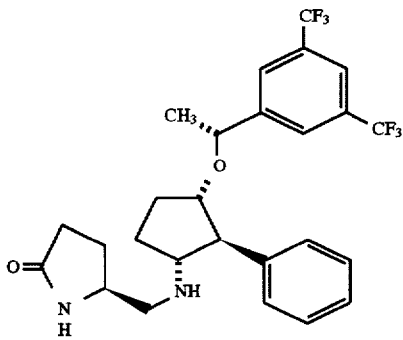

1-(S)-(1-(R)-(3,5-bis(trifluoromethyl)phenyl)ethoxy)-2-(S)-
phenyl-3-(R)-(((S)-(2-pyrrolidon-5-yl))-methylamino)
cyclopentane;

24

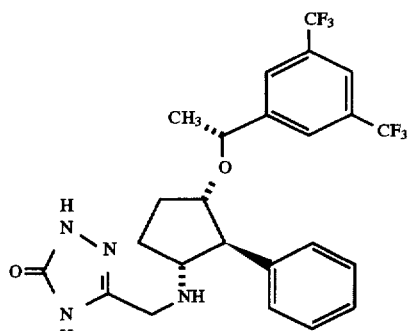

1-(S)-(1-(R)-(3,5-bis(trifluoromethyl)phenyl)ethoxy)-2-(S)-
phenyl-3-(R)-(3-(5-oxo-1H,4H-1,2,4-triazolo)
methylamino)cyclopentane;

and pharmaceutically acceptable salts and individual diasteromers thereof.

Preferred compounds within the present invention include:

1-(S)-(1-(R)-(3,5-bis(trifluoromethyl)phenyl)ethoxy)-2-(S)-
(4-fluorophenyl)-3-(R)-(2-methoxyethylamino)
cyclopentane;

1-(S)-(1-(R)-(3,5-bis(trifluoromethyl)phenyl)ethoxy)-2-(S)-
(4-fluorophenyl)-3-(R)-(N-(aminocarbonylmethyl)-N-(2-
methoxyethyl)-amino)cyclopentane;

methyl 3-(S)-((2-methoxy-5-(1-tetrazolyl)phenyl)
methylamino)-2-(S)-(4-fluorophenyl)cyclopentane-1-(S)-
carboxylate;

1-(S)-((2-methoxy-5-(1-tetrazolyl)phenyl)methylamino)-2-
(S)-(4-fluorophenyl)-3-(S)-(aminocarbonyl)
cyclopentane;

1-(S)-((2-methoxy-5-(1-tetrazolyl)phenyl)methylamino)-2-
(S)-(4-fluorophenyl)-3-(S)-(dimethylaminocarbonyl)
cyclopentane;

1-(S)-((2-methoxy-5-(1-tetrazolyl)phenyl)methylamino)-2-
(S)-(4-fluorophenyl)-3-(S)-(morpholin-4-ylcarbonyl)
cyclopentane;

1-(S)-((2-methoxy-5-(1-tetrazolyl)phenyl)methylamino)-2-
(S)-(4-fluorophenyl)-3-(S)-(t-butylaminocarbonyl)
cyclopentane;

1-(S)-((2-methoxy-5-(1-tetrazolyl)phenyl)methylamino)-2-
(S)-(4-fluorophenyl)-3-(S)-(aminocarbonylmethylamino)
cyclopentane;

1-(S)-((2-methoxy-5-(1-tetrazolyl)phenyl)methylamino)-2-
(S)-(4-fluorophenyl)-3-(S)-(methoxycarbonylamino)
cyclopentane;

1-(S)-((2-methoxy-5-(1-tetrazolyl)phenyl)methylamino)-2-
(S)-(4-fluorophenyl)-3-(S)-
(dimethylaminocarbonylamino)cyclopentane;

1-(S)-((2-methoxy-5-(1-tetrazolyl)phenyl)methylamino)-2-
(S)-(4-fluorophenyl)-3-(S)-(methylaminocarbonylamino)
cyclopentane;

1-(S)-((2-methoxy-5-(1-tetrazolyl)phenyl)methylamino)-2-
(S)-(4-fluorophenyl)-3-(S)-(ethylsulfonylamino)
cyclopentane;

1-(S)-((2-methoxy-5-(1-tetrazolyl)phenyl)methylamino)-2-(S)-(4-fluorophenyl)-3-(S)-(pyrrolidin-1-ylmethyl) cyclopentane;

1-(S)-((2-methoxy-5-(5-trifluoromethyltetrazol-1-yl) phenyl)methylamino)-2-(S)-(4-fluorophenyl)-3-(S)-(pyrrolidin-1-ylmethyl)cyclopentane;

1-(S)-((2-methoxy-5-(1-tetrazolyl)phenyl)methylamino)-2-(S)-(4-fluorophenyl)-3-(S)-(1,2,3-triazol-1-ylmethyl) cyclopentane;

1-(S)-((2-methoxy-5-(5-trifluoromethyltetrazol-1-yl) phenyl)methylamino)-2-(S)-(4-fluorophenyl)-3-(S)-(2-methyl-5-tetrazol-5-ylmethyl)cyclopentane;

methyl 3-(SR)-(2-methoxy-5-((5-trifluoromethyl)tetrazol-1-yl)phenyl)methylamino-2-(SR)-(4-fluorophenyl)-cyclopentane-1-(SR)-carboxylate;

N-((2-methoxy-5-trifluoromethoxy)phenylmethyl)-3-(SR)-(5-methyl-1,3,4-oxadiazol-2-yl)-2-(SR)-(4-fluorophenyl) cyclopentan-1-(SR)-amine;

methyl 3-(S)-{[2-isopropoxy-5-(1-methyl-1H-tetrazol-5-yl) -phenyl]-methylamino}-2-(S)-(4-fluorophenyl)-cyclopentane-1-(S)-carboxylate;

3-(SR)-((2-isopropoxy-5-(5-trifluoromethyltetrazol-1-yl) phenyl)methylamino)-2-(SR)-(4-fluorophenyl) cyclopentane-1-(SR)carboxamide;

methyl 3-(SR)-((2-cyclobutyloxy-5-(1-tetrazolyl)phenyl) methylamino)-2-(SR)-(4-fluorophenyl)cyclopentane-1-(SR)carboxylate;

3-(SR)-((2-isopropoxy-5-(tetrazol-1-yl)phenyl) methylamino)-2-(SR)-(4-fluorophenyl)cyclopentane-1-(SR)carboxamide;

1S-(1'S-methyl-(3,5-bistrifluoromethyl)benzyloxy)-2S-phenyl-3R-hydroxymethylcyclohexane;

1S-((1'R-(3,5-bistrifluoromethyl)phenyl)ethoxy)-2S-phenyl-3S-(N-methyl-N-(5-oxo-1,2,4-triazol-2-yl) methylamino))-cyclohexane;

1S-((1'R-(3,5-bistrifluoromethyl)phenyl)ethoxy)-2S-phenyl-3S-(N-methyl-N-(5-(1,2,4-triazolylmethyl) amino))-cyclohexane;

1S-((1'R-(3,5-bistrifluoromethyl)phenyl)ethoxy)-2S-phenyl-3S-aminocyclohexane;

1S-(1'R-(3,5-bistrifluoromethyl)phenyl)ethoxy)-2S-phenyl-3S-(amino-aminocarbonyl methyl amino-cyclohexane;

1S-(1'R-(3,5-bistrifluoromethyl)phenyl)ethoxy)-2S-phenyl-3S-(N-(2-pyrrolidinone-5-(S)-yl-methyl)) aminocyclohexane;

1S-(N-2-methoxy-5-(5-trifluoromethyl-1,2,3,4-tetrazol-1-yl))benzylamino-2S-phenyl-3S-hydroxymethylcyclohexane;

1S-(N-2-methoxy-5-(1,2,3,4-tetrazol-1-yl))benzylamino-2S-phenyl-3S-methylamino-cyclohexane;

1(S)-N-(2-methoxy-5-(trifluoromethyl-1,2,3,4-tetrazol-1-yl))benzyl-2(S)-phenyl-3(S)-(pyrrolidin-1-yl-methyl) cyclohexane;

1(S)-N-(2-methoxy-5-(trifluoromethyl-1,2,3,4-tetrazol-1-yl))benzyl-2(S)-phenyl-3(S)-methoxymethylcyclohexane;

1(S)-N-(2-methoxy-5-(1-tetrazolyl))-benzylamino-2(S)-phenylcyclohexane;

1(S)-N-(2-methoxy-5-(trifluoromethyl-1,2,3,4-tetrazol-1-yl))benzyl-2(S)-phenylcyclohexane;

1S-[(N-benzyloxycarbonyl)-(N-2-methoxy-5-(5-trifluoromethyl-1,2,3,4-tetrazol-1-yl))]benzylamino-2S-phenyl-3S-(2-hydroxyethyl)cyclohexane;

and pharmaceutically acceptable salts and individual diastereomers thereof.

Even more preferred compounds within the present invention include:

3-(S)-(2-methoxy-5-((5-trifluoromethyl)tetrazol-1-yl) phenyl)-methylamino-2-(S)-(4-fluorophenyl) cyclopentane-1-(S)-(N-t-butyl)carboxamide;

3-(SR)-(2-methoxy-5((5-trifluoromethyl)tetrazol-1-yl) phenyl)methylamino-2-(SR)-(4-fluorophenyl)-cyclopentane-1-(SR)-(N-t-butyl)carboxamide;

1-(S)-((2-isopropoxy-5-(5-trifluoromethyltetrazol-1-yl) phenyl)methylamino)-2-(S)-(4-fluorophenyl)-3-(S)-(pyrrolidin-1-ylmethyl)-cyclopentane;

1-(S)-((2-methoxy-5-(5-trifluoromethyltetrazol-1-yl) phenyl)methylamino)-2-(S)-(4-fluorophenyl)-3-(S)-(2-(S)-(aminocarbonyl)pyrrolidin-1-ylmethyl)cyclopentane;

1-(S)-((2-methoxy-5-(5-trifluoromethyltetrazol-1-yl) phenyl)-methylamino)-2-(S)-(4-fluorophenyl)-3-(S)-(1-methyl-5-tetrazol-5-ylmethyl)-cyclopentane;

N-(2-methoxy-5-((5-trifluoromethyl)tetrazol-1-yl)phenyl) methyl)-3-(SR)-(imidazol-2-yl)-2-(SR)-(4-fluorophenyl) cyclopentan-1-(SR)-amine;

N-(2-methoxy-5-((5-trifluoromethyl)tetrazol-1-yl)phenyl) methyl)-3-(SR)-((1-methyl)imidazol-2-yl)-2-(SR)-(4-fluorophenyl)cyclopentan-1-(SR)-amine;

N-(2-methoxy-5-((5-trifluoromethyl)tetrazol-1-yl)phenyl) methyl)-3-(SR)-(thiazol-2-yl)-2-(SR)-(4-fluorophenyl) cyclopentan-1-(SR)-amine;

N-(2-methoxy-5-((5-trifluoromethyl)tetrazol-1-yl)phenyl) methyl)-3-(S)-(thiazol-2-yl)-2-(S)-(4-fluorophenyl) cyclopentan-1-(S)-amine;

N-(2-methoxy-5-((5-trifluoromethyl)tetrazol-1-yl)phenyl) methyl)-3-(SR)-(isoxazol-3-yl)-2-(SR)-(4-fluorophenyl) cyclopentan-1-(SR)-amine;

N-(2-methoxy-5-((5-trifluoromethyl)tetrazol-1-yl)phenyl) methyl)-3-(S)-(5-methyl-1,3,4-oxadiazol-2-yl)-2-(S)-(4-fluorophenyl)cyclopentan-1-(S)-amine;

N-(2-methoxy-5-((5-trifluoromethyl)tetrazol-1-yl)phenyl) methyl)-3-(SR)-(tetrazol-1-yl)-2-(RS)-(4-fluorophenyl) cyclopentan-1-(SR)-amine;

N-(2-methoxy-5-((5-trifluoromethyl)tetrazol-1-yl)phenyl) methyl)-3-(SR)-(1,2,4-triazol-4-yl)-2-(SR)-(4-fluorophenyl)cyclopentan-1-(SR)-amine;

(1RS,2RS,3RS)-3-((5-(3,5-Dimethylisoxazol-4-yl)-2-methoxyphenyl)-methylamino)-2-(4-fluorophenyl) cyclopentane-carboxylic acid methyl ester;

methyl 3-(S,R)-(($^2$-methoxy-5-(5-trifluoromethyl-tetrazol-1-yl)-3-pyridine)methylamino)-2-(S,R)-(4-fluorophenyl) cyclopentane-1-(S,R)-carboxylate;

methyl 3-(S,)-(5-(5-trifluoromethyl-1-tetrazol-1-yl)-(7-benzofuran)-methylamino)-2-(S,)-(4-fluorophenyl) cyclopentane-1-(S,)-carboxylate;

methyl 3-(S)-[(5-cyano-2-isopropoxy-phenyl)-methylamino]-2-(S)-(4-fluorophenyl)-cyclopentane-1-(S) -carboxylate;

1-(S)-[(5-Cyano-2-isopropoxy-phenyl)-methylamino]-2-(S) -(4-fluorophenyl)-3-(S)-(2-thiazol-2-yl)-cyclopentane;

methyl 3-(SR)-((2-isopropoxy-5-(tetrazol-1-yl) phenyl) methylamino)-2-(SR)-(4-fluorophenyl)cyclopentane-1-(SR)carboxylate;

3-(SR)-((2-isopropoxy-5-(tetrazol-1-yl) phenyl) methylamino)-2-(SR)-(4-fluorophenyl) cyclopentane-1-(SR)-tert-butyl-carboxamide;

methyl 3-(SR)-((2-isopropoxy-5-(5-trifluoromethyltetrazol-1-yl) phenyl)methylamino)-2-(SR)-(4-fluorophenyl) cyclopentane-1-(SR) carboxylate;

methyl 3-(S)-((2-methylsulfanyl-5-(5-trifluoromethyltetrazol-1-yl)phenyl) methylamino)-2-(S)-(4-fluorophenyl) cyclopentane-1-(S)carboxylate;

1(S)-N-(2-methoxy-5-(1-tetrazolyl))-benzylamino-2(S)-phenyl-3(S)-carboxymethylcyclohexane;

1(S)-N-(2-methoxy-5-(trifluoromethyl-1,2,3,4-tetrazol-1-yl))benzyl-2(S)-phenyl-3(S)-imidazole cyclohexane;

1(S)-N-(2-methoxy-5-(1-tetrazolyl))-benzylamino-2(S)-phenyl-3(S)-ethyl cyclohexane;

and pharmaceutically acceptable salts and individual diasteromers thereof.

There are several acceptable methods of naming the compounds discussed herein.

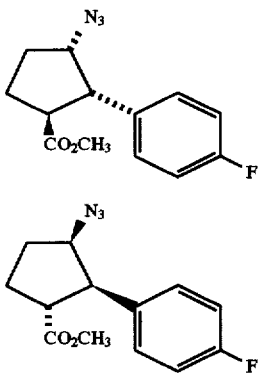

For example, the racemic mixture of A and B shown above can be named either as "(1RS,2RS,3RS)-2-(4-fluorophenyl)-3-azidocyclopentanecarboxylic acid methyl ester" or as "methyl 3-(SR)-azido-2-(SR)-(4-fluoro)phenyl-1-(SR)-carboxylate".

Throughout the instant application, the following abbreviations are used with the following meanings:

| Reagents: | |
|---|---|
| Cbz-Cl | benzyl chloroformate |
| BOP | benzotriazol-1-yloxy tris(dimethylamino)-phosphonium hexafluorophosphate |
| CDI | 1,1'-carbonyldiimidazole |
| ACE-Cl | alpha-chloroethyl chloroformate |
| MCPBA | m-chloroperbenzoic acid |
| DBU | 1,8-diazabicyclo[5.4.0]undec-7-ene |
| DCC | N,N'-dicyclohexylcarbodiimide |
| DCU | N,N'-dicyclohexylurea |
| DIBAL | diisobutylaluminum hydride |
| iPr$_2$NEt or DIPEA | N,N-diisopropylethylamine |
| EDC | 1-(3-dimethylaminopropyl)-3-ethylcarbodiimide hydrochloride |
| DMAP | 4-dimethylaminopyridine |
| Me$_2$SO$_4$ | dimethyl sulfate |
| EDAC | 1-ethyl-3-(3-dimethylaminopropyl)carbo- diimide hydrochloride |
| HOBt | 1-hydroxybenzotriazole hydrate |
| NHS | N-hydroxysuccinimide |
| LAH | lithium aluminum hydride |
| LHMDS | lithium bis(trimethylsilyl)amide |
| NMM | N-methylmorpholine |
| KHMDS | potassium bis(triethylsilyl)amide |
| NaOEt | sodium ethoxide |
| Et$_3$N | triethylamine |
| Ph$_3$P | triphenylphosphine |
| TFA | trifluoroacetic acid |
| Solvents: | |
| AcOH | acetic acid |
| MeCN | acetonitrile |
| AmOH | n-amyl alcohol |
| DMSO | dimethylsulfoxide |
| DMF | N,N-dimethylformamide |
| EtOH | ethanol |
| MeOH | methanol |
| THF | tetrahydrofuran |
| Others: | |

| | |
|---|---|
| Am | n-amyl |
| Ar | aryl |
| BOC | tert-butoxycarbonyl |
| Bn | benzyl |
| Bu | butyl |
| Cbz | carbobenzyloxy (benzyloxycarbonyl) |
| calc. | calculated |
| cat. | catalytic |
| EI-MS | electron ion-mass spectroscopy |
| Et | ethyl |
| eq. | equivalent(s) |
| FAB-MS | fast atom bombardment mass spectrometry |
| HPLC | high pressure liquid chromatography |
| iPr | isopropyl |
| MPLC | medium pressure liquid chromatography |
| Me | methyl |
| MHz | megahertz |
| MF | molecular formula |
| NMR | nuclear magnetic resonance |
| Ph | phenyl |
| PTC | phase transfer catalyst |
| prep. | prepared or preparative |
| Pr | propyl |
| rt | room temperature |
| TLC | thin layer chromatography |
| TMS | tetramethylsilane |

The preparation of compounds of Formula I of the present invention may be carried out in sequential or convergent synthetic routes. Syntheses detailing the preparation of the compounds of Formula I in a sequential manner are presented in the following reaction schemes. The skills required in carrying out the reaction and purification of the resulting reaction products are known to those in the art. Purification procedures includes crystallization, normal phase or reverse phase chromatography.

Several methods for preparing the compounds of this invention are illustrated in the following Schemes and Examples wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are as defined above.

SCHEME 1

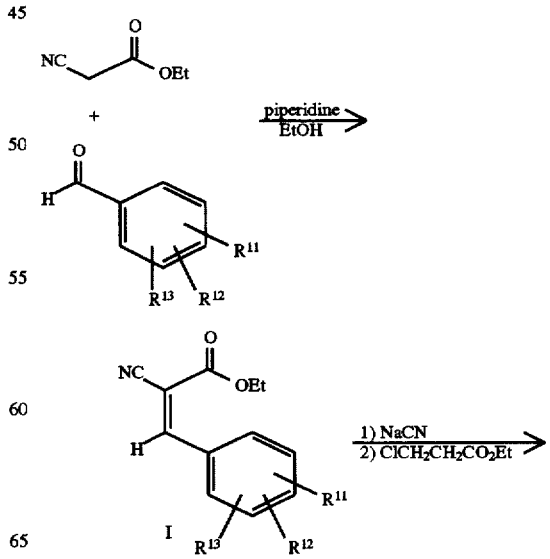

SCHEME 1

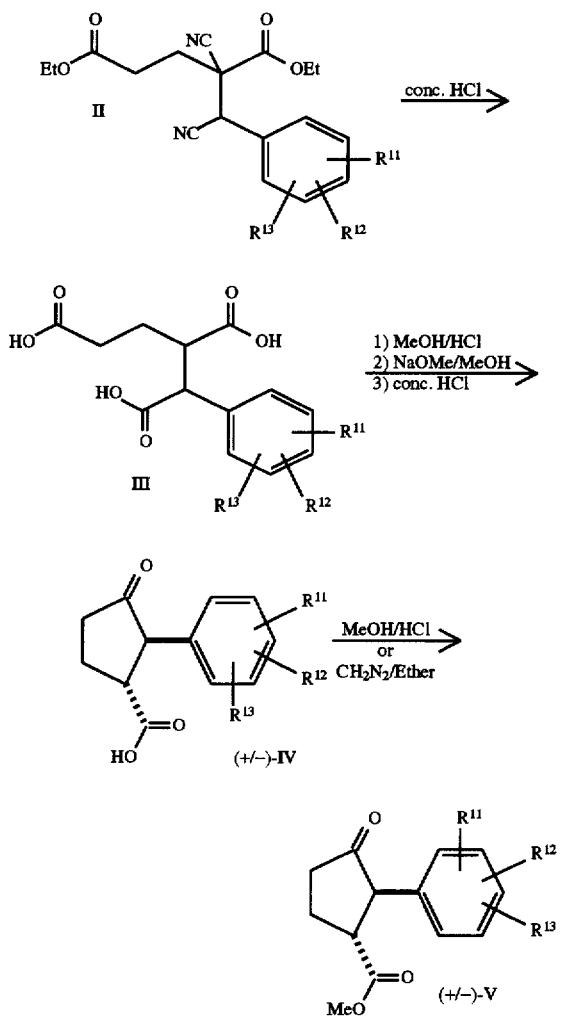

Intermediates for preparation of the compounds of the present invention in which the central ring is 5-membered may be synthesized by the general route outlined in Scheme 1. Thus, according to the procedure of Baker and Leeds (*J. Chem. Soc* 1948, 974), condensation of ethyl cyanoacetate and benzaldehyde (with or without substituents) in the presence of a base such as piperidine provides the unsaturated derivative I. Exposure of this olefin to sodium cyanide followed by ethyl 3-chloropropionate gives the dicyano derivative II, which after aqueous acidic hydrolysis yields triacid III. After esterification with acidic methanol, the triester may be cyclized by heating with sodium methoxide in dry methanol followed by treatment with aqueous HCl, to provide racemic cyclopentanone IV. The methyl ester V may be formed from ketone IV by treatment with acidic methanol or diazomethane in ether.

SCHEME 2

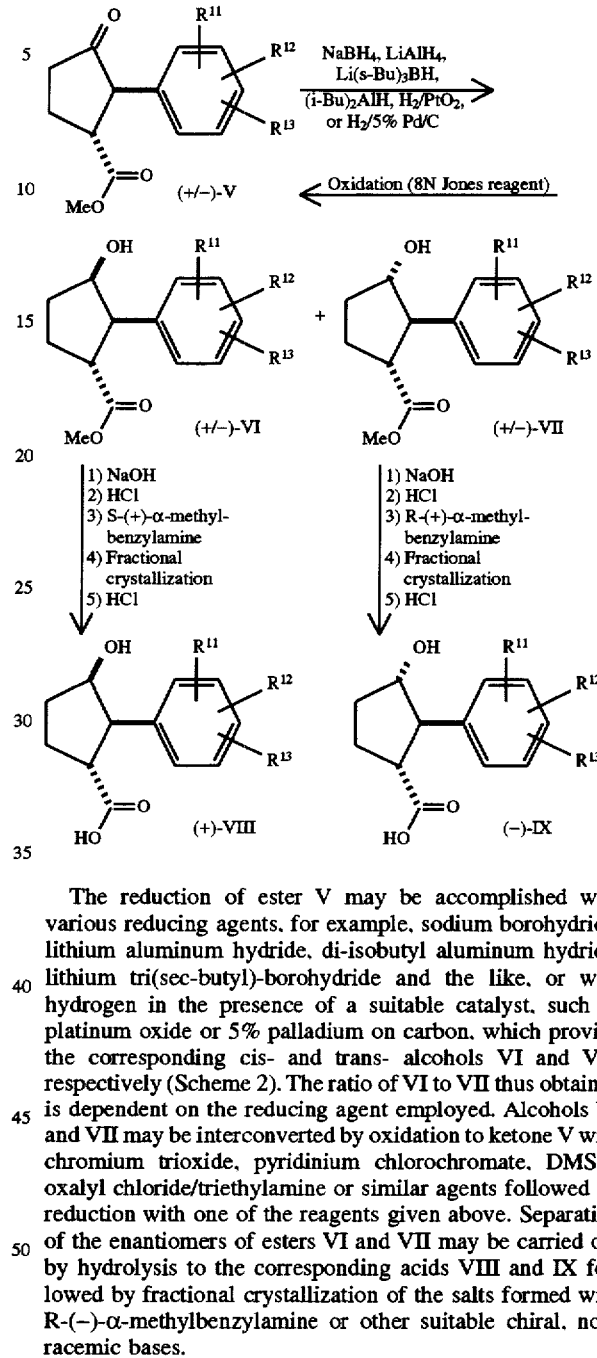

The reduction of ester V may be accomplished with various reducing agents, for example, sodium borohydride, lithium aluminum hydride, di-isobutyl aluminum hydride, lithium tri(sec-butyl)-borohydride and the like, or with hydrogen in the presence of a suitable catalyst, such as platinum oxide or 5% palladium on carbon, which provide the corresponding cis- and trans- alcohols VI and VII, respectively (Scheme 2). The ratio of VI to VII thus obtained is dependent on the reducing agent employed. Alcohols VI and VII may be interconverted by oxidation to ketone V with chromium trioxide, pyridinium chlorochromate, DMSO/oxalyl chloride/triethylamine or similar agents followed by reduction with one of the reagents given above. Separation of the enantiomers of esters VI and VII may be carried out by hydrolysis to the corresponding acids VIII and IX followed by fractional crystallization of the salts formed with R-(−)-α-methylbenzylamine or other suitable chiral, non-racemic bases.

SCHEME 3

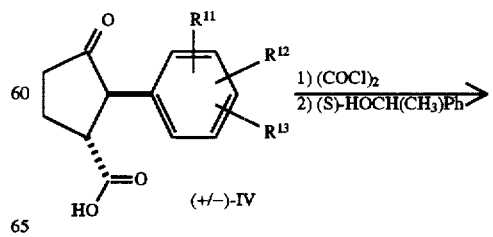

SCHEME 3

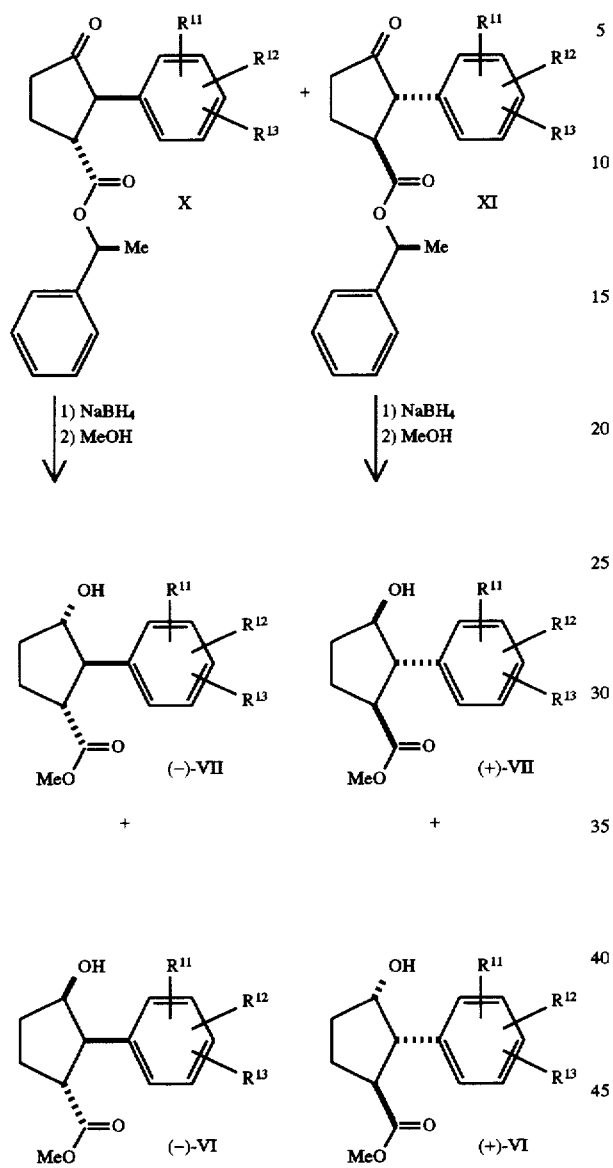

SCHEME 4

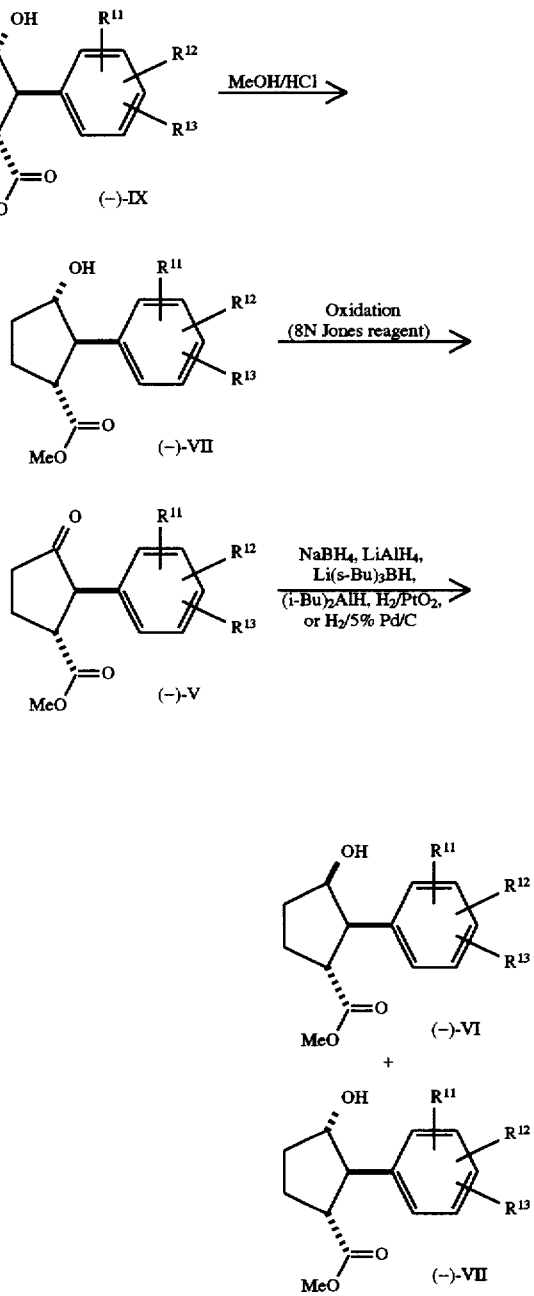

An alternative method of resolution is shown in Scheme 3. The racemic acid (+/−)-IV is activated with, for example, oxalyl chloride, DCC, EDAC/HOBt or similar condensing reagents, and then allowed to react with a chiral, non-racemic alcohol, such as (S)-alpha-methylbenzyl alcohol, to give the esters X and XI. After separating these diastereomers, they are individually treated with a suitable reducing agent, such as sodium borohydride, to give mixtures of the corresponding alcohols, which are then trans-esterified with methanol to provide the separate enantiomers of esters VI and VII.

Conversion of the free acids to the methyl esters is accomplished as shown in Scheme 4. Interconversion of the non-racemic cis and trans alcohols VI and VII may be carried out by oxidation to the non-racemic ketone V followed by reduction with an appropiate reducing agent as given above.

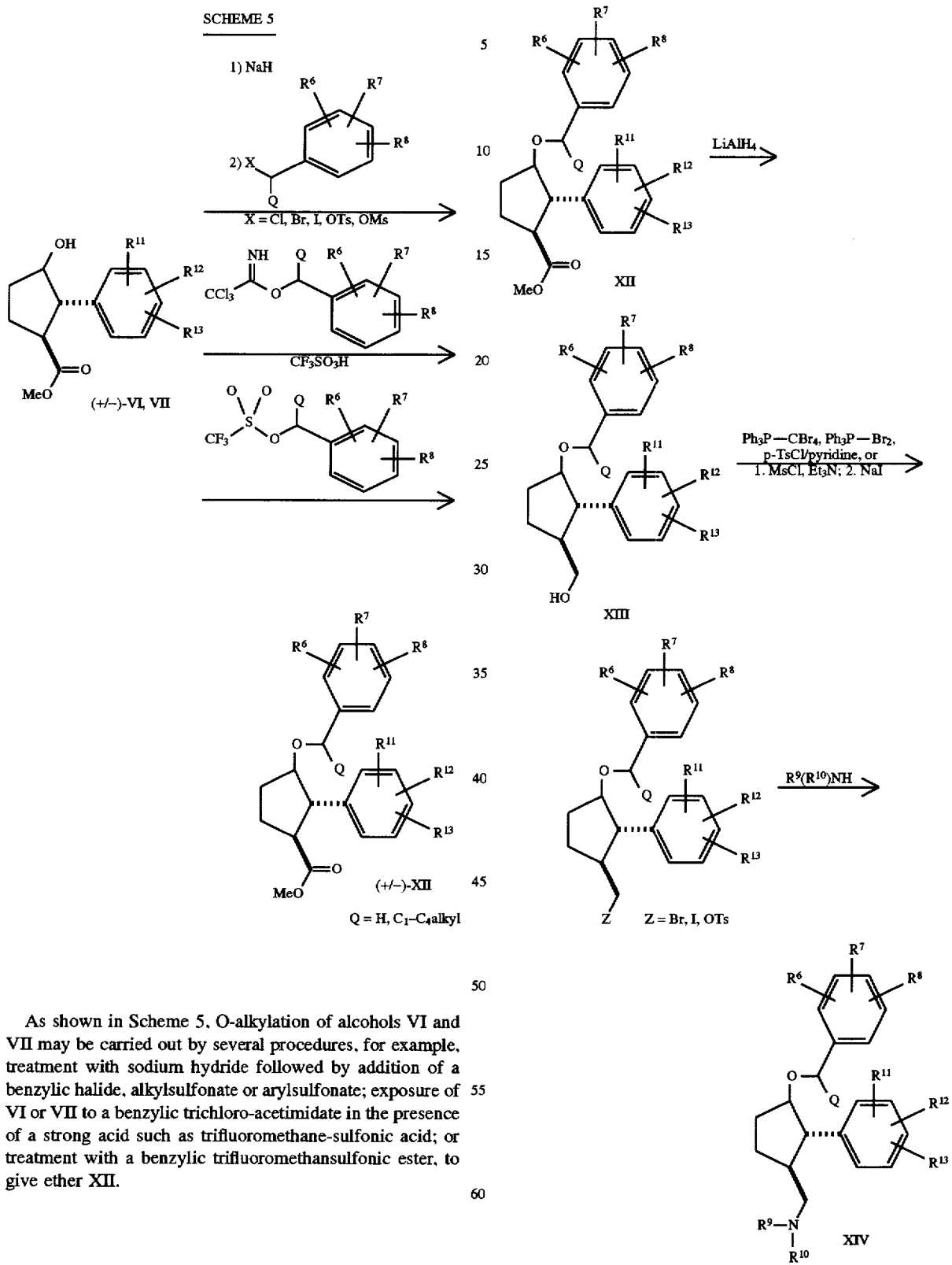

As shown in Scheme 5, O-alkylation of alcohols VI and VII may be carried out by several procedures, for example, treatment with sodium hydride followed by addition of a benzylic halide, alkylsulfonate or arylsulfonate; exposure of VI or VII to a benzylic trichloro-acetimidate in the presence of a strong acid such as trifluoromethane-sulfonic acid; or treatment with a benzylic trifluoromethansulfonic ester, to give ether XII.

Ester XII may be reduced with a hydride-reducing agent such as lithium aluminum hydride, lithium borohydride or di-isobutylaluminum hydride to provide the primary alcohol XIII, which may be further functionalized by standard acylation or etherification, reactions (Scheme 6). Alternatively, the hydroxyl group may be replaced by a leaving group such as a bromide (by exposure to triphenylphosphine-bromine or triphenylphosphine-carbon tetrabromide), an iodide (by treatment with methanesulfonyl chloride followed by sodium iodide) or a p-toluenesulfonate (by treatment with p-TsCl in the presence of a suitable base such as pyridine). The leaving group may then be displaced by a variety of nucleophiles such as unsubstituted, mono- or disubstituted amines $R^9(R^{10})NH$, to give amine XIV.

SCHEME 7

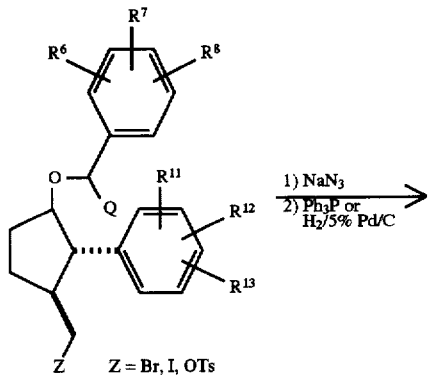

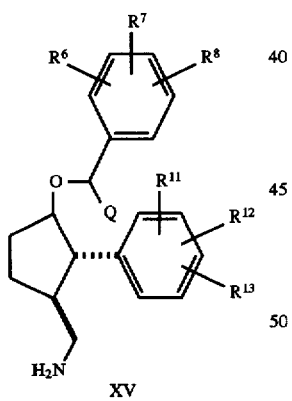

SCHEME 8

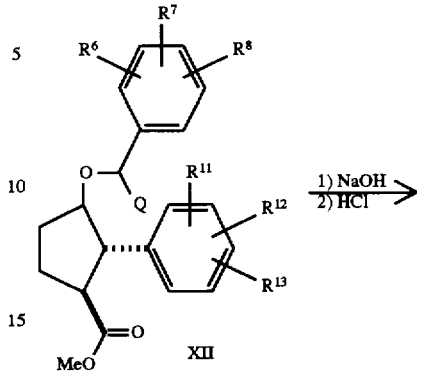

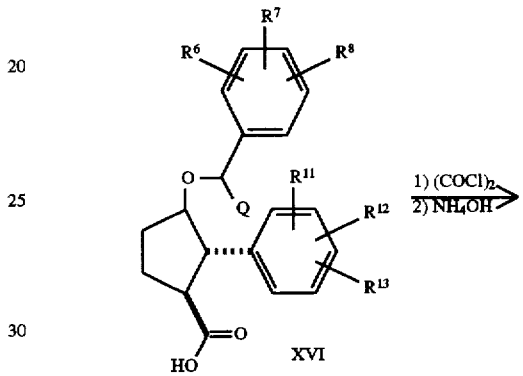

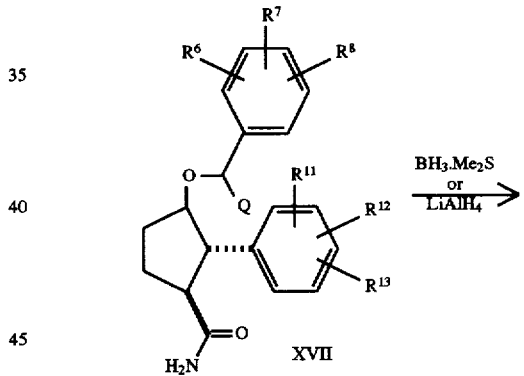

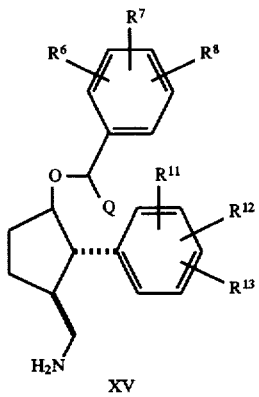

Alternatively, as shown in Scheme 7 the leaving group may be displaced by azide anion and the azide group reduced by treatment with either triphenylphosphine/water or hydrogenation in the presence of a suitable metal catalyst to give the primary amine XV.

Primary amine XV may also be prepared by the route shown in Scheme 8. Hydrolysis of ester XII to the acid XVI, followed by formation of the acid chloride and exposure to aqueous ammonia, provides primary amide XVII. Reduction with borane-methyl sulfide, lithium aluminum hydride, or a similar reagent then gives amine XV.

SCHEME 9

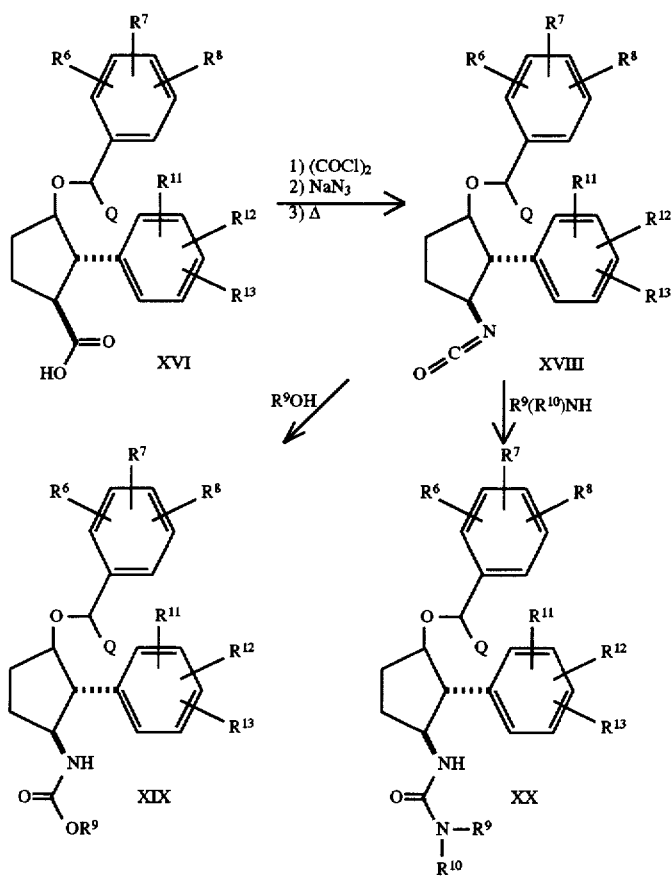

Treatment of acid XVI with oxalyl chloride and then sodium azide provides the corresponding acyl azide, which upon thermolysis provides isocyanate XVIII (Scheme 9). Treatment of XVIII with an alcohol $R^9OH$ gives the carbamate XIX, while reaction of XVIII with an amine $R^9(R^{10})$NH provides the urea XX.

SCHEME 10

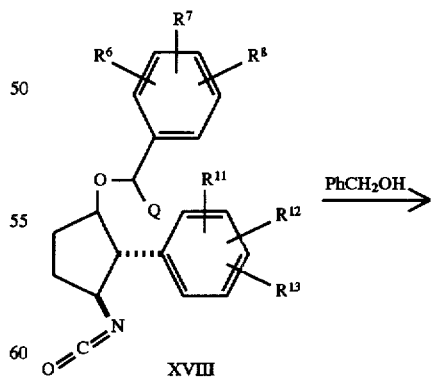

-continued
SCHEME 10

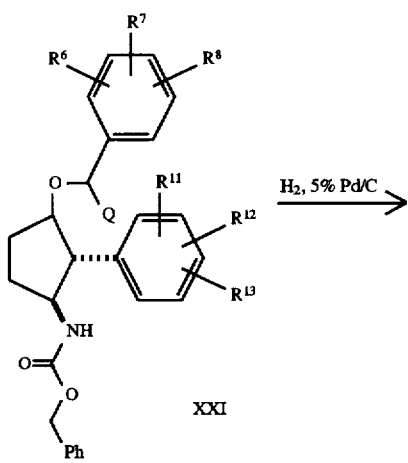

XXI

In the specific case where R⁹OH=PhCH₂OH, the CBZ-protected amine XXI is obtained, which may be de-protected under standard conditions (for example, H₂, 10% Pd/C) to afford primary amine XXII (Scheme 10).

SCHEME 11

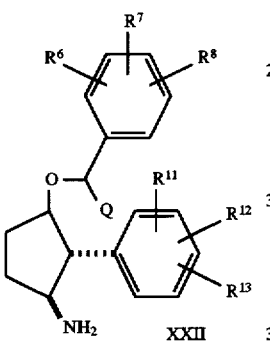

(+/−)-XVIII

-continued
SCHEME 11

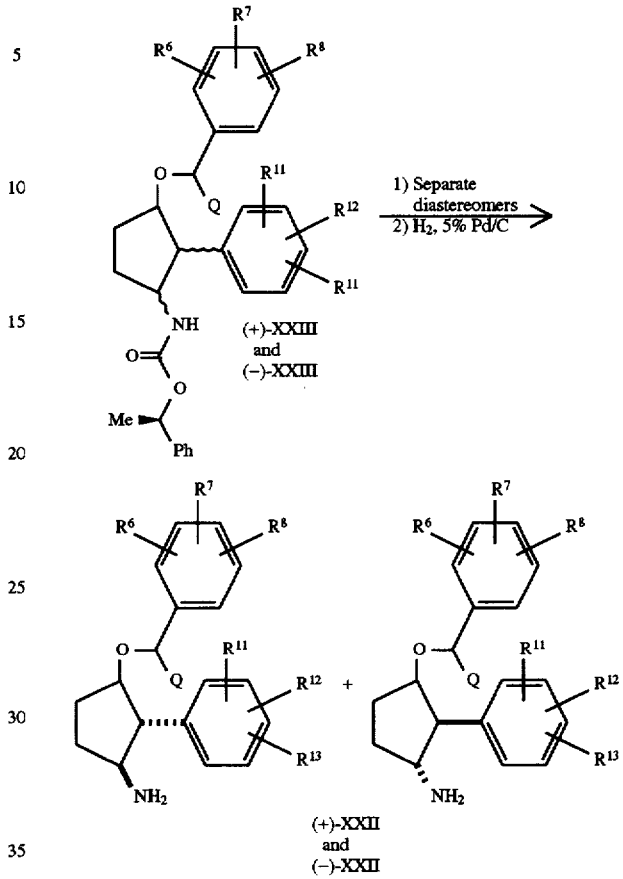

(+)-XXIII and (−)-XXIII (+)-XXII and (−)-XXII

If the enantiomers have not been separated up to this point, the isocyanate may be treated with a chiral, non-racemic alcohol such as (R)-(+)-alpha-methylbenzyl alcohol to form diastereomeric carbamates XXIII, which after diastereomer separation by, for example, fractional crystallization or chromatography, may be converted to the non-racemic primary amine XXII by reduction or hydrolysis (Scheme 11).

SCHEME 12

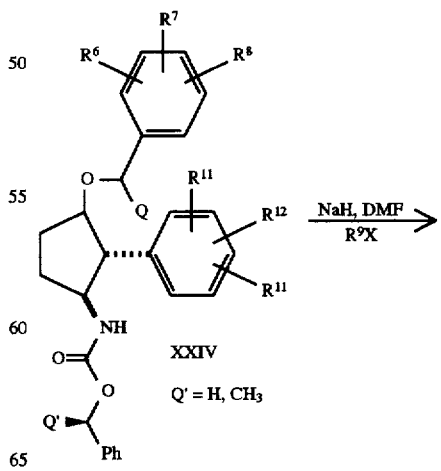

XXIV

Q' = H, CH₃

41
-continued
SCHEME 12

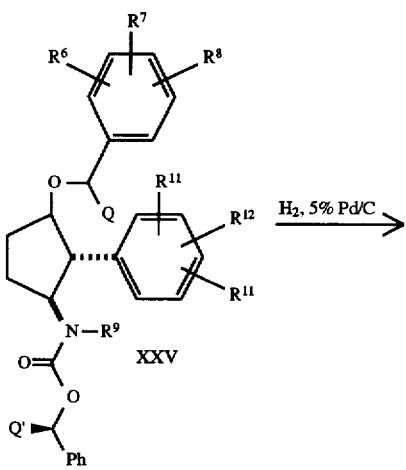

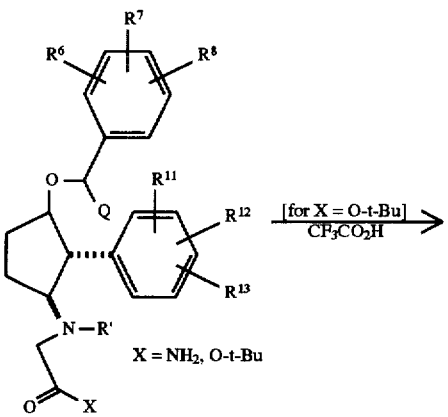

42
-continued
SCHEME 13

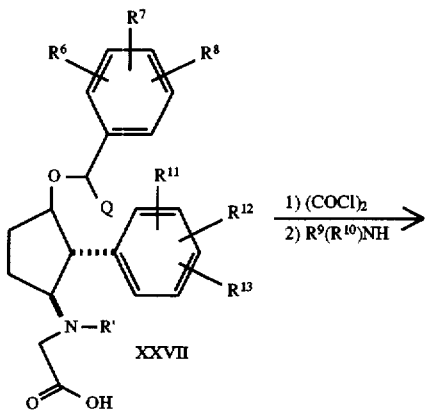

Alkylation of carbamate XXIV may be carried out by treatment with a suitable base such as sodium hydride followed by addition of an alkylating agent $R^9X$, where X=Cl, Br, I, OMs, or OTs, to afford XXV (Scheme 12). Cleavage of the carbamate under conditions described previously gives secondary amine XXVI.

SCHEME 13

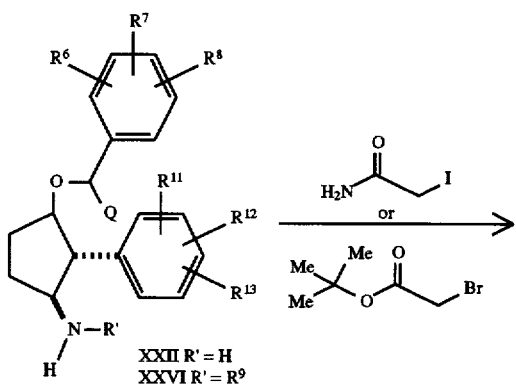

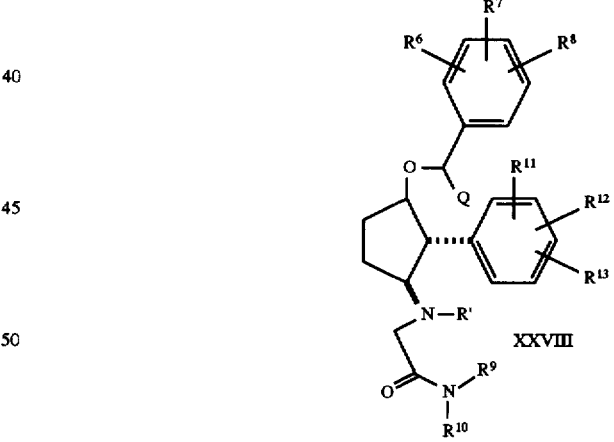

Alkylation of amine XXII or amine XXVI may be carried out by treatment with a number of reagents, such as iodoacetamide or t-butyl bromoacetate (Scheme 13). With the latter compound, the t-butyl ester may be cleaved by exposure to trifluoroacetic acid, to provide the carboxylic acid XXVII, which after treatment with coupling reagents such as oxalyl chloride, DCC or EDAC/HOBt, followed by addition of a primary or secondary amine $R^9(R^{10})NH$ gives carboxamide XXVIII.

SCHEME 14

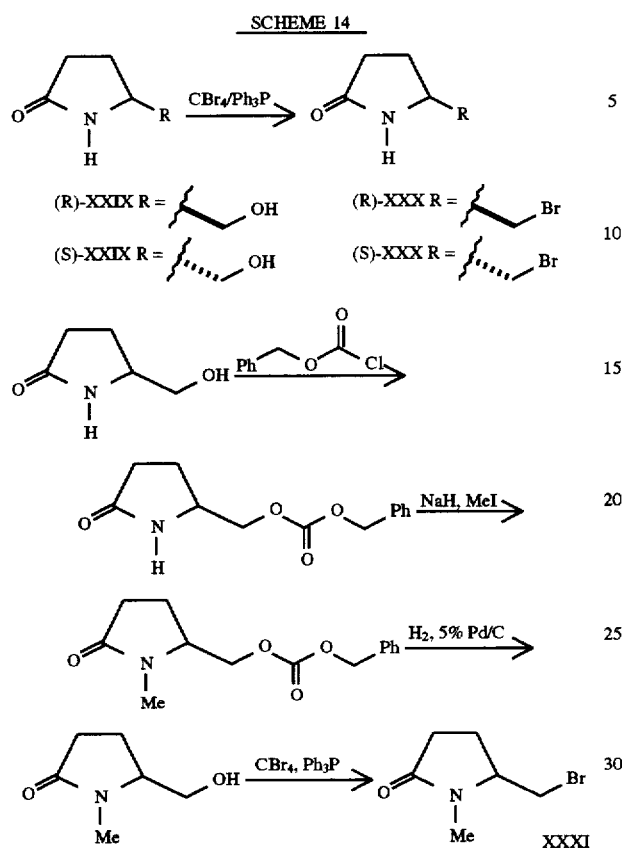

Alkylation of amines XXII and XXVI may also be accomplished with groups containing cyclic amides. Preparation of the appropriate intermediates is shown in Scheme 14. For example, the commercially available non-racemic pyrrolidone derivatives (R)-XXIX or (S)-XXIX may be converted into the corresponding bromide (R)-XXX by treatment with triphenylphosphine/carbon tetrabromide. Alternatively, the N-methyl derivative of XXX may be prepared by protecting the hydroxyl group of XXIX with a carbobenzyloxy group, then methylating the sodium salt of the intermediate amide, followed by cleavage of the protecting group under standard reductive conditions. Treatment as above with triphenylphosphine/carbon tetrabromide affords the primary bromide XXXI.

SCHEME 15

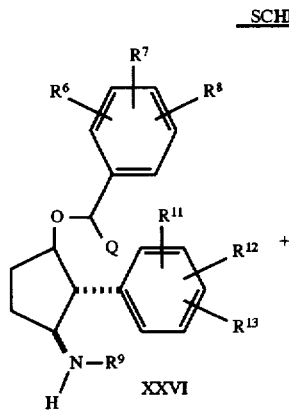

SCHEME 15

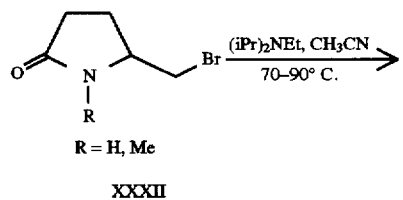

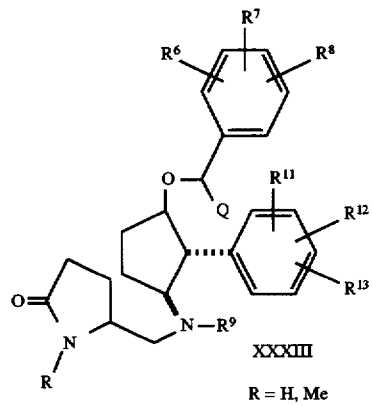

The bromides produced above may be employed to alkylate amine XXII and XXVI. For example, treatment of amine XXVI with bromide XXXII in acetonitrile in the presence of a suitable base such as di-isopropylethylamine affords the N-alkylated product XXXIII (Scheme 15). If the amine is racemic, alkylation with the chiral, non-racemic bromides (R)- or (S)-XXXII provides a mixture of diastereomers that may be separated by standard techniques.

SCHEME 16

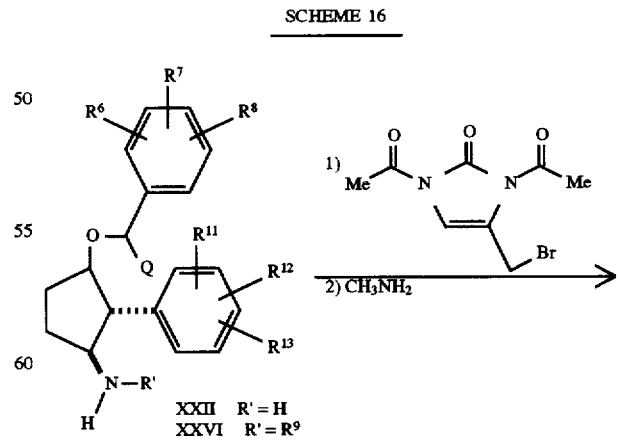

-continued
SCHEME 16

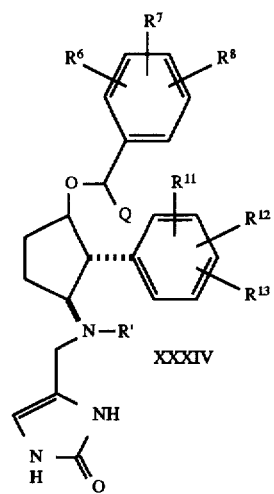

XXXIV

The cyclopentyl amines XXII and XXVI may also be alkylated with heteroarylalkyl subunits (Scheme 16). For example, treatment of amines XXII or XXVI with 4-(bromomethyl)-1,3-diacetyl-1H,3H-2-oxo-imidazole (prepared according to the procedure of R. Duschinsky and L. A. Dolan, *J. Am. Chem. Soc.*, 70, 657 (1948)) followed by de-acetylation with methylamine gives the cyclopentylamine derivative XXXII.

SCHEME 17

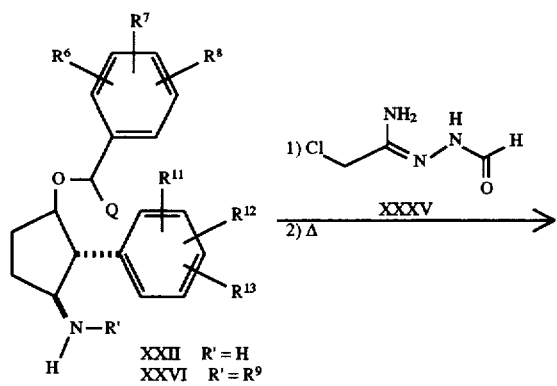

XXII R' = H
XXVI R' = R⁹

-continued
SCHEME 17

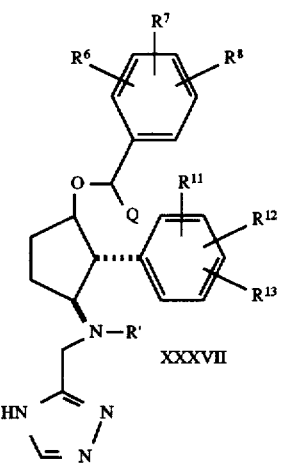

XXXVII

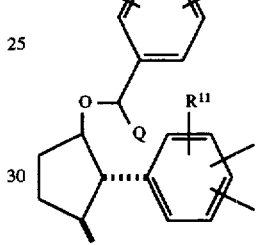

XXII R' = H
XXVI R' = R⁹

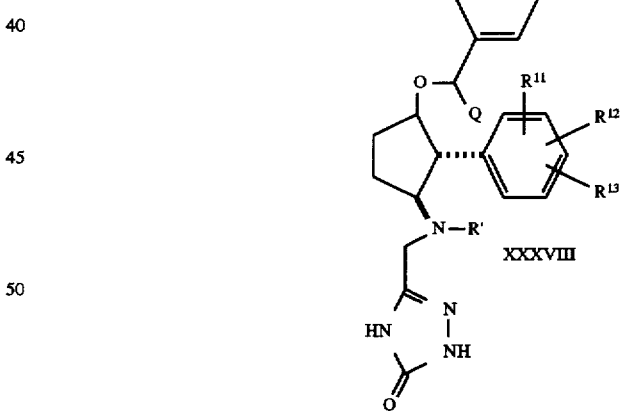

XXXVIII

Similarly, alkylation with the acyclic reagents XXXV or XXXVI followed by heating provides the N-(triazolomethyl) derivative XXXVII and the N-(triazolonomethyl) derivative XXXVIII, respectively (Scheme 17).

SCHEME 18

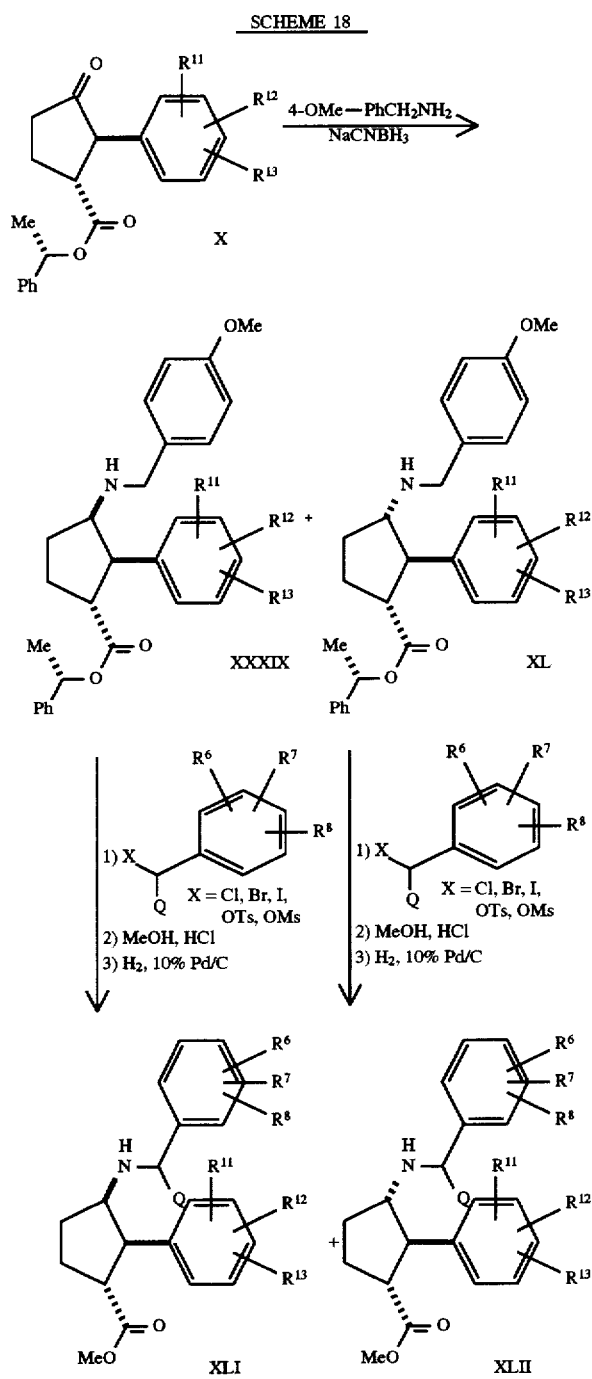

Benzylamine derivatives may be prepared as shown in Scheme 18. Treatment of ketone X with 4-methoxybenzylamine in the presence of a suitable reducing agent such as sodium cyanoborohydride provides a mixture of the cis and trans amines XXXIX and XL.

Alkylation with a benzyl halide, benzyl alkylsulfonate or benzyl arylsulfonate followed by acidic methanolysis and then hydrogenolysis with 10% Pd/C provides the N-benzylated derivatives XLI and XLII.

SCHEME 19

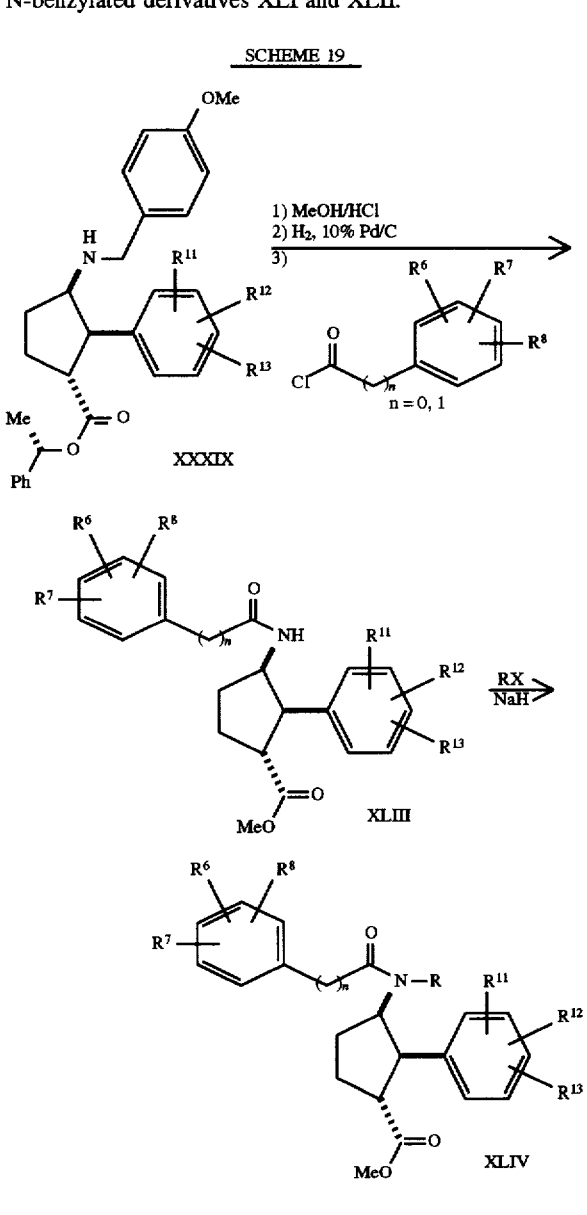

Amide derivatives may be prepared as shown in Scheme 19. Methanolysis of ester XXXIX, followed by removal of the para-methoxybenzyl protecting group with hydrogen and palladium on carbon and then acylation with an activated acyl derivative such as an acid chloride, provides amide XLIII. Optionally, the amide nitrogen may be alkylated with an alkyl halide such as methyl iodide in the presence of sodium hydride, to give tertiary amide XLIV.

SCHEME 20

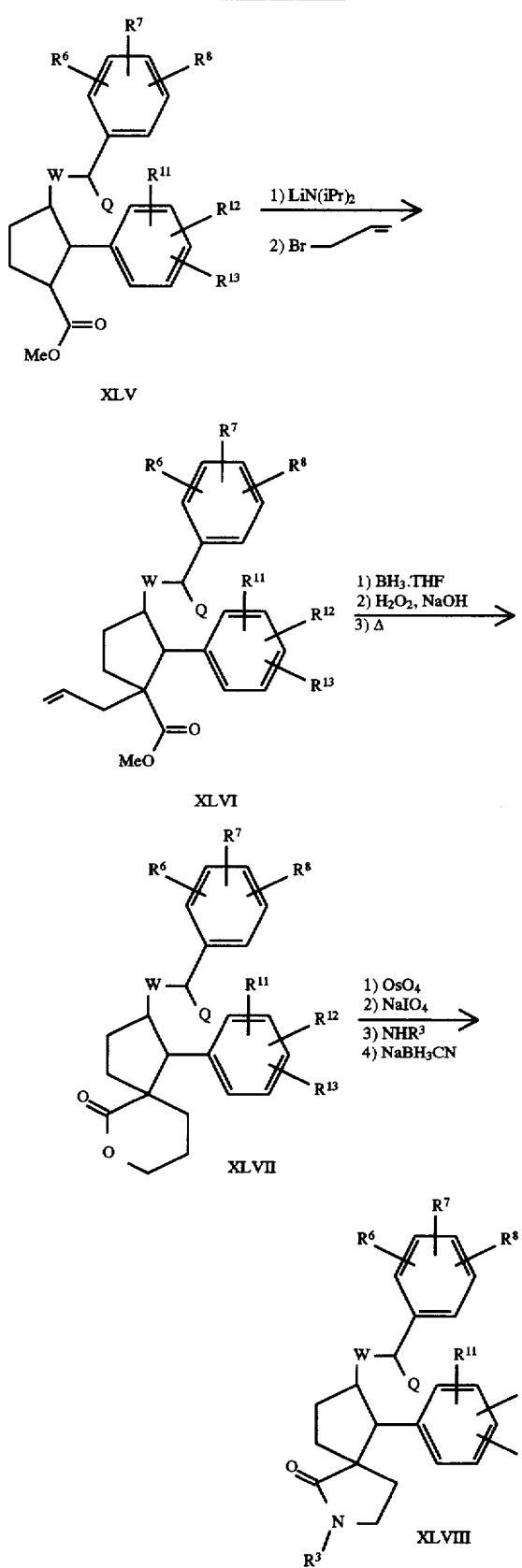

Derivatives with an additional substituent at the ring carbon to which Y is attached may be prepared as shown in Scheme 20. For example, treatment of XLV (which can be intermediates XII, XLI, or XLII) with a strong anhydrous base, such as lithium diisopropylamide, LHMDS, sodium hydride, or potassium hydride, followed by addition of an electrophile, such as an alkyl halide or alkyl sulfonate ester, or an allylic halide or allylic sulfonate ester, provides a compound with the alkyl group linked to the ring. If allyl bromide is employed, compound XLVI may be obtained by this procedure. The olefin can be hydroborated under standard conditions and the trialkylborane oxidized with hydrogen peroxide to provide the 3-hydroxypropyl substituent. Heating this compound with or without strong acid catalysis may provide the lactone XLVII. Alternatively, allyl-ester XLVI can be exposed to oxidizing conditions such as osmium tetroxide and then sodium periodate, or ozone gas at low temperature followed by dimethyl sulfide, or potassium permanganate, to provide the corresponding 2-oxo-ethyl substituent. Treatment of this aldehyde with an amine $NH_2R^3$ (wherein $R^3$ is as defined herein) followed by addition of a suitable reducing agent (such as sodium cyanoborohydride, sodium tris(acetoxy)borohydride, sodium borohydride, or hydrogen gas in the presence of a metal catalyst), provides the corresponding reductive amination product, which may either spontaneously cyclize to the lactam XLVIII or which may be induced to cyclize by heating or with an acid catalyst.

SCHEME 21

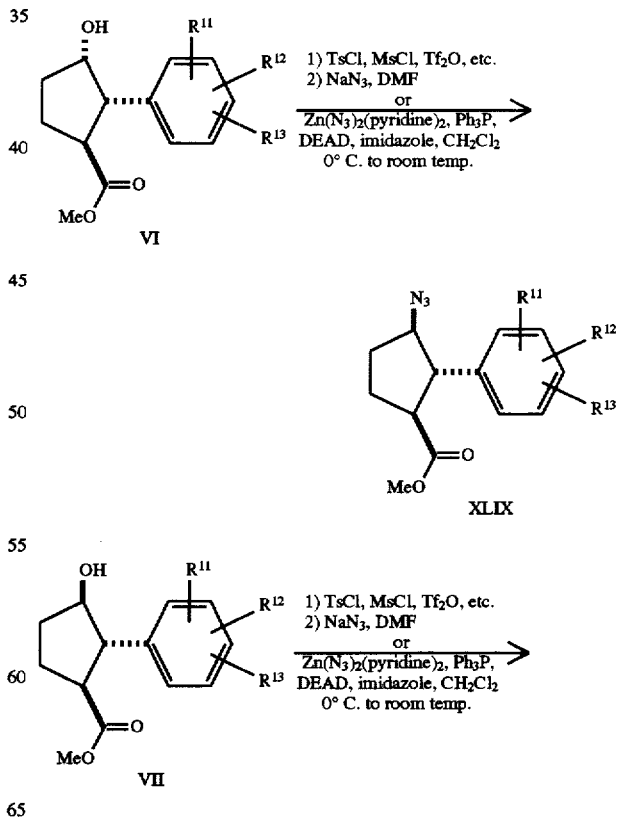

SCHEME 21 (continued)

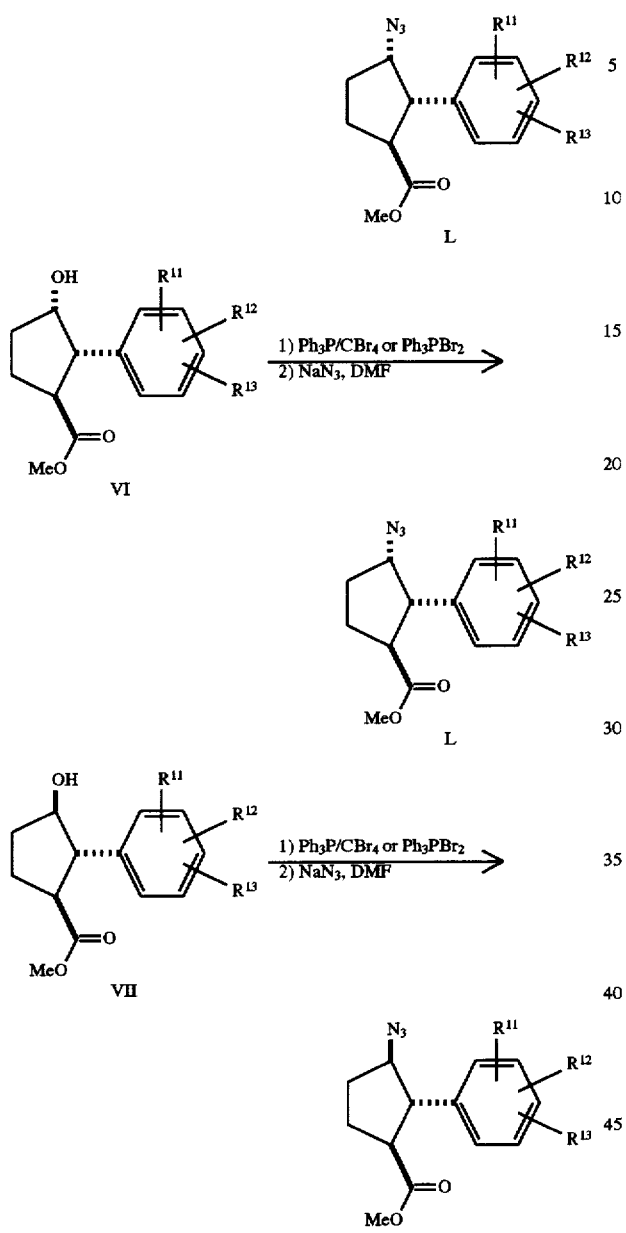

An alternative method for the synthesis of a 3-amino derivative is shown in Scheme 21. Treatment of hydroxy esters VI or VII with an activating agent, such as p-toluenesulfonyl chloride, methanesulfonyl chloride, trifluoromethanesulfonic anhydride, or similar agents, followed by treatment with sodium azide in DMF, provides the azide XLIX or L, respectively, in which the stereochemistry of the starting hydroxyl group has been inverted. Alternatively, activation of the alcohol VI or VII with a halogenating agent, for example triphenylphosphine/carbon tetrabromide or triphenylphosphine dibromide, followed by displacement with azide, results in formation of azides XLIX or L with overall retention of hydroxyl stereochemistry. Another method to produce the azide with inversion of stereochemistry involves treating the alcohol with triphenylphosphine, diethyl azodicarboxylate and zinc azide bis(pyridine) complex, in the presence of 2 equivalents of imidazole.

SCHEME 22

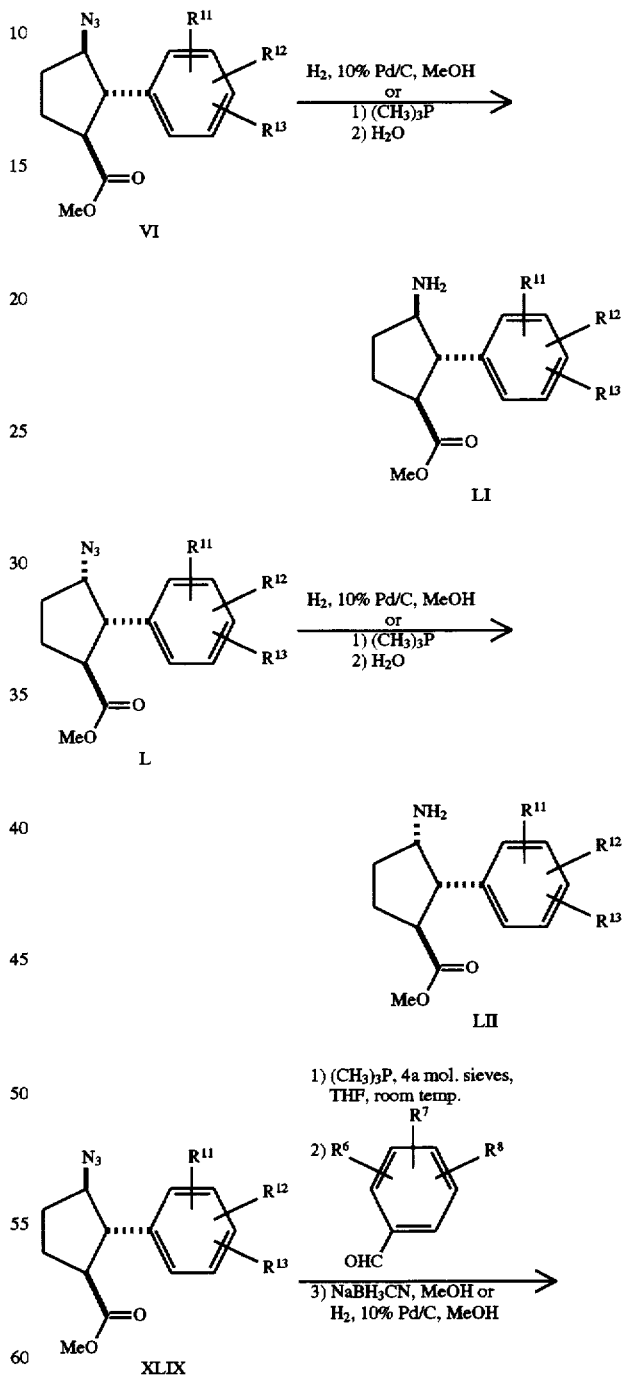

SCHEME 22 -continued

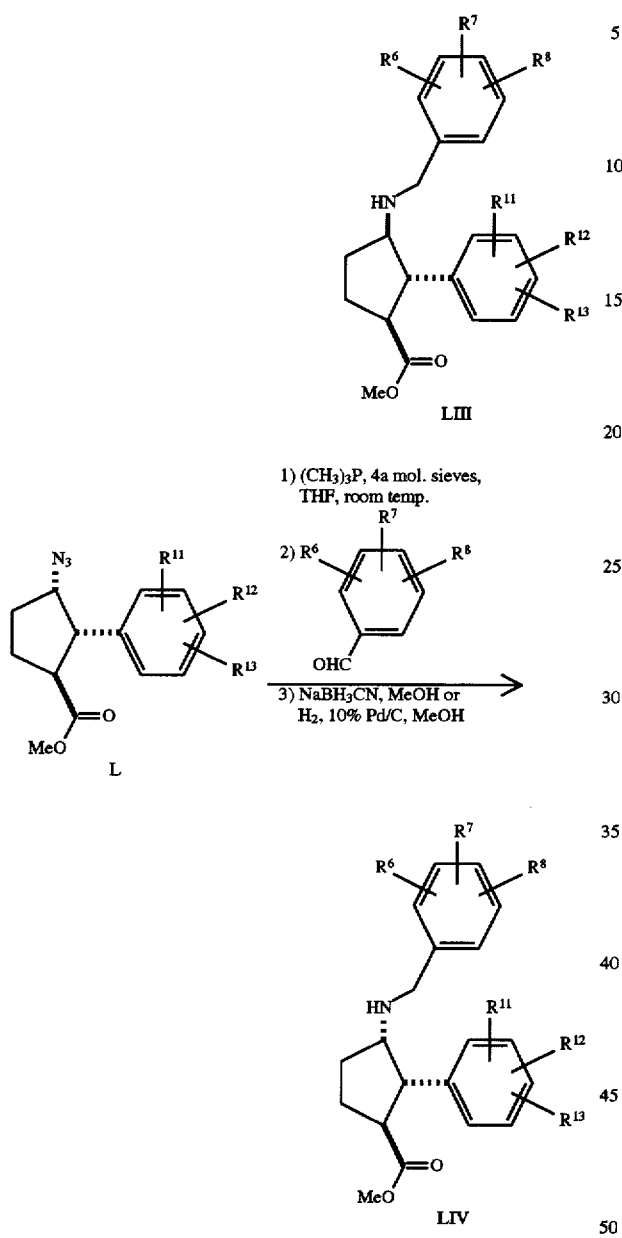

The azides XLIX and L can be converted directly to the primary amines LI and LII by either catalytic reduction, for example, with hydrogen and 10% Pd/C in methanol, or by treatment with a trialkyl- or triaryl-phosphine, followed by hydrolysis (Scheme 22). Alternatively, azides XLIX and L can be treated with trimethylphosphine in THF in the presence of 4A molecular sieves followed by direct addition of an aryl or heteroaryl aldehyde, to produce the intermediate imine. This can be reduced by taking up the imine in methanol and adding sodium cyanoborohydride, sodium tris(acetoxy)borohydride, or sodium borohydride in the presence of acetic acid, or by hydrogenating in the presence of a palladium on carbon catalyst, to provide the secondary amine LIII and LIV, respectively.

SCHEME 23

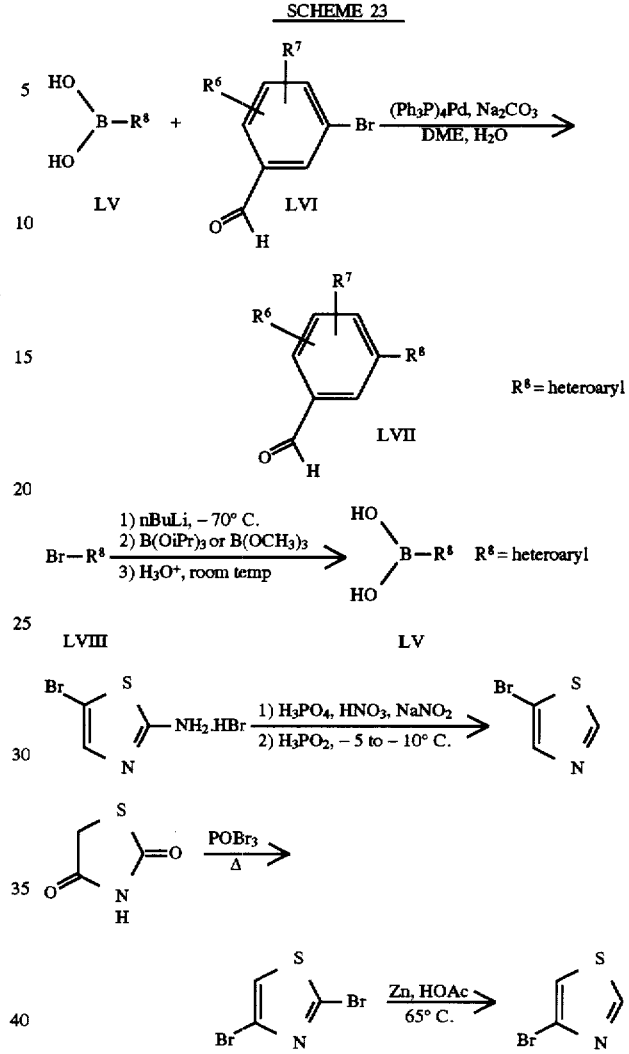

Preparation of heteroaryl substituted benzaldehydes are described in Scheme 23. When the desired heteroaryl boronic acids LV are commercially available, they can be coupled directly with 3-bromobenzaldehyde derivatives LVI, by treatment with a palladium (0) reagent, such as tetrakis(triphenylphosphine)palladium, in the presence of aqueous sodium carbonate in dimethoxyethane, to give the biaryl product LVII. If the heteroaryl boronic acid is not available but the corresponding bromide (LVIII) is, then the bromide can be converted into the desired boronic acid by treatment with an alkyllithium reagent in THF at low temperature followed by addition of trimethyl or triisopropyl borate. Hydrolysis to the boronic acid can be effected by treatment of the intermediate with aqueous base and then acid. Preparation of some heteroaryl bromides can be carried out by removing unneeded functionality from available precursors. For example, 5-bromothiazole can be prepared by diazotizing 2-amino-5-bromothiazole, followed by reduction with hypophosphorus acid. Treatment of 2,4-thiazolidinedione with phosphorus oxybromide, followed by selective reduction with zinc in acetic acid provides the isomeric 4-bromothiazole.

SCHEME 24

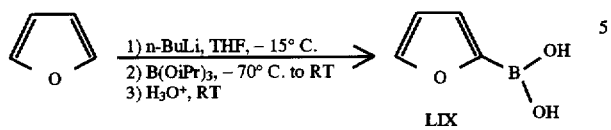

Several heteroaryl boronic acids can be prepared by direct metallation of the parent heterocycle. For example, as shown in Scheme 24, furan can be metallated with n-butyllithium at the 2-position. Treatment with triisopropyl borate and workup as above provides the desired boronic acid LIX.

SCHEME 25

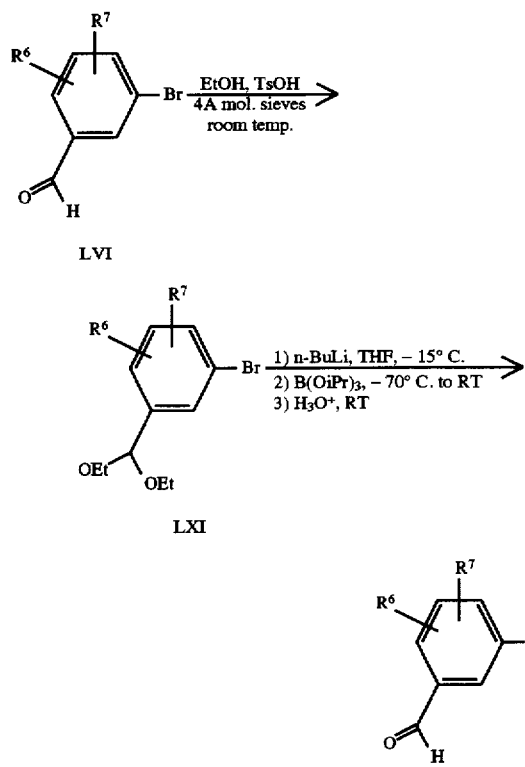

Alternatively, the 3-bromobenzaldehyde LVI can be converted into the corresponding boronic acid LX by protection of the aldehyde functionality, for example as the diethyl acetal LXI, followed by metal-halogen exchange with n-butyllithium and then treatment with a trialkyl borate. Hydrolytic workup then yields LX, which can then be coupled directly with heteroaryl bromides under the palladium catalyzed conditions given above.

SCHEME 26

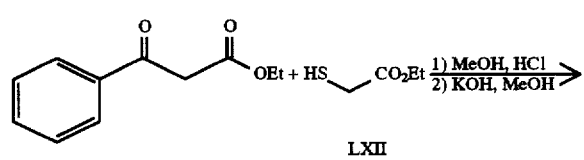

SCHEME 26 -continued

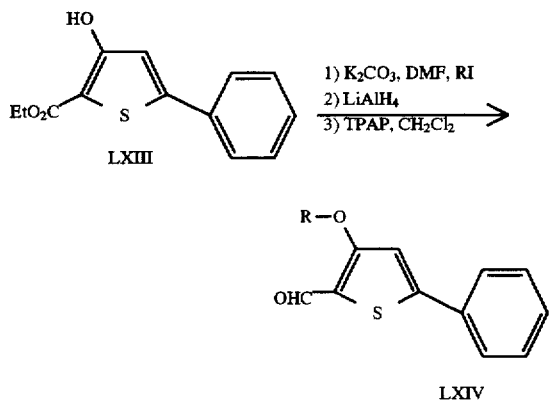

Preparation of thiophene-2-carboxaldehyde derivatives is shown in Scheme 26. Condensation of ethyl benzoylacetate with thiol LXII followed by acid and base treatment provides the thiophene LXIII. Alkylation of the hydroxy group under standard conditions is followed by conversion of the ester to the desired aldehyde intermediate LXIV. This latter reaction can be achieved either by controlled reduction of the ester with an agent such as DIBALH or else reduction to the primary alcohol followed by mild reoxidation, for example under Swern conditions or by reaction with TPAP+ NMMO.

SCHEME 27

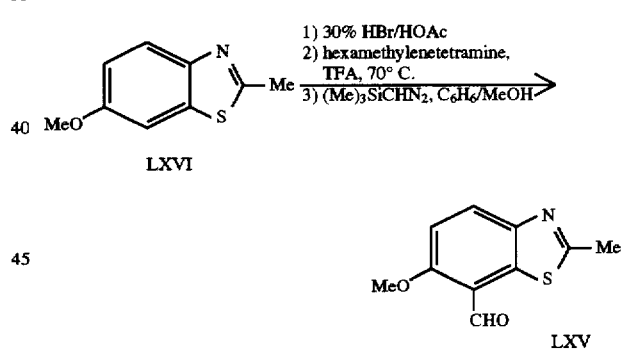

The benzothiazole carboxaldehyde LXV can be prepared as shown in Scheme 27. The commercially available benzothiazole LXVI is first demethylated with HBr in acetic acid. Reaction with hexamethylenetetramine in TFA followed by reformation of the methyl ether with trimethylsilyldiazomethane provides aldehyde LXV.

SCHEME 28

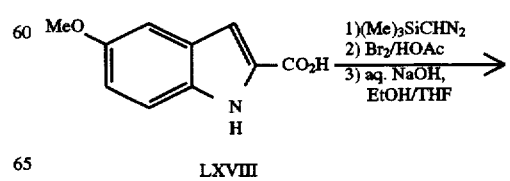

SCHEME 28

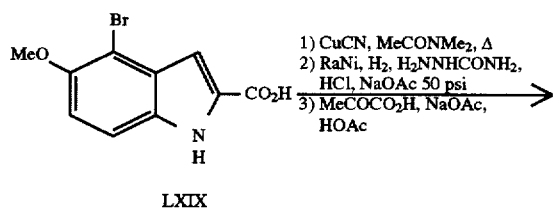

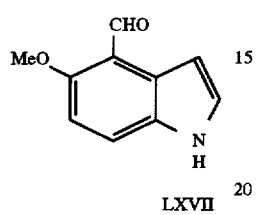

The indole derivative LXVII is prepared by esterification of 5-methoxy-indole-2-carboxylic acid (LXVIII), bromination and then hydrolysis to provide the 4-bromo derivative LXIX (Scheme 28). Sequential treatment with copper cyanide in refluxing dimethylacetamide, then hydrogenation in the presence of Raney nickel and semicarbazide, and finally hydrolysis with pyruvic acid in acetic acid yields the desired aldehyde intermediate LXVII.

SCHEME 29

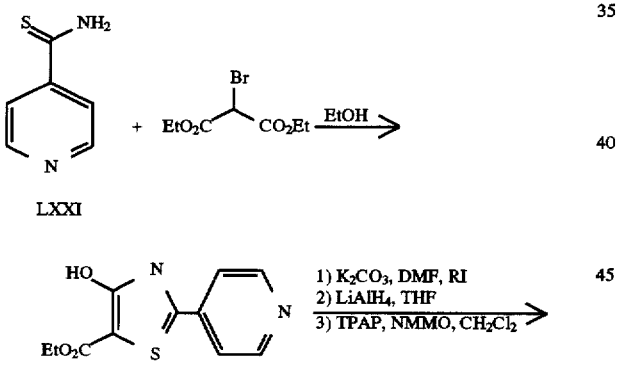

The 2-substituted thiazole LXX is prepared as outlined in Scheme 29. Condensation of the pyridine derivative LXXI and diethyl bromomalonate yields the thiazole LXXII. Alkylation of the hydroxyl group under standard conditions, followed by reduction and mild reoxidation then provides the aldehyde LXX.

SCHEME 30

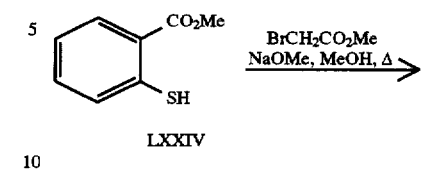

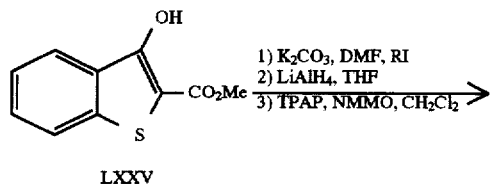

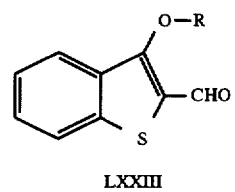

Benzothiophene LXXIII is synthesized according to the route given in Scheme 30. S-alkylation of thiol LXXIV with methyl bromoacetate provides the benzothiophene LXXV. Alkylation of the hydroxyl under standard conditions followed by reduction and mild reoxidation then provides the aldehyde LXXIII.

SCHEME 31

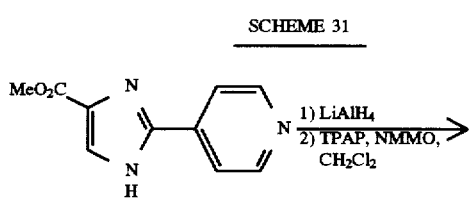

Reduction of the known imidazole ester LXXVI followed by mild reoxidation gives the 2-(pyridin-4-yl)-imidazolecarboxaldehyde LXXVII (Scheme 31).

SCHEME 32

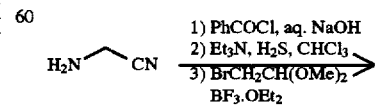

SCHEME 32 (continued)

Preparation of the bicyclic heteroaryl carboxaldehyde LXXVIII is given in Scheme 32. Sequential reaction of aminoacetonitrile with benzoyl chloride, hydrogen sulfide in the presence of triethylamine, and then bromoacetaldehyde dimethyl acetal in the presence of boron trifluoride etherate provided the thiazole derivative LXXIX. Cyclization with phosphorus oxychloride in refluxing benzene followed by formylation with phosphorus oxychloride and DMF then yielded the desired aldehyde LXXVIII.

SCHEME 33

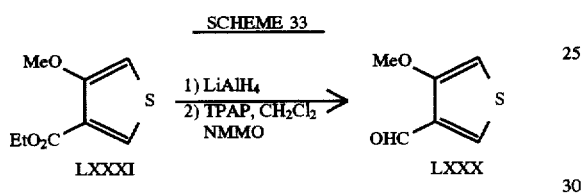

Synthesis of 4-methoxy-3-thiophenecarboxaldehyde (LXXX) can be carried out as shown in Scheme 33. Reduction of commercially available ester LXXXI with lithium aluminum hydride followed by reoxidation with TPAP (Tetrapropylammonium perruthenate(VII)) and NMMO gives the aldehyde LXXX.

SCHEME 34

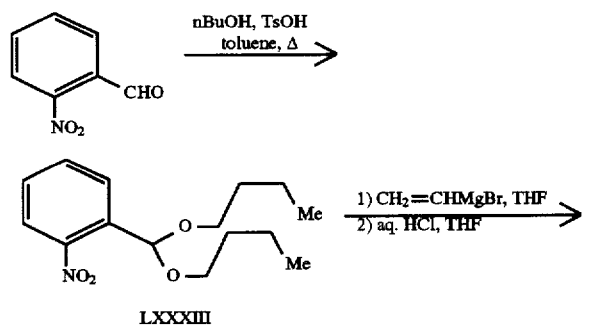

The indole derivative LXXXII is prepared according to the procedure of Dobson et. al (Dobson, D. R.; Gilmore, J. Long, D. A. *Syn. Lett.* 1992, 79) outlined in Scheme 34. Protection of the aldehyde in 2-nitrobenzaldehyde by ketal formation under standard conditions provides the dibutyl acetal LXXXIII. Treatment with vinyl magnesium bromide followed by aqueous acid then yields the desired aldehyde.

SCHEME 35

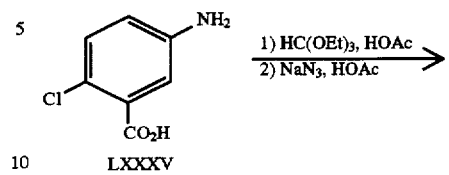

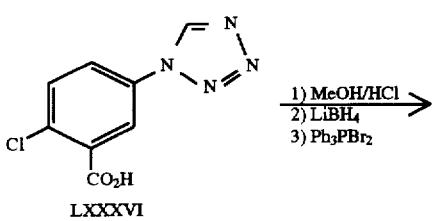

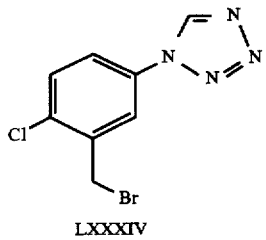

The tetrazole intermediate LXXXIV was prepared as shown in Scheme 35. The commercially available amino acid LXXXV is treated with triethyl orthoformate in warm acetic acid followed by addition of sodium azide to give tetrazole acid LXXXVI. Esterification and then reduction with lithium borohydride provided the alcohol, which was converted to the bromide LXXXIV with triphenylphosphine dibromide.

SCHEME 36

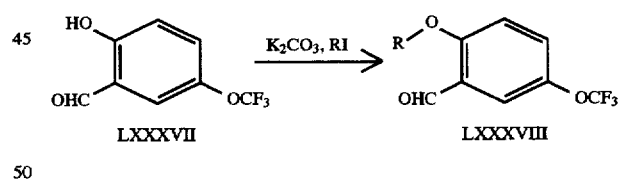

Preparation of a 2-alkoxy-5-trifluoromethoxy derivative LXXXVII is carried out by alkylation of the commercially available aldehyde LXXXVIII (Scheme 36).

SCHEME 37

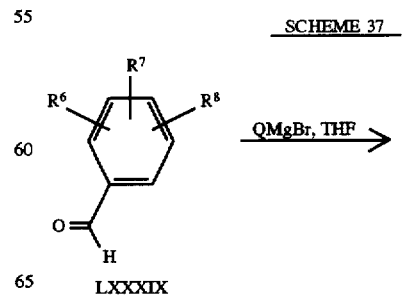

SCHEME 37 -continued

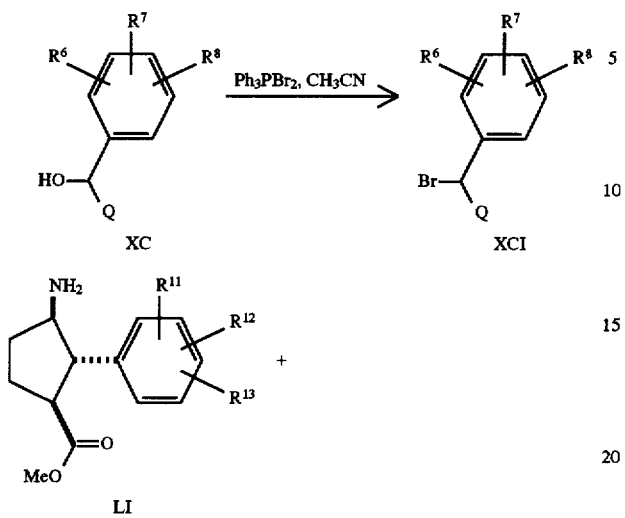

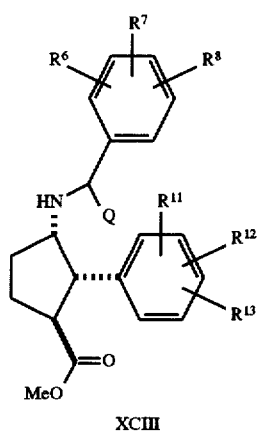

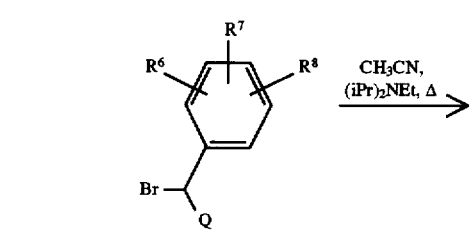

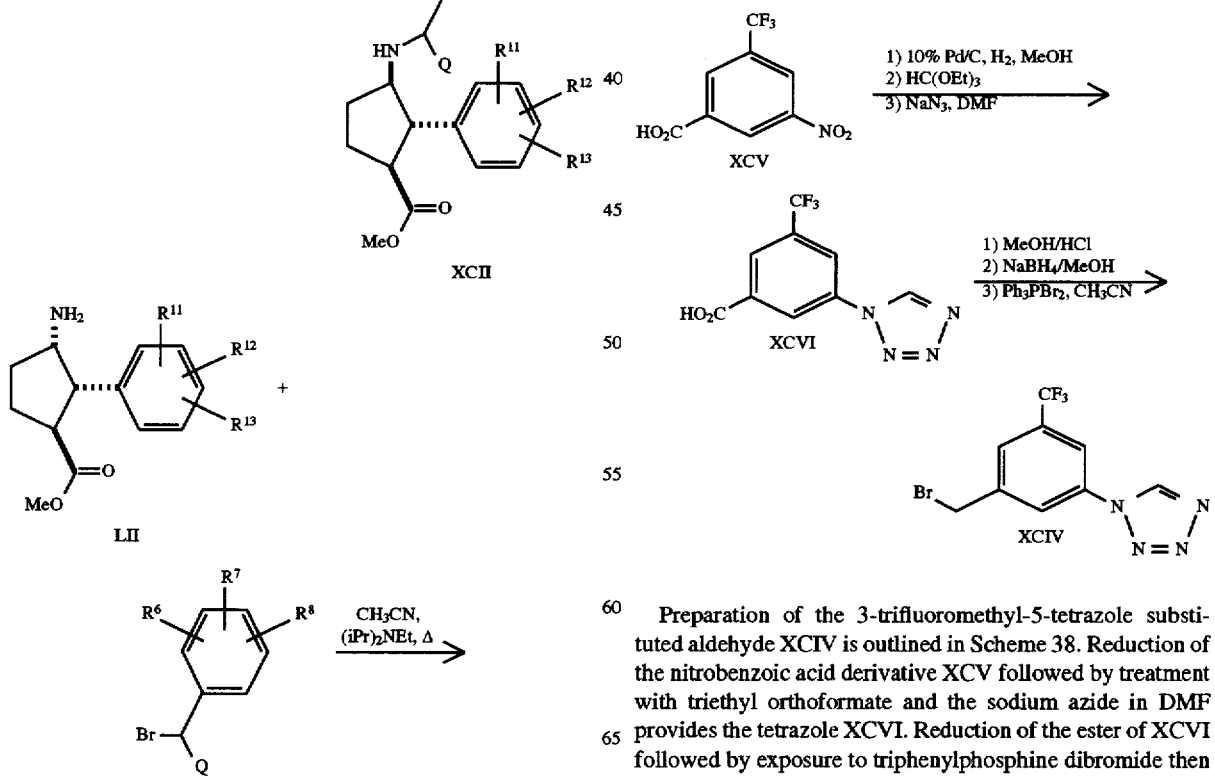

Preparation of derivatives wherein an alkyl chain Q is present at the benzylic position are prepared according to the procedure in Scheme 37. Addition of an alkyl magnesium halide or alkyllithium reagent to the aldehyde intermediate LXXXIX provides secondary alcohol XC. Conversion of the hydroxyl group to a leaving group, for example by formation of the tosylate, mesylate, triflate, bromide or iodide produces an intermediate XCI (when the leaving group is bromide) that can be used to alkylate amines LI and LII in refluxing acetonitrile in the presence of a suitable hindered amine base, such as DIEA, to give XCII and XCIII, respectively.

Preparation of the 3-trifluoromethyl-5-tetrazole substituted aldehyde XCIV is outlined in Scheme 38. Reduction of the nitrobenzoic acid derivative XCV followed by treatment with triethyl orthoformate and the sodium azide in DMF provides the tetrazole XCVI. Reduction of the ester of XCVI followed by exposure to triphenylphosphine dibromide then produces the desired bromide XCIV.

SCHEME 39

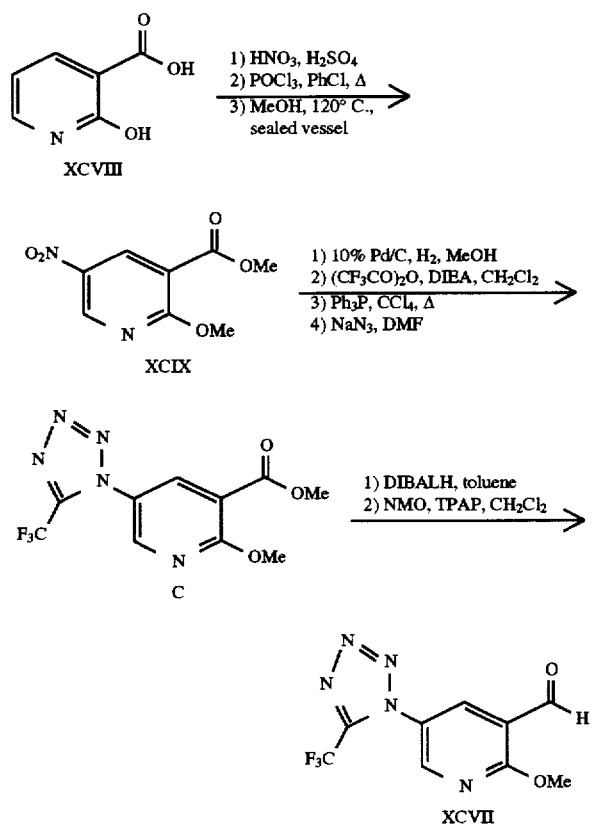

Preparation of the 2-methoxypyridine XCVII was carried out as shown in Scheme 39. The pyridinecarboxylic acid XCVIII was sequentially nitrated with nitric acid, chlorinated with phosphorus oxychloride, and then allowed to react with methanol at high temperature to provide the 2-methoxypyridine XCIX.: Reduction of the nitro group was followed by formation of the 5-(5-(trifluoro-methyl)tetrazol-1-yl)pyridine by exposure to trifluoroacetic anhydride, then triphenylphosphine and carbon tetrachloride, and then sodium azide in DMF, to give C. Reduction of the ester and mild reoxidation then gave the targetted aldehyde intermediate XCVII.

SCHEME 40

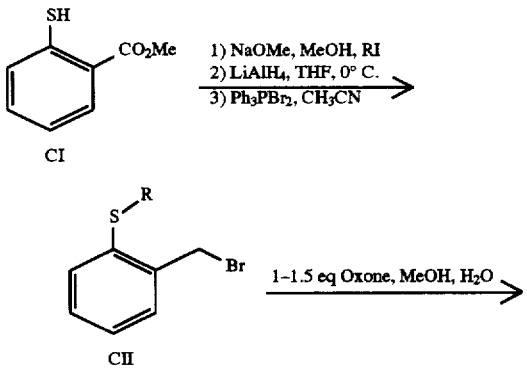

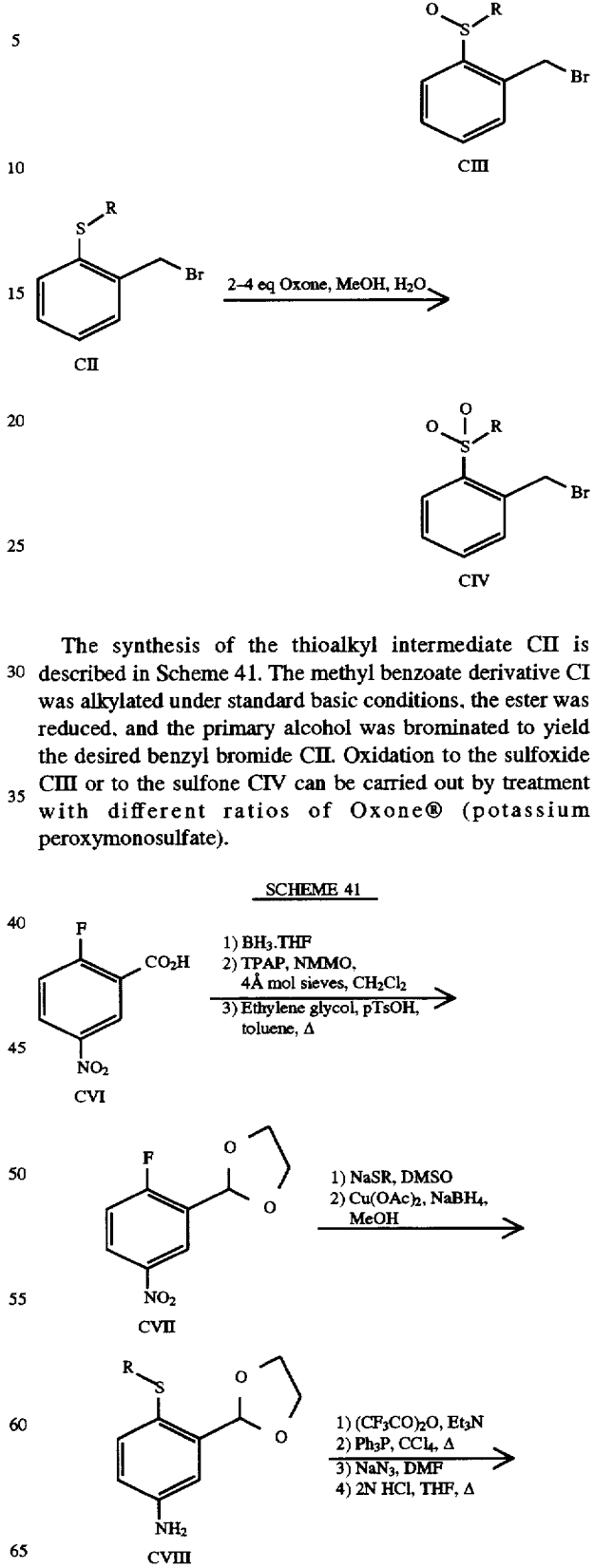

The synthesis of the thioalkyl intermediate CII is described in Scheme 41. The methyl benzoate derivative CI was alkylated under standard basic conditions, the ester was reduced, and the primary alcohol was brominated to yield the desired benzyl bromide CII. Oxidation to the sulfoxide CIII or to the sulfone CIV can be carried out by treatment with different ratios of Oxone® (potassium peroxymonosulfate).

SCHEME 41

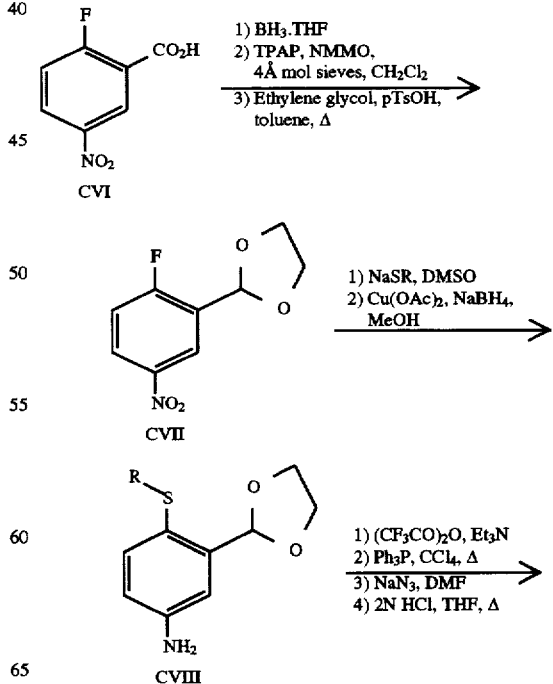

SCHEME 41 -continued

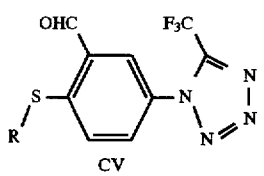

Synthesis of the tetrazole-substituted thioalkyl intermediate CV was carried out by the route outlined in Scheme 41. The fluoronitro derivative CVI was first carried through a sequence entailing carboxyl reduction, mild oxidation, and protection as the dioxolane, to provide CVII. Displacement of fluoride with a thioalkyl group, followed by reduction of the nitro group with sodium borohydride in the presence of copper diacetate gives aniline CVIII. The usual protocol for conversion into a 5-(trifluoromethyl)tetrazole then gives benzaldehyde CV.

SCHEME 42

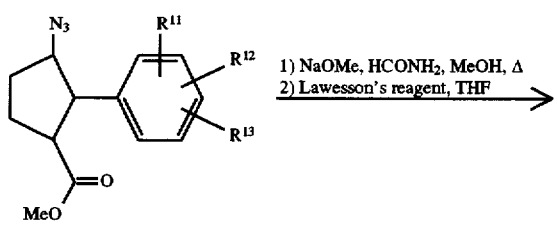

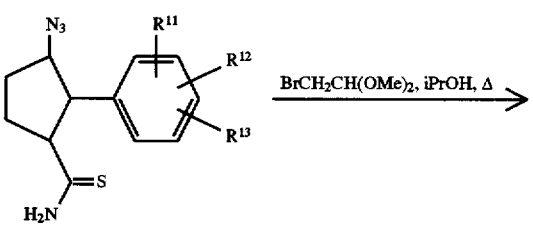

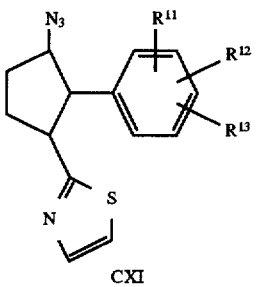

Preparation of derivatives where Y is a single bond, Z is absent and $R^3$ is a thiazol-2-yl group is shown in Scheme 42. Treatment of ester CIX with formamide and sodium methoxide in methanol followed by Lawesson's reagent (2,4-bis (4-methoxyphenyl)-1,3-dithia-2,4-diphosphetane-2,4-disulfide) gave the thioamide CX. Heating with bromoacetaldehyde dimethylacetal in isopropanol then produces the desired thiazole intermediate CXI.

SCHEME 43

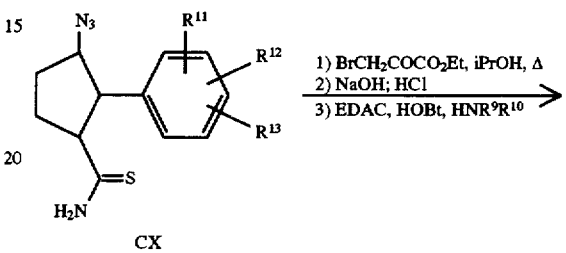

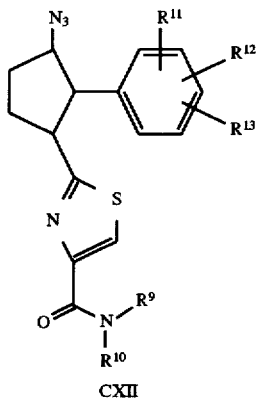

Preparation of thiazoles related to CXI are given in Scheme 43. Reaction of intermediate CX with ethyl bromopyruvate, followed by standard hydrolysis and amide formation, provides the thiazole amide CXII.

SCHEME 44

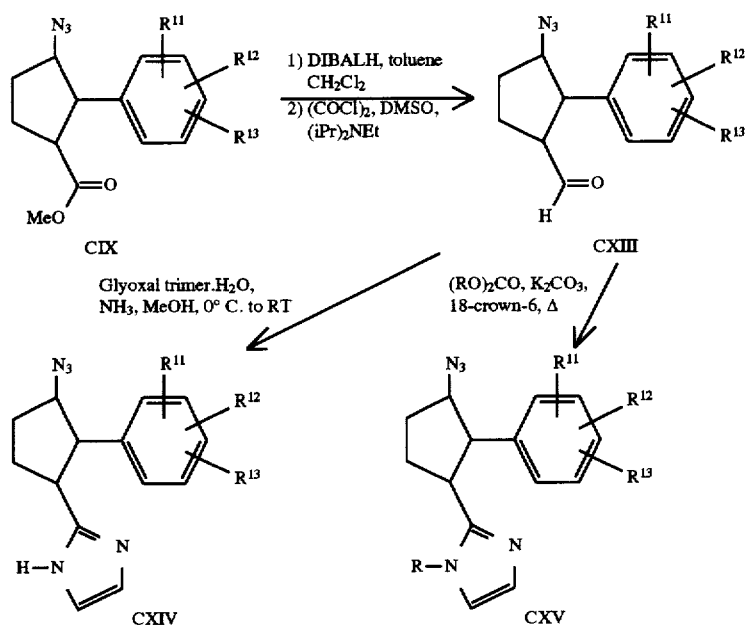

Preparation of intermediates which lead to analogs where Y is a single bond, Z is absent and $R^3$ is a imidazol-2-yl group is shown in Scheme 44. Reduction of ester CIX with DIBALH followed by mild reoxidation under Swern conditions provides the aldehyde CXIII. Reaction with glyoxal trimer dihydrate and ammonia provides the imidazole CXIV, which can be optionally alkylated on nitrogen with a dialkylcarbonate, potassium carbonate and 18-crown-6 at elevated temperature, to give N-alkyl imidazole CXV.

SCHEME 45

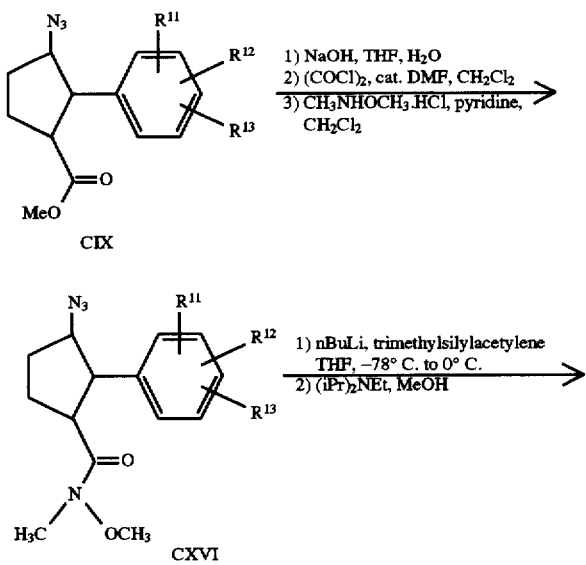

-continued
SCHEME 45

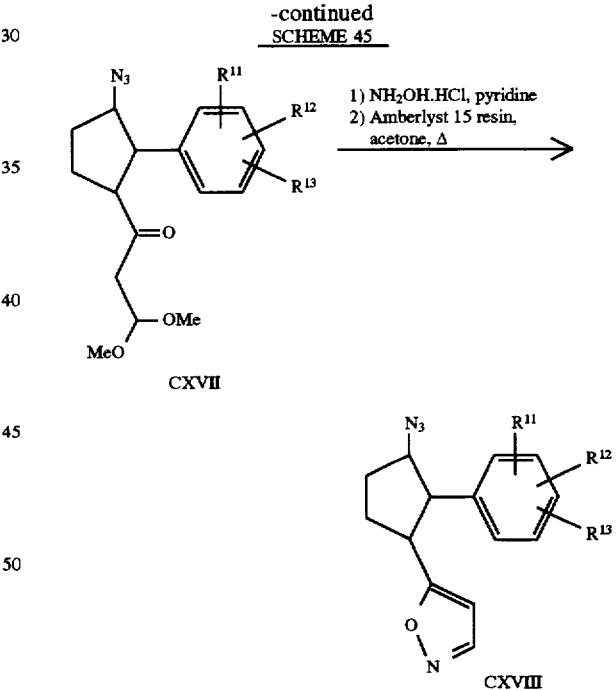

Preparation of intermediates which lead to analogs where Y is a single bond, Z is absent and $R^3$ is a isoxazol-3-yl group is shown in Scheme 45. Hydrolysis of ester CIX, followed by acid chloride formation and reaction with N,O-dimethylhydroxylamine hydrochloride gives amide CXVI. Reaction with the lithium salt of trimethylacetylene and then warm basic methanol yields the dimethyl acetal CXVII. Treatment with hydroxylamine hydrochloride in the presence of pyridine and then Amberlyst resin in refluxing acetone then provides the desired isoxazole CXVIII.

SCHEME 46

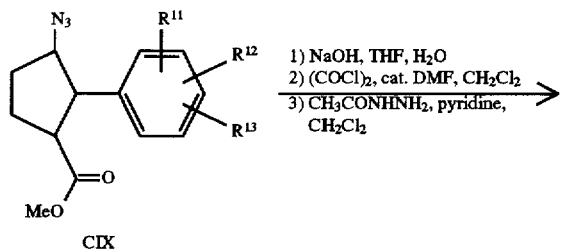

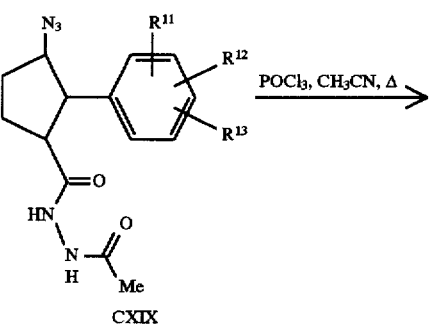

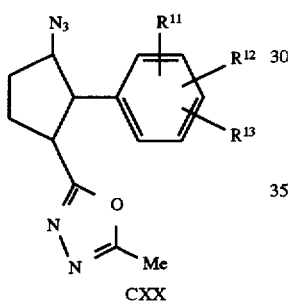

Preparation of intermediates which lead to analogs where Y is a single bond, Z is absent and R³ is a oxadiazo-2-yl group is shown in Scheme 46. Hydrolysis of ester CIX, followed by acid chloride formation and reaction with acetic hydrazide led to compound CXIX. Heating with phosphorus oxychloride in acetonitrile then gives the desired intermediate CXX.

SCHEME 47

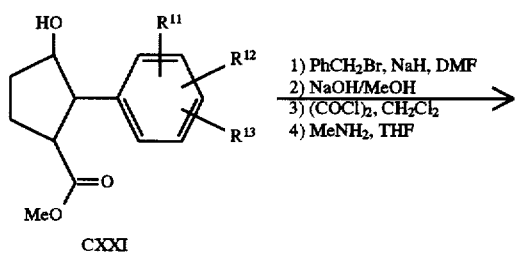

SCHEME 47 -continued

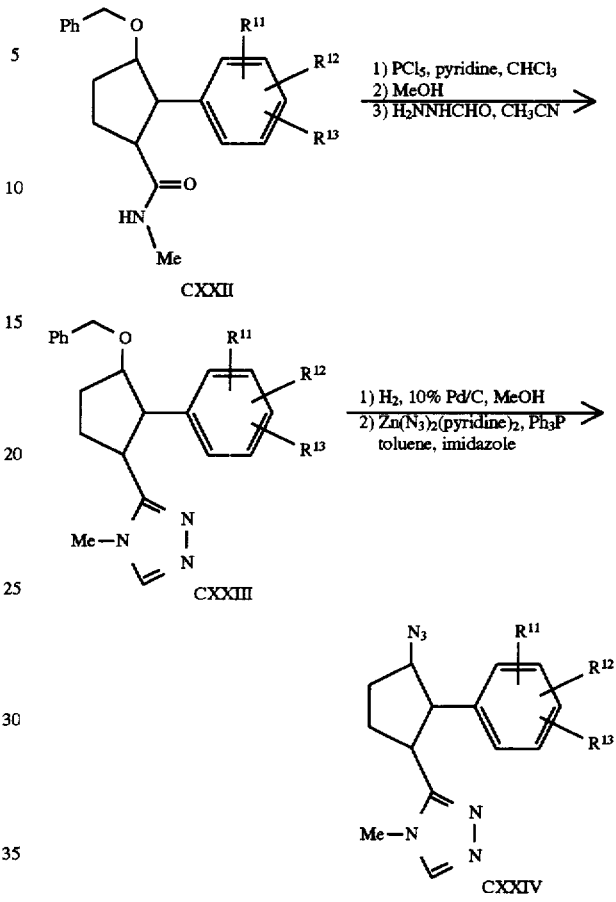

Preparation of intermediates which lead to analogs where Y is a single bond, Z is absent and R³ is a 1,2,4-triazol-3-yl group is shown in Scheme 47. Protection of the free hydroxyl of ester CXXI with a benzyl group under standard conditions, followed by basic hydrolysis of the ester, acid chloride formation, and exposure to methylamine gives amide CXXII. Treatment with phosphorus pentachloride, then methanol, and finally formic hydrazide in acetonitrile provides N-methyl triazole CXXIII. Hydrogenolytic removal of the benzyl group followed by treatment with zinc diazide bis(pyridine) complex and imidazole in the presence of diethyl azodicarboxylate and triphenylphosphine then yields azido triazole CXXIV.

SCHEME 48

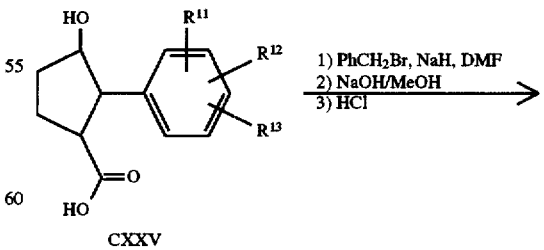

71
-continued
SCHEME 48

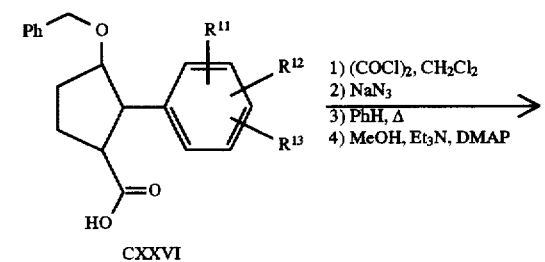

CXXVI 1) (COCl)₂, CH₂Cl₂
2) NaN₃
3) PhH, Δ
4) MeOH, Et₃N, DMAP

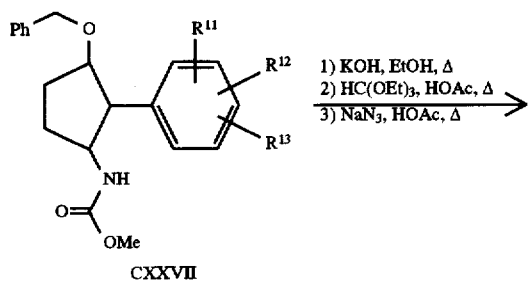

CXXVII

1) KOH, EtOH, Δ
2) HC(OEt)₃, HOAc, Δ
3) NaN₃, HOAc, Δ

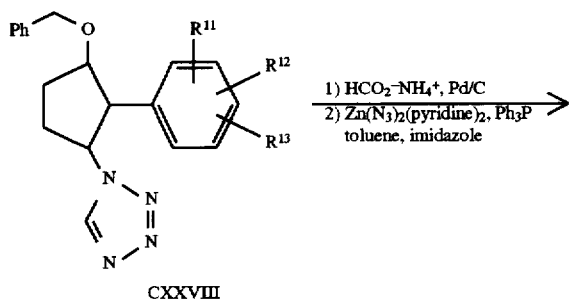

CXXVIII

1) HCO₂⁻NH₄⁺, Pd/C
2) Zn(N₃)₂(pyridine)₂, Ph₃P
toluene, imidazole

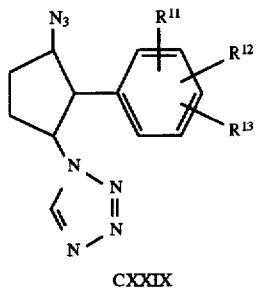

CXXIX

Preparation of intermediates which lead to analogs where Y is a single bond, Z is absent and R³ is a tetrazol-1-yl group is shown in Scheme 48. Protection of the hydroxyl group of acid CXXV with a benzyl group, followed by basic hydrolysis and acidification gives benzyl ether CXXVI. Generation of the acid chloride, acyl azide formation, and thermolysis provides the rearranged isocyanate, which is allowed to react with methanol under mildly basic conditions to yield the carbamate CXXVII. Hydrolysis under strongly basic conditions, followed by treatment with triethyl orthoformate and then sodium azide in acetic acid gives tetrazole CXXVIII. Cleavage of the benzyl group by hydrogenolysis followed by treatment with zinc diazide bis(pyridine) complex and imidazole in the presence of diethylazodicarboxylate and triphenylphosphine then yields azido tetrazole CXXIX.

72

SCHEME 49

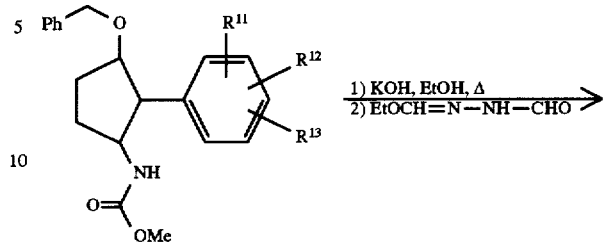

CXXVII

1) KOH, EtOH, Δ
2) EtOCH=N—NH—CHO

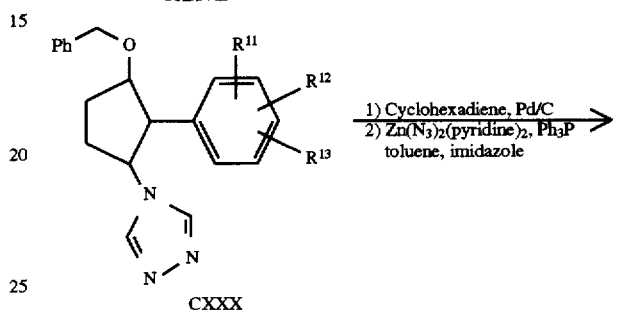

CXXX

1) Cyclohexadiene, Pd/C
2) Zn(N₃)₂(pyridine)₂, Ph₃P
toluene, imidazole

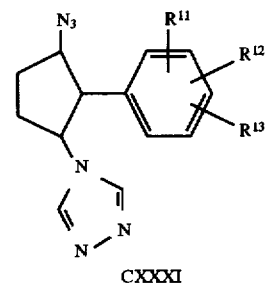

CXXXI

Preparation of intermediates which lead to analogs where Y is a single bond, Z is absent and R³ is a 1,2,4-triazol-4-yl group is shown in Scheme 49. Basic hydrolysis of carbamate CXXVII followed by treatment with the adduct from formyl hydrazide and triethyl orthoformate yields the triazole CXXX. Deprotection of the hydroxyl group is followed by treatment with zinc diazide bis(pyridine) complex and imidazole in the presence of diethylazodicarboxylate and triphenylphosphine to provide azido triazole CXXXI.

SCHEME 50

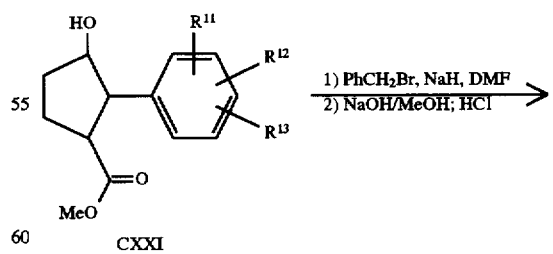

CXXI

1) PhCH₂Br, NaH, DMF
2) NaOH/MeOH; HCl

-continued
SCHEME 50

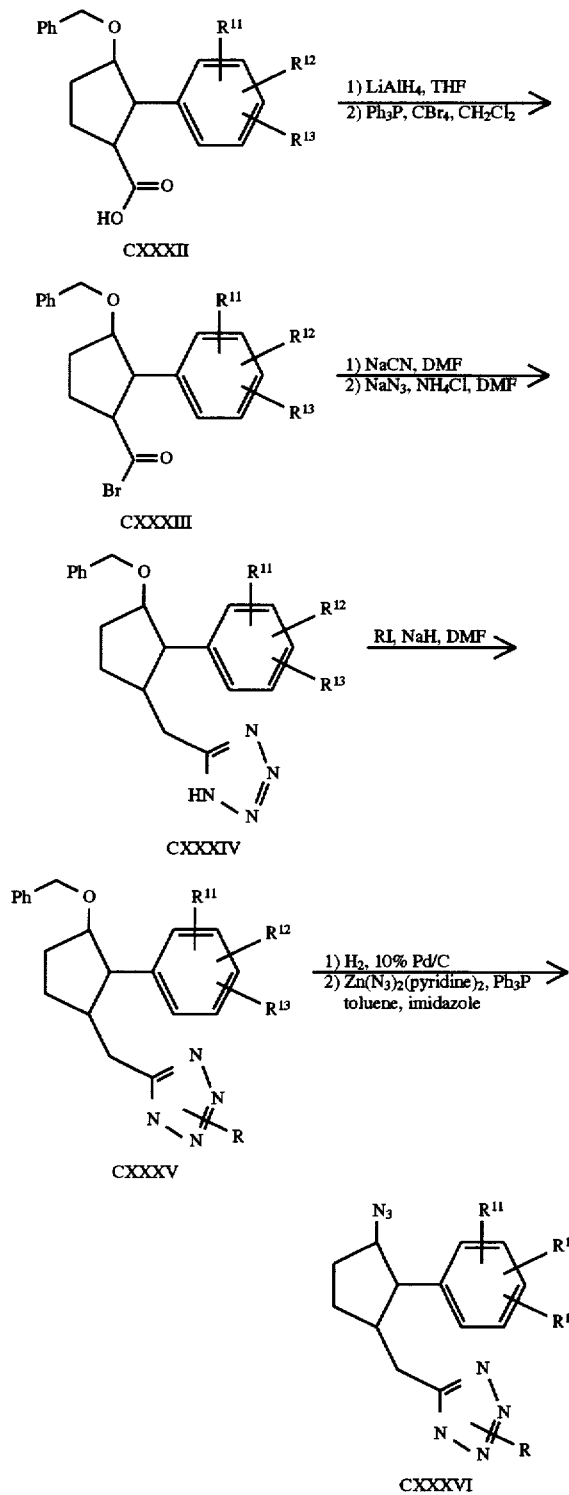

Preparation of intermediates which lead to analogs where Y is a methylene group, Z is absent and R³ is an N-alkyl tetrazo-5-yl group is shown in Scheme 50. Protection of the hydroxyl group of ester CXXI followed by basic hydrolysis gives benzyl ether CXXXII. Reduction with lithium aluminum hydride and then treatment with triphenylphosphine and carbon tetrabromide affords bromide CXXXIII. Dis-placement with sodium cyanide and then treatment with sodium azide in the presence of ammonium chloride in DMF provides tetrazole CXXXIV. Alkylation under basic conditions provides a mixture of 1-alkyl- and 2-alkyl tetrazoles CXXXV, which can be converted to the desired azide intermediates by hydrogenolytic deprotection and then by treatment with zinc diazide bis(pyridine) complex and imidazole in the presence of diethylazodicarboxylate and triphenylphosphine to provide azido tetrazoles CXXXVI.

SCHEME 51

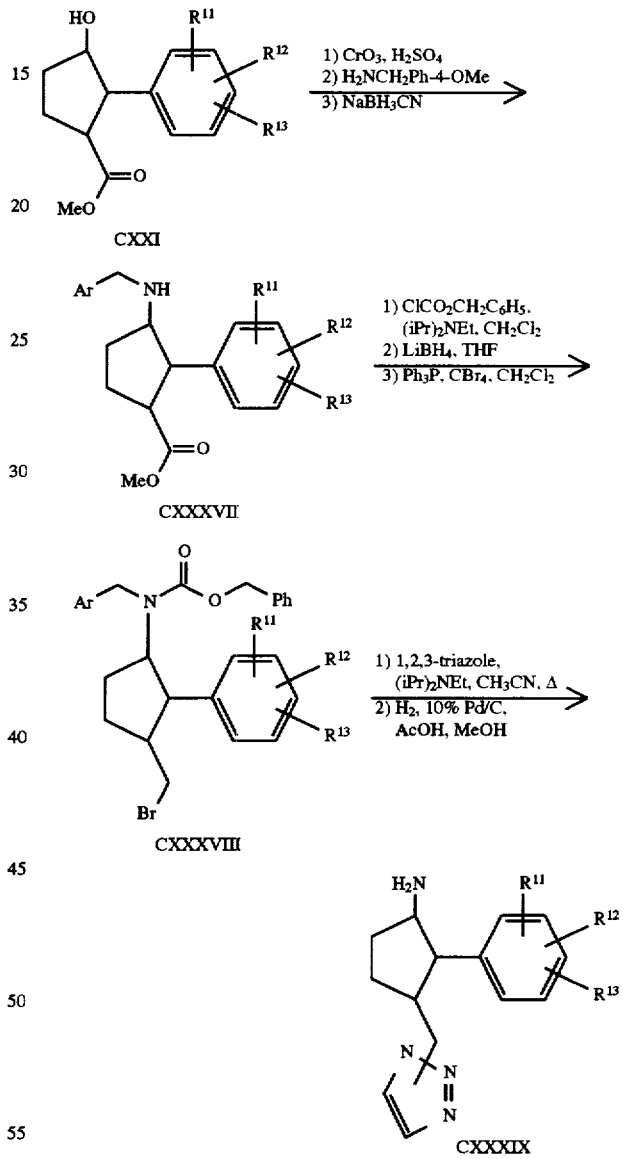

Preparation of intermediates which lead to analogs where Y is a methylene group, Z is absent and R³ is an 1,2,3-triazol-1-yl group is shown in Scheme 51. Oxidation of ester CXXI and then reductive amination with 4-methoxybenzylamine provides ester CXXXVII. Acylation with benzyl chloroformate, reduction with lithium borohydride and treatment with triphenylphosphine and carbon tetrabromide yields bromide CXXXVIII. Displacement with 1,2,3-triazole provides the 1- and 2-triazole derivatives, which upon treatment with hydrogen and palladium on carbon in the presence of acetic acid affords the desired free amine CXXXIX.

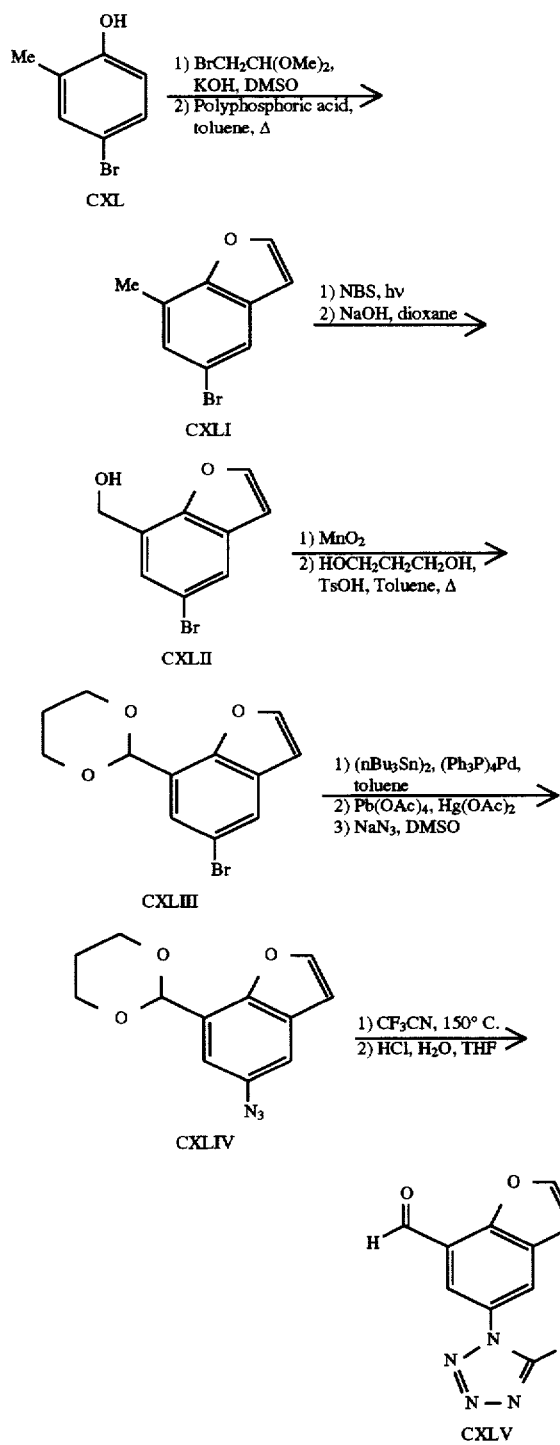

An alternative for the aromatic ring bearing $R^6$, $R^7$, and $R^8$ is the substituted benzofuran whose synthesis is outlined in Scheme 52. Alkylation of the available phenol derivative CXL with bromoacetaldehyde dimethyl acetal under basic conditions, followed by cyclization under acidic conditions provides benzofuran CXLI. Radical bromination and then hydroxide displacement provides benzyl alcohol CXLII.

After mild oxidation, protection of the aldehyde is accomplished by treatment with 1,3-propylene glycol and catalytic acid in refluxing toluene, yielding CXLIII. Successive exchange of the bromide for a trimethyltin group, then exchange of the tin moiety for a lead triacetate ligand, and finally displacement with sodium azide, provides aryl azide CXLIV. Thermolysis in the presence of trifluoroacetonitrile followed by acidic hydrolysis then provides aldehyde CXLV.

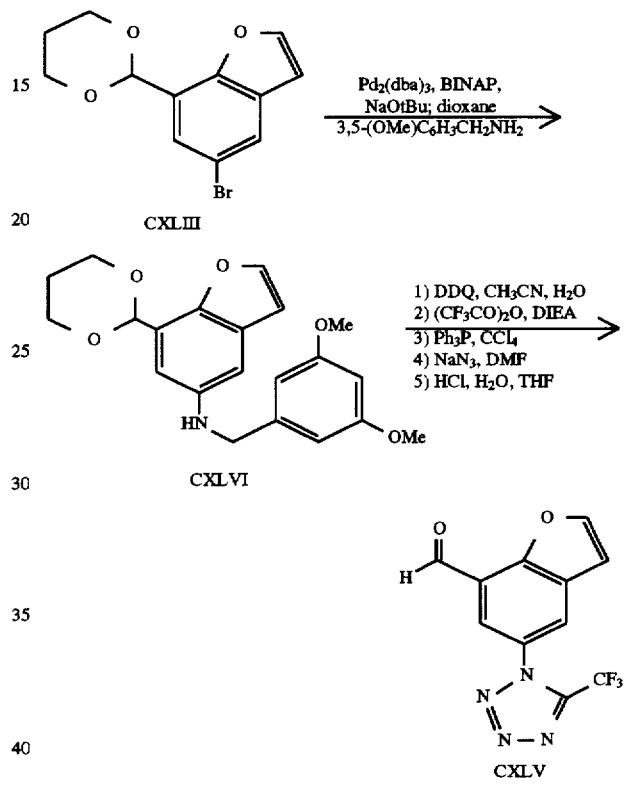

Another method for preparing aldehyde CXLV starts from acetal CXLIII (Scheme 53). Palladium catalyzed amination under Buchwald's conditions (Wolfe, J. P.; Wagaw, S.; Buchwald, S. L. *J. Am. Chem. Soc.* 1996, 118, 7215) with 3,5-dimethoxybenzylamine provides aniline derivative CXLVI. Removal of the 3,5-dimethoxybenzyl group with DDQ followed by standard protocols for 5-(trifluoromethyl) tetrazole formation and then acidic deprotection provides benzaldehyde CXLV.

It is noted that in some cases the order of carrying out the foregoing reaction schemes may be varied to facilitate the reaction or to avoid unwanted reaction products.

Tachykinin Antagonism Assay

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assays.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/mil Herring sperm DNA at 300 V and 950 uF using the IBI GENEZA-PPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol Using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

In particular, the intrinsic tachykinin receptor antagonist activities of the compounds of the present invention may be demonstrated by this assay. The compounds of the following examples have activity in the aforementioned assay in the range of 0.05 nM to 10 µM. The activity of the present compounds may also be demonstrated by the assay disclosed by Lei, et al., *British J. Pharmacol.*, 105, 261–262 (1992).

The compounds of the present invention are useful in the prevention and treatment of a wide variety of clinical conditions which are characterized by the presence of an excess of tachykinin, in particular substance P, activity. These conditions may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic neuropathy, chemotherapy-induced neuropathy, and postherpetic and other neuralgias; small cell carcinomas such as small cell lung cancer; respiratory diseases, particularly those associated with excess mucus secretion, such as chronic obstructive airways disease, bronchopneumonia, chronic bronchitis, acute bronchitis, diffuse panbronchilitis, emphysema, cystic fibrosis, asthma, and bronchospasm; airways disease modulated by neurogenic inflammation; laryngopharhngitis; bronchiectasis; conoisis; whooping cough; pulmonary tuberculosis; diseases associated with decreased glandular secretions, including lacrimation, such as Sjogren's syndrome, hyperlipoproteinemias IV and V, hemochromatosis, sarcoidosis, or amyloidosis; iritis; inflammatory diseases such as inflammatory bowel disease, inflammatory intestinal disease, psoriasis, fibrositis, ocular inflammation, osteoarthritis, rheumatoid arthritis, pruritis, and sunburn; hepatitis; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; hemodialysis-associated itching; lichen planus; oedema, such as oedema caused by thermal injury; addiction disorders such as alcoholism; mental disease, particularly anxiety and depression; stress related somatic disorders; reflex sympathetic dystrophy such as shoulder/hand syndrome; dysthymic disorders; tenalgia attended to hyperlipidemia; post-operative neuroma, particularly of mastectomy; vulvar vestibulitis; amniogenesis; adverse immunological reactions such as rejection of transplanted tissues and disorders related to immune enhancement or suppression, such as systemic lupus erythmatosus; gastrointestinal (GI) disorders, including inflammatory disorders, and diseases of the GI tract, such as gastritis, gastroduodenal ulcers, gastric carcinomas, gastric lymphomas, disorders associated with the neuronal control of viscera such as ulcerative colitis, Crohn's disease, irritable bowel syndrome, nausea, and emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure, in particular, for example, drug or radiation induced emesis or post-operative nausea and vomiting; disorders of bladder function such as cystitis, bladder detrusor hyperreflexia, and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, chronic pain or that attributable to or associated with any of the foregoing conditions especially the transmission of pain in migraine, or such as headache, toothache, cancerous pain, back pain, post-operative pain, neuritic pain symptoms, fibromyalgia and superficial pain on congelation, burn, herpes zoster or diabetic neuropathy. Hence, these compounds may be readily adapted to therapeutic use for the treatment of physiological disorders associated with an excessive stimulation of tachykinin receptors, especially neurokinin-1, and as neurokinin-1 antagonists in the control and/or treatment of any of the aforesaid clinical conditions in mammals, including humans.

The compounds of the present invention are also of value in the treatment of a combination of the above conditions, in particular in the treatment of combined post-operative pain and post-operative nausea and vomiting.

The compounds of the present invention are particularly useful in the treatment of nausea or emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure. Most especially, the compounds are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates and other compounds with an alkylating action such as nitrosoureas, cisplatin, and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for example, by D. J. Stewart in "Nausea and Vomiting: Recent Research and Clinical Advances", Eds. J. Kucharczyk, et al., CRC Press Inc., Boca Raton, Fla., USA (1991), pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, and chlorambucil [R. J. Gralla, et al., *Cancer Treatment Reports*, 68(1), 163–172 (1984)].

The compounds of the present invention are also of use in the treatment of emesis induced by radiation including radiation therapy such as in the treatment of cancer, or radiation sickness, and in the treatment of post-operative nausea and vomiting.

The compounds of the present invention are also of use in the prevention or treatment of disorders of the central nervous system such as anxiety, psychosis and schizophrenia; neurodegenerative disorders such as senile dementia of the Alzheimer type, Alzheimer's disease and Down's syndrome; respiratory diseases, particularly those associated with excess mucus secretion, such as chronic obstructive airways disease, broncho-pneumonia, chronic bronchitis, cystic fibrosis and asthma, and bronchospasm; inflammatory diseases such as inflammatory bowel disease, osteoarthritis, rheumatoid arthritis and fibromyalgia; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine (both prophylaxis and acute treatment).

The compounds of the present invention are also particularly useful in the treatment of pain or nociception and/or inflammation and disorders associated therewith such as, for example: neuropathy, such as diabetic or peripheral neuropathy and chemotherapy-induced neuropathy; postherpetic and other neuralgias; inflammatory bowel disease; acute and chronic pain, such as post-operative pain, cancer-related pain, neuritic pain syndromes, and fibromyalgia; asthma; osteoarthritis; rheumatoid arthritis; psoriasis; and especially migraine, either alone or in combination or co-administration with other antiinflammatory or analgesic agents.

The compounds of the present invention are also particularly useful in the treatment of diseases characterized by neurogenic mucus secretion, especially cystic fibrosis.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like.

The pharmaceutical compositions of this invention may be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

The present invention is further directed to a method for the manufacture of a medicament for antagonizing the effect of substance P or another tachykinin at its receptor site or for the blockade of neurokinin-1 receptors or other tachykin receptors in a mammal comprising combining a compound of the present invention with a pharmaceutical carrier or diluent.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of certain conditions it may be desirable to employ a compound of the present invention in conjunction with another pharmacologically active agent(s). A compound of the present invention and the other pharmacologically active agent(s) may be administered to a patient simultaneously, sequentially or in combination. For example, the present compound may employed directly in combination with the other active agent(s), or it may be administered prior, concurrent or subsequent to the administration of the other active agent(s). In general, the currently available dosage forms of the known therapeutic agents for use in such combinations will be suitable.

For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above.

Similarly, for the treatment or prevention of pain or inflammatory diseases, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; an antiitussive such as codeine, hydrocodone, caramiphen, carbetapentane, or dextramethorphan; a diuretic; and a sedating or non-sedating antihistamine.

Also, for the treatment of respiratory diseases, such as asthma, a compound of the present invention may be used in conjunction with a bronchodilator, such as a $\beta_2$-adrenergic receptor agonist or a tachykinin antagonist which acts at neurokinin-2 receptors. Suitable $\beta_2$-adrenergic receptor agonist include: Bambuterol (U.S. Pat. No. 4,419,364 issued to Draco on Dec. 6, 1983); Bitolterol mesylate (U.S. Pat. No. 4,138,581 issued to Sterling Feb. 6, 1979); Brosaterol (U.S. Pat. No. 4,276,299 issued to Zambon Jun. 30, 1981 and U.S. Pat. No. 4,520,200 issued to Zambon May 28, 1985); Carbuterol (U.S. Pat. No. 3,763,232 issued to Smith Kline Oct. 2, 1973); Clenbuterol (U.S. Pat. No. 3,536,712 issued to Boehringer Ingelheim Oct. 27, 1970); Cimaterol (U.S. Pat. No. 4,407,819 issued to American Cyanamid Oct. 4, 1983); Docarpamine (U.S. Pat. No. 4,228,183 issued to Tanabe Oct. 14, 1980); Dopexamine (U.S. Pat. No. 4,645,768 issued to Fisons Feb. 24, 1987); Formoterol (U.S. Pat. No. 3,994,974 issued to Yamanouchi Nov. 30, 1976); Mabuterol (U.S. Pat. No. 4,119,710 issued to Boehringer Ingelheim Oct. 10, 1978); Pirbuterol hydrochloride (U.S. Pat. No. 3,700,681 issued to Pfizer Oct. 24, 1972); Procaterol hydrochloride (U.S. Pat. No. 4,026,897 issued to Otsuka May 31, 1977); Ritodrine hydrochloride (U.S. Pat. No. 3,410,944 issued to North American Philips Nov. 12, 1968); or Salmeterol (U.S. Pat. No. 4,992,474 issued to Glaxo Feb. 21, 1991 and U.S. Pat. No. 5,091,422 issued to Glaxo Feb. 25, 1992).

Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis; neuropathy, such as diabetic or peripheral neuropathy and chemotherapy-induced neuropathy; osteoarthritis; rheumatoid arthritis; and migraine, a compound of the present invention may be used in conjunction with a tachykinin antagonist which acts at neurokinin-2 receptors, or with tachykinin receptor antagonist which acts at both neurokinin-1 and neurokinin-2 receptors.

Likewise, a compound of the present invention may be employed with a leucotriene antagonist, such a leucotriene $D_4$ antagonist, exemplified by those disclosed in Patent Pub. EP 0,480,717, published Apr. 15, 1992; Patent Pub. EP 0 604,114, published Jun. 1994; U.S. Pat. No. 5,270,324, issued Dec. 14, 1993; and U.S. Pat. No. 4,859,692, issued Aug. 22, 1989. This combination is particularly useful in the treatment of respiratory diseases such as asthma, chronic bronchitis and cough.

A compound of the present invention further may be used in conjunction with a corticosteroid such as Dexamethasone, Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712.

Similarly, for the prevention or treatment of emesis a compound of the present invention may be used in conjunction with other anti-emetic agents, especially $5HT_3$ receptor antagonists, such as ondansetron, granisetron, tropisetron, decadron, and zatisetron, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan.

Likewise, for the treatment of behavioral hyperalgesia, a compound of the present invention may be used in conjunction with an antagonist of N-methyl D-aspartate (NMDA), such as dizocilpine. For the prevention or treatment of inflammatory conditions in the lower urinary tract, especially cystitis, a compound of the present invention may be used in conjunction with an antiinflammatory agent, such as a bradykinin receptor antagonist. The compound of the present invention and the other pharmacologically active agent may be administered to a patient simultaneously, sequentially or in combination.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to 25 mg/kg per day, preferably about 0.05 to 10 mg/kg per day, and especially about 0.1 to 5 mg/kg per day. A compound may be administered on a regimen of multiple times per day, such as 1 to 4 times per day, preferably once or twice per day. In the treatment of emesis using an injectable formulation, a suitable dosage level is about 0.001 to 10 mg/kg per day, preferably about 0.005 to 5 mg/kg per day, and especially about 0.05 to 5 mg/kg per day. A compound may be administered on a regimen of multiple times per day, such as 1 to 4 times per day, preferably once or twice per day.

The following examples are provided for the purpose of further illustration only and are not intended to be limitations on the disclosed invention.

EXAMPLE 1

Methyl trans-(+/−)-2-phenylcyclopentan-3-one-1-carboxylate

The title compound was prepared as shown in Scheme 1 and using the procedures of W. Baker and W. G. Leeds, J. Chem. Soc. 974 (1948).

Step A:

γ-δ-Dicarboxy-δ-phenyl-n-valeric acid

A mixture of 47 g of benzaldehyde and 50 g of ethyl cyanoacetate in 200 mL of absolute ethanol was treated with 2 mL of piperidine and the reaction was gently warmed. After the initial exothermic reaction had subsided, the reaction was heated to 60° C. (internal temperature) and then allowed to cool to room temperature. After 1 h, 22 g of powdered sodium cyanide was added in portions over 25 min and a mild exotherm ensued. The reaction was heated to an internal temperature of 80° C. and then allowed to cool to 35° C. before slow addition of 60 g of ethyl β-chloropropionate over 10 min. After heating in an oil bath at 80° C. for 5 h, the reaction was cooled and filtered to remove the precipitated sodium chloride. The filtrate was concentrated and to the residue was added 500 mL of concentrated HCl and 250 mL of water. The mixture was heated at reflux for 48 h and, while still hot, was treated with charcoal and filtered through Celite to remove some insoluble tarry material. On cooling, 25.8 g of title compound as a pale yellow solid was obtained after filtration and air drying. The filtrate was extracted with ethyl acetate, washed with brine, dried with sodium sulfate and evaporated to provide an additional 32.8 g of less pure product which could be used directly.

Step B:

Trimethyl γ-δ-dicarboxy-δ-phenyl-n-valerate

Into a solution of 21.2 g of the above triacid dissolved in 200 mL of methanol was bubbled 48.6 g of HCl gas. After heating at reflux overnight, the cooled reaction was concentrated and diluted with toluene. Most of the aqueous bottom phase was removed via pipette and the toluene was evaporated. The residue was taken up in 200 mL of methanol and resaturated with HCl gas (53.5 g). After heating for another 20 h, the reaction was concentrated and the residue was dissolved in ether and washed with water, saturated $NaHCO_3$, and brine, then dried with sodium sulfate, and evaporated to provide 25.7 g of an oil which crystallized in the freezer. Trituration with 5% ethyl acetate in hexanes and filtration gave 18.4 g of the title triester as a white solid.
Step C:

trans-(+/−)-2-Phenylcyclopentan-3-one-1-carboxylic acid

To 50 mL of anhydrous methanol was added a solution of 26 mL of 25% by wt sodium methoxide in methanol followed by 18.4 g of the above triester dissolved in 25 mL of methanol. After heating at reflux for 5.5 h, the solvent was evaporated and the residue was dissolved in 150 mL of concentrated HCl and 75 mL of water and heated at reflux overnight. The reaction, while still hot, was treated with charcoal and filtered through Celite. After cooling, 7.65 g of title compound was obtained as a white solid after filtration and air drying. An additional 4.76 g of triacid was recovered by extraction of the filtrate with ethyl acetate.
Step D:

Methyl trans-(+/−)-2-phenylcyclopentan-3-one-1-carboxylate

A solution of 4.17 g of above acid in 200 mL of methanol was saturated with HCl gas and stirred overnight. The reaction was concentrated to a wet solid. This was taken up in ethyl acetate and washed with water, saturated NaHCO$_3$ solution, and brine, then dried with sodium sulfate and evaporated to furnish 4.4 g of the title product as a white solid. NMR (CDCl$_3$): δ 2.0–2.15 (m, 1H), 2.3–2.5 (m, 2H), 2.62 (br dd, 1H), 3.25 (dt, 1H), 3.65 (s, 3H), 3.70 (br d, 1H), 7.12 (m, 2H), 7.24 (m, 1H), 7.32 (m, 2H).

EXAMPLE 2

Methyl 3-(SR)-(hydroxy)-2-(SR)-phenylcyclopentane-1-(SR)-carboxylate (Racemic 2,3-cis isomer) and methyl 3-(SR)-(hydroxy)-2-(RS)-phenylcyclopentane-1-(RS)-carboxylate (Racemic 2,3-trans isomer)

Method A:

To a solution of 4.43 g of methyl trans-(+/−)-2-phenylcyclopentan-3-one-1-carboxylate from Example 1, Step D in 65 mL of absolute methanol cooled in an ice/ethanol bath was added 807 mg of NaBH$_4$ in portions. After 1 h, the reaction was quenched with aqueous NH$_4$Cl. The solvent was evaporated and the residual oil was partitioned between ethyl acetate and water. The organic layer was washed with brine, dried with sodium sulfate and evaporated. The residue was purified by Prep LC eluting first with 20% ethyl acetate in hexanes to provide 1.18 g of the higher R$_f$ 2,3-cis isomer.

NMR (CDCl$_3$): δ 1.8–2.0 (m, 2H), 2.05–2.2 (m, 1H), 2.3–2.4 (m, 1H), 3.3–3.45 (m, 2H), 3.59 (s, 3H), 4.30 (m, 1H), 7.2–7.35 (m, 5H). Further elution with 40% ethyl acetate in hexanes provided 3.90 g of the lower R$_f$ 2,3-trans isomer. NMR (CDCl$_3$): δ 1.82 (m, 1H), 2.10 (m, 3H), 2.95 (q, 1H), 3.22 (dd, 1H), 3.60 (s, 3H), 4.20 (q, 1H), 7.22 (m, 3H), 7.31 (m, 2H).

Method B:

To a solution of 100 mg of methyl trans-(+/−)-2-phenylcyclopentan-3-one-1-carboxylate from Example 1, Step D in 5 mL of dry THF under N$_2$ and cooled in a dry ice/acetone bath was added dropwise 0.55 mL of 1M L-Selectride in THF. After 1 h, the reaction was quenched with dilute HCl. The mixture was extracted twice with ether and the organic layers were washed with brine, combined, dried with sodium sulfate and evaporated. The residue was purified by flash chromatography eluting with 20% ethyl acetate in hexanes to give only the higher R$_f$ 2,3-cis product isomer. The NMR was same as the higher R$_f$ isomer in Method A.

EXAMPLE 3

Methyl 3-(SR)-(3,5-bis(trifluoromethyl)phenyl)methoxy)-2-(RS)-phenylcyclopentane-1-(RS)-carboxylate (Racemic 2,3-trans isomer)

To a solution of 250 mg of the lower 2,3-trans alcohol from Example 2, Method A and 525 mg of 3,5-bis(trifluoromethyl)-benzyl bromide in 5 mL of DMF at room temperature was added 91 mg of 60% NaH in mineral oil. After 3 h, the reaction was quenched with dilute HCl and extracted twice with ether. The organic layers were washed with a portion of brine, combined, dried with sodium sulfate and evaporated. The residue was purified by flash chromatography eluting with 10 to 20% ethyl acetate in hexanes to obtain 230 mg of title compound. NMR (CDCl$_3$): δ 1.85–2.0 (m, 1H), 2.0–2.2 (m, 3H), 2.90 (q, 1H), 3.46 (dd, 1H), 3.59 (s, 3H), 4.05 (q, 1H), 4.47 (ABq, 2H), 7.2–7.25 (m, 3H), 7.25–7.35 (m, 2H), 7.59 (s, 2H), 7.72 (s, 1H).

EXAMPLE 4

Methyl 3-(SR)-(3,5-bis(trifluoromethyl)phenyl)methoxy)-2-(SR)-phenylcyclopentane-1-(SR)-carboxylate (Racemic 2,3-cis isomer)

Using essentially the same procedure as in Example 3 but using 200 mg of the higher 2,3-cis alcohol from Example 2, Method A, 250 mg of the title compound was obtained. NMR (CDCl$_3$): δ 1.85–2.0 (m, 1H), 2.05–2.2 (m, 2H), 2.25–2.35 (m, 1H), 3.35–3.5 (m, 2H), 3.58 (s, 3H), 4.05 (m, 1H), 4.10 (d, 1H), 4.43 (d, 1H), 7.2–7.35 (m, 5H), 7.41 (s, 2H), 7.68 (s, 1H).

EXAMPLE 5

3-(SR)-(3,5-Bis(trifluoromethyl)phenyl)methoxy)-2-(SR)-phenylcyclopentyl-1-(RS)-isocyanate (Racemic 2,3-trans isomer)

Step A:

3-(SR)-(3,5-Bis(trifluoromethyl)phenyl)methoxy)-2-(RS)-phenylcyclopentane-1-(RS)-carboxylic acid To a solution of 250 mg of methyl 3-(SR)-(3,5-bis(trifluoromethyl)phenyl)methoxy)-2-(RS)-phenylcyclopentane-1-(RS)-carboxylate from Example 3 in 5 mL of ethanol was added 1.2 mL of 2N NaOH. The reaction was heated at 80° C. for 3 h, cooled, diluted with water and acidified with 2N HCl. The mixture was extracted twice with ether and the organic layers were washed with a portion of brine, combined, dried with sodium sulfate and evaporated. The residue was purified by flash chromatography eluting with 20% ethyl acetate in hexanes then 1% HOAc in 20% ethyl acetate/hexanes to obtain 230 mg of title compound as a semi-solid.

Step B:

3-(SR)-(3,5-Bis(trifluoromethyl)phenyl)methoxy)-2-(SR)-phenylcyclopentyl-1-(RS)-isocyanate To a solution of 230 mg of the above carboxylic acid in 5 mL of methylene chloride containing a catalytic amount of DMF was added 0.10 mL of oxalyl chloride. The reaction was stirred at room temperature for 1h and evaporated to dryness. The above residue was taken up in 5 mL of acetone and cooled in an ice bath and a solution of 70 mg of sodium azide in 5 mL of water was added. The reaction was stirred for 0.5 h, diluted with ice water and extracted twice with toluene. The organic layers were washed with a portion of brine, combined, dried with sodium sulfate and concentrated to 10 mL with a minimum of heating. (Note: The acyl azide is unstable and should not be concentrated to dryness.) The

EXAMPLE 6

1-(SR)-(3,5-Bis(trifluoromethyl)phenyl)methoxy-2-(SR)-phenyl-3-(RS)-(aminocarbonylamino)cyclopentane To a solution of 25 mg of isocyanate from Example 5 in 5 mL of toluene was added 1 mL of dioxane and 0.10 mL of 7.4N ammonium hydroxide. After 15 min, the reaction was diluted with water and extracted twice with ether. The organic layers were washed with a portion of brine, combined, dried with sodium sulfate and concentrated. The residue was purified on a 1 mm preparative silica gel plate eluted with ethyl acetate. Mass spec ($NH_3/CI$): 447 (M+1).

EXAMPLE 7

1-(SR)-(3,5-Bis(trifluoromethyl)phenyl)methoxy-2-(SR)-phenyl-3-(RS)-(methoxycarbonylamino)cyclopentane A solution of 150 mg of isocyanate from Example 5 and 0.10 mL of DIPEA in 10 mL of methanol was stirred at room temperature for 2 h. The solvent was evaporated and the residue was purified by flash chromatography eluting with 30 to 50% ethyl acetate in hexanes to obtain 150 mg of title compound. Mass spec ($NH_3/CI$): 462 (M+1).

EXAMPLE 8

1-(SR)-(3,5-Bis(trifluoromethyl)phenyl)methoxy-2-(SR)-phenyl-3-(RS)-(benzyloxycarbonylamino)cyclopentane A solution of isocyanate prepared from 1.3 g of acid as in Example 5, a catalytic amount of DMAP, 1 mL of DIPEA and 3 mL of benzyl alcohol in 3 mL of toluene was stirred at 80° C. for 20 h. The volatiles were removed in vacuo and the residue was purified by flash chromatography eluting with 25% ethyl acetate in hexanes to obtain 1.10 g of title compound after precipitation from 10% ethyl acetate in hexanes.

NMR (CDCl3): δ 1.7–1.85 (m, 1H), 1.85–2.0 (m, 1H), 2.0–2.2 (m, 1H), 2.2–2.4 (m, 1H), 2.90 (br t, 1H), 3.97 (dt, 1H), 4.1–4.2 (m, 1H), 4.54 (ABq, 2H), 4.83 (br d, 1H), 4.98 (ABq, 2H), 7.2–7.4 (m, 10H), 7.59 (s, 2H), 7.72 (s, 1H).

EXAMPLE 9

1-(SR)-(3,5-Bis(trifluoromethyl)phenyl)methoxy-2-(SR)-phenyl-3-(RS)-aminocyclopentane Method A:

To a solution of 130 mg of methyl carbamate prepared in Example 7 in 5 mL of ethanol was added 0.7 mL of 2N NaOH. The reaction was heated at 80° C. for 30 h, then diluted with water and extracted twice with ether. The organic layers were washed with a portion of brine, dried with sodium sulfate and evaporated. The residue was purified on a 1 mm preparative silica gel plate eluted with 10% MeOH in ethyl acetate to obtain 80 mg of title compound as an oil. Mass spec ($NH_3/CI$): 404 (M+1).

Method B:

A solution of 200 mg of benzyl carbamate prepared in Example 8 in 5 mL of methanol was hydrogenated over 50 mg of 10% Pd/C for 2 h. The reaction was filtered and concentrated. The residue was purified on a 1 mm preparative silica gel plate eluted with 10% MeOH in ethyl acetate to obtain 120 mg of title compound.

EXAMPLE 10

1-(SR)-(3,5-Bis(trifluoromethyl)phenyl)methoxy-2-(SR)-phenyl-3-(RS)-(aminocarbonylmethylamino)cyclopentane A solution of 30 mg of amine prepared in Example 9, Method A, 16 mg of iodoacetamide and 0.05 mL of DIPEA in 0.5 mL of acetonitrile was heated in a sealed vial at 50° C. for 4 h. The volatiles were evaporated under a stream of nitrogen and the residue was purified on a 1 mm preparative silica gel plate eluted with 5% MeOH in ethyl acetate to afford 23 mg of title compound as a sticky oil. Mass spec ($NH_3/CI$): 461 (M+1).

EXAMPLE 11

1-(SR)-(3,5-Bis(trifluoromethyl)phenyl)methoxy-2-(SR)-phenyl-3-(RS)-(methylamino)cyclopentane Step A:

1-(SR)-(3,5-Bis(trifluoromethyl)phenyl)methoxy-2-(SR)-phenyl-3-(RS)-(N-(benzyloxycarbonyl)-N-methylamino)cyclopentane To a solution of 500 mg of benzyl carbamate prepared in Example 8 and 0.12 mL of iodomethane in 5 mL of DMF was added 60 mg of 60% NaH in mineral oil. After 2 h, the reaction was quenched with 2N HCl and water and extracted twice with ethyl acetate. The organic layers were washed with a portion of brine, combined, dried over sodium sulfate and evaporated. The residue was purified by flash chromatography eluting with 25% ethyl acetate in hexanes to obtain 500 mg of title compound as an oil. NMR (CDCl3): δ 1.80–2.0 (m, 3H), 2.0–2.2 (m, 1H), 2.80 and 2.87 (2 br s, 3H), 3.05–3.15 (m, 1H), 3.9–4.0 (m, 1H), 4.36 and 4.40 (2 s, 1H), 4.4–4.55 (m, 1H), 4.55–4.85 (2 br m, 1H), 4.91 and 5.03 (2 br s, 2H), 7.0–7.3 (m, 10H), 7.58 (br s, 2H), 7.72 (s, 1H).

Step B:

1-(SR)-(3,5-Bis(trifluoromethyl)phenyl)methoxy-2-(SR)-phenyl-3-(RS)-(methyl amino)cyclopentane A solution of 475 mg of the above benzyl carbamate in 5 mL of 1:1 methanol:ethyl acetate was hydrogenated over 100 mg of 10% Pd/C for 2 h. The reaction was filtered and concentrated to afford the title compound as an oil.

Mass spec ($NH_3/CI$): 418 (M+1).

EXAMPLE 12

1-(SR)-(3,5-Bis(trifluoromethyl)phenyl)methoxy-2-(SR)-phenyl-3-(RS)-(N-(aminocarbonylmethyl)-N-methylamino)cyclopentane A solution of 50 mg of amine prepared in Example 11, 33 mg of iodoacetamide and 0.05 mL of DIPEA in 0.5 mL of acetonitrile was heated in a sealed vial at 50° C. for 2 h (or room temperature for 16 h). The volatiles were evaporated under a stream of nitrogen and the residue was purified on a 1 mm preparative silica gel plate eluted with 5% MeOH in methylene chloride to afford 70 mg of title compound. Mass spec ($NH_3/CI$): 475 (M+1).

EXAMPLE 13

1-(SR)-(3,5-Bis(trifluoromethyl)phenyl)methoxy-2-(SR)-phenyl-3-(RS)-(N-acetyl-N-methylamino)cyclopentane To a solution of 25 mg of amine prepared in Example 11 and 0.05 mL of DIPEA in 0.5 mL of methylene chloride was added 7 mg of acetyl chloride. After 1.5 h in a sealed vial, the volatiles were evaporated under a stream of nitrogen and the residue was purified on a 1 mm preparative silica gel plate eluted with ethyl acetate to afford 25 mg of title compound. Mass spec (NH$_3$/CI): 460 (M+1).

EXAMPLE 14

1-(SR)-(3,5-Bis(trifluoromethyl)phenyl)methoxy-2-(SR)-phenyl-3-(RS)-(N-(methoxycarbonyl)-N-methylamino)cyclopentane To a solution of 25 mg of amine prepared in Example 11 and 0.05 mL of DIPEA in 0.5 mL of methylene chloride was added 12 mg of methyl chloroformate. After 1.5 h in a sealed vial, the volatiles were evaporated under a stream of nitrogen and the residue was purified on a 1 mm preparative silica gel plate eluted with ethyl acetate to afford 20 mg of title compound. Mass spec (NH$_3$/CI): 476 (M+1).

EXAMPLE 15

1-(SR)-(3,5-Bis(trifluoromethyl)phenyl)methoxy-2-(SR)-phenyl-3-(RS)-(N-(methylaminocarbonyl)-N-methylamino)cyclopentane To a solution of 25 mg of amine prepared in Example 11 and 0.05 mL of DIPEA in 0.5 mL of methylene chloride was added 15 mg of methyl isocyanate. After 1.5 h in a sealed vial, the volatiles were evaporated under a stream of nitrogen and the residue was purified on a 1 mm preparative silica gel plate eluted with ethyl acetate to afford 25 mg of title compound. Mass spec (NH$_3$/CI): 475 (M+1).

EXAMPLE 16

1-(SR)-(3,5-Bis(trifluoromethyl)phenyl)methoxy-2-(SR)-phenyl-3-(RS)-(N-(dimethylaminocarbonyl)-N-methylamino)cyclopentane To a solution of 25 mg of amine prepared in Example 11 and 0.05 mL of DIPEA in 0.5 mL of methylene chloride was added 15 mg of dimethylcarbamoyl chloride. After 2 h at 50° C. in a sealed vial, the volatiles were evaporated under a stream of nitrogen and the residue was purified on a 1 mm preparative silica gel plate eluted with ethyl acetate to afford 25 mg of title compound. Mass spec (NH$_3$/CI): 489 (M+1).

EXAMPLE 17

1-(SR)-(3,5-Bis(trifluoromethyl)phenyl)methoxy-2-(SR)-phenyl-3-(RS)-(methylaminocarbonylamino)cyclopentane To a solution of 20 mg of amine prepared in Example 9, Method B and 0.05 mL of DIPEA in 0.5 mL of methylene chloride was added 20 mg of methyl isocyanate. After 1 h at 50° C. in a sealed vial, the volatiles were evaporated under a stream of nitrogen and the residue was purified on a 1 mm preparative silica gel plate eluted with ethyl acetate to afford 22 mg of title compound. Mass spec (NH$_3$/CI): 461 (M+1).

EXAMPLE 18

1-(SR)-(3,5-Bis(trifluoromethyl)phenyl)methoxy-2-(SR)-phenyl-3-(RS)-(dimethylaminocarbonylamino)cyclopentane To a solution of 20 mg of amine prepared in Example 9, Method B and 0.05 mL of DIPEA in 0.5 mL of methylene chloride was added 15 mg of dimethylcarbamoyl chloride. After 3 h at 50° C. in a sealed vial, the volatiles were evaporated under a stream of nitrogen and the residue was purified on a 1 mm preparative silica gel plate eluted with ethyl acetate to afford 20 mg of title compound. Mass spec (NH$_3$/CI): 475 (M+1).

EXAMPLE 19

1-(SR)-(3,5-Bis(trifluoromethyl)phenyl)methoxy-2-(SR)-phenyl-3-(RS)-(N-((2-oxo-1H,3H-1,3-imidazol-4-yl)methyl)-N-methylamino)cyclopentane To a solution of 25 mg of amine prepared in Example 11 and 0.05 mL of DIPEA in 0.5 mL of acetonitrile was added 25 mg of (1,3-diacetyl-2-oxo-1H,3H-1,3-imidazol-4-yl)methyl bromide. After 16 h at room temperature in a sealed vial, 0.1 mL of 40% aqueous methylamine was added and the mixture was aged for 15 min. The volatiles were evaporated under a stream of nitrogen and the residue was taken up in water and extracted twice with ethyl acetate. The organic layers were washed with a portion of brine, combined, dried over sodium sulfate and evaporated. The reside was purified on a 1 mm preparative silica gel plate eluted with 10% methanol in methylene chloride to afford 20 mg of title compound. Mass spec (NH$_3$/CI): 514 (M+1).

A small amount of a higher $R_f$ acylated product 1-(SR)-(3,5-bis(trifluoromethyl)phenyl)methoxy-2-(RS)-phenyl-3-(SR)-(N-acetyl-N-methylamino)cyclopentane was also obtained which was the same as that of Example 13.

EXAMPLE 20

1-(SR)-(3,5-Bis(trifluoromethyl)phenyl)methoxy-2-(SR)-phenyl-3-(RS)-(N-((5-oxo-1H,4H-1,2,4-triazol-3-yl)methyl)-N-methylamino)cyclopentane To a solution of 50 mg of amine prepared in Example 11 and 0.05 mL of DIPEA in 0.5 mL of acetonitrile was added 20 mg of N-methoxycarbonyl-2-chloroacetamidrazone. After 16 h at room temperature in a sealed vial, the volatiles were evaporated under a stream of nitrogen and the residue was purified by flash chromatography eluting with 5 to 10% methanol in ethyl acetate. The product fractions were combined and evaporated. The residue was then taken up in 15 mL of xylenes and heated at 150° C. for 2 h. The volatiles were evaporated and the residue was purified on a 1 mm preparative silica gel plate eluted with 5% methanol in ethyl acetate to afford 20 mg of title compound. Mass spec (NH$_3$/CI): 515 (M+1).

EXAMPLE 21

1-(SR)-(3,5-Bis(trifluoromethyl)phenyl)methoxy-2-(SR)-phenyl-3-(RS)-(N-((1 2,4-triazol-3-yl)methyl)-N-methylamino)cyclopentane To a solution of 50 mg of amine prepared in Example 11 and 0.05 mL of DIPEA in 0.5 mL of acetonitrile was added 17 mg of N-carboxaldehyde-2-chloroacetamidrazone. After 16 h at room temperature in a sealed vial, the volatiles were evaporated under a stream of nitrogen and the residue was purified by flash chromatography eluting with ethyl acetate, then 5 to 10% methanol in ethyl acetate. The product fractions were combined and evaporated. The residue was then taken up in 15 mL of xylenes and heated at 150° C. for 2 h. The volatiles were evaporated and the residue was purified on a 1 mm preparative silica gel plate eluted with 5% methanol in ethyl acetate to afford 28 mg of title compound. Mass spec (NH$_3$/CI): 499 (M+1).

EXAMPLE 22

Starting with the racemic 2,3-cis methyl ester from Example 4 and using essentially the same procedures as in Examples 5 thru 9, the following compounds were prepared:

3-(SR)-(3,5-Bis(trifluoromethyl)phenyl)methoxy-2-(RS)-phenylcyclopentyl-1-(SR)-isocyanate (Racemic 2,3-cis isomer)

1-(SR)-(3,5-Bis(trifluoromethyl)phenyl)methoxy-2-(RS)-phenyl-3-(SR)-(aminocarbonylamino)cyclopentane Mass spec ($NH_3$/CI): 447 (M+1).

1-(SR)-(3,5-Bis(trifluoromethyl)phenyl)methoxy-2-(RS)-phenyl-3-(SR)-(methoxycarbonylamino)cyclopentane Mass spec ($NH_3$/CI): 462 (M+1).

1-(SR)-(3,5-Bis(trifluoromethyl)phenyl)methoxy-2-(RS)-phenyl-3-(SR)-(benzyloxycarbonylamino)cyclopentane Mass spec ($NH_3$/CI): 538 (M+1).

1-(SR)-(3,5-Bis(trifluoromethyl)phenyl)methoxy-2-(RS)-phenyl-3-(SR)-aminocyclopentane Mass spec ($NH_3$/CI): 404 (M+1).

EXAMPLE 23

Starting with the benzyl carbamate from Example 22 and using essentially the same procedures as in Examples 11, 12 and 20, the following compounds were prepared.

1-(SR)-(3,5-Bis(trifluoromethyl)phenyl)methoxy-2-(RS)-phenyl-3-(SR)-(methylamino)cyclopentane Mass spec ($NH_3$/CI): 418 (M+1).

1-(SR)-(3,5-Bis(trifluoromethyl)phenyl)methoxy-2-(RS)-phenyl-3-(SR)-(N-(aminocarbonylmethyl)-N-methylamino)cyclopentane Mass spec ($NH_3$/CI): 475 (M+1).

1-(SR)-(3,5-Bis(trifluoromethyl)phenyl)methoxy-2-(RS)-phenyl-3-(SR)-(N-((5-oxo-1H,4H-1,2,4-triazol-3-yl)methyl)-N-methylamino)-cyclopentane Mass spec ($NH_3$/CI): 515(M+1).

EXAMPLE 24

Methyl 3-(SR)-(1-(SR)-(3,5-bis(trifluoromethyl)phenyl)ethoxy)-2-(RS)-phenylcyclopentane-1-(RS)-carboxylate (higher $R_f$ α-methyl isomer) and methyl 3-(SR)-(1-(RS)-(3,5-bis(trifluoromethyl)phenyl) ethoxy)-2-(RS)-phenylcyclopentane-1-(RS)-carboxylate (lower $R_f$ α-methyl isomer) (Racemic 2,3-trans isomers)

Step A:
(+/−)-1-(3,5-Bis(trifluoromethy)phenyl)-1-hydroxyethane

To a solution of 17.8 g of 3',5'-bis(trifluoromethyl) acetophenone in 300 mL of absolute ethanol was added 1.32 g of $NaBH_4$ while stirring in an ice bath. After 30 min the ice bath was removed and stirring was continued for an additional 1.5 h. The reaction was quenched using excess 2N HCl and the solvent was mostly evaporated in vacuo. The residue was partitioned between ethyl acetate and aq. HCl and the aqueous layer was extracted again with ethyl acetate. The separate organic layers were sequentially washed with brine, then combined, dried over $MgSO_4$ and evaporated to provide 16.74 g of the title compound as a white solid after vacuum drying.

Step B:
(+/−)-(1-(3,5-Bis(trifluoromethyl)phenyl)ethyl) trichloroacetamidate

To 40 mL of anhydrous ether was added 160 mg of 60% sodium hydride in mineral oil. After stirring 10 min, 10.3 g of the above racemic alcohol dissolved in 25 mL of ether was added. The reaction was warmed slightly and stirred until a homogeneous solution was obtained. After a further 10 min, the solution was added via canula to a solution of 4.0 mL of trichloroacetonitrile in 10 mL of ether cooled in an ice bath. After 1 h an amber color was produced and the reaction was concentrated to give 15.6 g of the title product as an amber oil.

Step C:
(+/−)-1-(3,5-Bis(trifluoromethyl)phenyl)ethyl bromide

To a solution of 1.89 g of (+/−)-1-(3,5-bis(trifluoromethy)-phenyl)-1-hydroxyethane prepared as in Example 5, Step A in 50 mL of acetonitrile at room temperature was added 5.15 g of triphenylphosphine dibromide. After 1.5 h, the reaction was partitioned between ether and water and the ether layer was washed with brine, dried with sodium sulfate and evaporated. The product was triturated with hexanes, filtered to remove the solid and reconcentrated. The residue was purified by flash chromatography using hexanes to provide 1.75 g of title compound as an oil.

Step D:
Methyl 3-(SR)-(1-(SR)-(3,5-bis(trifluoromethyl)phenylethoxy)-2-(RS)-phenylcyclopentane-1-(RS)-carboxylate (higher $R_f$ α-methyl isomer)and methyl 3-(SR)-(1-(RS)-(3,5-bis(trifluoromethyl)phenyl)-ethoxy)-2-(RS)-phenylcyclopentane-1-(RS)-carboxylate (lower $R_f$ α-methyl isomer) (Racemic 2,3-trans isomers)

Method A:
To a solution of 153 mg of the lower $R_f$ 2,3-trans alcohol isomer from Example 2 in 2.0 mL of dry dichloromethane was added 600 mg of the above trichloroacetamidate in 2.0 mL of cyclohexane. After stirring for 10 min, 0.015 mL of triflic acid was added. After 2 h the reaction was filtered to remove any insoluble white solid. The filtrate was diluted with dichloromethane and washed with saturated $NaHCO_3$, water and brine, and then dried with sodium sulfate and concentrated. The crude solid was purified by flash chromatography using 2 to 5% ethyl acetate in hexanes to provide first 145 mg of the higher $R_f$ α-methyl isomer. Mass spec ($NH_3$/CI): 461 (M+1). NMR ($CDCl_3$): δ 1.2 (d, 3H), 1.8–2.1 (m, 4H), 2.8 (m, 1H), 3.4 (dd, 1H), 3.58 (s, 3H), 3.78 (q, 1H), 4.3 (q, 1H), 7.16–7.3 (m, 5H), 7.43 (s, 2H), 7.7 (s, 1H). Further elution afforded 148 mg of the lower $R_f$ α-methyl isomer. Mass spec ($NH_3$/CI): 461 (M+1). NMR ($CDCl_3$): δ 1.34 (d, 3H), 1.86–1.92 (m, 1H), 2.05–2.1 (m, 3H), 2.80 (q, 1H), 3.34 (dd, 1H), 3.78 (q, 1H), 4.46 (q, 1H), 7.04–7.24 (m, 5H), 7.43 (s, 2H), 7.64 (s, 1H).

Method B:
To a solution of 219 mg of the lower $R_f$ 2,3-trans alcohol isomer from Example 2 and 642 mg of above bromide in 3.0 mL of dry DMF at room temperature was added 80 mg of 60% NaH in mineral oil in portions over 10 min. After 2 h, additional bromide (321 mg) and NaH (40 mg) were added and stirring was continued another 2 h. The reaction was then quenched with dilute HCl. The mixture was extracted twice with ether and the organic layers were washed with brine, combined, dried with sodium sulfate and evaporated. The residue was purified by flash chromatography eluting with hexanes and then 5% ethyl acetate in hexanes to give first the higher $R_f$ product isomer (50 mg) and then the lower product isomer (47 mg). The NMR of each was the same as in Method A.

EXAMPLE 25

Methyl 3-(SR)-(1-(SR)-(3,5-Bis(trifluoromethyl)phenyl) ethoxy)-2-(SR)-phenylcyclopentane-1-(SR)-carboxylate (higher $R_f$ α-methyl isomer) and methyl 3-(SR)-(1-(RS)-(3,5-bis(trifluoromethyl)phenyl)ethoxy)-2-(SR)-phenylcyclopentane-1-(SR)-carboxylate (lower $R_f$ α-methyl isomer) (Racemic 2,3-cis isomers)

Following essentially the same procedure as in Example 24, Step D, Method A but employing methyl 3-(SR)-

(hydroxy)-2-(SR)-phenylcyclopentane-1-(SR)-carboxylate (racemic 2,3-cis isomer) (1.06 g), the title compounds (378 and 712 mg) were obtained.

Higher $R_f$ isomer: NMR (CDCl$_3$): δ 1.04 (d, 3H), 1.75–1.89 (m, 2H), 1.95–2.04 (m, 1H), 195–2.04 (m, 1H), 3.34 (m, 2H), 3.6 (s, 3H), 3.87–3.96 (m, 2H), 7.05 (m, 2H), 7.34 (m, 2H), 7.6 (s, 2H), 7.75 (s, 1H). Lower $R_f$ isomer: NMR (CDCl$_3$): δ 1.3 (d, 3H), 1.92–2.04 (m, 3H), 2.28–2.37 (m, 1H), 3.24 (dd, 1H), 3.36–3.44 (m, 1H), 3.58 (s, 3H), 3.72 (m, 1H), 4.4 (q, 1H), 6.94 (m, 2H), 7.18–7.22 (m, 4H), 7.63 (s, 1H).

EXAMPLE 26

1-(R)-(1-(S)-(3,5-Bis(trifluoromethyl)phenyl) ethoxy-2-(R)-phenyl-3-(S)-((1-(S)-phenyl) ethoxycarbonylamino) cyclopentane (higher $R_f$ isomer) and 1-(S)-(1-(R)-(3,5-bis(trifluoromethyl) phenyl)ethoxy-2-(S)-phenyl-3-(R)-((1-(S)-phenyl) ethoxycarbonylamino)cyclopentane (lower $R_f$ isomer)

The title compounds were prepared essentially the same as in Examples 5 and 8 except that (S)-α-methylbenzyl alcohol was reacted with the intermediate isocyanate and the diastereomers were chromatographically separated.
Step A:
To a solution of 905 mg of the methyl ester lower isomer from Example 24, Step D, Method A in 20 mL of methanol was added 5 mL of 2.0N NaOH. After heating at reflux for 2 h, the methanol was evaporated, and the residual liquid was acidified with 2N HCl. The aqueous phase was washed twice with ethyl acetate. The separate organic layers were washed with brine, combined, dried with sodium sulfate and evaporated to furnish 943 mg of the carboxylic acid.
Step B:
A solution of 855 mg of the above acid in 20 mL of dry dichloromethane was treated with 2 drops of DMF followed by 0.36 mL of oxalyl chloride. After 1 h the reaction was evaporated and the residual yellow oil was concentrated twice more from dichloromethane.
Step C:
The above acid chloride was then taken up in 20 mL of acetone and added to a solution of 248 mg of sodium azide in 20 mL of water stirring in an ice bath. After 30 min the reaction was partitioned between benzene an cold water. The aqueous layer was washed again with benzene and the separate organic layers were washed with brine, combined, dried with sodium sulfate and then evaporated to approximately 10 mL (DO NOT EVAPORATE TO DRYNESS!!!).
Step D:
Another 40 mL of dry benzene was added to the above solution of acyl azide and the solution was heated at 80° C. for 2 h and then evaporated to give crude isocyanate as an oil.
Step E:
The above isocyanate was dissolved in 8 mL of toluene and treated with 1 g of (S)-(−)-α-methylbenzyl alcohol, 0.66 mL of diisopropylamine and 15 mg of dimethylaminopyridine. The resulting solution was heated at 100° C. overnight and then evaporated. Purification on a silica gel flash column (5 to 20% ethyl acetate in hexanes) gave 193 mg of pure higher $R_f$ isomer and 180 mg of pure lower $R_f$ isomer.

Higher $R_f$ isomer. NMR (CDCl$_3$): δ 1.37 (d, 6H), 1.68–2.3 (m, 4H), 2.85 (m, 1H), 3.74 (q, 1H), 4.02 (q, 1H), 4.48 (q, 1H), 4.76 (br s, 1H), 5.67 (q, 1H), 7.06–7.4 (m, 10H), 7.46 (s, 2H), 7.67 (s, 1H). Lower $R_f$ isomer. NMR (CDCl$_3$): δ 1.37 (d, 3H), 1.47 (m, 3H), 1.7–1.94 (m, 2H), 2.02–2.12 (m, 1H), 2.24–2.36 (m, 1H), 2.84 (m, 1H), 3.74 (m, 1H), 4.0 (q, 1H), 4.49 (q, 1H), 4.77 (br s, 1H), 5.67 (m, 1H), 7.02 (br s, 2H), 7.16–7.32 (m, 8H), 7.46 (s, 2H), 7.67 (s, 1H).

EXAMPLE 27

1-(R)-(1-(S)-(3,5-Bis(trifluoromethyl)phenyl) ethoxy)-2-(R)-phenyl-3-(S)-aminocyclopentane To 185 mg of the higher $R_f$ isomer from Example 26, Step E dissolved in 5 mL of ethanol was added 40 mg of 10% Pd on carbon and the mixture was hydrogenated on the Parr shaker. The reaction was filtered over Celite and the filtrate was evaporated to provide 111 mg of the title compound as a white solid. Mass spec (NH$_3$/CI): 418 (M+1).

EXAMPLE 28

1-(S)-(1-(R)-(3,5-Bis(trifluoromethyl)phenyl) ethoxy)-2-(S)-phenyl-3-(R)-aminocyclopentane To 174 mg of the lower $R_f$ isomer from Example 26, Step E dissolved in 5 mL of ethanol was added 40 mg of 10% Pd on carbon and the mixture was hydrogenated on the Parr shaker. The reaction was filtered thru Celite and the filtrate was evaporated to provide 106 mg of the title compound as a white solid. Mass spec (NH$_3$/CI): 418 (M+1).

EXAMPLE 29

1-(R)-(1-(S)-(3,5-Bis(trifluoromethyl)phenyl) ethoxy)-2-(R)-phenyl-3-(S)-(aminocarbonylmethylamino)cyclopentane The title compound was prepared using the amine from Example 27 and iodoacetamide using essentially the same procedure as Example 10. Mass spec (NH$_3$/CI): 475 (M+1).

EXAMPLE 30

1-(S)-(1-(R)-(3,5-Bis(trifluoromethyl)phenyl) ethoxy)-2-(S)-phenyl-3-(R)-(aminocarbonylmethylamino)cyclopentane The title compound was prepared using the amine from Example 28 and iodoacetamide using essentially the same procedure as Example 10. Mass spec (NH$_3$/CI): 475 (M+1).

EXAMPLE 31

Methyl trans-(+/−)-2-(4-fluorophenyl)cyclopentan-3-one-1-carboxylate

Using essentially the same procedures as described in Example 1 but starting with 4-fluorobenzaldehyde, the title compound was prepared. NMR (CD$_3$OD): δ 2.0–2.2 (m, 1H), 2.3–2.5 (m, 2H), 2.56–2.76 (m, 1H), 3.1–3.3 (m, 1H), 3.68 (s, 3H), 3.72 (br d, 1H), 6.98–7.16 (m, 4H).

EXAMPLE 32

Methyl 3-(SR)-(hydroxy)-2-(SR)-(4-fluorophenyl) cyclopentane-1-(SR)-carboxylate (Racemic 2,3-cis isomer) and methyl 3-(SR)-(hydroxy)-2-(RS)-(4-fluorophenyl)cyclopentane-1-(RS)-carboxylate (Racemic 2,3-trans isomer)

Using essentially the same procedures as described in Example 2 but starting with the 4-fluorophenyl derivative, the title compounds were prepared. Higher $R_f$ isomer. NMR (CDCl$_3$): δ 1.86–2.0 (m, 2H), 2.1–2.2 (m, 1H), 2.29–2.36

(m, 1H), 3.28–3.4 (m, 2H), 3.6 (s, 3H), 4.28 (m, 1H), 7.0 (m, 2H), 7.24 (m, 2H). Lower $R_f$ isomer. NMR (CDCl$_3$): δ 1.80–1.86 (m, 1H), 2.06–2.17 (m, 3H), 2.87 (q, 1H), 3.19 (dd, 1H), 3.6 (s, 3H), 4.14 (q, 1H), 6.99 (m, 2H) 7.18 (m, 2H).

EXAMPLE 33

Methyl 3-(S)-(hydroxy)-2-(R)-(4-fluorophenyl) cyclopentane-1-(R)-carboxylate (from R-salt) and methyl 3-(R)-(hydroxy)-2-(S)-(4-fluorophenyl) cyclopentane-1-(S)-carboxylate (from S-salt). (Non-racemic 2,3-trans isomers)

Step A:

(R)-(+/−)-α-Methylbenzylammonium 3-(S)-(hydroxy)-2-(R)-(4-fluorophenyl)cyclopentane-1-(R)-carboxylate To a solution of 3.0 g of the lower $R_f$ trans alcohol of Example 32 in 20 mL of methanol was added 13 mL of 5N NaOH. The reaction was stirred at room temperature for 20 h and then concentrated in vacuo. The residue was taken up in water, acidified with 2N HCl, and extracted with three portions of ethyl acetate. The organic layers were washed with a portion of brine, combined, dried over sodium sulfate and evaporated to afford the crude acid as a white solid. To a warm solution of 2.3 g of the above crude acid in 35 mL of isopropanol was added 930 mg (0.75 eq) of (R)-(+/−)-α-methylbenzyl amine. The solution was seeded and aged at room temperature for 4 h, the solid was filtered, washed with isopropanol and then ether, and air dried to give 1.8 g white solid. Recrystallization from another 30 mL of isopropanol afforded 1.1 g of the title compound as a white solid. $[\alpha]_D$ (EtOH)=−11.3 (c=0.37).

Step B:

(S)-(−)-α-Methylbenzylammonium 3-(R)-(hydroxy)-2-(S)-(4-fluorophenyl)cyclopentane-1-(S)-carboxylate The mother liquors from Step A were combined and concentrated. The residue was taken up in water and acidified with 2N HCl and was extracted with 3 portions of ethyl acetate. The organic layers were washed with a portion of brine, combined, dried sodium sulfate and evaporated. The residue was dissolved in 25 mL of isopropanol and 0.75 g (0.95 eq) of (S)-(−)-α-methylbenzyl amine was added. The solution was seeded and left at room temperature overnight after which the solid was filtered, washed with isopropanol and then ether, and air dried to give 1.56 g white solid. Recrystallization from another 30 mL of isopropanol afforded 1.3 g of the title compound as a white solid. $[\alpha]_D$ (EtOH)=+12.5 (c=0.44).

Step C:

3-(S)-(Hydroxy)-2-(R)-(4-fluorophenyl)cyclopentane-1-(R)-carboxylic acid

The salt from Step A was dissolved in water and acidified with 2N HCl and was extracted with 3 portions of ethyl acetate. The organic layers were washed with a portion of brine, combined, dried over sodium sulfate and evaporated to give a white solid. $[\alpha]_D$ (EtOH)=−19.9 (c=0.675).

Step D:

3-(R)-(Hydroxy)-2-(S)-(4-fluorophenyl)cyclopentane-1-(S)-carboxylic acid

The salt from Step B was dissolved in water and acidified with 2N HCl and was extracted with 3 portions of ethyl acetate. The organic layers were washed with a portion of brine, combined, dried over sodium sulfate and evaporated to give a white solid. $[\alpha]_D$ (EtOH)=+21.6 (c=2.55).

Step E:

Methyl 3-(S)-(hydroxy)-2-(R)-(4-fluorophenyl) cyclopentane-1-(R)-carboxylate

Method A:

The salt from Step A was converted to the free acid as in Step C and dissolved in ether and a solution of diazomethane was added portionwise until the yellow color persisted. The excess diazomethane was quenched with acetic acid and the volatiles were removed in vacuo. The residue was purified by flash chromatography eluting with 20 to 40% ethyl acetate in hexanes to obtain 800 mg of title compound as an oil. $[\alpha]_D$ (EtOH)=−30 (c=0.390).

Method B:

(R)-salt (8.7 g) obtained as in Step A was converted to the free acid as in Step C to give 5.7 g of crude acid. $[\alpha]_D$ (EtOH)=−19.9 (c=0.675). This was taken up in 200 mL of methanol and saturated with HCl gas. The solution was stirred at room temperature for 16 h and then concentrated in vacuo. The residue was dissolved in water and extracted twice with ether. The organic layers were washed with a portion of brine, combined, dried over sodium sulfate and evaporated to give 6.0 g of oil. $[\alpha]_D$ (EtOH)=−30.5 (c=0.98).

Step F:

Methyl 3-(R)-(hydroxy)-2-(S)-(4-fluorophenyl) cyclopentane-1-(S)-carboxylate

Using essentially the same procedures as in Step E, the acid from the (S)-salt (7.50 g) afforded 4.92 g of the title compound as an oil. $[\alpha]_D$ (EtOH)=+37 (c=1.05).

EXAMPLE 34

Methyl 3-(S)-(hydroxy)-2-(S)-(4-fluorophenyl) cyclopentane-1-(S)-carboxylate (from R-salt) and methyl 3-(R)-(hydroxy)-2-(R)-(4-fluorophenyl) cyclopentane-1-(R)-carboxylate (from S-salt). (Non-racemic 2,3-cis isomers)

Using essentially the same procedures as in Example 33, the title compounds were prepared from the higher $R_f$ 2,3-cis alcohol from Example 32.

Step A:

(R)-(+/−)-α-Methylbenzylammonium 3-(S)-(hydroxy)-2-(S)-(4-fluorophenyl)cyclopentane-1-(S)-carboxylate $[\alpha]_D$ (EtOH)=+84 (c=0.375).

Step B:

(S)-(−)-α-Methylbenzylammonium 3-(R)-(hydroxy)-2-(R)-(4-fluorophenyl)cyclopentane-1-(R)-carboxylate $[\alpha]_D$ (EtOH)=−81 (c=0.335).

Step C:

3-(S)-(Hydroxy)-2-(S)-(4-fluorophenyl)cyclopentane-1-(S)-carboxylic acid

From Step A. $[\alpha]_D$ (EtOH)=+126 (c=0.915).

Step D:

3-(R)-(Hydroxy)-2-(R)-(4-fluorophenyl)cyclopentane-1-(R)-carboxylic acid

From Step B. $[\alpha]_D$ (EtOH)=−108 (c=0.810).

Step E:

Methyl 3-(S)-(hydroxy)-2-(S)-(4-fluorophenyl) cyclopentane-1-(S)-carboxylate

From Step C. $[\alpha]_D$ (EtOH)=+133 (c=1.81).

EXAMPLE 35

Methyl 3-(S)-(hydroxy)-2-(S)-(4-fluorophenyl) cyclopentane-1-(S)-carboxylate (Non-racemic 2,3-cis isomer, Alternante Method)

Step A:

Methyl 2-(S)-(4-fluorophenyl)cyclopentan-3-one-1-(S)-carboxylate

Method A:

To a solution of 3.35 g of non-racemic alcohol obtained as in Example 33, Step F was added dropwise 5.8 mL of 8N Jones reagent over 1 min. After stirring at room temperature for 30 min, the reaction was concentrated in vacuo. The residue was diluted with water and extracted twice with ether. The organic layers were washed with a portion of brine, combined, dried over sodium sulfate and evaporated to give 3.55 g of oil. Flash chromatography with 20 to 40% ethyl acetate in hexanes afforded 2.63 g of title compound as a white solid. $[\alpha]_D$ (EtOH)=+25 (c=0.62).

Method B:

A solution of 20.25 mL of oxalyl chloride in 200 mL of methylene chloride was cooled to<−70° C. in a dry ice/acetone bath. A solution of 32 mL of DMSO in 50 mL of methylene chloride was added dropwise while maintaining the temperature at<−60° C. After a further 15 min of stirring, a solution of 21.75 g of non-racemic alcohol obtained as in Example 33, Step F in 100 mL of methylene chloride was added dropwise while maintaining the temperature at<−60° C. After a further 60 min of stirring, a solution of 127 mL of DIPEA in 100 mL of methylene chloride was added dropwise while maintaining the temperature at<−60° C. The ice bath was then removed and the reaction was allowed to warm to 0° C. over 1 h. The reaction was then slowly added (some gas evolution) to a mixture of 500 mL of ice water and 250 mL of 2N HCl. The layers were separated and the aqueous layer was extracted with a second portion of methylene chloride. The organic layers were each washed with brine, dried over sodium sulfate, combined and evaporated. The residue was purified by flash chromatography using a gradient of 20 to 30% ethyl acetate/hexanes as eluent. Evaporation of the product fractions afforded 21.7 g of title product as a white solid. $[\alpha]_D$ (EtOH)=+27 (c=0.84).

Step B:

Methyl 3-(S)-(hydroxy)-2-(S)-(4-fluorophenyl)-cyclopentane-1-(S)-carboxylate

A solution of 0.55 g of crude ketone prepared as in Step A in 30 mL of THF was cooled in an ice bath and 3.2 mL of 1M L-Selectride was added. The ice bath was removed and the reaction was stirred at room temperature for 2 h before being quenched with 2N HCl. The mixture was extracted twice with ethyl acetate and the organic layers were washed with a portion of brine, combined, dried over sodium sulfate and evaporated. TLC analysis (30% ethyl acetate in hexanes) indicated that very little if any 2,3-trans alcohol was formed. The residue was purified by flash chromatography eluting with 10 to 20% ethyl acetate in hexanes to obtain 210 mg of title compound as an oil. $[\alpha]_D$ (EtOH)=+107 (c=0.79).

EXAMPLE 36

Methyl 3-(SR)-(hydroxy)-2-(RS)-(4-fluorophenyl) phenylcyclopentane-1-(RS)-carboxylate (Racemic 2,3-trans isomer)

Additional quantities of the title 2,3-trans alcohol were obtained from the minor 2,3-cis alcohol obtained as in Example 32 thru oxidation to the ketone as in Example 35, Step A, Method A and subsequent reduction with sodium borohydride as in Example 32. Thus, 4.35 g of 2,3-cis alcohol was converted to 2.35 g of pure 2,3-trans product.

EXAMPLE 37

1-(S)-(1-(S)-(3,5-Bis(trifluoromethyl)phenyl)ethoxy)-2-(R)-(4-fluorophenyl)-3-(R)-(methoxycarbonyl) cyclopentane (higher $R_f$ α-methyl isomer) and 1-(S)-(1-(R)-(3,5-bis(trifluoromethyl)-phenyl)ethoxy)-2-(R)-(4-fluorophenyl)-3-(R)-(methoxycarbonyl)-cyclopentane (lower $R_f$ α-methyl isomer) (non-racemic 2,3-trans isomers)

Following essentially the same procedure as in Example 24 but using non-racemic alcohol from Example 33, Step E, the title compounds were prepared.

EXAMPLE 38

1-(S)-(1-(S)-(3,5-Bis(trifluoromethyl)phenyl)ethoxy)-2-(S)-(4-fluorophenyl)-3-(S)-(methoxycarbonyl) cyclopentane (higher $R_f$ α-methyl isomer) and 1-(S)-(1-(R)-(3,5-bis(trifluoromethyl)phenyl)-ethoxy)-2-(S)-(4-fluorophenyl)-3-(S)-(methoxycarbonyl) cyclopentane (lower $R_f$ α-methyl isomer) (non-racemic 2,3-cis isomers)

Following essentially the same procedure as in Example 24 but using non-racemic alcohol from Example 34, Step E, the title compounds were prepared.

EXAMPLE 39

Following essentially the same procedures as in Example 5, 8, 9 (Method B), 11, 19, 20 and 21, but using non-racemic ether from Example 37 (lower $R_f$ α-methyl isomer), the title compounds were prepared.

1-(S)-(1-(R)-(3,5-Bis(trifluoromethyl)phenyl)ethoxy)-2-(S)-(4-fluorophenyl)-3-(R)-aminocyclopentane 1-(S)-(1-(R)-(3,5-Bis(trifluoromethyl)phenyl)ethoxy)-2-(S)-(4-fluorophenyl)-3-(R)-(methylamino)cyclopentane 1-(S)-(1-(R)-(3,5-Bis(trifluoromethyl)phenyl)ethoxy)-2-(S)-(4-fluorophenyl)-3-(R)-(N-(aminocarbonylmethyl)-N-methylamino)cyclopentane 1-(S)-(1-(R)-(3,5-Bis(trifluoromethyl)phenyl)ethoxy)-2-(S)-(4-fluorophenyl)-3-(R)-(N-((2-oxo-1H,3H-1,3-imidazol-4-yl)methyl)-N-methylamino)cyclopentane 1-(S)-(1-(R)-(3,5-Bis(trifluoromethyl)phenyl)ethoxy)-2-(S)-(4-fluorophenyl)-3-(R)-(N-((5-oxo-1H,4H-1,2,4-triazol-3-yl)methyl)-N-methylamino)cyclopentane 1-(S)-(1-(R)-(3,5-Bis(trifluoromethyl)phenyl)ethoxy)-2-(S)-(4-fluorophenyl)-3-(R)-(N-((1,2,4-triazol-3-yl)methyl)-N-methylamino)cyclopentane

EXAMPLE 40

Following essentially the same procedures as in Example 5, 8, 9 (Method B), 11, 19, 20 and 21, but using non-racemic ether from Example 38 (lower $R_f$ α-methyl isomer), the following compounds were prepared.

1-(S)-(1-(R)-(3,5-Bis(trifluoromethyl)phenyl)ethoxy)-2-(R)-(4-fluorophenyl)-3-(S)-(methylamino)cyclopentane 1-(S)-(1-(R)-(3,5-Bis(trifluoromethyl)phenyl)ethoxy)-2-(R)-(4-fluorophenyl)-3-(S)-(N-((1,2,4-triazol-3-yl)methyl)-N-methylamino)cyclopentane Mass spec (NH$_3$/CI): 531 (M+1). NMR (CDCl$_3$): δ 1.32 (d, 3H), 1.7–1.85 (m, 1H), 1.85–2.05 (m, 2H), 2.05–2.2 (m, 1H), 2.24 (s, 3H), 2.95 (m, 1H), 3.64 (m, 1H), 3.75 (ABq, 2H), 3.80 (q, 1H), 4.40 (q, 1H), 6.97 (t, 2H), 7.15 (s, 2H), 7.18 (m, 2H), 7.60 (s, 1H), 7.89 (s, 1H).

EXAMPLE 41

1-(S)-(1-(R)-(3,5-Bis(trifluoromethyl)phenyl) ethoxy)-2-(R)-(4-fluorophenyl)-3-(R)-(hydroxymethyl)cyclopentane To a solution of 2.0 g of non-racemic ether/ester from Example 37 (lower $R_f$ α-methyl isomer) in 50 mL of THF cooled to 0°C. in an ice bath was added 80 mg of LAH. After 15 min the ice bath was removed and the reaction was stirred for another 30 min. At this time the reaction was not complete and an additional 60 mg of LAH was added and stirring was continued for another 1 h. The reaction was quenched by the addition of ethyl acetate, poured into water containing 10 mL of 2N HCl and extracted twice with ether. The organic layers were washed with a portion of brine, combined, dried over sodium sulfate and evaporated to give 1.92 g of title compound as an oil. Mass spec (NH$_3$/CI): 451(M+1).

EXAMPLE 42

1-(S)-(1-(R)-(3,5-Bis(trifluoromethyl)phenyl) ethoxy)-2-(R)-(4-fluorophenyl)-3-(R)-(bromomethyl)cyclopentane Method A:

To a solution of 1.9 g of alcohol from Example 41 in 50 mL of dry acetonitrile at room temperature was added 2.0 g of triphenylphosphine dibromide. After 1 h an additional 700 mg of triphenylphosphine dibromide was added and the reaction was stirred a further 1 h. The reaction was quenched with sodium bicarbonate solution and extracted twice with ether. The organic layers were washed with a portion of brine, combined, dried over sodium sulfate and evaporated. The residue was purified by flash chromatography eluting with 10% ethyl acetate in hexanes to obtain 708 mg of title compound and 484 mg of recovered strating material.

Method B:

To a solution of 520 mg of alcohol from Example 41 in 20 mL of dry methylene chloride at room temperature was added 452 mg of triphenylphosphine and then 574 mg of carbon tetrabromide and stirred for 1–2 h. The reaction was diluted with hexanes and filtered through Celite. The filtrate was concentrated and the residue was purified by flash chromatography eluting with 10% ethyl acetate in hexanes to obtain 519 mg of title compound as a waxy white solid. Mass spec (NH$_3$/CI): 513 (M+1), 433 (M+1–HBr).

EXAMPLE 43

1-(S)-(1-(R)-(3,5-Bis(trifluoromethyl)phenyl)ethoxy)-2-(R)-(4-fluorophenyl)-3-(R)-((imidazol-1-yl)methyl)cyclopentane To a solution of 35 mg of bromide from Example 42 in 0.5 mL of acetonitrile was added 20 mg of imidazole and 0.035 ML of DIPEA. The reaction was heated at 50° C. for 5 days and then 90° C. for 24 h. The volatiles were removed under a stream of nitrogen and the residue was purified on a 1 mm preparative silica gel plate eluted with 5% methanol in methylene chloride to give 16 mg of title compound. Mass spec (NH$_3$/CI): 501 (M+1).

EXAMPLE 44

1-(S)-(1-(R)-(3,5-Bis(trifluoromethyl)phenyl) ethoxy)-2-(R)-(4-fluorophenyl)-3-(R)-((2-(S)-(aminocarbonyl)pyrrolidin-1-yl)methyl)cyclopentane To a solution of 35 mg of bromide from Example 42 in 0.5 mL of acetonitrile was added 15 mg of L-proline amide and 0.035 mL of DIPEA. The reaction was heated at 90° C. for 24 h. The volatiles were removed under a stream of nitrogen and the residue was purified on a 1 mm preparative silica gel plate eluted with 5% methanol in methylene chloride to give 16 mg of title compound. Mass spec (NH$_3$/CI): 503 (M+1–44 (CONH$_2$)).

EXAMPLE 45

Following essentially the same procedure as in Example 44 using the bromide from Example 42, the following compounds were prepared.

1-(S)-(1-(R)-(3,5-Bis(trifluoromethyl)phenyl)ethoxy)-2-(R)-(4-fluorophenyl)-3-(R)-((morpholin-4-yl)methyl)cyclopentane Mass spec (NH$_3$/CI): 520 (M+1).

1-(S)-(1-(R)-(3,5-Bis(trifluoromethyl)phenyl)ethoxy)-2-(R)-(4-fluorophenyl)-3-(R)-((pyrrolidin-1-yl)methyl)cyclopentane Mass spec (NH$_3$/CI): 504 (M+1).

1-(S)-(1-(R)-(3,5-Bis(trifluoromethyl)phenyl)ethoxy)-2-(R)-(4-fluorophenyl)-3-(R)-((2-(RS)-(3-pyridinyl)pyrrolidin-1-yl)methyl)cyclopentane Mass spec (NH$_3$/CI): 581 (M+1).

1-(S)-(1-(R)-(3,5-Bis(trifluoromethyl)phenyl)ethoxy)-2-(R)-(4-fluorophenyl)-3-(R)-((2-(S)-(dimethylaminocarbonyl)pyrrolidin-1-yl)methyl)cyclopentane Mass spec (NH$_3$/CI): 575 (M+1).

1-(S)-(1-(R)-(3,5-Bis(trifluoromethyl)phenyl)ethoxy)-2-(R)-(4-fluorophenyl)-3-(R)-((2-(S)-(methylaminocarbonyl)pyrrolidin-1-yl)methyl)cyclopentane Mass spec (NH$_3$/CI): 561 (M+1).

1-(S)-(1-(R)-(3,5-Bis(trifluoromethyl)phenyl)ethoxy)-2-(R)-(4-fluorophenyl)-3-(R)-((2-(S)-(morpholin-4-ylcarbonyl)pyrrolidin-1-yl)methyl)cyclopentane Mass spec (NH$_3$/CI): 617 (M+1).

1-(S)-(1-(R)-(3,5-Bis(trifluoromethyl)phenyl)ethoxy)-2-(R)-(4-fluorophenyl)-3-(R)-((2-(S)-(pyrrolidin-1-ylcarbonyl)pyrrolidin-1-yl)methyl)cyclopentane Mass spec (NH$_3$/CI): 617 (M+1).

1-(S)-(1-(R)-(3,5-Bis(trifluoromethyl)phenyl)ethoxy)-2-(R)-(4-fluorophenyl)-3-(R)-((2-(R)-(aminocarbonyl)pyrrolidin-1-yl)methyl)cyclopentane Mass spec (NH$_3$/CI): 547 (M+1).

1-(S)-(1-(R)-(3,5-Bis(trifluoromethyl)phenyl)ethoxy)-2-(R)-(4-fluorophenyl)-3-(R)-((2-(R)-(methylaminocarbonyl)pyrrolidin-1-yl)methyl)cyclopentane Mass spec (NH$_3$/CI): 561 (M+1).

1-(S)-(1-(R)-(3,5-Bis(trifluoromethyl)phenyl)ethoxy)-2-(R)-(4-fluorophenyl)-3-(R)-((2-(S)-(t-butoxycarbonyl)pyrrolidin-1-yl)methyl)cyclopentane Mass spec (NH$_3$/CI): 604 (M+1).

1-(S)-(1-(R)-(3,5-Bis(trifluoromethyl)phenyl)ethoxy)-2-(R)-(4-fluorophenyl)-3-(R)-((3-(RS)-(t-butoxycarbonyl)pyrrolidin-1-yl)methyl)cyclopentane Mass spec (NH$_3$/CI): 604 (M+1).

1-(S)-(1-(R)-(3,5-Bis(trifluoromethyl)phenyl)ethoxy)-2-(R)-(4-fluorophenyl)-3-(R)-(((4-piperidin-1-yl)piperidin-1-yl)methyl)cyclopentane Mass spec (NH$_3$/CI): 601 (M+1).

1-(S)-(1-(R)-(3,5-Bis(trifluoromethyl)phenyl)ethoxy)-2-(R)-(4-fluorophenyl)-3-(R)-(((4-t-butyl)piperidin-1-yl)methyl)cyclopentane Mass spec (NH$_3$/CI): 574 (M+1).

1-(S)-(1-(R)-(3,5-Bis(trifluoromethyl)phenyl)ethoxy)-2-(R)-(4-fluorophenyl)-3-(R)-(((4-aminocarbonyl)piperidin-1-yl)methyl)cyclopentane Mass spec (NH$_3$/CI): 543 (M+1-H$_2$O).

1-(S)-(1-(R)-(3,5-Bis(trifluoromethyl)phenyl)ethoxy)-2-(R)-(4-fluorophenyl)-3-(R)-(((4-methylaminocarbonyl)piperidin-1-yl)methyl)cyclopentane Mass spec (NH$_3$/CI): 575 (M+1).

1-(S)-(1-(R)-(3,5-Bis(trifluoromethyl)phenyl)ethoxy)-2-(R)-(4-fluorophenyl)-3-(R)-(((4-(morpholin-4-yl)carbonyl)piperidin-1-yl)methyl)cyclopentane Mass spec (NH$_3$/CI): 631 (M+1).

EXAMPLE 46

Following essentially the same procedures as in Example 41, 42 (Method B) and 44, but using non-racemic ether/ester from Example 38 (lower R$_f$ α-methyl isomer), the following compounds were prepared.

1-(S)-(1-(R)-(3,5-Bis(trifluoromethyl)phenyl)ethoxy)-2-(S)-(4-fluorophenyl)-3-(S)-((2-(R)-aminocarbonylpyrrolidin-1-yl)methyl)cyclopentane Mass spec (NH$_3$/CI): 547 (M+1).

1-(S)-(1-(R)-(3,5-Bis(trifluoromethyl)phenyl)ethoxy)-2-(S)-(4-fluorophenyl)-3-(S)-((2-(S)-aminocarbonylpyrrolidin-1-yl)methyl)cyclopentane Mass spec (NH₃/CI): 547 (M+1).

1-(S)-(1-(R)-(3,5-Bis(trifluoromethyl)phenyl)ethoxy)-2-(S)-(4-fluorophenyl)-3-(S)-((morpholin-4-yl)methyl)cyclopentane Mass spec (NH₃/CI): 520 (M+1).

1-(S)-(1-(R)-(3,5-Bis(trifluoromethyl)phenyl)ethoxy)-2-(S)-(4-fluorophenyl)-3-(S)-(((4-aminocarbonyl)piperidin-1-yl)methyl)cyclopentane Mass spec (NH₃/CI): 543 (M+1-H₂O).

1-(S)-(1-(R)-(3,5-Bis(trifluoromethyl)phenyl)ethoxy)-2-(S)-(4-fluorophenyl)-3-(S)-(((4-phenyl)piperidin-1-yl)methyl)cyclopentane Mass spec (NH₃IC): 594 (M+1).

1-(S)-(1-(R)-(3,5-Bis(trifluoromethyl)phenyl)ethoxy)-2-(S)-(4-fluorophenyl)-3-(S)-(((4-t-butyl)piperidin-1-yl)methyl)cyclopentane Mass spec (NH₃/CI): 574 (M+1).

EXAMPLE 47

Following essentially the same procedures as in Examples 37, 41, 42 (Method B) and 44, but using (+/−)-1-(3-fluoro-5-trifluoromethyl-phenyl)ethyl bromide, prepared as in Example 24, the following compounds were prepared.

1-(S)-(1-(R)-(3-Fluoro-5-trifluoromethylphenyl)ethoxy)-2-(S)-(4-fluorophenyl)-3-(S)-((2-(S)-aminocarbonylpyrrolidin-1-yl)methyl)cyclopentane Mass spec (NH₃/CI): 497 (M+1).

1-(S)-(1-(R)-(3-Fluoro-5-trifluoromethylphenyl)ethoxy)-2-(S)-(4-fluorophenyl)-3-(S)-((2-(R)-aminocarbonylpyrrolidin-1-yl)methyl)cyclopentane Mass spec (NH₃/CI): 497 (M+1).

EXAMPLE 48

1-(S)-(1-(R)-(3,5-Bis(trifluoromethyl)phenyl)ethoxy)-2-(S)-(4-fluorophenyl)-3-(R)-((pyridin-3-yl)methylamino)cyclopentane To a solution of 75 mg of non-racemic 1-(S)-(1-(R)-(3,5-bis(trifluoromethyl)phenyl)ethoxy)-2-(S)-(4-fluorophenyl)-3-(R)-aminocyclopentane from Example 39 in 2 mL of acetonitrile was added 34 mg of 3-picolyl chloride hydrochloride and 0.090 mL of DIPEA. The reaction was heated at 50° C. for 3 days and then poured into water and extract twice with ethyl acetate. The organic layers were washed with a portion of brine, combined, dried over sodium sulfate and evaporated. The residue was purified on a 3×1 mm preparative silica gel plates eluted with 5% methanol in methylene chloride to give 40 mg of title compound as an oil. Mass spec (NH₃/CI): 527 (M+1).

EXAMPLE 49

1-(S)-(1-(R)-(3,5-Bis(trifluoromethyl)phenyl)ethoxy)-2-(S)-(4-fluorophenyl)-3-(R)-(N-((2-pyrrolidin-1-yl)carbonylmethyl)-N-methylamino) cyclopentane Step A:

1-(S)-(1-(R)-(3,5-Bis(trifluoromethyl)phenyl)ethoxy)-2-(S)-(4-fluorophenyl)-3-(R)-(N-(t-butoxycarbonylmethyl)-N-methylamino)cyclopentane To a solution of 250 mg of non-racemic 1-(S)-(1-(R)-(3,5-bis(trifluoromethyl)phenyl)ethoxy)-2-(S)-(4-fluorophenyl)-3-(R)-(methylamino)cyclopentane from Example 39 in 6 mL of acetonitrile was added 0.108 mL of t-butyl bromoacetate and 0.36 mL of DIPEA. The reaction was heated at 50° C. for 5 h and then poured into water and extract twice with ethyl acetate. The organic layers were washed with a portion of brine, combined, dried over sodium sulfate and evaporated. The residue was purified by flash chromatography eluting with 0 to 2.5% methanol in methylene chloride to give 294 mg of title compound as an oil. Mass spec (NH₃/CI): 564 (M+1).

Step B:

1-(S)-(1-(R)-(3,5-Bis(trifluoromethyl)phenyl)ethoxy)-2-(S)-(4-fluorophenyl)-3-(R)-(N-(carboxymethyl)-N-methylamino)cyclopentane To 280 mg of t-butyl ester from Step A was added 2 drops of anisole and 4 mL of TFA. After 75 min the volatiles were removed in vacuo followed by evaporation of two portions of methylene chloride. The residue was used directly in the Step C.

Step C:

1-(S)-(1-(R)-(3,5-Bis(trifluoromethyl)phenyl)ethoxy)-2-(S)-(4-fluorophenyl)-3-(R)-(N-(chlorocarbonylmethyl)-N-methylamino)cyclopentane The residue from Step B was taken up in methylene chloride and a trace of DMF was added followed by 0.21 mL of oxalyl chloride. The reaction was stirred at room temperature for 1 h and then evaporated and used in Step D.

Step D:

1-(S)-(1-(R)-(3,5-Bis(trifluoromethyl)phenyl)ethoxy)-2-(S)-(4-fluorophenyl)-3-(R)-(N-((2-pyrrolidin-1-yl)carbonyl-methyl)-N-methylamino)cyclopentane To a solution of ⅙ of the residue from Step C in 2 mL of methylene chloride was added 0.035 mL of pyrrolidine at room temperature. After 1 h the reaction was evaporated under a stream of nitrogen and the residue was purified on a 1 mm preparative silica gel plate eluted with 7% methanol in methylene chloride to give 27 mg of title compound. Mass spec (NH₃/CI): 561 (M+1).

EXAMPLE 50

Following essentially the same procedure as in Example 49, Step D, the following compounds were prepared using the appropriate amine.

1-(S)-(1-(R)-(3,5-Bis(trifluoromethyl)phenyl)ethoxy)-2-(S)-(4-fluorophenyl)-3-(R)-(N-((morpholin-4-yl)carbonylmethyl)-N-methylamino)cyclopentane Mass spec (NH₃/CI): 577 (M+1).

1-(S)-(1-(R)-(3,5-Bis(trifluoromethyl)phenyl)ethoxy)-2-(S)-(4-fluorophenyl)-3-(R)-(N-((4-methylpiperizin-1-yl)carbonylmethyl)-N-methylamino)cyclopentane Mass spec (NH₃/CI): 590 (M+1).

1-(S)-(1-(R)-(3,5-Bis(trifluoromethyl)phenyl)ethoxy)-2-(S)-(4-fluorophenyl)-3-(R)-(N-((2-methoxyethylamino)carbonylmethyl)-N-methylamino)cyclopentane Mass spec (NH₃/CI): 579 (M+1).

1-(S)-(1-(R)-(3,5-Bis(trifluoromethyl)phenyl)ethoxy)-2-(S)-(4-fluorophenyl)-3-(R)-(N-((methylamino)carbonylmethyl)-N-methylamino)cyclopentane Mass spec (NH₃/CI): 521 (M+1).

1-(S)-(1-(R)-(3,5-Bis(trifluoromethyl)phenyl)ethoxy)-2-(S)-(4-fluorophenyl)-3-(R)-(N-((dimethylamino)carbonylmethyl)-N-methylamino)cyclopentane Mass spec (NH₃/CI): 535 (M+1).

EXAMPLE 51

Following essentially the same procedures as in Example 49 but using non-racemic 1-(S)-(1-(R)-(3,5-bis(trifluoromethyl)phenyl)ethoxy)-2-(R)-(4-fluorophenyl)-3-(S)-(methylamino)cyclopentane prepared in Example 40, the following compounds were prepared.

1-(S)-(1-(R)-(3,5-Bis(trifluoromethyl)phenyl)ethoxy)-2-(R)-(4-fluorophenyl)-3-(R)-(N-((2-pyrrolidin-1-yl)

carbonylmethyl)-N-methylamino)cyclopentane Mass spec (NH$_3$/CI): 561 (M+1).

1-(S)-(1-(R)-(3,5-Bis(trifluoromethyl)phenyl)ethoxy)-2-(R)-(4-fluorophenyl)-3-(R)-(N-((morpholin-4-yl)carbonylmethyl)-N-methylamino)cyclopentane Mass spec (NH$_3$/CI): 577 (M+1).

1-(S)-(1-(R)-(3,5-Bis(trifluoromethyl)phenyl)ethoxy)-2-(R)-(4-fluorophenyl)-3-(R)-(N-((dimethylamino)carbonylmethyl)-N-methylamino)cyclopentane Mass spec (NH$_3$/CI): 535 (M+1).

1-(S)-(1-(R)-(3,5-Bis(trifluoromethyl)phenyl)ethoxy)-2-(R)-(4-fluorophenyl)-3-(R)-(N-((cyclopropylamino)carbonylmethyl)-N-methylamino)cyclopentane Mass spec (NH$_3$/CI): 547 (M+1).

1-(S)-(1-(R)-(3,5-Bis(trifluoromethyl)phenyl)ethoxy)-2-(R)-(4-fluorophenyl)-3-(R)-(N-((2-methoxyethylamino)carbonylmethyl)-N-methylamino)cyclopentane Mass spec (NH$_3$/CI): 579 (M+1).

1-(S)-(1-(R)-(3,5-Bis(trifluoromethyl)phenyl)ethoxy)-2-(R)-(4-fluorophenyl)-3-(R)-(N-((t-butylamino)carbonylmethyl)-N-methylamino)cyclopentane Mass spec (NH$_3$/CI): 563 (M+1).

1-(S)-(1-(R)-(3,5-Bis(trifluoromethyl)phenyl)ethoxy)-2-(R)-(4-fluorophenyl)-3-(R)-(N-((isopropylamino)carbonylmethyl)-N-methylamino)cyclopentane Mass spec (NH$_3$/CI): 549 (M+1).

EXAMPLE 52

1-(S)-(1-(R)-(3,5-Bis(trifluoromethyl)phenyl)ethoxy)-2-(S)-(4-fluorophenyl)-3-(R)-(N-((2-pyrrolidon-5-(S)-yl)methyl)-amino)cyclopentane To a solution of non-racemic 1-(S)-(1-(R)-(3,5-bis(trifluoro-methyl)phenyl)ethoxy)-2-(S)-(4-fluorophenyl)-3-(R)-(amino)cyclopentane from Example 39 in 0.5 mL of acetonitrile was added 50 mg of (2-pyrrolidon-5-(S)-yl)methylbromide and 0.10 mL of DIPEA. The reaction was heated in a sealed vial at 90° C. for 60 h and then evaporated. The residue was purified on a 2×1 mm preparative silica gel plates eluted with 2% TEA in methanol to afford 50 mg of title compound as a white solid. Mass spec (NH$_3$/CI): 533 (M+1).

EXAMPLE 53

Following essentially the same procedures as in Example 52, the following compounds were prepared. When a racemic amine was employed with the non-racemic bromide, the two resulting diastereomers were separable by silica gel chromatography.

1-(S)-(1-(R)-(3,5-Bis(trifluoromethyl)phenyl)ethoxy)-2-(S)-(4-fluorophenyl)-3-(R)-(N-((2-pyrrolidon-5-(S)-yl)methyl)-N-methylamino)cyclopentane Mass spec (NH$_3$/CI): 547 (M+1).

1-(R)-(1-(S)-(3,5-Bis(trifluoromethyl)phenyl)ethoxy)-2-(S)-(4-fluorophenyl)-3-(S)-(N-((2-pyrrolidon-5-(R)-yl)methyl)-N-methylamino)cyclopentane Mass spec (NH$_3$/CI): 547 (M+1).

1-(S)-(1-(R)-(3,5-Bis(trifluoromethyl)phenyl)ethoxy)-2-(R)-(4-fluorophenyl)-3-(R)-(N-((2-pyrrolidon-5-(R)-yl)methyl)-N-methylamino)cyclopentane Mass spec (NH$_3$/CI): 547 (M+1).

1-(S)-(1-(R)-(3,5-Bis(trifluoromethyl)phenyl)ethoxy)-2-(R)-(4-fluorophenyl)-3-(R)-((2-pyrrolidon-5-(S)-yl)methylamino)cyclopentane Mass spec (NH$_3$/CI): 533 (M+1).

1-(R)-(1-(S)-(3,5-Bis(trifluoromethyl)phenyl)ethoxy)-2-(S)-(4-fluorophenyl)-3-(S)-((2-pyrrolidon-5-(S)-yl)methylamino)cyclopentane Mass spec (NH$_3$/CI): 533 (M+1).

1-(R)-(1-(S)-(3,5-Bis(trifluoromethyl)phenyl)ethoxy)-2-(S)-(4-fluorophenyl)-3-(S)-((2-pyrrolidon-5-(R)-yl)methylamino)cyclopentane Mass spec (NH$_3$/CI): 533 (M+1).

1-(S)-(1-(R)-(3,5-Bis(trifluoromethyl)phenyl)ethoxy)-2-(R)-(4-fluorophenyl)-3-(R)-((2-pyrrolidon-5-(R)-yl)methylamino)cyclopentane Mass spec (NH$_3$/CI): 533 (M+1).

1-(S)-(1-(R)-(3,5-Bis(trifluoromethyl)phenyl)ethoxy)-2-(S)-(4-fluorophenyl)-3-(R)-(N-((1-methyl-2-pyrrolidon-5-(S)-yl)methyl)-N-methylamino)cyclopentane Mass spec (NH$_3$/CI): 561 (M+1).

1-(S)-(1-(R)-(3,5-Bis(trifluoromethyl)phenyl)ethoxy)-2-(R)-(4-fluorophenyl)-3-(R)-(N-((1-methyl-2-pyrrolidon-5-(S)-yl)methyl)-N-methylamino)cyclopentane Mass spec (NH$_3$/CI): 561 (M+1).

1-(S)-(1-(R)-(3,5-Bis(trifluoromethyl)phenyl)ethoxy)-2-(R)-(4-fluorophenyl)-3-(R)-(N-(1-methyl-2-pyrrolidon-5-(S)-yl)methylamino)cyclopentane Mass spec (NH$_3$/CI): 547 (M+1).

EXAMPLE 54

1-(S)-(1-(R)-(3,5-Bis(trifluoromethyl)phenyl)ethoxy)-2-(S)-(4-fluorophenyl)-3-(R)-(N-((1,4-dimethyl-5-oxo-1H,4H-1,2,4-triazol-3-yl)methyl)-N-methylamino)cyclopentane and 1-(S)-(1-(R)-(3,5-Bis(trifluoromethyl)phenyl)ethoxy)-2-(S)-(4-fluorophenyl)-3-(R)-(N-((1 or 4-methyl-5-oxo-1H, 4H-1,2,4-triazol-3-yl) methyl)-N-methylamino) cyclopentane To a solution of 25 mg of 1-(S)-(1-(R)-(3,5-bis(trifluoromethyl)phenyl)ethoxy)-2-(S)-(4-fluorophenyl)-3-(R)-(N-((5-oxo-1H, 4H-1,2,4-triazol-3-yl)methyl)-N-methylamino) cyclopentane from Example 39 in 0.5 mL of DMF was added 3.0 mg of 60% NaH in mineral oil. After 5 min, 7.2 mg of iodomethane was added. After stirring for 20 min, the reaction was quenched with water and extracted twice with ethyl acetate. The organic layers were washed with a portion of brine, combined, dried over sodium sulfate and evaporated. The residue was purified on a 1 mm preparative silica gel plate eluted with 4% methanol in methylene chloride to afford 2 product bands. The higher R$_f$ band of 8 mg was identified as the dialkylated product 1-(S)-(1-(R)-(3,5-bis(trifluoromethyl)phenyl)-ethoxy)-2-(S)-(4-fluorophenyl)-3-(R)-(N-((1,4-dimethyl-5-oxo-1H,4H-1,2,4-triazol-3-yl)methyl)-N-methylamino)cyclopentane. The lower R$_f$ band of 10 mg was monoalkylated product either at the 1 or 4 N, 1-(S)-(1-(R)-(3,5-bis(trifluoromethyl)phenyl)ethoxy)-2-(S)-(4-fluorophenyl)-3-(R)-(N-((1 or 4-methyl-5-oxo-1H,4H-1, 2,4-triazol-3-yl) methyl)-N-methyl-amino)-cyclopentane. Higher R$_f$ Mass spec (NH$_3$/CI): 575 (M+1). Lower R$_f$ Mass spec (NH$_3$/CI): 561 (M+1).

EXAMPLE 55

1-(S)-(1-(R)-(3,5-Bis(trifluoromethyl)phenyl)ethoxy)-2-(S)-(4-fluorophenyl)-3-(R)-(N-((1, 2 or 4-methyl-1,2,4-triazol-3-yl)methyl)-N-methylamino) cyclopentane To a solution of 50 mg of 1-(S)-(1-(R)-(3,5-bis(trifluoromethyl)phenyl)ethoxy)-2-(S)-(4-fluorophenyl)-3-(R)-(N-((1,2,4-triazol-3-yl)methyl)-N-methylamino)cyclopentane from Example 39 in 1.0 mL of DMF was added 10 mg of 60% NaH in mineral oil. After 5 min, 0.065 mL of iodomethane was added. After stirring for 1 h, the reaction was quenched with water and extracted twice with ether. The organic layers were washed with a portion of brine, combined, dried over sodium sulfate and evaporated. The residue was purified on a 1 mm preparative silica gel plate eluted with 5% methanol in methylene chloride to afford 16 mg of a mixture of two of the three methyl isomeric products. Mass spec (NH$_3$/CI): 545 (M+1).

EXAMPLE 56

1-(S)-(1-(R)-(3,5-Bis(trifluoromethyl)phenyl) ethoxy)-2-(S)-(4-fluorophenyl)-3-(R)-(ethylamino) cyclopentane Following essentially the same procedures as in Example 5, 8 and 11 but using non-racemic ether from Example 37 (lower R$_f$ α-methyl isomer) and iodoethane in Example 11, Step A, the title compound was prepared. Mass spec (NH$_3$/CI): 464 (M+1).

EXAMPLE 57

1-(S)-(1-(R)-(3,5-Bis(trifluoromethyl)phenyl) ethoxy)-2-(S)-(4-fluorophenyl)-3-(R)-(N-(aminocarbonylmethyl)-N-ethylamino)-cyclopentane Following essentially the same procedure as in Example 12 but using product from Example 56, the title compound was prepared. Mass spec (NH$_3$/CI): 521 (M+1).

EXAMPLE 58

1-(S)-(1-(R)-(3,5-Bis(trifluoromethyl)phenyl) ethoxy)-2-(S)-(4-fluorophenyl)-3-(R)-(N-((1,2,4-triazol-3-yl) methyl)-N-ethylamino)cyclopentane Following essentially the same procedure as in Example 21 but using product from Example 56, the title compound was prepared. Mass spec (NH$_3$/CI): 545 (M+1).

EXAMPLE 59A 1-(S)-(1-(R)-(3,5-Bis(trifluoromethyl)phenyl) ethoxy)-2-(S)-(4-fluorophenyl)-3-(R)-(2-methoxyethylamino)cyclopentane Following essentially the same procedures as in Example 5, 8 and 11 but using non-racemic ether from Example 37 (lower R$_f$ α-methyl isomer) and 2-methoxyethyl bromide in Example 11, Step A, the title compound was prepared. Mass spec (NH$_3$/CI): 494 (M+1).

EXAMPLE 59B 1-(S)-(1-(R)-(3,5-Bis(trifluoromethyl)phenyl) ethoxy)-2-(S)-(4-fluorophenyl)-3-(R)-(N-(aminocarbonylmethyl)-N-(2-methoxyethyl)-amino) cyclopentane Following essentially the same procedure as in Example 12 but using product from Example 59A, the title compound was prepared. Mass spec (NH$_3$/CI): 5 (M+1).

EXAMPLE 60

Methyl 3-(R)-((4-methoxyphenyl)methylamino)-2-(R)-(4-fluorophenyl)cyclopentane-1-(R)-carboxylate (higher R$_f$, cis) and methyl 3-(S)-((4-methoxyphenyl)methylamino)-2-(R)-(4-fluorophenyl) cyclopentane-1-(R)-carboxylate (lower R$_f$, trans) (Non-racemic 2,3-cis and 2,3-trans PMB isomers from R-salt).

To a solution of 5.0 g of methyl 2-(R)-(4-fluorophenyl)-cyclopentan-3-one-1-(R)-carboxylate ([α]$_D$ (EtOH)=−24.5 (c=0.56)), prepared from the (R)-salt as in Examples 33 and 36, in 60 mL of methanol was added 3.84 g of acetic acid, 15 g of 3A sieves and 8.7 g of 4-methoxybenzylamine. The reaction was stirred at room temperature for 30 min and then 4.0 g of sodium cyanoborohydride was added. The reaction was stirred for 20 h at room temperature and was then poured into water, made basic with 2N NaOH and extracted twice with ether. The organic layers were washed with a portion of brine, combined, dried over sodium sulfate and evaporated. The residue was purified by flash chromatography eluting with 20 to 70% ethyl acetate in hexanes to obtain 2.88 g of the higher R$_f$ 2,3-cis product and 3.15 g of the lower R$_f$ 2,3-trans product. Higher. [α]$_D$ (EtOH)=−91 (c=0.53). Lower. [α]$_D$ (EtOH)=−23 (c=0.485).

EXAMPLE 61

Methyl 3-(S)-((4-methoxyphenyl)methylamino)-2-(S)-(4-fluorophenyl)cyclopentane-1-(S)-carboxylate (higher R$_f$, cis) and methyl 3-(R)-((4-methoxyphenyl)methylamino)-2-(S)-(4-fluorophenyl) cyclopentane-1-(S)-carboxylate (lower R$_f$, trans) (Non-racemic 2,3-cis and 2,3-trans PMB isomers from S-salt)

Following essentially the same procedure as in Example 60 but starting with the (S)-salt from Example 33, 3.7 g of methyl 2-(S)-(4-fluorophenyl)cyclopentan-3-one-1-(S)-carboxylate afforded 2.38 g of the higher R$_f$ 2,3-cis product and 3.12 g of the lower R$_f$ 2,3-trans product. Higher. [α]$_D$ (EtOH)=+99 (c=0.53). Lower. [α]$_D$ (EtOH)=+26 (c=0.53).

EXAMPLE 62

Methyl 3-(S)-(amino)-2-(R)-(4-fluorophenyl) cyclopentane-1-(R)-carboxylate (Non-racemic 2,3-trans isomer from R-salt)

A solution of 1.5 g of lower R$_f$ PMB amine product from Example 60 in 15 mL of methanol containing 1 mL of acetic acid was hydrogenated with 500 mg of 10% Pd/C under 40 psi H$_2$ pressure for 24 h. The reaction was then filtered through Celite, concentrated in vacuo, diluted with water, made basic with 2N NaOH and extracted twice with ether. The organic layers were washed with a portion of brine, combined, dried over sodium sulfate and evaporated. The residue was purified by flash chromatography eluting with 0 to 10% methanol in methylene chloride to obtain 900 mg of title compound as an oil.

EXAMPLE 63

Methyl 3-(S)-(amino)-2-(S)-(4-fluorophenyl) cyclopentane-1-(S)-carboxylate (Non-racemic 2,3-cis isomer from S-salt)

A solution of 1.0 g of higher R$_f$ PMB amine product from Example 61 in 10 mL of methanol was hydrogenated with 300 mg of 10% Pd/C under 40 psi H$_2$ pressure for 60 h. The reaction was then filtered thru Celite and concentrated in vacuo. The residue was purified by flash chromatography eluting with 0 to 10% methanol in methylene chloride to obtain 500 mg of title compound as an oil.

EXAMPLE 64

Methyl 3-(S)-(1-(RS)-(3,5-bis(trifluoromethyl) phenyl) ethylamino)-2-(R)-(4-fluorophenyl) cyclopentane-1-(R)-carboxylate A solution of 200 mg of amine from Example 62, 0.3 mL of DIPEA and 350 mg of 1-(RS)-(3,5-bis(trifluoromethyl)

phenyl)ethyl bromide (prepared in Example 24) in 2 mL of acetonitrile was heated at 50° C. in a sealed vial for 40 h. The reaction was diluted with saturated sodium bicarbonate and extracted twice with methylene chloride. The organic layers were washed with a portion of brine, combined, dried over sodium sulfate and evaporated. The residue was purified by flash chromatography eluting with 10 to 15% ethyl acetate in hexanes to obtain 150 mg of title compound as a mixture of methyl isomers. Mass spec (NH$_3$/CI): 478 (M+1).

EXAMPLE 65

Methyl 3-(S)-((3,5-bis(trifluoromethyl)phenyl) methylamino)-2-(S)-(4-fluorophenyl)cyclopentane-1-(S)-carboxylate A solution of 20 mg of amine from Example 63, 0.050 mL of DIPEA and 30 mg of 3,5-bis(trifluoromethyl)benzyl bromide in 1 mL of acetonitrile was stirred for 20 h in a sealed vial and evaporated. The residue was purified on a 1 mm preparative silica gel plate eluted with 20% ethyl acetate in hexanes to obtain 28 mg of title compound as an oil. Mass spec (NH$_3$/CI): 464 (M+1).

EXAMPLE 66

Methyl 3-(S)-(1-(S)-(3,5-bis(trifluoromethyl)phenyl) ethylamino)-2-(S)-(4-fluorophenyl)cyclopentane-1-(S)-carboxylate (higher methyl isomer) and methyl 3-(S)-(1-(R)-(3,5-bis(trifluoromethyl)phenyl) ethylamino)-2-(S)-(4-fluorophenyl)cyclopentane-1-(S)-carboxylate (higher methyl isomer)

A solution of 250 mg of amine from Example 63, 0.40 mL of DIPEA and 500 mg of 1-(RS)-(3,5-bis(trifluoromethyl) phenyl)ethyl bromide (prepared in Example 24) in 5 mL of acetonitrile in a sealed vial was heated at 50° C. for 20 h and evaporated. The residue was purified by flash chromatography eluting with 10 to 15% ethyl acetate in hexanes to obtain 140 mg of the higher methyl isomer and 160 mg of the lower methyl isomer. Mass specs (NH$_3$/CI): 478 (M+1).

EXAMPLE 67

1-(S)-(1-(R)-(3,5-Bis(trifluoromethyl)phenyl) ethylamino)-2-(S)-(4-fluorophenyl)-3-(S)-(N-(aminocarbonylmethyl)-N-methylamino)-cyclopentane Step A:
3-(S)-(N-(4-Methoxybenzyl)-N-(benzyloxy-carbonyl) amino)-2-(S)-(4-fluorophenyl)cyclopentane-1-(S)-carboxylic acid To a solution of 1.3 g of higher PMB amine from Example 61 in 40 mL of methanol was added 7.3 mL of 2N NaOH. The reaction was heated to 80° C. for 2 h and then concentrated. The residue was taken up in 25 mL of water and 15 ml of acetone and then 1.25 g of benzyl chloroformate in 10 mL of acetone and an additional 1 mL of 2N NaOH were each added dropwise over 5 min. The mixture was stirred at room temperature for 16 h and then diluted with water and extracted twice with ether. The aqueous layer was acidified with 2N HCl and extracted 3 times with ethyl acetate. The organic layers were washed with a portion of brine, combined, dried over sodium sulfate and evaporated to afford 1.9 g of crude title acid which was used in the next step. T.l.c. (1% HOAc/20% ethyl acetate in hexanes) R$_f$=0.2.
Step B:
1-(S)-(N-(4-Methoxybenzyl)-N-(benzyloxycarbonyl)- amino)-2-(R)-(4-fluorophenyl)-3-(S)-(methoxycarbonyl- amino)-cyclopentane Following essentially the same procedures as Example 5 and 7, the product from Step A was converted to 1.33 g of title compound after flash chromatography eluting with 30 to 50% ethyl acetate in hexanes. T.l.c. (40% ethyl acetate in hexanes) R$_f$=0.3.
Step C:
1-(S)-(N-(4-Methoxybenzyl)-N-(benzyloxycarbonyl)- amino)-2-(R)-(4-fluorophenyl)-3-(S)-(N-(methoxy- carbonyl)-N-methylamino)cyclopentane Following essentially the same procedures as Example 11 A, the product from Step B was converted to 1.16 g of title compound after flash chromatography eluting with 30 to 40% ethyl acetate in hexanes. T.l.c. (40% ethyl acetate in hexanes) R$_f$=0.35.
Step D:
1-(S)-(Amino)-2-(S)-(4-fluorophenyl)-3-(S)-(N-(methoxycarbonyl)-N-methylamino)cyclopentane A solution of the product from Step C in 10 mL of methanol was hydrogenated over 200 mg of 10% Pd/C at 40 psi for 3 days to remove first the CBz and then the PMB group. The reaction was filtered and evaporated to give 550 mg of title compound. T.l.c. (5% Methanol in methylene chloride) R$_f$=0.5 (PMB intermediate) and 0.2 (amine product).
Step E:
1-(S)-(1-(S)-(3,5-Bis(trifluoromethyl)phenyl) ethylamino)-2-(S)-(4-fluorophenyl)-3-(S)-(N-(methoxycarbonyl)-N-methylamino)cyclopentane (Higher R$_f$) and 1-(S)-(1-(R)-(3,5-bis(trifluoromethyl)phenyl) ethylamino)-2-(S)-(4-fluorophenyl)-3-(S)-(N-(methoxycarbonyl)-N-methylamino)cyclopentane (Lower R$_f$)

A solution of 40 mg of amine from Step D, 80 mg of 1-(RS)-(3,5-bis(trifluoromethyl)phenyl)ethylbromide (prepared in Example 24) and 0.10 mL of DIPEA in 0.5 mL of acetonitrile was heated in a sealed vial at 80° C. for 20 h and evaporated. The residue was purified on a 2×1 mm preparative silica gel plates eluted with 40% ethyl acetate in hexanes to obtain 40 mg of the higher methyl isomer and 40 mg of the lower methyl isomer. Mass specs (NH$_3$/CI): 507 (M+1).
Step F:
1-(S)-(1-(R)-(3,5-Bis(trifluoromethyl)phenyl) ethylamino)-2-(S)-(4-fluorophenyl)-3-(S)-(methylamino) cyclopentane A solution of 350 mg of lower product from Step E and 3.5 mL of 2N NaOH in 5 mL of ethanol was heated at reflux for 60 h. The reaction was then diluted with water and extracted twice with ether. The organic layers were washed with a portion of brine, combined, dried over sodium sulfate and evaporated. The residue was purified by flash chromatography eluting with 30% ethyl acetate in hexanes to obtain 250 mg of recovered starting material. Further elution with 5 to 10% methanol in methylene chloride afforded 65 mg of title compound.
Step G:
1-(S)-(1-(R)-(3,5-Bis(trifluoromethyl)phenyl) ethylamino)-2-(S)-(4-fluorophenyl)-3-(S)-(N-(aminocarbonylmethyl)-N-methylamino)cyclopentane A solution of 40 mg of product from Step F, 25 mg of iodoacetamide and 0.10 mL of DIPEA in 0.5 ml of acetonitrile was stirred at room temperature for 16 h and then evaporated. The residue was purified on a 1 mm preparative silica gel plate eluted with 5% methanol in methylene chloride to give 30 mg of title compound as an oil. Mass specs (NH$_3$/CI): 506 (M+1).

EXAMPLE 68

1-(S)-(1-(RS)-(3,5-Bis(trifluoromethyl)phenyl) ethylamino)-2-(S)-(4-fluorophenyl)-3-(R)-(N-(methoxycarbonylmethyl)-N-methylamino) cyclopentane Following essentially the same procedures as in Example 67, but using non-racemic ester from Example 62 (lower R$_f$ isomer), the title compound was prepared as a mixture of methyl isomers. Mass specs (NH₃/CI): 507 (M+1).

EXAMPLE 69

Methyl 3-(S)-(N-((3,5-bis(trifluoromethyl)phenyl) carbonyl)-N-methylamino)-2-(R)-(4-fluorophenyl) cyclopentane-1-(R)-carboxylate Step A:

Methyl 3-(S)-((3,5-bis(trifluoromethyl)phenyl) carbonylamino)-2-(R)-($^4$-fluorophenyl)cyclopentane-1-(R)-carboxylate To a solution of 100 mg of amine from Example 62 in 5 mL of methylene chloride was added 0.2 mL of DIPEA and 175 mg of 3,5-bis(trifluoromethyl)benzoyl chloride. The reaction was stirred at room temperature for 1 h and was then poured into water and 2N HCl and extracted twice with methylene chloride. The organic layers were washed with a portion of brine, combined, dried over sodium sulfate and evaporated. The residue was purified by flash chromatography eluting with 30 to 50% ethyl acetate in hexanes to obtain 100 mg of title compound. NMR (CDCl₃): δ 1.8–1.9 (m, 1H), 2.05–2.2 (m, 1H), 2.2–2.4 (m, 2H), 3.08 (q, 1H), 3.42 (t, 1H), 3.67 (s, 3H), 4.65 (p, 1H), 6.80 (d, 1H), 6.99 (t, 2H), 7.22 (dd, 2H), 7.96 (s, 1H), 8.15 (s, 2H).

Step B:

Methyl 3-(S)-(N-((3,5-bis(trifluoromethyl)phenyl)-carbonyl)-N-methylamino)-2-(R)-(4-fluorophenyl)-cyclopentane-1-(R)-carboxylate To a solution of 100 mg of amide from Example 66 in 5 mL of DMF was added 0.05 mL of methyl iodide and 15 mg of 60% NaH. The reaction was stirred at room temperature for 5 h and was then poured into water and 2N HCl and extracted twice with ether. The organic layers were washed with a portion of brine, combined, dried over sodium sulfate and evaporated. The residue was purified by flash chromatography eluting with 20 to 40% ethyl acetate in hexanes to obtain 100 mg of title compound. NMR (CDCl₃): δ 1.8–2.0 (m, 1H), 2.0–2.2 (m, 3H), 3.75–3.95 (m, 1H), 2.76 and 3.10 (2s, 3H), 3.3–3.5 (m, 1H), 3.56 and 3.62 (2 s, 3H), 3.82 and 5.28 (2m, 1H), 6.8–7.1 (m, 3H), 7.15–7.35 and 7.49 (m and br s, 3H), 7.82 (s, 1H).

EXAMPLE 70

Following essentially the same procedures as in Example 68, the following compounds were prepared. (Note: Methylation of phenylacetamide derivatives afforded mixtures of N and C alkylation.)

Methyl 3-(S)-((3,5-bis(trifluoromethyl)phenyl) carbonylamino)-2-(S)-(4-fluorophenyl)cyclopentane-1-(S)-carboxylate Methyl 3-(S)-(N-((3,5-bis(trifluoromethyl)phenyl)carbonyl)-N-methylamino)-2-(S)-(4-fluorophenyl)cyclopentane-1-(S)-carboxylate Methyl 3-(R)-((3,5-bis(trifluoromethyl)phenyl) carbonylamino)-2-(S)-(4-fluorophenyl)cyclopentane-1-(S)-carboxylate Methyl 3-(R)-(N-((3,5-bis(trifluoromethyl)phenyl) carbonyl)-N-methylamino)-2-(S)-(4-fluorophenyl) cyclopentane-1-(S)-carboxylate Methyl 3-(R)-((3,5-bis(trifluoromethyl)phenyl)phenyl) carbonylamino)-2-(R)-(4-fluorophenyl)cyclopentane-1-(R)-carboxylate Methyl 3-(R)-(N-((3,5-bis(trifluoromethyl)phenyl) carbonyl)-N-methylamino)-2-(R)-(4-fluorophenyl) cyclopentane-1-(R)-carboxylate Methyl 3-(S)-((3,5-bis(trifluoromethyl)phenylmethyl) carbonylamino)-2-(S)-(4-fluorophenyl)cyclopentane-1-(S)-carboxylate Methyl 3-(S)-((1-(S)-(3,5-bis(trifluoromethyl)phenyl)ethyl) carbonyl-amino)-2-(S)-(4-fluorophenyl)cyclopentane-1-(S)-carboxylate Methyl 3-(S)-((1-(R)-(3,5-bis(trifluoromethyl)phenyl)ethyl) carbonyl-amino)-2-(S)-(4-fluorophenyl)cyclopentane-1-(S)-carboxylate Methyl 3-(S)-((1-(RS)-(N-3,5-bis(trifluoromethyl)phenyl) ethyl)-carbonyl)-N-methylamino)-2-(S)-(4-fluorophenyl) cyclopentane-1-(S)-carboxylate Methyl 3-(S)-((3,5-bis(trifluoromethyl)phenylmethyl) carbonylamino)-2-(R)-(4-fluorophenyl)cyclopentane-1-(R)-carboxylate Methyl 3-(S)-((1-(RS)-(N3,5-bis(trifluoromethyl)phenyl)-carbonyl)-N-methylamino)-2-(R)-(4-fluorophenyl) cyclopentane-1-(R)-carboxylate Methyl 3-(S)-(N-(3,5-bis(trifluoromethyl)phenylmethyl) carbonyl)-N-methylamino)-2-(R)-(4-fluorophenyl) cyclopentane 1-(R)-carboxylate

EXAMPLE 71

Methyl 3-(S)-((2-methoxy-5-(1-tetrazolyl)phenyl) methylamino)-2-(R)-(4-fluorophenyl)cyclopentane-1-(R)-carboxylate To a solution of 100 mg of amine from Example 62 in 2 mL of methanol was added 0.040 mL of acetic acid, 1 g of 3A sieves and 90 mg 2-methoxy-5-(1-tetrazolyl) benzaldehyde (prepared according to the procedures given in PCT International Application WO 95/08549, published 30 Mar. 1995; p. 33). The reaction was stirred at room temperature for 30 min and then 0.080 g of sodium cyanoborohydride was added. The reaction was stirred further for 20 h and was then poured into water, made basic with 2N NaOH and extracted twice with ether. The organic layers were washed with a portion of brine, combined, dried over sodium sulfate and evaporated. The residue was purified by flash chromatography eluting with 0 to 3% methanol in methylene chloride to obtain 100 mg of title compound.

NMR (CDCl₃): δ 1.68 (m, 1H), 1.95 (br s, NH/H₂O), 2.0–2.2 (m, 3H), 2.83 (q, 1H), 3.0–3.2 (m, 2H), 3.56 (s, 3H), 3.71 (s, 3H), 3.73 (ABq, 2H), 6.85–7.0 (m, 3H), 7.13 (m, 2H), 7.40 (d, 1H), 7.51 (dd, 1H), 8.82 (s, 1H).

EXAMPLE 72

Methyl 3-(S)-((2-methoxy-5-(1-tetrazolyl)phenyl) methylamino)-2-(S)-(4-fluorophenyl)cyclopentane-1-(S)-carboxylate To a solution of 100 mg of amine from Example 63 in 2 mL of methanol was added 0.040 mL of acetic acid, 1 g of 3A sieves and 94 mg 2-methoxy-5-(1-tetrazolyl) benzaldehyde (prepared according to the procedures given in PCT International Application WO 95/08549, published 30 Mar. 1995; p. 33). The reaction was stirred at room temperature for 30 min and then 0.080 g of sodium cyanoborohydride was added. The reaction was stirred further for 20 h and was then poured into water, made basic with 2N NaOH and extracted twice with ether. The organic layers were washed with a portion of brine, combined, dried over sodium sulfate and evaporated. The residue was purified by flash chromatography eluting with 0 to 3% methanol in methylene chloride to obtain 100 mg of title compound. NMR (CDCl₃): δ 1.5 (br s, NH/H₂O), 1.8–1.9 (m, 1H), 1.9–2.05 (m, 2H), 2.2–2.35 (m, 1H), 2.24 (m, 1H), 3.3–3.45 (m, 1H), 3.45–3.55 (m, 2H), 3.59 (s, 3H), 3.63 (s, 3H), 3.68 (d, 1H), 6.86 (d, 1H), 6.98 (t, 2H), 7.17 (m, 2H), 7.36 (d, 1H), 7.46 (dd, 1H), 8.85 (s, 1H).

EXAMPLE 73

1-(S)-((2-Methoxy-5-(1-tetrazolyl)phenyl) methylamino)-2-(S)-(4-fluorophenyl)3-(S)-(N-(methoxycarbonyl)-N-methylamino)cyclopentane Following essentially the same procedure as in Ex. 72, but using non-racemic 1-(S)-(amino)-2-(S)-(4-fluorophenyl)-3-(S)-(N-(methoxycarbonyl)-N-methylamino)cyclopentane from Ex. 67, Step D, the title compound was prepared. Mass spec (NH$_3$/CI): 455 (M+1).

EXAMPLE 74

1-(S)-((2-Methoxy-5-(1-tetrazolyl)phenyl) methylamino)-2-(S)-(4-fluorophenyl)-3-(S)-(aminocarbonyl)cyclopentane Step A:

Methyl 3-(S)-((N-(2-methoxy-5-(1-tetrazolyl)phenyl)-methyl)-N-(benzyloxocarbonyl)amino)-2-(S)-(4-fluorophenyl)cyclopentane-1-(S)-carboxylate To a solution of 1.25 g of methyl 3-(S)-((2-methoxy-5-(1-tetrazolyl)phenyl)methylamino)-2-(S)-(4-fluorophenyl) cyclopentane-1-(S)-carboxylate prepared as in Example 72 in 20 mL of methylene chloride was added 0.50 mL of benzyl chloroformate and 1 mL of DIPEA. After 2 h, the reaction was poured into water containing 3 mL of 2N HCl and was extracted with 3×methylene chloride. The organic layers were washed with a portion of brine, combined, dried over sodium sulfate and evaporated. The residue was purified by flash chromatography eluting with 50 to 60% ethyl acetate in hexanes to give 1.2 g of title compound. T.l.c. (70% ethyl acetate in hexanes) R$_f$=0.75.

Step B:

3-(S)-((N-(2-Methoxy-5-(1-tetrazolyl)phenyl)methyl)-N-(benzyloxocarbonyl)amino)-2-(S)-(4-fluorophenyl) cyclopentane-1-(S)-carboxylic acid To a solution of 1.2 g of product from Step A in 20 mL of methanol was added 5.4 mL of 2N NaOH and the reaction was stirred at room temperature for 16 h. The mixture was diluted with water, acidified with 2N HCl and extracted 3×with ethyl acetate. The organic layers were washed with a portion of brine, combined, dried over sodium sulfate and evaporated to obtain 1.15 g of title compound as a white solid. T.l.c. (1% HOAc/50% ethyl acetate in hexanes) R$_f$=0.3.

Step C:

1-(S)-((N-(2-Methoxy-5-(1-tetrazolyl)phenyl)methyl)-N-(benzyloxocarbonyl)amino)-2-(S)-(4-fluorophenyl)-3-(S)-(aminocarbonyl)cyclopentane To a solution of 500 mg of product from Step B in 10 mL of methylene chloride was added a drop of DMF and 0.12 mL of oxalyl chloride. After 2 h, the volatiles were removed in vacuo as well as two additional portions of methylene chloride. The residue was taken up in 5 mL of THF and to ¼ of this solution was added 0.095 mL of 7.4N ammonium hydroxide. After 1 h, the reaction was poured into water containing 2 mL of 2N HCl and was extracted 3 times with methylene chloride. The organic layers were washed with a portion of brine, combined, dried over sodium sulfate and evaporated. The residue was purified by flash chromatography eluting with 60 to 100% ethyl acetate in hexanes to obtain the title compound.

Step D:

1-(S)-((2-Methoxy-5-(1-tetrazolyl)phenyl)methylamino)-2-(S)-(4-fluorophenyl)-3-(S)-(aminocarbonyl)cyclopentane The product from Step C was taken up in 5 mL of methanol and hydrogenated over 20 mg of 10% Pd/C at 40 psi for 16 h. The mixture was filtered and evaporated. The residue was purified by flash chromatography eluting with 0 to 10% methanol in methylene chloride to obtain the title compound. Mass spec (NH$_3$/CI): 411 (M+1).

EXAMPLE 75

Following essentially the same procedure as in Example 74, Step D, but using the appropriate amine, the following compounds were prepared.

1-(S)-((2-Methoxy-5-(1-tetrazolyl)phenyl)methylamino)-2-(S)-(4-fluorophenyl)-3-(S)-(dimethylaminocarbonyl) cyclopentane Mass spec (NH$_3$/CI): 439 (M+1).

1-(S)-((2-Methoxy-5-(1-tetrazolyl)phenyl)methylamino)-2-(S)-(4-fluorophenyl)-3-(S)-(morpholin-4-ylcarbonyl) cyclopentane Mass spec (NH$_3$/CI): 481 (M+1).

1-(S)-((2-Methoxy-5-(1-tetrazolyl)phenyl)methylamino)-2-(S)-(4-fluorophenyl)-3-(S)-(t-butylaminocarbonyl) cyclopentane Mass spec (NH$_3$/CI): 439 (M+1).

EXAMPLE 76

Following essentially the same procedure as in Example 74, but using methyl 3-(S)-((2-methoxy-5-(1-tetrazolyl) phenyl)methylamino)-2-(R)-(4-fluorophenyl)cyclopentane-1-(R)-carboxylate from Example 71, the following compounds were prepared.

1-(S)-((2-Methoxy-5-(1-tetrazolyl)phenyl)methylamino)-2-(R)-(4-fluorophenyl)-3-(R)-(dimethylaminocarbonyl) cyclopentane Mass spec (NH$_3$/CI): 439 (M+1).

1-(S)-((2-Methoxy-5-(1-tetrazolyl)phenyl)methylamino)-2-(R)-(4-fluorophenyl)-3-(R)-(aminocarbonyl) cyclopentane Mass spec (NH$_3$/CI): 411 (M+1).

EXAMPLE 77

1-(S)-((2-Methoxy-5-(1-tetrazolyl)phenyl) methylamino)-2-(R)-(4-fluorophenyl)-3-(S)-(amino) cyclopentane Following essentially the same procedures as in Example 5, 8, 9 (Method B), but using non-racemic 3-(S)-((N-(2-methoxy-5-(1-tetrazolyl)-phenyl)methyl)-N-(benzyloxocarbonyl)amino)-2-(S)-(4-fluoro-phenyl) cyclopentane-1-(S)-carboxylic acid from Example 74, Step B, the title compound was prepared.

EXAMPLE 78

Following essentially the same procedures as in Example 10, 17 and 18, but using non-racemic 1-(S)-((2-methoxy-5-(1-tetrazolyl)phenyl)-methylamino)-2-(R)-(4-fluorophenyl)-3-(S)-(amino)cyclopentane from Example 77, the following compounds were prepared.

1-(S)-((2-Methoxy-5-(1-tetrazolyl)phenyl)methylamino)-2-(S)-(4-fluorophenyl)-3-(S)-(aminocarbonylmethylamino) cyclopentane Mass spec (NH$_3$/CI): 440 (M+1).

1-(S)-((2-Methoxy-5-(1-tetrazolyl)phenyl)methylamino)-2-(S)-(4-fluorophenyl)-3-(S)-(methoxycarbonylamino) cyclopentane Mass spec (NH$_3$/CI): 441 (M+1).

1-(S)-((2-Methoxy-5-(1-tetrazolyl)phenyl)methylamino)-2-(S)-(4-fluorophenyl)-3-(S)-(dimethylaminocarbonylamino)cyclopentane Mass spec (NH$_3$/CI): 454 (M+1).

1-(S)-((2-Methoxy-5-(1-tetrazolyl)phenyl)methylamino)-2-(S)-(4-fluorophenyl)-3-(S)-(methylaminocarbonylamino) cyclopentane Mass spec (NH$_3$/CI): 440 (M+1).

1-(S)-((2-Methoxy-5-(1-tetrazolyl)phenyl)methylamino)-2-(S)-(4-fluorophenyl)-3-(S)-(ethylsulfonylamino) cyclopentane Mass spec (NH$_3$/CI): 475 (M+1).

1-(S)-((2-Methoxy-5-(1-tetrazolyl)phenyl)methylamino)-2-(S)-(4-fluorophenyl)-3-(S)-(t-butylcarbonylamino)cyclopentane Mass spec (NH$_3$/CI): 467 (M+1).

EXAMPLE 79

2-Chloro-5-(1-tetrazolyl)benzyl bromide

Step A:

2-Chloro-5-(1-tetrazolyl)benzoic acid

A suspension of 5.15 g of 2-chloro-5-aminobenzoic acid in 50 mL of HOAc was heated to 75° C. under nitrogen and then 13.3 g of triethyl orthoformate was slowly added to give a thick slurry. After 2 h, 5.85 g of sodium azide was added in 5 portions over 75 min. After a further 40 min, the reaction was cooled and gave a precipitate. This was filtered, washed with ether and hexanes and air dried to give 22 g of solid. This was dissolved in 60 mL of water and acidified with 2N HCl. The resulting precipitate was filtered, washed with 0.1N HCl and ether and air dried to afford 4.38 g of the title compound. Mass spec (NH$_3$/CI): 226.7 (M+1).

Step B:

Methyl 2-chloro-5-(1-tetrazolyl)benzoate

A solution of 1.0 g of 2-chloro-5-(1-tetrazolyl)benzoic acid from Step A in 25 mL of methanol was saturated with HCl (gas) and stirred for 20 h. The solution was concentrated in vacuo, diluted with water and extracted twice with ether. The organic layers were washed with a portion of brine, combined, dried over sodium sulfate and evaporated to afford 1.0 g of title compound.

Step C:

2-Chloro-5-(1-tetrazolyl)benzyl alcohol

The product from Step B was taken up in 30 mL of THF and 160 mg of lithium borohydride was added. The reaction was stirred for 16 h and was then poured into dilute HCl solution and extracted twice with ethyl acetate. The organic layers were washed with a portion of brine, combined, dried over sodium sulfate and evaporated. When taken up in 50% ethyl acetate in hexanes, the product partially precipitated to give white solid after filtration. The mother liquor was concentrated and additional product was obtained by flash chromatography eluting with 1% HOAc/50% ethyl acetate in hexanes to obtain a total of 400 mg of title compound. T.l.c. (50% ethyl acetate in hexanes) R$_f$=0.4

Step D:

2-Chloro-5-(1-tetrazolyl)benzyl bromide

A suspension of triphenylphosphine-dibromide in acetonitrile was prepared by dissolving 160 mg of triphenylphosphine in 5 mL of acetonitrile and adding bromine until the color persisted. A small additional amount of triphenylphosphine was added to discharge the color. After 5 min, 100 mg of product from Step C was added and stirred for 2 h. The reaction was concentrated and the residue was purified by flash chromatography eluting with 25 to 40% ethyl acetate in hexanes to obtain 130 mg of title compound as a white solid. T.l.c. (30% ethyl acetate in hexanes) R$_f$=0.5

EXAMPLE 80

2-Chloro-5-(5-trifluoromethyltetrazol-1-yl)benzyl bromide

Step A:

Methyl 2-chloro-5-(amino)benzoate

A solution of 10 g of 2-chloro-5-(amino)benzoic acid in 250 mL of methanol was saturated with HCl (gas) and stirred for 16 h. The solution was concentrated in vacuo, diluted with water, made neutral with 5N NaOH and extracted twice with ether. The organic layers were washed with a portion of brine, combined, dried over sodium sulfate and evaporated to afford 10 g of title compound as a slightly pink solid.

Step B:

Methyl 2-chloro-5-(benzyloxycarbonylamino)benzoate

The product from Step A was taken up in 100 mL of methylene chloride and cooled in an ice bath. To the solution was added 7.6 mL of benzyl chloroformate and after 5 min 20 mL of DIPEA was added dropwise over 5 min. After stirring at r.t. for 3 h, the reaction was poured into water containing 50 mL of 2N HCl and was extracted twice with methylene chloride. The organics were washed with a portion of brine, combined, dried over sodium sulfate and evaporated to give a solid. This was triturated with hot 5% ethyl acetate in hexanes, cooled, filtered and air dried to afford 16.5 g of title compound as an off white solid. T.l.c. (30% ethyl acetate in hexanes) R$_f$=0.75

Step C:

2-Chloro-5-(benzyloxycarbonylamino)benzyl alcohol

To a solution of 16.5 g of product from Step B in 100 mL of THF was added 1.70 g of lithium borohydride. The reaction was stirred at room temperature for 4 days, then quenched by addition of dilute HCl and extracted twice with ethyl acetate. The organics were washed with a portion of brine, combined, dried over sodium sulfate and evaporated. The residue was purified by flash chromatography eluting with 20 to 30% ethyl acetate in hexanes to obtain 11.5 g of title compound. T.l.c. (25% ethyl acetate/hexanes) R$_f$=0.25

Step D:

2-Chloro-5-(benzyloxycarbonylamino)benzyl 4-methylbenzoate

The product from Step C was taken up in 100 mL of methylene chloride and cooled in an ice bath. To the solution was added 7.65 g of 4-methylbenzoyl chloride and after 5 min 7.7 gm of DIPEA was added dropwise over 5 min. The reaction was warmed until everything was in solution and stirred at room temperature for 16 h. The reaction was poured into water containing 25 mL of 2N HCl and was extracted twice with methylene chloride. The organic layers were washed with a portion of brine, combined, dried over sodium sulfate and evaporated to give a solid. This was triturated with hot 20% ethyl acetate in hexanes, cooled, filtered and air dried to afford 7.5 g of title compound as an off white solid. Flash chromatography of the mother liquor eluting with 15 to 25% ethyl acetate/hexanes afforded an addn'l 2.5 g of title compound. T.l.c. (25% ethyl acetate in hexanes) R$_f$=0.6

Step E:

2-Chloro-5-(amino)benzyl 4-methylbenzoate

Careful hydrogenation of the product from Step D was done in two batches of 5 g in 150 mL of ethyl acetate and 25 mL of methanol over 250 mg of 10% Pd/C at 40 psi. The hydrogenation was stopped after 25 to 35% of the theoretical uptake of hydrogen and the reaction was filtered and concentrated. Most of the remaining starting material was recovered by trituration with 20% ethyl acetate in hexanes and filtration. After 2 further cycles, the combined filtrates were concentrated and the residue was purified by flash chromatography eluting with 15% ethyl acetate in hexanes to obtain 3.0 g of recovered starting material and with 20 to 30% ethyl acetate in hexanes to afford 2.7 g of title compound. T.l.c. (25% ethyl acetate in hexanes) R$_f$=0.3

Step F:

2-Chloro-5-(trifluoromethylcarbonylamino)benzyl 4-methylbenzoate

The product from Step E was taken up in 40 mL of methylene chloride and to the solution was added 2.0 mL of TFAA and after 5 min 5.0 mL of DIPEA was added dropwise over 5 min. The reaction was stirred at room temperature for 2 h and another 0.5 mL of TFAA was added. After a further 1 h, the reaction was poured into water containing 15 mL of 2N HCl and was extracted twice with methylene chloride. The organic layers were washed with a portion of brine, combined, dried over sodium sulfate and evaporated. Flash chromatography of the residue eluting with 10 to 15% ethyl acetate in hexanes afforded 3.6 g of title compound as a white solid. T.l.c. (20% ethyl acetate in hexanes) $R_f$=0.6

Step G:

2-Chloro-5-(5-trifluoromethyltetrazol-1-yl)benzyl 4-methylbenzoate

The product from Step F was suspended in 75 mL of carbon tetrachloride, treated with 4.9 gm of triphenylphosphine and heated at 90° C. for 16 h. (T.l.c. (20% ethyl acetate in hexanes) $R_f$=0.8.) The reaction was concentrated and the residue was taken up in 40 mL of DMF. To this solution was added 1.2 g of sodium azide. The reaction was stirred at room temperature for 4 h and then diluted with water and extracted twice with ether. The organic layers were washed with a portion of brine, combined, dried over sodium sulfate and evaporated. Most of the triphenylphosphine oxide was precipitated with 10% ethyl acetate in hexanes and filtered. The filtrate was reconcentrated and the residue was purified by flash chromatography eluting with 10 to 15% ethyl acetate in hexanes to obtain 3.1 g of title compound. T.l.c. (20% ethyl acetate in hexanes) $R_f$=0.5

Step H:

2-Chloro-5-(5-trifluoromethyltetrazol-1-yl)benzyl alcohol

The product from Step G was suspended in 15 mL of methanol and 0.50 mL of 2N NaOH was added. The reaction was gently warmed for 30 min until all was in solution and stirred at room temperature for 1 h. The reaction was concentrated, diluted with water and 1 mL of 2N HCl and extracted twice with ether. The organic layers were washed with a portion of brine, combined, dried over sodium sulfate and evaporated. The residue was purified by chromatography eluting with 15 to 25% ethyl acetate/hexanes to give 1.5 g of the title compound. T.l.c. (20% ethyl acetate in hexanes) $R_f$=0.25

Step I:

2-Chloro-5-(5-trifluoromethyltetrazol-1-yl)benzyl bromide

A suspension of triphenylphosphine-dibromide in 10 mL of acetonitrile was prepared as in Example 79, Step D from 720 mg of triphenylphosphine. To this was added 500 mg of product from Step H. The reaction was stirred for 1 h and then concentrated. The residue was purified by flash chromatography eluting with 15% ethyl acetate in hexanes to obtain 500 mg of title compound. T.l.c. (15% ethyl acetate in hexanes) $R_f$=0.6

EXAMPLE 81

Methyl 3-(S)-((2-chloro-5-(1-tetrazolyl)phenyl) methylamino)-2-(S)-(4-fluorophenyl)cyclopentane-1-(S)-carboxylate A solution of 25 mg of amino ester from Example 63, 29 mg of bromide from Example 79 and 0.050 mL of DIPEA in 1 mL of acetonitrile was stirred in a sealed vial at 50° C. for 16 h and then evaporated. The residue was purified on a 1 mm preparative silica gel plate eluted with 5% methanol in methylene chloride to afford 23 mg of the title compound. Mass spec ($NH_3$/CI): 430 (M+1).

EXAMPLE 82

Following essentially the same procedures as in Example 79 or 80 or employing other available benzyl bromides, the following compounds were prepared using the amine from Example 63 according to the procedure of Example 81.

Methyl 3-(S)-((3-trifluoromethyl-5-(1-tetrazolyl)phenyl) methylamino)-2-(S)-(4-fluorophenyl)cyclopentane-1-(S)-carboxylate Mass spec ($NH_3$/CI): 464 (M+1).

Methyl 3-(S)-((2-fluoro-5-(1-tetrazolyl)phenyl) methylamino)-2-(S)-(4-fluorophenyl)cyclopentane-1-(S)-carboxylate Mass spec ($NH_3$/CI): 414 (M+1). NMR ($CDCl_3$): δ 1.7-1.85 (m, 1H), 1.85-2.0 (m, 1H), 2.0-2.1 (m, 1H), 2.2-2.3 (m, 1H), 3.3-3.4 (m, 2H), 3.55 (m, 1H), 3.63 (s, 3H), 3.69 (ABq, 2H), 7.00 (t, 2H), 7.23 (m, 2H), 7.52 (s, 1H), 7.70 (s, 1H), 7.80 (s, 1H), 8.99 (s, 1H).

Methyl 3-(S)-(1-(RS)-((2-methoxy-5-trifluoromethoxyphenyl)ethyl)-amino)-2-(S)-(4-fluorophenyl)cyclopentane-1-(S)-carboxylate Mass spec ($NH_3$/CI): 457 (M+1).

Methyl 3-(S)-(1-(RS)-((2-fluoro-3-trifluoromethylphenyl) ethyl)amino)-2-(S)-(4-fluorophenyl)cyclopentane-1-(S)-carboxylate Mass spec ($NH_3$/CI): 428 (M+1).

Methyl 3-(S)-((3-trifluoromethyl-5-methylcarbonylaminophenyl)-methylamino)-2-(S)-(4-fluorophenyl)cyclopentane-1-(S)-carboxylate Mass spec ($NH_3$/CI): 453 (M+1).

Methyl 3-(S)-((3-trifluoromethyl-5-(5-methyltetrazol-1-yl) phenyl)methylamino)-2-(S)-(4-fluorophenyl) cyclopentane-1-(S)-carboxylate Mass spec ($NH_3$/CI): 478 (M+1). NMR ($CDCl_3$): δ 1.7-1.85 (m, 1H), 1.85-2.0 (m, 1H), 2.0-2.1 (m, 1H), 2.2-2.3 (m, 1H), 2.59 (s, 3H), 3.4-3.5 (m, 2H), 3.5-3.6 (m, 1H), 3.63 (s, 3H), 3.67 (ABq, 2H), 6.98 (t, 2H), 7.21 (dd, 2H), 7.45 (s, 1H), 7.55 (s, 2H).

Methyl 3-(S)-((3-trifluoromethyl-5-(5-trifluoromethyltetrazol-1-yl)phenyl)methylamino)-2-(S)-(4-fluorophenyl)cyclopentane-1-(S)-carboxylate Mass spec ($NH_3$/CI): 532 (M+1). NMR ($CDCl_3$): δ 1.7-1.85 (m, 1H), 1.85-2.0 (m, 1H), 2.0-2.1 (m, 1H), 2.2-2.3 (m, 1H), 3.3-3.4 (m, 2H), 3.55 (dd, 1H), 3.60 (s, 3H), 3.70 (ABq, 2H), 6.98 (t, 2H), 7.21 (dd, 2H), 7.50 (s, 1H), 7.59 (s, 1H), 7.64 (s, 1H).

Methyl 3-(S)-((2-fluoro-3-trifluoromethyl-5-(5-trifluoromethyltetrazol-1-yl)phenyl)methylamino)-2-(S)-(4-fluorophenyl)cyclopentane-1-(S)-carboxylate Mass spec ($NH_3$/CI): 532 (M+1).

Methyl 3-(S)-((2-chloro-5-(5-trifluoromethyltetrazol-1-yl) phenyl)methylamino)-2-(S)-(4-fluorophenyl) cyclopentane-1-(S)-carboxylate Mass spec ($NH_3$/CI): 498 (M+1). NMR ($CDCl_3$): δ 1.7-1.85 (m, 1H), 1.85-2.0 (m, 1H), 2.0-2.1 (m, 1H), 2.2-2.3 (m, 1H), 3.3-3.4 (m, 2H), 3.52 (dd, 1H), 3.59 (s, 3H), 3.69 (ABq, 2H), 6.93 (t, 2H), 7.18 (dd, 2H), 7.28 (dd, 1H), 7.41 (d, 1H), 7.50 (d, 1H).

Methyl 3-(S)-(1-(RS)-((2-fluoro-3-methylphenyl)ethyl) amino)-2-(S)-(4-fluorophenyl)cyclopentane-1-(S)-carboxylate Mass spec ($NH_3$/CI): 360 (M+1).

Methyl 3-(S)-(1-(R and S)-((2,4-(bis-trifluoromethyl) phenyl)-ethyl)amino)-2-(S)-(4-fluorophenyl) cyclopentane-1-(S)-carboxylate Mass spec ($NH_3$/CI): 464 (M+1).

Methyl 3-(S)-(1-(R and S)-((2,5-(bis-trifluoromethyl) phenyl)-ethyl)amino)-2-(S)-(4-fluorophenyl) cyclopentane-1-(S)-carboxylate Mass spec ($NH_3$/CI): 464 (M+1).

Methyl 3-(S)-(1-(R and S)-((3-fluoro-5-trifluoromethylphenyl)ethyl)-amino)-2-(S)-(4-fluorophenyl)cyclopentane-1-(S)-carboxylate Mass spec ($NH_3$/CI): 464 (M+1).

EXAMPLE 83

Following essentially the same procedure as in Example 72 and employing other available substituted benzaldehydes or acetophenones, the following compounds were prepared using the amine from Ex. 63.

Methyl 3-(S)-(2-fluoro-5-trifluoromethylphenylmethyl) amino)-2-(S)-(4-fluorophenyl)cyclopentane-1-(S)-carboxylate Mass spec (NH₃/CI): 414 (M+1).

Methyl 3-(S)-(3-fluoro-5-trifluoromethylphenylmethyl) amino)-2-(S)-(4-fluorophenyl)cyclopentane-1-(S)-carboxylate Mass spec (NH₃/CI): 414 (M+1).

Methyl 3-(S)-(2-fluoro-3-trifluoromethylphenylmethyl) amino)-2-(S)-(4-fluorophenyl)cyclopentane-1-(S)-carboxylate Mass spec (NH₃/CI): 414 (M+1).

Methyl 3-(S)-((2-methoxy-5-trifluoromethoxyphenylmethyl)amino)-2-(S)-(4-fluorophenyl)cyclopentane-1-(S)-carboxylate Mass spec (NH₃/CI): 442 (M+1).

Methyl 3-(S)-(1-(R and S)-(3-(1-tetrazolylphenyl)ethyl) amino)-2-(S)-(4-fluorophenyl)cyclopentane-1-(S)-carboxylate Mass spec (NH₃/CI): 410(M+1).

Methyl 3-(S)-((2-cyclopropylmethyloxy-5-trifluoromethoxyphenyl-methyl)-amino)-2-(S)-(4-fluorophenyl)cyclopentane-1-(S)-carboxylate Mass spec (NH₃/CI): 482(M+1).

Methyl 3-(S)-((2-methoxyphenylmethyl)amino)-2-(S)-(4-fluorophenyl)-cyclopentane-1-(S)-carboxylate Mass spec (NH₃/CI): 358 (M+1).

Methyl 3-(S)-(1-(R and S)-(2-methoxyphenyl)ethyl)amino)-2-(S)-(4-fluorophenyl)cyclopentane-1-(S)-carboxylate Mass spec (NH₃/CI): 410(M+1).

EXAMPLE 84

1-(S)-((2-Methoxy-5-(1-tetrazolyl)phenyl) methylamino)-2-(S)-(4-fluorophenyl)-3-(S)-(pyrrolidin-1-ylmethyl)cyclopentane Step A:

Methyl 3-(S)-(N-(4-methoxybenzyl)-N-(benzyloxycarbonyl)-amino)-2-(S)-(4-fluorophenyl) cyclopentane-1-(S)-carboxylate To a solution of 3.1 g of methyl 3-(S)-(4-methoxybenzyl-amino)-2-(S)-(4-fluorophenyl)cyclopentane-1-(S)-carboxylate, prepared as in Example 61, in 50 mL of methylene chloride was added 1.36 mL of benzyl chloroformate and after 5 min 3.0 mL of DIPEA. After stirring at room temperature for 16 h, the reaction was poured into water containing 3 mL of 2N HCl and was extracted twice with methylene chloride. The organic layers were washed with a portion of brine, combined, dried over sodium sulfate and evaporated. The residue was purified by flash chromatography eluting with 10% ethyl acetate in hexanes to obtain 3.95 g of title compound as an oil. T.l.c. (10% ethyl acetate in hexanes) R$_f$=0.35

Step B:

1-(S)-(N-(4-Methoxybenzyl)-N-(benzyloxycarbonyl)-amino)-2-(S)-(4-fluorophenyl)-3-(S)-(hydroxymethyl)-cyclopentane To a solution of 2.0 g of product from Step A in 40 mL of THF was added 277 mg of lithium borohydride. The reaction was stirred at 40° C. for 2 h and then at room temperature for 16 h when it was quenched by addition of water and the mixture was extracted twice with ether. The organic layers were washed with a portion of brine, combined, dried over sodium sulfate and evaporated. The residue was purified by flash chromatography eluting with 30 to 50% ethyl acetate in hexanes to obtain 1.35 g of title compound as an oil. Mass spec (NH₃/CI): 464 (M+1).

Step C:

1-(S)-(N-(4-Methoxybenzyl)-N-(benzyloxycarbonyl)-amino)-2-(S)-(4-fluorophenyl)-3-(S)-(bromomethyl)-cyclopentane To a solution of 1.3 g of product from Step B in 40 mL of methylene chloride was added 1.1 g of triphenylphosphine and 1.39 g of carbon tetrachloride. The reaction was stirred at room temperature for 2 h and then diluted with hexanes to precipitate triphenylphosphine oxide. After filtration, the filtrate was concentrated and the residue was purified by flash chromatography eluting with 10% ethyl acetate in hexanes to obtain 1.35 g of title compound. Mass spec (NH₃/CI): 526 (M+1), 528 (M+3).

Step D:

1-(S)-(N-(4-Methoxybenzyl)-N-(benzyloxycarbonyl)-amino)-2-(S)-(4-fluorophenyl)-3-(S)-(pyrrolidin-1-ylmethyl)-cyclopentane To a solution of 500 mg of product from Step C in 3.0 mL of acetonitrile was added 0.40 mL of pyrrolidine. The reaction was heated at 90° C. for 3 days in a sealed vial and then concentrated. The residue was purified by flash chromatography eluting with 0 to 5% methanol in methylene chloride to obtain 483 mg of title compound. Mass spec (NH₃/CI): 517 (M+1).

Step E:

1-(S)-(Amino)-2-(S)-(4-fluorophenyl)-3-(S)-(pyrrolidin-1-yl-methyl)cyclopentane

A solution of 477 mg of product from Step D in 5 mL of methanol and 0.117 mL of HOAc was hydrogenated over 70 mg of 10% Pd/C at 40 psi for 18 h. The mixture was filtered and evaporated to afford 188 mg of oil. The residue was purified by flash chromatography eluting with 2 to 10% methanol in methylene chloride to obtain 108 mg of title compound. Mass spec (NH₃/CI): 263 (M+1).

Step F:

1-(S)-((2-Methoxy-5-(1-tetrazolyl)phenyl)methylamino)-2-(S)-(4-fluorophenyl)-3-(S)-(pyrrolidin-1-ylmethyl) cyclopentane Using the procedure from Example 72, 50 mg of product from Step E afforded 40 mg of the title compound after purification on a 1 mm preparative silica gel plate eluted with 10% methanol in methylene chloride. Mass spec (NH₃/CI): 451 (M+1).

EXAMPLE 85

Following essentially the same procedures as in Example 84, the following compounds were prepared.

1-(S)-((2-Methoxy-5-(1-tetrazolyl)phenyl)methylamino)-2-(R)-(4-fluorophenyl)-3-(R)-(pyrrolidin-1-ylmethyl) cyclopentane Mass spec (NH₃/CI): 451 (M+1).

1-(S)-((2-Methoxy-5-(1-tetrazolyl)phenyl)methylamino)-2-(S)-(4-fluorophenyl)-3-(S)-(4-(pyrrolidin-1-ylcarbonyl) piperidin-1-ylmethyl)cyclopentane Mass spec (NH₃/CI): 576 (M+1).

1-(S)-((2-Methoxy-5-(1-tetrazolyl)phenyl)methylamino)-2-(S)-(4-fluorophenyl)-3-(S)-(imidazol-1-ylmethyl) cyclopentane Mass spec (NH₃/CI): 448 (M+1).

1-(S)-((2-Methoxy-5-(5-trifluoromethyltetrazol-1-yl) phenyl)methylamino)-2-(S)-(4-fluorophenyl)-3-(S)-(pyrrolidin-1-ylmethyl)cyclopentane Mass spec (NH₃/CI): 519 (M+1).

1-(S)-((2-Methoxy-5-(1-tetrazolyl)phenyl)methylamino)-2-(S)-(4-fluorophenyl)-3-(S)-(1,2,3-triazol-1-ylmethyl) cyclopentane Mass spec (NH₃/CI): 517 (M+1).

1-(S)-((2-Methoxy-5-trifluoromethoxyphenyl) methylamino)-2-(S)-(4-fluorophenyl)-3-(S)-(pyrrolidin-1-ylmethyl)cyclopentane Mass spec (NH₃/CI): 467 (M+1).

1-(S)-(1-(R and S)-(3,5-bis(trifluoromethyl)phenyl) ethylamino)-2-(S)-(4-fluorophenyl)-3-(S)-(pyrrolidin-1-ylmethyl)cyclopentane Mass spec (NH₃/CI): 503 (M+1).

1-(S)-((2-Isopropoxy-5-(5-trifluoromethyltetrazol-1-yl)phenyl)methylamino)-2-(S)-(4-fluorophenyl)-3-(S)-(pyrrolidin-1-ylmethyl)cyclopentane Mass spec (NH$_3$/CI): 547 (M+1).

1-(S)-((2-Chloro-5-(5-trifluoromethyltetrazol-1-yl)phenyl)methylamino)-2-(S)-(4-fluorophenyl)-3-(S)-(pyrrolidin-1-ylmethyl)-cyclopentane Mass spec (NH$_3$/CI): 523 (M+1).

1-(S)-((2-Cyclopropylmethyloxy-5-trifluoromethoxyphenyl)-methylamino)-2-(S)-(4-fluorophenyl)-3-(S)-(pyrrolidin-1-ylmethyl)cyclopentane Mass spec (NH$_3$/CI): 507 (M+1).

1-(S)-((2-Methoxy-5-(5-trifluoromethyltetrazol-1-yl)phenyl)methylamino)-2-(S)-(4-fluorophenyl)-3-(S)-(2-(S)-(aminocarbonyl)pyrrolidin-1-ylmethyl)cyclopentane Mass spec (NH$_3$/CI): 562 (M+1).

EXAMPLE 86

1-(RS)-((2-Methoxy-5-(5-trifluoromethyltetrazol-1-yl)phenyl)methylamino)-2-(RS)-(4-fluorophenyl)-3-(RS)-(4-methyl-1,2,4-triazol-3-ylmethyl)-cyclopentane Step A:

3-(SR)-(Benzyloxy)-2-(RS)-(4-fluorophenyl)cyclopentane-1-(RS)-carboxylic acid

To a solution of 10.0 gm of methyl 3-(SR)-(hydroxy)-2-(RS)-(4-fluorophenyl)cyclopentane-1-(RS)-carboxylate prepared as in Example 32 (lower isomer) and 10.8 gm of benzyl bromide in 50 mL of DMF was added in portions over 30 min 2.0 gm of 60% NaH in mineral oil. The reaction was stirred for 2 h at room temperature and was then diluted with ether and quenched by slow addition to water containing 25 mL of 2N HCl. The mixture was extracted twice with ether and the organic layers were washed with a portion of brine, combined, dried over sodium sulfate and evaporated. By T.l.c. and NMR the crude product consisted of a mixture of desired benzylated starting material and dimer derived from transesterification. The crude product was taken up in 100 mL of methanol and 45 mL of 5N NaOH was added. The mixture was stirred at room temperature for 40 h residue was diluted with waste. The residue was diluted with water and extracted twice with ether and the ether layers washed with dilute NaOH. The combined aqueous layers were acidified with HCl (c) and extracted twice with ethyl acetate. The organic layers were washed with a portion of brine, combined, dried over sodium sulfate and evaporated to give 14 gm of title compound contaminated with some 3-(SR)-(hydroxy)-2-(RS)-(4-fluorophenyl)cyclopentane-1-(RS)-carboxylic acid. This could be further purified by flash chromatography eluting with 20% ethyl acetate in hexanes followed by 1% HOAc/20% ethyl acetate in hexanes. T.l.c. (1% HOAc/20% ethyl acetate in hexanes) R$_f$=0.4.

Step B:

1-(SR)-(Benzyloxy)-2-(RS)-(4-fluorophenyl)-3-(RS)-(methylaminocarbonylmethyl)cyclohexane To a solution of 2.5 gm of the crude product from Step A in 25 mL of methylene chloride was added a drop of DMF and 0.85 mL of oxalyl chloride. The reaction was stirred for 2 h and then concentrated followed by two portions of methylene chloride. The residue was taken up in 25 ml of THF and treated with 3.1 mL of 40% aqueous methylamine. After 2 h, the reaction was concentrated, poured into water and extracted twice with methylene chloride. The organic layers were washed with a portion of brine, combined, dried over sodium sulfate and evaporated. The residue was purified by flash chromatography eluting with 75 to 100% ethyl acetate in hexanes to obtain 1.8 mg of title compound as a white solid.

Step C:

1-(SR)-(Benzyloxy)-2-(RS)-(4-fluorophenyl)-3-(RS)-(1-methyl-1,2,4-triazol-3-yl)cyclopentane To a solution of 0.80 g of product from step B in 20 mL of chloroform was added 1.2 mL of pyridine and 660 mg of phosphorous pentachloride. After 6 h, the reaction was cooled in an ice bath and 0.60 mL of methanol was added. The ice bath was removed and the reaction was stirred at room temperature for 1 h. It was then diluted with methylene chloride, poured into water and extracted twice with methylene chloride. The organic layers were washed with a portion of brine, combined, dried over sodium sulfate and evaporated. The residue was rapidly purified by flash chromatography eluting with 25% ethyl acetate in hexanes. The imino ether was taken up in 10 mL of acetonitrile and 180 mg of formic hydrazide was added. The reaction was heated at 50° C. for 16 h and then poured into water and extracted twice with ether. The organic layers were washed with a portion of brine, combined, dried over sodium sulfate and evaporated. The residue was purified by flash chromatography eluting with 0 to 5% methanol in methylene chloride to obtain 280 mg of title compound as a white solid. Mass spec (NH$_3$/CI): 352 (M+1). NMR (CDCl$_3$): δ 2.0–2.2 (m, 3H), 2.3–2.5 (m, 1H), 3.0–3.1 (m, 1H), 3.10 (s, 3H), 3.52 (dd, 1H), 4.16 (q, 1H), 4.40 (s, 2H), 6.94 (t, 2H), 7.15 (m, 5H), 7.2–7.3 (m, 2H), 7.89 (s, 1H).

Step D:

1-(SR)-(Hydroxy)-2-(RS)-(4-fluorophenyl)-3-(RS)-(4-methyl-1,2,4-triazol-3-yl)cyclopentane A solution of 275 mg of product from Step C in 5 mL of methanol and 0.5 mL of TTA was stirred with 100 mg of 10% Pd/C under a hydrogen balloon for 60 h. The reaction was filtered and concentrated. The residue was purified by flash chromatography eluting with 5 to 10% methanol in methylene chloride to obtain 220 mg of title compound. T.l.c. (5% methanol in methylene chloride) R$_f$=0.25. Mass spec (NH$_3$/CI): 262 (M+1).

Step E:

1-(RS)-(Azido)-2-(RS)-(4-fluorophenyl)-3-(RS)-(4-methyl-1,2,4-triazol-3-yl)cyclopentane To a solution of 210 mg of the product from Step D, 392 mg of zinc azide bispyridine, 435 mg of triphenylphosphine and 115 mg of imidazole in 2.0 mL of methylene chloride was added over 5 min 300 mg of DEAD. The reaction was stirred at room temperature for 20 h and then diluted with methylene chloride and filtered. The solvent was removed and the residue was purified by flash chromatography eluting with 0 to 5% methanol in methylene chloride to obtain 90 mg of title compound. Further elution with 10% methanol in methylene chloride afford 50 mg of recovered starting material. T.l.c. (10% methanol in methylene chloride) R$_f$=0.5.

Step F:

1-(RS)-(Amino)-2-(RS)-(4-fluorophenyl)-3-(RS)-(4-methyl-1,2,4-triazol-3-yl)cyclopentane A solution of 90 mg of product from Step E in 5 mL of methanol was hydrogenated over 25 mg of 10% Pd/C at 40 psi for 2 h and then filtered and evaporated. The residue was purified by flash chromatography eluting with 1% NH$_4$OH/10% methanol in methylene chloride to obtain 20 mg of title compound. T.l.c. (5% methanol in methylene chloride) R$_f$=0.1.

Step G:

1-(RS)-((2-Methoxy-5-(5-trifluoromethyltetrazol-1-yl)phenyl)-methylamino)-2-(RS)-(4-fluorophenyl)-3-(RS)-(4-methyl-1,2,4-triazol-3-ylmethyl)-cyclopentane To a solution of 20 mg of product from Step F, 10 mg of HOAc, 41 mg of 2-methoxy-5-(5-trifluoromethyltetrazol-1- yl)benzaldehyde (prepared as in Example) in 3 mL of methanol were added 0.5 g of 3A sieves and after 30 min 15 mg of sodium cyanoborohydride. The mixture was stirred at room temperature for 16 h and then was diluted with water containing a drop of 2N NaOH and extracted three times with methylene chloride. The organic layers were washed with a portion of brine, combined, dried over sodium sulfate and evaporated. The residue was purified by flash chromatography eluting with 0 to 5% methanol in methylene chloride to obtain 20 mg of title compound. T.l.c. (5% methanol in methylene chloride) $R_f$=0.45. Mass spec (NH$_3$/CI): 517 (M+1). NMR (CDCl$_3$): δ 1.8–2.0 (m, 2H), 2.1–2.2 (m, 1H), 2.3–2.5 (m, 1H), 3.4–3.5 (m, 1H), 3.52 (s, 3H), 3.72 (s, 3H), 3.4–3.8 (2m, 3H), 3.98 (m, 1H), 6.90 (m, 3H), 7.17 (m, 2H), 7.23 (s, 1H), 7.40 (m, 1H), 7.86 (s, 1H).

EXAMPLE 87

1-(S)-((2-Methoxy-5-(5-trifluoromethyltetrazol-1-yl)phenyl)-methylamino)-2-(S)-(4-fluorophenyl)-3-(S)-(1-methyl-5-tetrazol-5-ylmethyl)-cyclopentane Step A:

3-(R)-(Benzyloxy)-2-(S)-(4-fluorophenyl)cyclopentane-1-(S)-carboxylic acid

To a solution of 10.0 gm of 3-(S)-(hydroxy)-2-(R)-phenylcyclopentane-1-(R)-carboxylic acid prepared as in Example 33 (from S-salt) and 15.2 gm of benzyl bromide in 150 mL of DMF was added in portions over 30 min 4.46 gm of 60% NaH in mineral oil. The reaction was stirred for 2 h at room temperature when an additional 300 mg of NaH was added. After a further 3 h, the reaction was diluted with ether and quenched by slow addition to water containing 25 mL of 2N HCl. The mixture was extracted twice with ether and the organic layers were washed with a portion of brine, combined, dried over sodium sulfate and evaporated. The residue was taken up in 25 mL of methanol and 25 mL of 5N NaOH and stirred at room temperature for 20 h. The mixture was concentrated and then acidified with 2N HCl and extract three times with ether. The organic layers were washed with a portion of brine, combined, dried over sodium sulfate and evaporated. The residue was purified by flash chromatography eluting with 20% ethyl acetate in hexanes to obtain 3.1 g of recovered starting material and then with 1% HOAc/20% ethyl acetate in hexanes to obtain 10.3 g of title compound. [α]$_D$ (EtOH)=+0.64 (c=2.5).

Step B:

1-(R)-(Benzyloxy)-2-(S)-(4-fluorophenyl)-3-(S)-(hydroxymethyl)-cyclopentane

A solution of 2.0 g of product from Step A in 40 mL of THF was cooled in an ice bath and treated in portions with 482 mg of LAH and then stirred at room temperature for 20 h. The reaction was quenched with 2N NaOH and sodium sulfate to give a white precipitate which was filtered off. The filtrate was concentrated and the residue was purified by flash chromatography eluting with 25% ethyl acetate in hexanes to obtain 1.46 g of title compound as an oil. T.l.c. (50% ethyl acetate in hexanes) $R_f$=0.45.

Step C:

1-(R)-(Benzyloxy)-2-(S)-(4-fluorophenyl)-3-(S)-(bromomethyl)-cyclopentane

To a solution of 1.4 g of product from Step B in 40 mL of methylene chloride was added 1.46 g of triphenylphosphine and 1.85 g of carbon tetrachloride. After 1.5 h, the reaction was concentrated and the residue was purified by flash chromatography eluting with 0 to 5% ethyl acetate in hexanes to obtain 1.09 g of title compound as a white solid. T.l.c. (20% ethyl acetate in hexanes) $R_f$=0.8. Mass spec (NH$_3$/CI): 363(M+1), 365 (M+3).

Step D:

1-(R)-(Benzyloxy)-2-(S)-(4-fluorophenyl)-3-(S)-(cyanomethyl)-cyclopentane

To a solution of 1.07 g of product from Step C in 12 mL of DMF was added 0.433 g of sodium cyanide. The reaction was stirred at room temperature for 20 h and then diluted with water and extracted twice with ethyl acetate. The organic layers were washed with a portion of brine, combined, dried over sodium sulfate and evaporated. The residue was purified by flash chromatography to obtain 879 mg of title compound as a white solid. Mass spec (NH$_3$/CI): 310(M+1).

Step E:

1-(R)-(Benzyloxy)-2-(S)-(4-fluorophenyl)-3-(S)-(tetrazol-5-ylmethyl)cyclopentane To a solution of 342 mg of product from Step D in 7 mL of DMF was added 215 mg of sodium azide and 176 mg of ammonium chloride. The reaction was heated at 125° C. for 4 days and then cooled and diluted with water and extracted twice with ether. The organic layers were washed with a portion of brine, combined, dried over sodium sulfate and evaporated. The residue was purified by flash chromatography with 5% methanol in methylene chloride to obtain 250 mg of title compound as a oil. T.l.c. (5% methanol in methylene chloride) $R_f$=0.2. Mass spec (NH$_3$/CI): 353(M+1).

Step F:

1-(R)-(Benzyloxy)-2-(S)-(4-fluorophenyl)-3-(S)-(1- and 2-methyltetrazol-5-ylmethyl)cyclopentane To a solution of 250 mg of product from Step E in 2.5 mL of DMF was added 10.092 mL of iodomethane and then 59 mg of 60% NaH in mineral oil. The reaction was stirred at room temperature for 20 h and then diluted with water and extracted twice with ethyl acetate. The organic layers were washed with a portion of brine, combined, dried over sodium sulfate and evaporated. The residue was purified by flash chromatography eluting with 20 to 40% ethyl acetate in hexanes to obtain 110 mg of the higher $R_f$ methylation product and 105 mg of the lower product. T.l.c. (40% ethyl acetate in hexanes) $R_f$=0.4 and 0.2. Mass specs (NH$_3$/CI): 367 (M+1).

Step G:

1-(R)-(Hydroxy)-2-(S)-(4-fluorophenyl)-3-(S)-(1- and 2-methyltetrazol-5-ylmethyl)cyclopentane A solution of 105 mg of the lower Rf product from Step F in 2 mL of methanol and 0.066 mL of HOAc was hydrogenated over 20 mg of 10% Pd/C at 40 psi for 20 h. The reaction was filtered and evaporated to afford 75 mg of the title compound as a white solid. T.l.c. (60% ethyl acetate in hexanes) $R_f$=0.2.

Step H:

1-(S)-(Azido)-2-(S)-(4-fluorophenyl)-3-(S)-(1- and 2-methyltetrazol-5-ylmethyl)cyclopentane To a solution of 130 mg of product from Step G in 4 mL of toluene was added 64 mg of imidazole, 246 mg of triphenylphosphine and 217 mg of zinc azide bispyridine. The solution was cooled in an ice bath and 0.155 mL of DEAD was slowly added via syringe. After 4.5 h, the reaction was filtered and concentrated. The residue was purified by flash chromatography eluting with 25% ethyl acetate in hexanes to obtain 80 mg of title compound as an oil. T.l.c. (60% ethyl acetate in hexanes) $R_f$=0.6.

Step I:

1-(S)-(Amino)-2-(S)-(4-fluorophenyl)-3-(S)-(1- and 2-methyltetrazol-5-ylmethyl)cyclopentane A solution of 80 mg of product from Step H in 2.5 mL of methanol was hydrogenated over 20 mg of 10% Pd/C at 40 psi for 20 h. The reaction was filtered and evaporated. T.l.c. (4% methanol in methylene chloride) R$_f$=0.1.

Step J:

1-(S)-((2-Methoxy-5-(5-trifluoromethyltetrazol-1-yl) phenyl)-methylamino)-2-(S)-(4-fluorophenyl)-3-(S)-(1-methyl-5-tetrazol-5-ylmethyl)-cyclopentane A solution of 40 mg of product from Step I, 0.028 mL of HOAc, 65 mg of 2-methoxy-5-(5-trifluoromethyltetrazol-1-yl)benzaldehyde (prepared as described in PCT Publication No. WO 95/08549, Intermediate 23 on page 35) and 1 g of 3A molecular sieves in 1.5 mL of methanol was stirred for 30 min and then 30 mg of sodium cyanoborohydride was added. The reaction was stirred at room temperature for 60 h and then quenched with 2N NaOH and extracted 3 times with methylene chloride. The organic layers were washed with a portion of brine, combined, dried over sodium sulfate and evaporated. The residue was purified on a 1 mm preparative silica gel plate eluting with 4% methanol in methylene chloride to obtain 15 mg of title compound. Mass spec (NH$_3$/CI): 532 (M+1). NMR (CDCl$_3$): δ 1.4–1.6 (m, 1H), 1.7–1.9 (m, 1H), 1.9–2.1 (m, 1H), 2.1–2.2 (m, 1H), 2.7–2.8 (m, 1H), 2.8–3.0 (m, 3H), 3.15 (m, 1H), 3.6 (ABq, 2H), 3.65 (s, 3H), 3.75 (s, 3H), 6.90 (d, 1H), 7.00 (t, 2H), 7.1–7.2 (m, 2H), 7.25 (d, 1H), 7.30 (dd, 1H).

EXAMPLE 88

1-(S)-((2-Methoxy-5-(5-trifluoromethyltetrazol-1-yl) phenyl)methylamino)-2-(S)-(4-fluorophenyl)-3-(S)-(2-methyl-5-tetrazol-5-ylmethyl)-cyclopentane Using essentially the same procedures as in Example 87, Steps G to J but using the higher product from Step F, the title compound was prepared. Mass spec (NH$_3$/CI): 532 (M+1). NMR (CDCl$_3$): δ 1.3–1.6 (m, 1H), 1.6–1.8 (m, 1H), 1.85–2.0 (m, 1H), 2.1–2.15 (m, 1H), 2.7–2.8 (m, 1H), 2.8–3.0 (m, 3H), 3.12 (m, 1H), 3.55 (ABq, 2H), 3.68 (s, 3H), 4.20 (s, 3H), 6.85 (d, 1H), 6.93 (t, 2H), 7.1–7.2 (m, 3H), 7.25 (dd, 1H).

EXAMPLE 89

Methyl 3-(S)-(2-methoxy-5-((5-trifluoromethyl) tetrazol-1-yl)phenyl)methylamino-2-(S)-(4-fluorophenyl)cyclopentane-1-(S)-carboxylate and methyl 3-(R)-(2-methoxy-5-((5-trifluoromethyl) tetrazol-1-yl)phenyl)methylamino-2-(R)-(4-fluorophenyl)cyclopentane-1-(R)-carboxylate Step A:

Methyl 3-(SR)-azido-2-(SR)-(4-fluorophenyl) cyclopentane-1-(SR)-carboxylate

A mixture of 5.00 g (8.5 mmol) of methyl 3-(RS)-hydroxy-2-(SR)-(4-fluoro)phenyl-1-(SR)-carboxylate (from Example 2), 11.00 g (42.0 mmol) of triphenylphosphine, 2.85 g (42.0 mmol) of imidazole and 9.70 g (31.5 mmol) zinc azide, bis(pyridine) complex in 150 mL of CH$_2$Cl$_2$ at 0° C. was treated with 7.30 g (42.0 mmol) of diethylazodicarboxylate. The cooling bath was removed and the reaction was stirred at rt for 20 h. The precipitated solids were filtered onto a pad of Celite and the filtrate was concentrated in vacuo. Flash chromatography on 400 g of silica gel afforded 4.52 g (82%) of the title compound as a solid. $^1$H NMR (500 MHz, CDCl$_3$): δ 1.96–2.02 (m, 2H), 2.17–2.22 (m, 1H), 2.26–2.32 (m, 1H), 3.22–3.28 (m, 1H), 3.49 (dd, J=4.5, 11.0, 1H), 3.61 (s, 3H), 4.13 (app t, J=5.0, 1H), 7.02 (t, J=8.5, 2H), 7.27 (t, J=8.5, 2H). IR (nujol): 2100 cm$^{-1}$.

Step B:

Methyl 3-(SR)-(2-methoxy-5-((5-trifluoromethyl) tetrazol-1-yl)phenyl)methylamino-2-(SR)-(4-fluorophenyl)-cyclopentane-1-(SR)-carboxylate A mixture of 150 mg of methyl 3-(SR)-azido-2-(SR)-(4-fluorophenyl)cyclopentane-1-(SR)-carboxylate (from Example 89, Step A) and 200 mg of 4A molecular sieves in 3 mL of THF was treated with 0.68 mL of 1.0M trimethylphosphine solution in THF and stirred at rt for 1h. 2-Methoxy-5-((5-trifluoromethyl)tetrazol-1-yl) benzaldehyde (186 mg) was added and the reaction allowed to stir at rt for 1 h. The volatiles were removed in vacuo. The residue was redissolved in 3 mL of MeOH, the reaction flask was flushed with nitrogen and 115 mg of Na(CN)BH$_3$ was added. After 30 min, the reaction was filtered through a short pad of celite, rinsed well with 200 mL of MeOH and concentrated in vacuo. The residue was partitioned between ethyl acetate and sat'd NaHCO$_3$ and the layers were separated. The organic layer was washed with a portion of brine, dried over MgSO$_4$ and concentrated. The residue was purified by flash chromatography eluting with 20% EtOAc in hexanes to obtain 176 mg of title compound as an oil. $^1$H NMR (500 MHz, CDCl$_3$): δ 1.82–1.85 (m, 1H), 1.94–2.05 (m, 2H), 2.27–2.33 (m, 1H), 3.23–3.24 (m, 1H), 3.41 (br q, 1H), 3.50–3.52 (m, 2H), 3.61 (s, 3H), 3.71 (s, 3H), 3.69–3.74 (m, 1H), 6.91–6.99 (m, 2H), 7.17–7.32 (m, 5H). Mass Spectrum (NH$_3$-CI): m/z 494 (M+H, 100%).

Step C:

Methyl 3-(S)-(2-methoxy-5-((5-trifluoromethyl)tetrazol-1-yl)phenyl)methylamino-2-(S)-(4-fluorophenyl)-cyclopentane-1-(S)-carboxylate and methyl 3-(R)-(2-methoxy-5-((5-trifluoromethyl)tetrazol-1-yl)phenyl) methylamino-2-(R)-(4-fluorophenyl)-cyclopentane-1-(R)-carboxylate The enantiomers of methyl 3-(SR)-(2-methoxy-5-((5-trifluoromethyl)tetrazol-1-yl)phenyl)methylamino-2-(SR)-(4-fluorophenyl)cyclopentane-1-(SR)-carboxylate (from Example 89, Step B) were resolved using semi-preparative HPLC. Conditions: Chiralpak AD® 2.0×25 cm column, 75/25 v/v hexanes/iPrOH, 9.0 mL/min, 220 nm. Retention times: Methyl 3-(S)-(2-methoxy-5-((5-trifluoromethyl)-tetrazol-1-yl)phenyl)methylamino-2-(S)-(4-fluorophenyl) cyclopentane-1-(S)-carboxylate, 13.6 min; methyl 3-(R)-(2-methoxy-5-((5-trifluoromethyl)tetrazol-1-yl)phenyl) methylamino-2-(R)-(4-fluorophenyl)-cyclopentane-1-(R)-carboxylate, 17.4 min.

EXAMPLE 90

3-(S)-(2-Methoxy-5-((5-trifluoromethyl)tetrazol-1-yl)phenyl)-methylamino-2-(S)-(4-fluorophenyl) cyclopentane-1-(S)-(N-t-butyl)carboxamide and 3-(R)-(2-methoxy-5-((5-trifluoromethyl)-tetrazol-1-yl) -phenyl)methylamino-2-(R)-(4-fluorophenyl) cyclopentane-1-(R)-(N-t-butyl)carboxamide Step A:

3-(SR)-Azido-2-(SR)-(4-fluorophenyl)cyclopentane-1-(SR)-(N-t-butyl)carboxamide

A solution of 147 mg of methyl 3-(SR)-azido-2-(SR)-(4-fluorophenyl)cyclopentane-1-(SR)-carboxylate (from Example 89, Step A) in 5 mL of MeOH was treated with 2.0 mL of 5.0N NaOH. The reaction was stirred at rt for 18 h, diluted with H$_2$O and acidified with 2.0N HCl. The mixture was extracted twice with ether and the organic layers were washed with sat'd NaCl, combined, dried with MgSO$_4$ and evaporated. The residue was redissolved in 3 mL of CH$_2$Cl$_2$, cooled to 0° C. and treated with 0.66 mL of oxalyl chloride and 2 drops of DMF. After 30 minutes, the cooling bath was removed and the volatiles were evaporated under a stream of nitrogen. The residue was taken up in 5 mL of CH$_2$Cl$_2$, cooled to 0° C. and treated with 0.61 mL of t-butylamine. After 45 min, the reaction was diluted with water and acidified with 2.0N HCl. The mixture was extracted twice with ether and the organic layers were washed with a portion of sat'd NaHCO$_3$ and then sat'd NaCl, combined, dried with MgSO$_4$ and evaporated. The residue was purified by flash chromatography eluting with 25% EtOAc in hexanes to obtain 159 mg of title compound as an oil. $^1$H NMR (500 MHz, CDCl$_3$): δ 1.18 (m, 9H), 1.98–2.02 (m, 1H), 2.10–2.22 (m, 3H), 2.81 (q, 1H), 3.37 (dd, 1H), 4.14 (br t, 1H), 4.99 (br s, 1H), 7.05 (t, 2H), 7.30–7.33 (m, 2H). Mass Spectrum (NH$_3$-CI): m/z 305 (M+H, 20%).

Step B:

3-(SR)-(2-Methoxy-5-((5-trifluoromethyl)tetrazol-1-yl) phenyl)methylamino-2-(SR)-(4-fluorophenyl)-cyclopentane-1-(SR)-(N-t-butyl)carboxamide The title compound was prepared from 3-(SR)-azido-2-(SR)-(4-fluorophenyl)-cyclopentane-1-(SR)-(N-t-butyl) carboxamide (from Example 90, Step A) using a procedure analogous to that described in Example 89, Step B. $^1$H NMR (500 MHz, CDCl$_3$): δ 1.22 (s, 9H), 1.8–1.85 (m, 1H), 1.98–2.06 (m, 2H), 2.16–2.20 (m, 1H), 3.00 (br q, 1H), 3.25–3.28 (m, 1H), 3.45–3.48 (m, 1H), 3.53 (d, 1H), 3.73 (s, 3H), 3.73–3.75 (m, 1H), 5.11 (br s, 1H), 6.92 (d, 1H), 7.00 (t, 2H), 7.21–7.33 (m, 4H). Mass Spectrum (NH$_3$-CI): m/z 535 (M+H, 100%).

Step C:

3-(S)-(2-Methoxy-5-((5-trifluoromethyl)tetrazol-1-yl) phenyl)methylamino-2-(S)-(4-fluorophenyl)cyclopentane-1-(S)-(N-t-butyl)carboxamide and 3-(R)-(2-methoxy-5-((5-trifluoromethyl)tetrazol-1-yl)phenyl)-methylamino- 2-(R)-(4-fluorophenyl)cyclopentane-1-(R)-(N-t-butyl) carboxamide The enantiomers of 3-(SR)-(2-methoxy-5-((5-trifluoromethyl)tetrazol-1-yl)phenyl)methylamino-2-(SR)-(4-fluorophenyl)cyclopentane-1-(SR)-(N-t-butyl) carboxamide (from Example 90, Step B) were resolved using semi-preparative HPLC. Conditions: Chiralpak AD® 2.0×25 cm column, 75/25 v/v hexanes/iPrOH, 9.9 mL/min, 220 nm. Retention times: 3-(S)-(2-Methoxy-5-((5-trifluoromethyl)tetrazol-1-yl)phenyl)methylamino-2-(S)-(4-fluorophenyl)cyclopentane-1-(S)-(N-t-butyl)carboxamide, 10.4 min; 3-(R)-(2-methoxy-5-((5-trifluoromethyl)tetrazol-1-yl)phenyl)methylamino-2-(R)-(4-fluorophenyl) cyclopentane-1-(R)-(N-t-butyl)carboxamide, 17.4 min.

EXAMPLE 91

N-(2-Methoxy-5-((5-trifluoromethyl)tetrazol-1-yl) phenyl)methyl)-3-(SR)-(imidazol-2-yl)-2-(SR)-(4-fluorophenyl)cyclopentan-1-(SR)-amine Step A:

3-(SR)-azido-2-(SR)-(4-fluorophenyl)-cyclopentanemethanol-1-(SR)-methanol

A solution of 694 mg (2.6 mmol) of methyl 3-(SR)-azido-2-(SR)-(4-fluorophenyl)cyclopentane-1-(SR)-carboxylate (from Example 89, Step A) in 10 mL of CH$_2$Cl$_2$ at 0° C. was treated with 4.0 mL of 1.5M diisobutylaluminum hydride solution in toluene. The cooling bath was removed and the reaction mixture was stirred at rt for 3 h. The reaction was quenched with 10 mL of saturated sodium potassium tartrate solution; the resulting mixture was diluted with 20 mL of ether and 10 mL of H$_2$O and stirred at rt for 1 h. The mixture was partitioned between 100 mL of ether and 25 mL of H$_2$O and the layers were separated. The organic layer was washed with 25 mL of sat'd NaCl and dried over MgSO$_4$. The aqueous layers were combined and extracted with 100 mL of ether; the extract was dried and combined with the original organic extract. The combined extracts were concentrated in vacuo. Flash chromatography on 30 g of silica gel using 3:1 v/v hexanes/ether as the eluant gave 515 mg (83%) of the title cpd. as an oil. $^1$H NMR (500 MHz, CDCl$_3$): δ 1.43 (br s, 1H), 1.60–1.68 (m, 1H), 1.91–1.98 (m, 1H), 2.04–2.15 (m, 2H), 2.52 (m, 1H), 2.96 (dd, J=10.5, 5.0, 1H), 3.47 (dd, J=11.0, 5.0, 1H), 3.63 (dd, J=11.0, 5.0, 1H), 4.02–4.04 (m, 1H), 7.02 (app t, J=8.5, 2H), 7.26–7.29 (m, 2H).

Step B:

3-(SR)-Azido-2-(SR)-(4-fluorophenyl)-(SR)-cyclopentanecarboxaldehyde

A solution of 0.38 mL (4.4 mmol) of oxalyl chloride in 15 mL of CH$_2$Cl$_2$ at –78° C. was treated with a solution of 0.46 mL (6.6 mmol) of DMSO in 1.0 mL of CH$_2$Cl$_2$, maintaining the temperature of the reaction mixture at <–60° C. The resulting mixture was stirred cold for 5 min, then was treated with a solution of 510 mg (2.2 mmol) of 3-(SR)-azido-2-(SR)-(4-fluorophenyl)-cyclopentane-1-(SR)-methanol (from Example 91, Step A) in 3 mL of CH$_2$Cl$_2$, maintaining the temperature of the reaction mixture at <–60° C. The resulting mixture was stirred cold for 30 min, then was treated with 3.80 mL (22.0 mmol) of N,N-diisopropylethylamine, maintaining the temperature of the reaction mixture at <–60° C. The resulting mixture was stirred cold for 5 min, warmed to 0° C. and quenched with 15 mL of 2.0N HCl solution. The mixture was partitioned between 60 mL of CH$_2$Cl$_2$ and 15 mL H$_2$O and the layers were separated. The aqueous layer was extracted with 30 mL of CH$_2$Cl$_2$ and the organic layers were combined. The combined organic layers were washed with 2×30 mL of H$_2$O , dried over MgSO$_4$ and concentrated in vacuo. Flash chromatography on 25 g of silica gel using 9:1 v/v hexanes/ether afforded 445 mg (88%) of the title cpd. as an oil. $^1$H NMR (500 MHz, CDCl$_3$): δ 2.00–2.10 (m, 3H), 2.17–2.24 (m, 1H), 3.28–3.34 (m, 1H), 3.46 (dd, J=10.5, 5.0, 1H), 4.14–4.17 (m, 1H), 7.04 (app t, J=8.5, 2H), 7.28–7.32 (m, 2H), 9.65 (d, J=2.5, 1H).

Step C:

1-(SR)-Azido-2-(SR)-(4-fluoro)phenyl-3-(SR)-(imidazol-2-yl)cyclopentane

A mixture of 290 mg (1.24 mmol) of 3-(SR)-azido-2-(SR) -(4-fluorophenyl)-(SR)-cyclopentanecarboxaldehyde (from Example 91, Step B) and 90 mg (0.43 mmol) of glyoxal trimer dihydrate in 5 mL of MeOH at 0° C. was treated with 2.0 mL of 2.0M ammonia in MeOH solution. The cooling bath was removed and the reaction mixture was stirred at rt for 20 h. The reaction mixture was concentrated in vacuo . Flash chromatography on 12 g of silica gel using 40:1:0.1 CH$_2$Cl$_2$/MeOH/NH$_4$OH as the eluant afforded 250 mg (70%) of the title compound as a solid. $^1$H NMR (500 MHz, CDCl$_3$): δ 2.00–2.06 (m, 1H), 2.20–2.34 (m, 2H), 2.36–2.44 (m, 1H), 3.51 (dd, J=11.5, 5.0, 1H), 3.61–3.66 (m, 1H), 4.16–4.19 (m, 1H), 6.56 (s, 2H), 7.00 (app t, J=8.5, 1H), 7.27–7.30 (m, 2H). Mass Spectrum (NH$_3$-CI): m/z 272 (M+H, 10%), 244 (M-N$_2$+H, 100%).

Step D:

N-(2-Methoxy-5-((5-trifluoromethyl)tetrazol-1-yl) phenyl)methyl)-3-(SR)-(imidazol-2-yl)-2-(SR)-(4-fluorophenyl)cyclopentane-1-(SR)-amine A mixture of 114 mg (0.42 mmol) of 1-(SR)-azido-2-(SR) -(4-fluoro)phenyl-3-(SR)-(imidazol-2-yl)cyclopentane (from Example 91, Step C) and 250 mg of powdered 4 Å molecular sieves in 4 mL of THF under N$_2$ was treated with 0.50 mL of 1.0M of trimethyl-phosphine solution in THF. After 1 h, 125 mg (0.46 mmol) of 2-methoxy-5-((5-trifluoromethyl)tetrazol-1-yl)benzaldehyde was added to the reaction mixture in one portion as a solid and the resulting mixture was stirred at rt for 1 h. The reaction mixture was concentrated in vacuo and the residue was taken up in 4 mL of MeOH. The resulting mixture was treated with 62 mg (1.0 mmol) of Na(CN)BH$_3$ and 60 μL (1.0 mmol) of HOAc and stirred at rt for 0.5 h. The reaction mixture was filtered through a pad of Celite; the reaction flask and filtered solids were rinsed well with MeOH (~100 mL) and the filtrate was concentrated in vacuo. The residue was partitioned between 50 mL 1:1 v/v EtOAc/ether and 25 mL of sat'd NaHCO$_3$ and the layers were separated. The organic layer was washed with 25 mL of sat'd NaCl, dried over MgSO$_4$ and concentrated in vacuo. Flash chromatography on 10 g of silica gel using 50:1:0.1 v/v/v CH$_2$Cl$_2$/MeOH/NH$_4$OH afforded 174 mg (83%) of the title cpd. as a foam. $^1$H NMR (500 MHz, CDCl$_3$): δ 1.80–1.86 (m, 1H), 2.08–2.17 (m, 2H), 2.37–2.45 (m, 1H), 3.29–3.31 (m, 1H), 3.49 (d, J=15.0, 1H), 3.55 (dd, J=11.0, 6.0, 1H), 3.72 (s, 3H), 3.72 (d, J=15.0, 1H), 3.76–3.82 (m, 1H), 6.86 (s, 2H), 6.91 (d, J=9.0, 1H), 6.95 (app t, J=8.5, 2H), 7.20–7.23 (m, 3H), 7.30 (dd, J=8.5, 2.5, 1H). Mass Spectrum (NH$_3$-CI): m/z 502 (M+H, 15%).

EXAMPLE 92

N-(2-Methoxy-5-((5-trifluoromethyl)tetrazol-1-yl) phenyl)methyl)-3-(SR)-((1-methyl)imidazol-2-yl)-2-(SR)-(4-fluorophenyl)cyclopentane-1-(SR)-amine Step A:

1-(SR)-Azido-2-(SR)-(4-fluoro)phenyl-3-(SR)-((1-methyl)imidazol-2-yl)cyclopentane A mixture of 106 mg (0.39 mmol) of 1-(SR)-azido-2-(SR)-(4-fluoro)phenyl-3-(SR)-(imidazol-2-yl)cyclopentane (from Example 91, Step C), 81 mg (0.59 mmol) of K$_2$CO$_3$ and 11 mg (0.04 mmol) of 18-crown-6 in 3 mL of dimethylcarbonate was stirred in an oil bath set at 90° C. The reaction mixture was treated with additional portions of K$_2$CO$_3$ (200 mg) and 18-crown-6 (25 mg) after 4 h and after 20 h. After 6 h, the reaction mixture was cooled, partitioned between 50 mL of ether and 25 mL of H$_2$O and the layers were separated. The organic layer was dried over MgSO$_4$. The aqueous layer was extracted with 50 mL of CH$_2$Cl$_2$; the extract was dried and combined with the original organic extract. The combined extracts were concentrated in vacuo. Flash chromatography on 7 g of silica gel using 200:3:0.3 v/v/v CH$_2$Cl$_2$/MeOH/NH$_4$OH as the eluant afforded 99 mg (89%) of the title compound as a solid. $^1$H NMR (500 MHz, CDCl$_3$): δ 2.01–2.08 (m, 2H), 2.31–2.39 (m, 2H), 3.43 (s, 3H), 3.57 (app q, J=9.0, 1H), 3.82 (dd, J=10.5, 5.0, 1H), 4.24 (m, 1H), 6.68 (s, 1H), 6.90 (s, 1H), 6.96 (app t, J=8.5, 2H), 7.26 (app t, J=8.5, 2H). Mass Spectrum (NH$_3$-CI): m/z 286 (M+H, 15%), 258 (M-N$_2$+H).

Step B:

N-(2-Methoxy-5-((5-trifluoromethyl)tetrazol-1-yl) phenyl)methyl)-3-(SR)-((1-methyl)imidazol-2-yl)-2-(SR)-(4-fluorophenyl)cyclopentane-1-(SR)-amine The title compound was prepared in 89% yield from 1-(SR)-azido-2-(SR)-(4-fluoro)phenyl-3-(SR)-((1-methyl) imidazol-2-yl)cyclopentane (from Example 92, Step A) using a procedure analogous to that described in Example 91, Step D.

EXAMPLE 93

N-(2-Methoxy-5-((5-trifluoromethyl)tetrazol-1-yl) phenyl)methyl)-3-(SR)-(thiazol-2-yl)-2-(SR)-(4-fluorophenyl)cyclopentan-1-(SR)-amine Step A:

3-(SR)-Azido-2-(SR)-(4-fluorophenyl)cyclopentane-1-(SR)-carboxamide

A mixture of 775 mg (2.9 mmol) of methyl 3-(SR)-azido-2-(SR)-(4-fluoro)phenyl-1-(SR)-carboxylate (from Example 89, Step A), 5 mL of 2.0M sodium methoxide in methanol and 3 mL of formamide was stirred at 70° C. for 2 h. The reaction was cooled and partitioned between 100 mL of 1:1 v/v ether/EtOAc and 50 mL of 50% sat'd NaHCO$_3$ and the layers were separated. The organic layer was washed with 3×50 mL of water, dried over MgSO$_4$ and concentrated in vacuo. Flash chromatography on 30 g of silica gel using 4:1 v/v CH$_2$Cl$_2$/EtOAc as the eluant afforded 701 mg (97%) of the title compound as a solid. $^1$H NMR (400 MHz, CDCl$_3$): δ 1.97–2.26 (m, 4H), 3.00–3.08 (m, 2H), 3.45 (dd, J=4.8, 10.8, 1H), 4.12–4.14 (m, 1H), 5.34 (br s, 1H), 5.58 (br s, 1H), 7.01–7.06 (m, 2H), 7.29–7.33 (m, 2H). Mass Spectrum (NH$_3$-CI): m/z 249 (M+H, 18%), 174 (100%).

Step B:

3-(SR)-Azido-2-(SR)-(4-fluorophenyl)cyclopentane-1-(SR)-thiocarboxamide

A mixture of 643 mg (2.6 mmol) of 3-(SR)-azido-2-(SR)-(4-fluoro)phenyl-1-(SR)-carboxamide (from Example 93, Step A) and 600 mg (1.5 mmol) of Lawesson's reagent in 8 mL of THF was stirred at rt for 20 h. The reaction mixture was partitioned between 100 mL of ether and 50 mL sat'd NaHCO$_3$ and the layers were separated. The organic layer was washed with 50 mL of sat'd NaCl, dried over MgSO$_4$ and concentrated in vacuo. Flash chromatography on 25 g of silica gel using 2:1 v/v hexanes/ether as the eluant afforded 410 mg (60%) of the title cpd. as a solid. $^1$H NMR (500 MHz, CDCl$_3$): δ 2.00–2.04 (m, 1H), 2.23–2.34 (m, 3H), 3.30–3.35 (m, 1H), 3.66 (dd, J=5.0, 11.0, 1H), 4.17 (app t, J=10.0, 1H), 6.70 (br s, 1H), 7.02 (app t, J=8.5, 2H), 7.31 (m, 2H). Mass Spectrum (NH$_3$-CI): m/z 265 (M+H, 15%), 203 (100%).

Step C:

1-(SR)-Azido-2-(SR)-(4-fluoro)phenyl-3-(SR)-(thiazol-2-yl)cyclopentane

A solution of 264 mg (1.0 mmol) of 3-(SR)-azido-2-(SR)-(4-fluorophenyl)cyclopentane-1-(SR)-thiocarboxamide (from Example 93, Step B) and 0.50 mL of bromoacetaldehyde, dimethyl acetal in 8 mL of iPrOH was stirred at 100° C. for 20 h. The reaction mixture was cooled and partitioned between 75 mL of ether and 25 mL of sat'd NaHCO$_3$. The layers were separated and the organic layer was washed with 25 mL of sat'd NaCl, dried over MgSO$_4$ and concentrated in vacuo. Flash chromatography on 15 g of silica gel using 20:1 v/v then 9:1 v/v hexanes/ether as the eluant afforded 211 mg (73%) of the title compound as a solid. $^1$H NMR (500 MHz, CDCl$_3$): δ 2.02–2.08 (m, 1H), 2.12–2.20 (m, 1H), 2.32–2.39 (m, 1H), 2.48–2.56 (m, 1H), 3.57 (dd, J=11.5, 5.0, 1H), 3.99 (app q, J=11.5, 1H), 4.21 (app t, J=5.5, 1H), 7.00 (app t, J=11.5, 2H), 7.09 (d, J=3.5, 1H), 7.28–7.31 (m, 2H), 7.63 (d, J=3.5, 1H). Mass Spectrum (NH$_3$-CI): m/z 289 (M+H, 15%), 261 (M-N$_2$+H, 100%).

Step D:

N-(2-Methoxy-5-((5-trifluoromethyl)tetrazol-1-yl) phenyl)methyl)-3-(SR)-(thiazol-2-yl)-2-(SR)-(4-fluorophenyl)cyclopentan-1-(SR)-amine The title compound was prepared in 90% yield from 1-(SR)-azido-2-(SR)-(4-fluoro)phenyl-3-(SR)-(thiazol-2-yl) cyclopentane (from Example 93, Step C) using a procedure analogous to that described in Example 91, Step D. $^1$H NMR (500 MHz, CDCl$_3$): δ 1.34 (br s, 1H), 1.82–1.92 (m, 1H), 2.04–2.18 (m, 2H), 2.48–2.56 (m, 1H), 3.31–3.33 (m, 1H), 3.52 (d, J=15.0, 1H), 3.59 (dd, J=11.0, 5.5, 1H), 3.71 (s, 3H), 3.75 (d, J=15.0, 1H), 4.15 (app q, J=9.5, 1H), 6.91 (d, J=8.5, 1H), 6.95 (t, J=8.5, 2H), 7.09 (d, J=3.0, 1H), 7.20–7.25 (m, 2H), 7.31 (dd, J=8.5, 1H), 7.61 (d, J=3.0, 1H).

EXAMPLE 94

N-(2-Methoxy-5-((5-trifluoromethyl)tetrazol-1-yl)
phenyl)methyl)-3-(S)-(thiazol-2-yl)-2-(S)-(4-
fluorophenyl)cyclopentan-1-(S)-amine Step A:

1-(S)-Azido-2-(S)-(4-fluoro)phenyl-3-(S)-(thiazol-2-yl)
cyclopentane

The enantiomers of 1-(SR)-azido-2-(SR)-(4-fluoro)
phenyl-3-(SR)-(thiazol-2-yl)cyclopentane (from Example 93, Step C) were resolved using semi-preparative HPLC. Conditions: Chiralpak AD® 2.0×25 cm column, 95/5 v/v hexanes/iPrOH, 9.0 mL/min, 240 nm. Retention times: 1-(S)-azido-2-(S)-(4-fluoro)phenyl-3-(S)-(thiazol-2-yl) cyclopentane, 13.8 min; 1-(R)-azido-2-(R)-(4-fluoro) phenyl-3-(R)-(thiazol-2-yl)cyclopentane, 17.4 min.

Step B:

N-(2-Methoxy-5-((5-trifluoromethyl)tetrazol-1-yl)
phenyl)methyl)-3-(S)-(thiazol-2-yl)-2-(S)-(4-fluorophenyl)
cyclopentan-1-(S)-amine The title compound was prepared in 89% yield from 1-(S)-azido-2-(S)-(4-fluoro)phenyl-3-(S)-(thiazol-2-yl) cyclopentane (from Example 94, Step A) using a procedure analogous to that described in Example 91, Step D. HPLC: Zorbax C8 Rx column, 50/50 to 100/0 MeCN/$H_2O$ gradient over 20 min, 1.0 mL/min, 210 nm. Retention time: 4.7 min.

EXAMPLE 95

N-(2-Methoxy-5-((5-trifluoromethyl)tetrazol-1-yl)
phenyl)methyl)-3-(SR)-(4-((N-methyl)carboxamido)
thiazol-2-yl)-2-(SR)-(4-fluorophenyl)cyclopentan-1-
(SR)-amine Step A:

1-(SR)-Azido-2-(SR)-(4-fluoro)phenyl-3-(SR)-(4-
(carboethoxy)thiazol-2-yl)cyclopentane A solution of 508 mg (1.9 mmol) of 3-(SR)-azido-2-(SR)
-(4-fluorophenyl)cyclopentane-1-(SR)-thiocarboxamide (from Example 93, Step B) and 0.5 mL (4.0 mmol) of ethyl bromopyruvate in 10 mL of iPrOH was stirred at 80° C. for 30 min. The mixture was cooled and concentrated in vacuo. The residue was partitioned between 75 mL of ether and 25 mL of sat'd $NaHCO_3$ and the layers were separated. The organic layer was washed with 25 mL of 0.5N $KHSO_4$, 25 mL of sat'd NaCl, dried over $MgSO_4$ and concentrated in vacuo. Flash chromatography on 20 g of silica gel using 2:1 v/v, then 1:1 v/v hexanes/ether as the eluant afforded 398 mg (58%) of the title compound as an oil. $^1$H NMR (400 MHz, $CDCl_3$): δ 1.38 (t, J=6.8, 3H), 2.14–2.19 (m, 1H), 2.34–2.46 (m, 3H), 3.85 (app t, J=7.2, 1H), 4.09–4.15 (m, 1H), 4.39 (q, J=7.2, 2H), 4.39–4.46 (m, 1H), 6.87–6.92 (m, 2H), 7.00–7.05 (m, 2H), 7.89 (s, 1H). Mass Spectrum ($NH_3$-CI): m/z 361 (M+H, 70%), 333 (M-$N_2$+H, 100%).

Step B:

1-SR)-Azido-2-(SR)-(4-fluoro)phenyl-3-(SR)-(4-(N-
methyl)carboxamido)-thiazol-2-yl)cyclopentane A solution of 395 mg (1.1 mmol) of 1-(SR)-azido-2-(SR) -(4-fluoro)phenyl-3-(SR)-(4-(carboethoxy)thiazol-2-yl) cyclopentane (from Example 95, Step A) in 5 mL of EtOH at 0° C. was treated with 1.0 mL of 5.0N NaOH, the cooling was removed and the resulting solution was stirred rt for 30 min. The reaction mixture was concentrated in vacuo to ~1 mL volume, partitioned between 50 mL of EtOAc and 25 mL of 2.0N HCl and the layers were separated. The organic layer was washed with 25 mL of sat'd NaCl, dried over $MgSO_4$ and concentrated in vacuo. A solution of the crude carboxylic acid in 5 mL of $CH_2Cl_2$ was treated with 0.5 mL of oxalyl chloride and 1 drop of DMF and stirred at rt for 30 min. The solution was concentrated in vacuo. The residue was redissolved in 2×20 mL ether and concentrated in vacuo. A solution of the crude acid chloride in 5.0 mL of THF at 0° C. was treated with 10.0 mL of 2.0M $CH_3NH_2$, the cooling was removed and the resulting solution was stirred at rt for 30 min. The reaction mixture was partitioned between 50 mL of EtOAc and 25 mL of 2.0N HCl and the layers were separated. The organic layer was washed with 25 mL sat'd $NaHCO_3$, 25 mL of sat'd NaCl, dried over $MgSO_4$ and concentrated in vacuo. Flash chromatography on 20 g of silica gel using 1:1 v/v, then 3:1 v/v EtOAc hexanes afforded 292 mg (77%) of the title compound as an oil. $^1$H NMR (500 MHz, $CDCl_3$): δ 2.16–2.23 (m, 1H), 2.28–2.42 (m, 2H), 2.53–2.61 (m, 1H), 2.98 (d, J=5.0, 3H), 3.75 (app t, J=7.5, 1H), 3.93 (app q, J=8.5, 1H), 4.36 (app q, J=6.5, 1H), 6.87 (t, J=8.5, 2H), 6.97–7.00 (m, 2H), 7.18 (br s, 1H), 7.82 (s, 1H). Mass Spectrum ($NH_3$-CI): m/z 318 (M-$N_2$+H, 100%).

Step C:

N-(2-Methoxy-5-((5-trifluoromethyl)tetrazol-1-yl)
phenyl)-methyl)-3-(SR)-(4-((N-methyl)carboxamido)
thiazol-2-yl)-2-(SR)-(4-fluorophenyl)cyclopentan-1-(SR)-
amine The title compound was prepared in 79% yield from 1-(S)-azido-2-(S)-(4-fluoro)phenyl-3-(S)-(4-((N-methyl) carboxamido)thiazol-2-yl)cyclopentane (from Example 95, Step B) using a procedure analogous to that described in Example 93, Step D. $^1$H NMR (500 MHz, $CDCl_3$): δ 1.86–1.96 (m, 1H), 2.31–2.43 (m, 3H), 2.97 (d, 3H), 3.77 (s, 3H), 3.67–3.93 (m, 5H), 6.88–7.37 (m, 8H), 7.77 (s, 1H). Mass Spectrum ($NH_3$-CI): m/z 576 (M+H, 100%).

EXAMPLE 96

N-(2-Methoxy-5-((5-trifluoromethyl)tetrazol-1-yl)
phenyl)methyl)-3-(SR)-(4-((N,N-dimethyl)
carboxamido)thiazol-2-yl)-2-(SR)-(4-fluorophenyl)
cyclopentan-1-(SR)-amine The title compound was prepared using procedures analogous to those described in Example 95 substituting dimethylamine for methylamine in Step B. $^1$H NMR (500 MHz, $CDCl_3$): δ 1.87–1.93 (m, 1H), 2.32–2.48 (m, 3H), 2.95 & 3.04 (br d, 6H), 3.79 (s, 3H), 3.67–3.99 (m, 5H), 6.86–7.37 (m, 8H), 7.56 (s, 1H). Mass Spectrum ($NH_3$-CI): m/z 590 (M+H, 100%).

EXAMPLE 97

N-(2-Methoxy-5-((5-trifluoromethyl)tetrazol-1-yl)
phenyl)methyl)-3-(SR)-(isoxazol-3-yl)-2-(SR)-(4-
fluorophenyl)cyclopentan-1-(SR)-amine Step A:

N-Methyl-N-methoxy 3-(SR)-azido-2-(SR)-(4-
fluorophenyl)cyclopentane-1-(SR)-carboxamide A solution of 500 mg (1.9 mmol) methyl 3-(SR)-azido-2-(SR)-(4-fluorophenyl)-cyclopentane-1-(SR)-carboxylate (from Example 89, Step A) in 10 mL of 1:1 v/v THF/MeOH at 0° C. was treated with 3.0 mL of 5.0N NaOH. The cooling bath was removed and the mixture was stirred at rt for 45 min. The reaction was concentrated to ~3 mL volume in vacuo, acidified with 20 mL of 2.0N HCl and extracted with 75 mL of EtOAc. The extract was washed with 25 mL of sat'd NaCl, dried over $MgSO_4$ and concentrated in vacuo. A solution of the crude carboxylic acid in 15 mL of $CH_2Cl_2$ was treated with 2.5 mL of oxalyl chloride and 2 drops of DMF. The resulting solution was stirred at rt for 1 h and concentrated in vacuo. The residue was dissolved in 2×25 mL of ether and concentrated in vacuo. A mixture of 488 mg

131

(5.0 mmol) of O,N-dimethylhydroxylamine×HCl in 5 mL of 1:1 v/v $CH_2Cl_2$/pyridine at 0° C. was treated with a solution of the crude acid chloride in 5 mL of $CH_2Cl_2$. The cooling bath was removed and the reaction mixture was stirred at rt for 2 h. The reaction was concentrated in vacuo and the residue was partitioned between 75 mL of ether and 25 mL of 2.0N HCl and the layers were separated. The organic layer was washed with 25 mL of sat'd $NaHCO_3$, 25 mL of sat'd NaCl, dried over $MgSO_4$ and concentrated in vacuo. Flash chromatography on 25 g of silica gel using 3:2 v/v hexanes/ether as the eluant afforded 518 mg (93%) of the title compound as an oil. $^1H$ NMR (400 MHz, $CDCl_3$): δ 1.82–1.92 (m, 1H), 1.98–2.06 (m, 1H), 2.16–2.34 (m, 2H), 3.13 (s, 3H), 3.63 (s, 3H), 3.64–3.67 (m, 1H), 4.16–4.20 (m, 1H), 7.00 (t, J=8.4, 2H), 7.28–7.31 (m, 2H).

Step B:

3-(SR)-Azido-2-(SR)-(4-fluorophenyl)-1-(SR)-(3-1-oxo-2-propynyl)cyclopentane

A solution of 515 mg (1.8 mmol) of N-methyl-N-methoxy 3-(SR)-azido-2-(SR)-(4-fluorophenyl)cyclopentane-1-(SR)-carboxamide (from Example 97, Step A) in 8 mL of THF at −78° C. was treated with 2.2 mmol of lithio trimethylsilylacetylene (prepared by treating a solution of 250 mg (2.5 mmol) of trimethylsilylacetylene in 3 mL of THF at −78° C. with 1.4 mL of 1.6M-n-butyllithium solution in hexanes). The reaction was warmed to −15° C. and stirred for 30 min. The reaction mixture was quenched with 25 mL of sat'd $NH_4Cl$ and extracted with 75 mL of ether. The extract was washed with 25 mL of sat'd NaCl, dried over $MgSO_4$ and concentrated in vacuo. Flash chromatography on 25 g of silica gel using 17:3 v/v, then 2:1 v/v hexanes/$CH_2Cl_2$ afforded 343 mg (25%) of the title compound as an oil.

$^1H$ NMR (500 MHz, $CDCl_3$): δ 0.18 (s, 9H), 1.98–2.06 (m, 1H), 2.08–2.20 (m, 2H), 2.26–2.38 (m, 1H), 3.42–3.62 (m, 2H), 4.12–4.18 (m, 1H), 7.03 (t, J=8.5, 2H), 7.27–7.30 (m, 2H).

Step C:

3-(SR)-Azido-2-(SR)-(4-fluorophenyl)-1-(SR)-(3,3-dimethoxy-1-oxo-propyl)cyclopentane A solution of 340 mg (1.1 mmol) 3-(SR)-azido-2-(SR)-(4-fluorophenyl)-1-(SR)-(3-trimethylsilyl-1-oxo-2-propynyl)cyclopentane (from Example 97, Step B) and 0.50 mL (2.9 mmol) of N,N-diisopropylethylamine in 5 mL of MeOH was stirred at rt for 20 h. The reaction mixture was partitioned concentrated in vacuo, the residue was partitioned between 50 mL of ether and 25 mL of 0.5N $KHSO_4$ and the layers were separated. The organic layer was washed with 25 mL of sat'd $NaHCO_3$, 25 mL of sat'd NaCl, dried over $MgSO_4$ and concentrated in vacuo. Flash chromatography on 12 g of silica gel using 4:1 v/v hexanes/ether as the eluant afforded 133 mg (37%) of the title compound as an oil. $^1H$ NMR (500 MHz, $CDCl_3$): δ 1.84–1.94 (m, 1H), 1.98–2.14 (m, 2H), 2.22–2.32 (m, 1H), 2.61–2.70 (m, 2H), 3.26 (s, 3H), 3.29 (s, 3H), 3.42–3.53 (m, 2H), 4.10–4.12 (m, 1H), 4.70 (t, J=6.0, 1H), 7.01 (t, J=8.5, 2H), 7.26–7.28 (m, 2H).

Step D:

3-(SR)-Azido-2-(SR)-(4-fluorophenyl)-1-(SR)-(isoxazol-3-yl)cyclopentane

A solution of 130 mg (0.40 mmol) of 3-(SR)-azido-2-(SR)-(4-fluorophenyl)-1-(SR)-(3,3-dimethoxy-1-oxo-propyl)cyclopentane (from Example 97, Step C) in 3 mL of pyridine was treated with 150 mg (2.2 mmol) of hydroxylamine×HCl and stirred at rt for 3 h. The reaction mixture was partitioned between 50 mL of ether and 25 mL of 2.0N HCl and the layers were separated. The organic layer was washed with 25 mL of sat'd $NaHCO_3$, 25 mL of

132 sat'd NaCl, dried over $MgSO_4$ and concentrated in vacuo. A mixture of the crude ketoxime and 200 mg of Amberlyst 15 $H^+$ resin in 4 mL of acetone was heated at reflux for 2 h. The mixture was cooled, the resin filtered and the filtrate concentrated in vacuo. Flash chromatography on 7 g of silica gel using 10:1 v/v hexanes/ether as the eluant afforded 79 mg (72%) of the title compound.

$^1H$ NMR (500 MHz, $CDCl_3$): δ 2.02–2.08 (m, 2H), 2.26–2.34 (m, 1H), 2.40–2.48 (m, 1H), 3.38 (dd, J=6.5, 5.0, 1H), 3.71–3.77 (m, 1H), 4.18–4.20 (m, 1H), 6.00 (d, J=1.5, 1H), 7.01 (t, J=8.5, 2H), 7.25–7.30 (m, 2H), 8.22 (d, J=1.5, 1H). Mass Spectrum ($NH_3$-CI): m/z 273 (M+H, 25%).

Step E:

N-(2-Methoxy-5-((5-trifluoromethyl)tetrazol-1-yl) phenyl)methyl)-3-(SR)-(isoxazol-3-yl)-2-(SR)-(4-fluorophenyl)cyclopentan-1-(SR)-amine The title compound was prepared in 86% yield from 1-(SR)-azido-2-(SR)-(4-fluoro)phenyl-3-(SR)-(isoxazol-3-yl)cyclopentane (from Example 97, Step D) using a procedure analogous to that described in Example 91, Step D. $^1H$ NMR (500 MHz, $CDCl_3$): δ 1.48 (br s, 1H), 1.84–1.98 (m, 2H), 2.04–2.12 (m, 1H), 2.44–2.54 (m, 1H), 2.27–2.30 (m, 1H), 3.40 (dd, J=11.0, 6.0, 1H), 3.52 (d, J=15.0, 1H), 3.71 (s, 3H), 3.75 (d, J=15.0, 1H), 3.90 (app q, J=10.0, 1H), 6.07 (s, 1H), 6.91 (d, J=9.0, 1H), 6.95 (t, J=8.5, 2H), 7.19–7.21 (m, 3H), 7.31 (d, J=9.0, 1H), 8.22 (s, 1H). Mass Spectrum ($NH_3$-CI): m/z 503 (M+H, 100%).

EXAMPLE 98

N-(2-Methoxy-5-((5-trifluoromethyl)tetrazol-1-yl) phenyl)methyl)-3-(S)-(5-methyl-1,3,4-oxadiazol-2-yl)-2-(S)-(4-fluorophenyl)cyclopentan-1-(S)-amine Step A:

3-(SR)-(2-Acetylhydrazin-1-yl)-2-(SR)-(4-fluorophenyl)-1-(SR)-(azido)cyclopentane A solution of 201 mg of methyl 3-(SR)-azido-2-(SR)-(4-fluorophenyl)cyclopentane-1-(SR)-carboxylate (from Example 89, Step A) in 5 mL of 1:1 v/v THF/MeOH was added 1.0 mL of 5.0N NaOH. After 30 min, the solvent was reduced to ~20% the original volume and acidified with 2.0N HCl. The mixture was extracted twice with EtOAc and the organic layers were washed with a portion of sat'd NaCl, combined, dried over $MgSO_4$ and concentrated in vacuo. The residue was dissolved in 5 mL of $CH_2Cl_2$ and treated with 0.5 mL of oxalyl chloride and 2 drops of DMF. After 30 min, the volatiles were evaporated under a stream of nitrogen. The residue was taken up in 2 mL of $CH_2Cl_2$ and added to a mixture of 142 mg of acetic hydrazine in 1 mL of pyridine and 3 mL of $CH_2Cl_2$ at 0° C. After 2 h, the mixture was and concentrated in vacuo and the residue was partitioned between ether and 2.0N HCl and the organic layer was separated. The organics were washed with sat'd $NaHCO_3$ and sat'd NaCl. The ether layer was filtered and the precipitated product was collected and dried to give 145 mg of title compound as a white solid. $^1H$ NMR (500 MHz, $CD_3OD$): δ 1.92 (s, 3H), 1.93–1.99 (m, 2H), 2.20–2.28 (m, 2H), 3.21 (br q, 1H), 3.57 (dd, 1H), 4.21 (br t, 1H), 7.03 (br t, 2H), 7.35–7.38 (m, 2H). Mass Spectrum ($NH_3$-CI): m/z 306 (M+H, 20%)

Step B:

3-(SR)-(5-Methyl-1,2,4-oxadiazol-2-yl)-2-(SR)-(4-fluorophenyl)-1-(SR)-(azido)cyclopentane A solution of 50 mg of 3-(SR)-(2-acetylhydrazin-1-yl)-2-(SR)-(4-fluorophenyl)-1-(SR)-(azido)cyclopentane (from Example 98, Step A) in 1 mL of MeCN was treated with 0.12 mL of phosphorous oxychloride and heated at reflux for 2 h. The reaction was cooled, quenched with 500 mg of ice and partitioned between EtOAc and H$_2$O and the layers were separated. The organic layer was washed with sat'd NaCl, dried over MgSO$_4$ and concentrated in vacuo. The residue was purified by flash chromatography eluting with 25% EtOAc in hexanes to obtain 36 mg of title compound as an oil. $^1$H NMR (500 MHz, CHCl$_3$): δ 2.05–2.15 (m, 2H), 2.28–2.34 (m, 1H), 2.43 (s, 3H), 2.44–2.51 (m, 1H), 3.63 (dd, 1H), 3.83 (br q, 1H), 4.22 (br t, 1H), 7.03 (br t, 2H), 7.30–7.33 (m, 2H). Mass Spectrum (ESI): m/z 288 (M+H, 20%)

Step C:

N-(2-Methoxy-5-((5-trifluoromethyl)tetrazol-1-yl) phenyl)methyl)-3-(SR)-(5-methyl-1,3,4-oxadiazol-2-yl)-2-(SR)-(4-fluorophenyl)cyclopentan-1-(SR)-amine The title compound was prepared in 74% yield from 3-(SR)-(5-methyl-1,3,4-oxadiazol-2-yl)-2-(SR)-(4-fluorophenyl)-1-(SR)-(azido)cyclopentane (from Example 98, Step B) using a procedure analogous to that described in Example 91, Step D.

$^1$H NMR (500 MHz, CDCl$_3$): δ 1.62 (br s, 1H), 1.88–1.95 (m, 1H), 2.06–2.11 (m, 2H), 2.44 (s, 3H), 2.45–2.50 (m, 1H), 3.29–3.34 (m, 1H), 3.53 (d, 1H), 3.62 (dd, 1H), 3.72 (s, 3H), 3.73–3.77 (m, 1H), 4.00 (br q, 1H), 6.92–7.00 (m, 3H), 7.21–7.34 (m, 4H). Mass Spectrum (NH$_3$-CI): m/z 518 (M+H, 100%).

EXAMPLE 99

N-((2-Methoxy-5-trifluoromethoxy)phenylmethyl)-3-(SR)-(5-methyl-1,3,4-oxadiazol-2-yl)-2-(SR)-(4-fluorophenyl)cyclopentan-1-(SR)-amine The title compound was prepared in 85% yield from 3-(SR)-(5-methyl-1,3,4-oxadiazol-2-yl)-2-(SR)-(4-fluorophenyl)-1-(SR)-(azido)cyclopentane (from Example 98, Step B) and 2-methoxy-5-trifluoromethoxybenzaldehyde (prepared from 5-(trifluoromethoxy)-salicylaldehyde by treatment with potassium carbonate and methyl iodide) using a procedure analogous to that described in Example 91, Step D. $^1$H NMR (500 MHz, CDCl$_3$): δ 1.92–2.09 (m, 4H), 2.44 (s, 3H), 2.45–2.51 (m, 1H), 3.28–3.30 (m, 1H), 3.45 (d, 1H), 3.58 (s, 3H), 3.59–3.61 (m, 1H), 4.02 (br q, 1H), 6.72 (d, 1H), 6.93–7.07 (m, 4H), 7.21–7.24 (m, 2H). Mass Spectrum (NH$_3$-CI): m/z 466 (M+H, 100%).

EXAMPLE 100

N-((2-Cyclopropylmethoxy-5-trifluoromethoxy) phenylmethyl)-3-(SR)-(5-methyl-1,3,4-oxadiazol-2-yl)-2-(SR)-(4-fluorophenyl)cyclopentan-1-(SR)-amine The title compound was prepared in 78% yield from 3-(SR)-(5-methyl-1,3,4-oxadiazol-2-yl)-2-(SR)-(4-fluorophenyl)-1-(SR)-(azido)cyclopentane (from Example 93, Step C) and 2-cyclopropylmethoxy-5-trifluoromethoxybenzaldehyde (by analogy to the preparation of the corresponding 2-methoxy derivative given in Example 99) using a procedure analogous to that described in Example 91, Step D. $^1$H NMR (500 MHz, CDCl$_3$): δ 0.22 (br t, 2H), 0.56 (d, 2H), 0.98–1.01 (m, 1H), 1.94–2.11 (m, 4H), 2.44 (s, 3H), 2.45–2.50 (m, 1H), 3.32 (br t, 1H), 3.46 (d, 1H), 3.59 (dd, 1H), 3.63 (dd, 1H), 3.73 (d, 1H), 4.02 (br q, 1H), 6.70 (d, 1H), 6.94–7.04 (m, 4H), 7.20–7.23 (m, 2H). Mass Spectrum (NH$_3$-CI): m/z 506 (M+H, 100%).

EXAMPLE 101

N-((2-Cyclopropylmethoxy-5-trifluoromethoxy) phenylmethyl)-3-(SR)-(thiazol-2-yl)-2-(SR)-(4-fluorophenyl)cyclopentan-1-(SR)-amine The title compound was prepared in 74% yield from 3-(SR)-(thiazol-2-yl)-2-(SR)-(4-fluorophenyl)-1-(SR)-(azido)cyclopentane (from Example 93, Step C) and 2-cyclopropylmethoxy-5-trifluoromethoxybenzaldehyde (from Example 100) using a procedure analogous to that described in Example 91, Step D. $^1$H NMR (500 MHz, CDCl$_3$): δ 0.22 (br s 2H), 0.56 (d, 2H), 0.99–1.02 (m, 1H), 1.54 (br s, 1H), 1.92–1.96 (m, 1H), 2.06–2.19 (m, 2H), 2.53–2.58 (m, 1H), 3.35 (br t, 1H), 3.46 (d, 1H), 3.57 (dd, 1H), 3.64 (dd, 1H), 3.73 (d, 1H), 4.18 (br q, 1H), 6.69 (d, 1H), 6.95–7.10 (m, 4H), 7.22–7.25 (m, 3H), 7.62–7.63 (m, 1H). Mass Spectrum (NH$_3$-CI): m/z 507 (M+H, 100%).

EXAMPLE 102

N-(2-Methoxy-5-((5-trifluoromethyl)tetrazol-1-yl) phenyl)methyl)-3-(SR)-(tetrazol-1-yl)-2-(RS)-(4-fluorophenyl)cyclopentan-1-(SR)-amine Step A:

3-(RS)-Benzyloxy-2-(SR)-4-fluorophenyl-1-(SR)-(tetrazol-1-yl)cyclopentane

A solution of 0.59 g of 3-(R)-benzyloxy-2-(S)-4-fluorophenyl-1-(S)-cyclopentylamine (prepared by analogy to the procedure given in Example 9, Method A) in 10 ml of acetic acid was added slowly 0.92 g of triethyl orthoformate. The mixture was heated at 75° C. (oil bath) for 3 h and then 0.403 g of sodium azide was added portionwise over 1.5 h. The reaction mixture was heated at 75° C. overnight, then concentrated in vacuo. The residue was extracted between ethyl acetate and saturated sodium bicarbonate solution (50 ml), the aqueous layer separated and extracted again with ethyl acetate. The combined organic layers were dried over sodium sulfate and concentrated in vacuo. Chromatography of the residue on silica gel (120 ml column) using 10–50% ethyl acetate in methylene chloride gave 0.163 g. Mass Spectrum (NH$_3$-CI): m/z 339 (M+H, 100%).

Step B:

2-(SR)-4-Fluorophenyl-3-(SR)-(tetrazol-1-yl)-1-(SR)-cyclopentanol

A mixture of 0.160 g of 3-(R)-benzyloxy-2-(S)-4-fluorophenyl-1-(S)-(tetrazol-1-yl)cyclopentane (from Example 102, Step A), 0.5 mL of water, 0.5 mL of acetic acid, 1.0 g of ammonium formate and 0.05 g of 10% Pd/C in 15 ml of ethanol was heated at 70° C. (oil bath) overnight. When TLC indicated only partial reduction, 0.5 ml of trifluoroacetic acid and 1.0 g of ammonium formate were added and heating continued. After 6 h another 0.5 ml of trifluoracetic acid, 1.5 g of ammonium formate and 0.05 g of 10% Pd/C were added and heating continued overnight. The reaction mixture was filtered through Celite and concentrated in vacuo. The residue was taken up between 50 ml ethyl acetate and 50 ml saturated sodium bicarbonate solution. The aqueous layer was extracted with 25 ml ethyl acetate and the combined organic layers were dried over sodium sulfate and concentrated to dryness. Chromatography of the residue on silica gel (30 ml column) and elution with 10–80% ethyl acetate in methylene chloride gave 0.036 g of starting material and 0.078 g of the title compound. Mass Spectrum (NH$_3$-CI): m/z 249 (M+H, 100%).

Step C:

1-(SR)-Azido-2-(RS)-4-fluorophenyl-3-(SR)-(tetrazol-1-yl)cyclopentane

The title compound was prepared from 2-(SR)-4-fluorophenyl-3-(SR)-(tetrazol-1-yl)-1-(SR)-cyclopentanol (from Example 102, Step B) using a procedure analogous to that described in Example 89, Step A. Mass Spectrum (ESI): m/z 274 (M+H, 25%).

Step D:

1-(SS)-Amino-2-(RS)-4-fluorophenyl-3-(SR)-(tetrazol-1-yl)cyclopentane

The title compound was prepared from 1-(RS)-azido-2-(S)-4-fluorophenyl-3-(SR)-(tetrazol-1-yl)cyclopentane (from Example 102, Step C) by catalytic hydrogenation with 10% palladium on carbon in methanol. Mass Spectrum (NH$_3$-CI): m/z 248 (M+H, 100%).

Step E:

N-(2-Methoxy-5-((5-trifluoromethyl)tetrazol-1-yl)phenyl)methyl)-3-(SR)-(tetrazol-1-yl)-2-(RS)-(4-fluorophenyl)cyclopentan-1-(SR)-amine The title compound was prepared from 1-(SR)-amino-2-(RS)-4-fluorophenyl-3-(SR)-(tetrazol-1-yl)cyclopentane (from Example 102, Step D) using a procedure analogous to that described in Example 71. $^1$H NMR (500 MHz, CDCl$_3$): δ 1.69 (br s, 1H), 1.96–2.04 (m, 1H), 2.24–2.36 (m, 2H), 2.68–2.74 (m, 1H), 3.39–3.42 (m, 1H), 3.55 (d, J=15.0, 1H), 3.73 (s, 3H), 3.76 (d, J=15.0, 1H), 3.81 (dd, J=11.0, 5.5, 1H), 5.52–5.57 (m, 1H), 6.95 (d, J=8.5, 1H), 7.00 (t, J=8.5, 2H), 7.20–7.23 (m, 2H), 7.26 (d, J=2.5, 1H), 7.35 (dd, J=8.5, 2.5, 1H), 8.47 (s, 1H). Mass Spectrum (ESI): m/z 501 (M+H, 100%).

EXAMPLE 103

N-(2-Methoxy-5-((5-trifluoromethyl)tetrazol-1-yl)phenyl)methyl)-3-(SR)-(1,2,4-triazol-4-yl)-2-(SR)-(4-fluorophenyl)cyclopentan-1-(SR)-amine Step A:

3-(RS)-Benzyloxy-2-(SR)-4-fluorophenyl-1-(SR)-(1,2,4-triazol-4-yl)cyclopentane

A mixture of 0.182 g of formic hydrazide and 0.450 g of triethyl orthoformate in 15 ml of anhydrous methanol was heated at reflux for 4 h after which time 0.452 g of 3-(RS)-benzyloxy-2-(SR)-4-fluorophenyl-1-(SR)-cyclopentylamine (from Example 102, Step A) was added. The reaction mixture was refluxed overnight and then concentrated in vacuo. Chromatography of the residue on silica gel (100 ml column) and elution with ethyl acetate saturated with water gave 0.219 g of the title compound. Mass Spectrum (NH$_3$-CI): m/z 338 (M+H, 100%).

Step B:

2-(SR)-4-Fluorophenyl-3-(SR)-(1,2,4-triazol-4-yl)-1-(RS)-cyclopentanol

A mixture of 0.215 g of 3-(RS)-benzyloxy-2-(SR)-4-fluorophenyl-1-(SR)-(1,2,4-triazol-4-yl)cyclopentane (from Example CPD2, Step A), 0.5 g of 10% Pd/C and 3 mL of 1,4-cyclohexadiene in 15 mL of methanol was refluxed under nitrogen for 7 h. Another 1.0 mL of 1,4-cyclohexadiene was added and refluxing continued until TLC indicated completion of the reduction. The reaction mixture was filtered through Celite and concentrated in vacuo to give 0.155 g of the title compound. Mass Spectrum (NH$_3$-CI): m/z 248 (M+H, 100%).

Step C:

1-(SR)-Azido-2-(SR)-4-fluorophenyl-3-(SR)-(1,2,4-triazol-4-yl)cyclopentane

The title compound was prepared from 2-(SR)-4-fluorophenyl-3-(SR)-(1,2,4-triazol-4-yl)-1-(SR)-cyclopentanol (from Example 103, Step B) using a procedure analogous to that described in Example 89, Step A. Mass Spectrum (NH$_3$-CI): m/z 273 (M+H, 25%).

Step D:

1-(SR)-Amino-2-(SR)-4-fluorophenyl-3-(SR)-(1,2,4-tetrazol-4-yl)cyclopentane

The title compound was prepared from 1-(SR)-azido-2-(SR)-4-fluorophenyl-3-(SR)-(1,2,4-tetrazol-4-yl)cyclopentane (from Example 103, Step C) using a procedure analogous to that described in Example 102, Step D.

Step E:

N-(2-Methoxy-5-((5-trifluoromethyl)tetrazol-1-yl)phenyl)methyl)-3-(SR)-(1,2,4-triazol-4-yl)-2-(SR)-(4-fluorophenyl)cyclopentan-1-(SR)-amine The title compound was prepared from 1-(SR)-amino-2-(SR)-4-fluorophenyl-3-(RS)-(1,2,4-triazol-4-yl)cyclopentane (from Example 103, Step D) using a procedure analogous to that described in Example 102, Step E. $^1$H NMR (500 MHz, CDCl$_3$): δ 1.78 (br s, 1H), 1.91–2.06 (m, 2H), 2.21–2.28 (m, 1H), 2.64–2.71 (m, 1H), 3.34–3.37 (dt, J=2.5, 11.0, 1H), 3.48 (dd, J=11.0, 5.5, 1H), 3.50 (d, J=15.0, 1H), 3.72 (s, 3H), 3.73 (d, J=15.0, 1H), 5.11–5.17 (m, 1H), 6.94 (d, J=9.0, 1H), 7.03 (t, J=8.5, 2H), 7.18–7.22 (m, 3H), 7.34 (dd, J=9.0, 2.5, 1H), 8.01 (s, 2H). Mass Spectrum (NH$_3$-CI): m/z 503 (M+H, 100%).

EXAMPLE 104

(1RS,2RS,3RS)-2-(4-Fluorophenyl)-3-((2-methoxy-5-(thiophen-3-yl)phenyl)methylamino)cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the known 2-methoxy-5-(thiophen-3-yl)benzaldehyde (P. J. Ward, D. R. Armour, D. E. Bays, B. Evans, G. M. P. Giblin, N. Hernon, T. Hubbard, K. Liang, D. Middlemiss, J. Mordaunt, A. Naylor, N. A. Pegg, M. V. Vinder, S. P. Watson, C. Bountra, and D. C. Evans, J. Med. Chem. 1995, 38, 4985–92).

NMR (400 MHz, CDCl$_3$): δ 7.42 (d, 1H, J=8.2 Hz), 7.37 (dd, 1H, J=5.4 Hz), 7.31–7.28 (m, 2H), 7.23 (d, 1H, J=2 Hz), 7.18 (dd, 2H, J=9, 5 Hz), 7.00 (t, 2H, J=9 Hz), 6.76 (d, 1H, J=8 Hz), 3.74 (d, 1H, J=13 Hz), 3.61 (s, 3H), 3.55 (s, 3H), 3.52–3.38 (m, 3H), 3.27–3.22 (m, 1H), 2.41–2.28 (m, 1H), 2.20–1.87 (m, 3H). Mass spectrum (NH$_3$/CI): 440 (M+1).

EXAMPLE 105

(1RS,2RS,3RS)-2-(4-Fluorophenyl)-3-((2-methoxy-5-(thiophen-2-yl)phenyl)methylamino)cyclopentanecarboxylic acid methyl ester Step A:

2-Methoxy-5-(thiophen-2-yl)benzaldehyde 5-Bromo-2-methoxybenzaldehyde (500 mg, 2.33 mmol), thiophene-2-boronic acid (360 mg, 2.81 mmol), and tetrakis(triphenylphosphine)palladium(0) (50 mg, 0.043 mmol) were added to stirred mixture of sodium carbonate (560 mg, 5.28 mmol), water (5.0 mL) and ethylene glycol dimethyl ether (5.0 mL). The mixture was heated in an oil bath at 80° C. for 4 h, and additional tetrakis(triphenylphosphine)palladium(0) (25 mg, 0.022 mmol) was then added. Heating at 80° C. was continued for another 5.5 h. The mixture was allowed to stand overnight at 25° C., and was then partitioned between water (5 mL) and ethyl acetate (30 mL). The aqueous layer was extracted with 2×30 mL of ethyl acetate and the combined organic extracts were dried (sodium sulfate), decanted, and evaporated. The residue was purified by flash column chromatography on silica gel, eluting with 25–40% dichloromethane in hexane. A second flash column chromatography on silica gel, eluting with 5% ethyl acetate in hexane gave the title compound at 180 mg (37% yield) of light yellow solid. NMR (400 MHz, CDCl$_3$): δ 10.47 (s, 1H), 8.04 (d, 1H, J=3 Hz), 7.77 (dd, 1H, J=9.3 Hz), 7.27–7.23 (m, 2H), 7.05 (dd, 1H, J=5.4 Hz), 7.00 (d, 1H, J=9 Hz), 3.95 (s, 3H). Mass spectrum (NH$_3$/CI): 219 (M+1).

Step B:

(1RS,2RS,3RS)-2-(4-Fluorophenyl)-3-((2-methoxy-5-(thiophen-2-yl)phenyl)methylamino)cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the aldehyde from Step A above.

NMR (400 MHz, CDCl$_3$): δ 7.43 (dd, 1H, J=9.2 Hz), 7.26 (d, 1H, J=2 Hz), 7.22 (dd, 1H, J=5.1 Hz), 7.19 (dd, 2H, J=9.5 Hz), 7.16 (dd, 1H, J=4.1 Hz), 7.06 (dd, 1H, J=5.4 Hz), 7.01 (t, 2H, J=9 Hz), 6.75 (d, 1H, J=9 Hz), 3.72 (d, 1H, J=13 Hz), 3.61 (s, 3H), 3.53–3.38 (m, 2H), 3.55 (s, 3H), 3.46 (d, 1H, J=13 Hz), 3.47–3.38 (m, 1H), 3.27–3.22 (m, 1H), 2.38–2.29 (m, 1H), 2.02–1.87 (m, 3H), 1.61 (br, 1H). Mass spectrum (NH$_3$/CI): 440 (M+1).

EXAMPLE 106

(1RS,2RS,3RS)-2-(4-Fluorophenyl)-3-((5-(furan-2-yl)-2-methoxyphenyl)methylamino)cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the known 5-(furan-2-yl)-2-methoxybenzaldehyde (P. J. Ward, et al., J. Med. Chem. 1995, 38, 4985–92).

NMR (400 MHz, CDCl$_3$): δ 7.47 (dd, 1H, J=9.2 Hz), 7.41 (dd, 1H, J=2.1 Hz), 7.28 (d, 1H, J=2 Hz), 7.15 (dd, 2H, J=9.5 Hz), 6.97 (t, 2 H, J=9 Hz), 6.72 (d, 1H, J=9 Hz), 6.46 (dd, 1H, J=3.1 Hz), 6.42 (dd, 1H, J=3.2H), 3.70 (d, 1H, J=13 Hz), 3.59 (s, 3H), 3.52 (s, 3H), 3.49–3.36 (m, 2H), 3.42 (d, 1H, J=13 Hz), 3.23–3.18 (m, 1H), 2.38–2.26 (m, 1H), 1.98–1.84 (m, 3H), 1.54 (br, 1H). Mass spectrum (NH$_3$/CI): 424 (M+1).

EXAMPLE 107

(1RS,2RS,3RS)-2-(4-Fluorophenyl)-3-((5-(furan-3-yl)-2-methoxyphenyl)methylamino)cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the known 5-(furan-3-yl)-2-methoxybenzaldehyde (P. J. Ward, et al., J. Med. Chem. 1995, 38, 4985–92). NMR (400 MHz, CDCl$_3$): δ 7.63–7.61 (m, 1H), 7.46 (t, 1H, J=2 Hz), 7.31 (dd, 1H, J=9.2 Hz), 7.18 (dd, 2H, J=9.5 Hz), 7.12 (d, 1H, J=2 Hz), 7.01 (t, 2H, J=9 Hz), 6.75 (d, 1H, J=9 Hz), 6.62 (dd, 1H, J=2.1 Hz), 3.73 (d, 1H, J=13 Hz), 3.61 (s, 3H), 3.54 (s, 3H), 3.53–3.38 (m, 2H), 3.45 (d, 1H, J=13 Hz), 3.27–3.22 (m, 1H), 2.41–2.29 (m, 1H), 2.02–1.87 (m, 3H), 1.69 (br, 1H). Mass spectrum (NH$_3$/CI): 424 (M+1).

EXAMPLE 108

(1RS,2RS,3RS)-3-((5-Butyl-2-methoxyphenyl)methylamino)-2-(4-fluorophenyl)cyclopentanecarboxylic acid methyl ester hydrochloride Step A:

5-Butyl-2-methoxybenzaldehyde n-BuLi in hexane (1.6M, 15.4 mL, 24.6 mmol) was added dropwise over 15 min to a –70° C. solution of 5-bromo-2-methoxybenzaldehyde diethylacetal in 50 mL of THF. Once the addition was complete, the mixture was stirred and allowed to warm up to 0° C. over 1.5 h. The mixture was then cooled to –70° C. and a solution of trimethylborate (5.4 mL, 48 mmol) in 25 mL of THF was added rapidly through a double-ended needle. The reaction was kept at –70° C. for 4 h and was then allowed to warm to 0° C. slowly before being quenched by the addition of 70 mL of 2.0N aqueous hydrochloric acid. After the mixture had been stirred for 1 h, the layers were separated and the aqueous layer was extracted with 3×100 mL of ethyl acetate. The combined organic layers were dried (sodium sulfate), decanted, and evaporated. The residue was then dissolved in ethyl acetate (100 mL) and extracted with 4×44 mL of 2.0N sodium hydroxide. The ethyl acetate layer was dried (sodium sulfate), decanted, and evaporated. The crude material was purified by flash column chromatography on silica gel, eluting with 10–20% dichloromethane in hexane to yield 5-butyl-2-methoxybenzaldehyde (1.87 g, 43% yield) as an amber liquid.

NMR (400 MHz, CDCl$_3$): δ 10.43 (s, 1H), 7.62 (d, 1H, J=2 Hz), 7.34 (dd, 1H, J=9.2 Hz), 6.89 (d, 1H, J=9 Hz), 3.89 (s, 3H), 2.55 (t, 2H, J=8 Hz), 1.59–1.50 (m, 2H), 1.31 (sextet, 2H, J=8 Hz), 0.89 (t, 3H, J=8 Hz). Mass spectrum (NH$_3$/CI): 193 (M+1).

Step B:

(1RS,2RS,3RS)-3-((5-Butyl-2-methoxyphenyl)methylamino)-2-(4-fluorophenyl)cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the aldehyde from the preceeding step.

NMR (400 MHz, CD$_3$OD): δ 7.20 (dd, 2H, J=9.5 Hz), 7.07 (t, 2H, J=9 Hz), 7.01 (dd, 1H, J=9.2 Hz), 6.84 (d, 1H, J=2 Hz), 6.72 (d, 1H, J=9 Hz), 3.64 (d, 1H, J=13 Hz), 3.58 (s, 3H), 3.50 (dd, 1H, J=11.6 Hz), 3.44 (s, 3H), 3.42–3.36 (m, 1H), 3.39 (d, 1H, J=13 Hz), 3.22 (td, 1H, J=6.2 Hz), 2.49 (t, 2H, J=8 Hz), 2.35–2.24 (m, 1H), 2.10–2.00 (m, 1H), 1.98–1.85 (m, 2H), 1.52 (quintet, 2H, J=8 Hz), 1.32 (sextet, 2H, J=8 Hz), 0.92 (t, 3H, J=8 Hz). Mass spectrum (NH$_3$/CI): 414 (M+1).

Step C:

(1RS,2RS,3RS)-3-((5-Butyl-2-methoxyphenyl)methylamino)-2-(4-fluorophenyl)cyclopentanecarboxylic acid methyl ester hydrochloride Exposure of the product from Step B above to 1.5 equivs of HCl in ethyl ether followed by evaporation provided the title compound.

NMR (400 MHz, CD$_3$OD): δ 7.37 (dd, 1H, J=9.5 Hz), 7.22 (dd, 1H, J=9.2 Hz), 7.21 (t, 2H, J=9 Hz), 7.03 (d, 1H, J=2 Hz), 6.92 (d, 1H, J=9 Hz), 4.16 (d, 1H, J=13 Hz), 4.00 (d, 1H, J=13 Hz), 3.90–3.83 (m, 2H), 3.64 (s, 3H), 3.63 (s, 3H), 3.39–3.30 (m, 1H), 2.54 (t, 2H, J=8 Hz), 2.47–2.34 (m, 2H), 2.14–1.95 (m, 2H), 1.54 (quintet, 2H, J=8 Hz), 1.33 (sextet, 2H, J=8 Hz), 0.92 (t, 3H, J=8 Hz).

EXAMPLE 109

(1RS,2RS,3RS)-2-(4-Fluorophenyl)-3-((2-methoxy-5-(pyrimidin-5-yl)phenyl)methylamino)cyclopentane carboxylic acid methyl ester The title compound was prepared by employing the method described in Example 91, Step D with (1RS,2RS,3RS)-2-(4-fluorophenyl)-3-azidocyclopentanecarboxylic acid methyl ester (from Ex. 89, Step A) and the known 2-methoxy-5-(pyrimidin-5-yl)benzaldehyde (P. J. Ward, et al., J. Med. Chem. 1995, 38, 4985–92). $^1$H NMR (400 MHz, CD$_3$OD): δ 9.07 (s, 1H), 8.99 (s, 2H), 7.61 (dd, 1H, J=9.2 Hz), 7.45 (d, 1H, J=2 Hz), 7.22 (dd, 2H, J=9.5 Hz), 7.07 (t, 2H, J=9 Hz), 7.02 (d, 1H, J=9 Hz), 3.76 (d, 1H, J=13 Hz), 3.59 (s, 3H), 3.56 (s, 3H), 3.55–3.49 (m, 1H), 3.53 (d, 1H, J=13 Hz), 3.45–3.36 (m, 1H), 3.26 (td, 1H, J=6.2 Hz), 2.36–2.26 (m, 1H), 2.12–2.01 (m, 1H), 1.99–1.88 (m, 2H). Mass spectrum (NH$_3$/CI): 436 (M+1).

EXAMPLE 110

(1RS,2RS,3RS)-2-(4-Fluorophenyl)-3-((2-methoxy-5-(thiazol-2-yl)phenyl)methylamino)cyclopentanecarboxylic acid methyl ester hydrochloride Step A:

(1RS,2RS,3RS)-2-(4-Fluorophenyl)-3-((2-methoxy-5-(thiazol-2-yl)phenyl)methylamino)cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the known 2-methoxy-5-(thiazol-2-yl)benzaldehyde (P. J. Ward, et al., J. Med. Chem. 1995, 38, 4985–92).

NMR (400 MHz, CD$_3$OD): δ 7.82 (dd, 1H, J=9.2 Hz), 7.79 (d, 1H, J=3 Hz), 7.66 (d, 1H, J=2 Hz), 7.52 (d, 1H, J=3 Hz), 7.21 (dd, 2H, J=9.5 Hz), 7.07 (t, 2H, J=9 Hz), 6.96 (d, 1H, J=9 Hz), 3.75 (d, 1H, J=13 Hz), 3.58 (s, 3H), 3.56 (s, 3H), 3.52 (dd, 1H, J=11.6 Hz), 3.49 (d, 1H, J=13 Hz), 3.45–3.37 (m, 1H), 3.25 (td, 1H, J=6.2 Hz), 2.36–2.27 (m, 1H), 2.10–2.02 (m, 1H), 1.99–1.88 (m, 2H). Mass spectrum (NH$_3$/CI): 441 (M+1).

Step B:

(1RS,2RS,3RS)-2-(4-Fluorophenyl)-3-((2-methoxy-5-(thiazol-2-yl)phenyl)methylamino)cyclopentanecarboxylic acid methyl ester hydrochloride Exposure of the product from Step A above to 1.0 equivalent of HCl in methanol/ethyl ether followed by evaporation provided the title compound. NMR (400 MHz, CD$_3$OD): δ 8.01 (dd, 1H, J=9.2 Hz), 7.87 (d, 1H, J=2 Hz), 7.86 (d, 1H, J=3 Hz), 7.60 (d, 1H, J=3 Hz), 7.40 (dd, 2H, J=9.5 Hz), 7.21 (t, 2H, J=9 Hz), 7.17 (d, 1H, J=9 Hz), 4.25 (d, 1H, J=13 Hz), 4.11 (d, 1H, J=13 Hz), 3.97–3.86 (m, 2H), 3.79 (s, 3H), 3.63 (s, 3H), 3.38 (quartet, 1H, J=9 Hz), 2.51–2.36 (m, 2H), 2.19–1.97 (m, 2H).

EXAMPLE 111

(1RS,2RS,3RS)-2-(4-Fluorophenyl)-3-((2-methoxy-5-(thiazol-4-yl)phenyl)methylamino)cyclopentanecarboxylic acid methyl ester hydrochloride Step A:

2-Methoxy-5-(thiazol-4-yl)benzaldehyde (3-Formyl-4-methoxyphenyl)boronic acid (309 mg, 1.71 mmol), 4-bromothiazole (250 mg, 1.52 mmol, prepared as described by J. Trybulski and H. J. Brabander, U.S. Pat. No. 4,990,520, 1991), and tetrakis(triphenylphosphine)palladium(0) (88 mg, 0.076 mmol) were added to a mixture of water (3.5 mL), ethylene glycol dimethyl ether (3.5 mL), and sodium carbonate (805 mg, 7.6 mmol). The mixture was heated in an oil bath at 80° C. for 3 h, allowed to cool to 25° C., and partioned between ethyl acetate (40 mL) and water (20 mL). The aqueous layer was extracted with 2×40 mL of dichloromethane and the combined organic layers dried (sodium sulfate), decanted, and evaporated. The residue was purified by flash column chromatography on silica gel, eluting with 10% ethyl acetate in hexane to give 182 mg (55% yield) of the title compound as a white solid. NMR (400 MHz, CDCl$_3$): δ 10.51 (s, 1H), 8.88 (d, 1H, J=2 Hz), 8.32 (d, 1H, J=2 Hz), 8.24 (dd, 1H, J=9.2 Hz), 7.54 (d, 1H, J=2 Hz), 7.09 (d, 1H, J=9 Hz), 3.99 (s, 3H). Mass spectrum (NH$_3$/CI): 220 (M+1).

Step B:

(1RS,2RS,3RS)-2-(4-Fluorophenyl)-3-((2-methoxy-5-(thiazol-4-yl)phenyl)methylamino)cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the aldehyde from the preceeding step. NMR (400 MHz, CD$_3$OD): δ 9.01 (d, 1H, J=2 Hz), 7.80 (dd, 1H, J=9.2 Hz), 7.70 (d, 1H, J=2 Hz), 7.64 (d, 1H, J=2 Hz), 7.20 (dd, 2H, J=9, 5 Hz), 7.07 (t, 2H, J=9 Hz), 6.91 (d, 1H, J=9 Hz), 3.75 (d, 1H, J=13 Hz), 3.58 (s, 3H), 3.52 (s, 3H), 3.53–3.38 (m, 2H), 3.48 (d, 1H, J=13 Hz), 3.25 (td, 1H, J=5.2 Hz), 2.36–2.27 (m, 1H), 2.31–2.00 (m, 1H), 1.99–1.88 (m, 2H). Mass spectrum (NH$_3$/CI): 441 (M+1).

Step C:

(1RS,2RS,3RS)-2-(4-Fluorophenyl)-3-((2-methoxy-5-(thiazol-4-yl)phenyl)methylamino)cyclopentanecarboxylic acid methyl ester hydrochloride Exposure of the product from Step B above to 1.0 equivalent of HCl in methanol/ethyl ether followed by evaporation provided the title compound as a white solid. NMR (400 MHz, CD$_3$OD): δ 9.06 (d, 1H, J=2 Hz), 7.99 (dd, 1H, J=9.2 Hz), 7.85 (d, 1H, J=2 Hz), 7.79 (d, 1H, J=2 Hz), 7.39 (dd, 2H, J=9.5 Hz), 7.22 (t, 2H, J=9 Hz), 7.12 (d, 1H, J=9 Hz), 4.25 (d, 1H, J=13 Hz), 4.10 (d, 1H, J=13 Hz), 3.96–3.85 (m, 2H), 3.75 (s, 3H), 3.63 (s, 3H), 3.38 (quartet, 1H, J=8 Hz), 2.51–2.36 (m, 2H), 2.18–1.96 (m, 2H).

EXAMPLE 112

(1RS,2RS,3RS)-2-(4-Fluorophenyl)-3-((2-methoxy-5-(thiazol-5-yl)phenyl)methylamino)cyclopentanecarboxylic acid methyl ester hydrochloride Step A:

2-Methoxy-5-(thiazol-5-yl)benzaldehyde

The title compound was prepared by employing the method described in Example 111, Step A with (3-formyl-4-methoxyphenyl)boronic acid and the known 5-bromothiazole (E. J. Trybulski and H. J. Brabander, U.S. Pat. No. 4,990,520, 1991). NMR (400 MHz, CDCl$_3$): δ 10.48 (s, 1H), 8.76 (s, 1H), 8.04 (s, 1H), 8.01 (d, 1H, J=2 Hz), 7.75 (dd, 1H, J=9.2 Hz), 7.05 (d, 1H, J=9 Hz), 3.97 (s, 3H). Mass spectrum (NH$_3$/CI): 220 (M+1).

Step B:

(1RS,2RS,3RS)-2-(4-Fluorophenyl)-3-((2-methoxy-5-(thiazol-5-yl)phenyl)methylamino)cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the aldehyde from the step A. NMR (400 MHz, CD$_3$OD): δ 8.89 (s, 1H), 8.03 (s, 1H), 7.51 (dd, 1H, J=9.2 Hz), 7.36 (d, 1H, J=2 Hz), 7.22 (dd, 2H, J=9,5 Hz), 7.08 (t, 2H, J=9 Hz), 6.92 (d, 1H, J=9 Hz), 3.71 (d, 1H, J=13 Hz), 3.58 (s, 3H), 3.74 (s, 3H), 3.51 (dd, 1H, J=11.6 Hz), 3.47 (d, 1H, J=13 Hz), 3.45–3.36 (m, 1H), 3.24 (td, 1H, J=6.2 Hz), 2.36–2.24 (m, 1H), 2.11–2.00 (m, 1H), 1.99–1.87 (m, 2H). Mass spec. (NH$_3$/CI):441 (M+1).

Step C:

(1RS ,2RS ,3RS)-2-(4-Fluorophenyl)-3-((2-methoxy-5-(thiazol-5-yl)phenyl)methylamino)cyclopentanecarboxylic acid methyl ester hydrochloride Exposure of the product from Step A above to 1.0 equivalent of HCl in methanol/ethyl ether followed by evaporation provided the title compound. NMR (400 MHz, CD$_3$OD): δ 9.01 (s, 1H), 8.11 (s, 1H), 7.73 (dd, 1H, J=9.2 Hz), 7.59 (d, 1H, J=2 Hz), 7.40 (dd, 2H, J=9.5 Hz), 7.22 (t, 2H, J=9 Hz), 7.13 (d, 1H, J=9 Hz), 4.23 (d, 1H, J=13 Hz), 4.09 (d, 1H, J=13 Hz), 3.96–3.86 (m, 2H), 3.76 (s, 3H), 3.63 (s, 3H), 3.38 (quartet, 1H, J=9 Hz), 2.50–2.36 (m, 2H), 2.18–1.96 (m, 2H).

EXAMPLE 113

(1RS,2RS ,3RS)-2-(4-Fluorophenyl)-3-((2-methoxy-5-(pyridin-2-yl)phenyl)methylamino)cyclopentanecarboxylic acid methyl ester dihydrochloride Step A:

2-Methoxy-5-(pyridin-2-yl)benzaldehyde

The title compound was prepared by employing the method described in Example 111, Step A with (3-formyl-4-methoxyphenyl)boronic acid and the commercially available 2-bromopyridine.

NMR (400 MHz, DMSO-d6): δ 10.41 (8.43H), 8.64 (d, 1H, J=5 Hz), 8.43 (d, 1H, J=2 Hz), 8.39 (dd, 1H, J=9.2 Hz), 7.97 (d, 1H, J=8 Hz), 7.87 (td, 1H, J=8.2 Hz), 7.38 (d, 1H, J=9 Hz), 7.33 (dd, 1H, J=8.5 Hz). Mass spectrum (NH$_3$/CI): 214 (M+1)

Step B:

(1RS ,2RS ,3RS)-2-(4-Fluorophenyl)-3-((2-methoxy-5-(pyridin-2-yl)phenyl)methylamino)cyclopentanecarboxylic acid methyl ester The title compound was prepared by employing the method described in Example 91, Step D with (1RS,2RS, 3RS)-2-(4-fluorophenyl)-3-azidocyclopentanecarboxylic acid methyl ester (from Example 89, Step A) and the aldehyde from the preceeding step.

NMR (400 MHz, CD$_3$OD): δ 8.55 (d, 1H, J=5 Hz), 7.85 (dt, 1H, J=8.2 Hz), 7.83 (dd, 1H, J=9.2 Hz), 7.75 (d, 1H, J=8 Hz), 7.66 (d, 1H, J=2 Hz), 7.30 (dd, 1H, J=8.5 Hz), 7.20 (dd, 2H, J=8.5 Hz), 7.06 (t, 2H, J=9 Hz), 6.96 (d, 1H, J=9 Hz), 3.78 (d, 1H, J=13 Hz), 3.58 (s, 3H), 3.55 (s, 3H), 3.55–3.37 (m, 2H), 3.50 (d, 1H, J=13 Hz), 3.26 (td, 1H, J=6.2 Hz), 2.36–2.26 (m, 1H), 2.10–2.01 (m, 1H), 1.98–1.88 (m, 2H). Mass spectrum (NH$_3$/CI): 435 (M+1).

Step C:

(1RS,2RS,3RS)-2-(4-Fluorophenyl)-3-((2-methoxy-5-(pyridin-2-yl)phenyl)methylamino)cyclopentanecarboxylic acid methyl ester dihydrochloride Exposure of the product from Step B above to 2.2 equivalents of HCl in methanol/ethyl ether followed by evaporation provided the title compound. NMR (400 MHz, CD$_3$OD): δ 8.81 (d, 1H, J=5 Hz), 8.64 (td, 1H, J=8.1 Hz), 8.35 (d, 1H, J=8 Hz), 8.06 (dd, 1H, J=9.2 Hz), 8.02–7.96 (m, 2H), 7.45 (dd, 2H, J=9.5 Hz), 7.34 (d, 1H, J=9 Hz), 7.20 (t, 2H, J=9 Hz), 4.31 (d, 1H, J=13 Hz), 4.15 (d, 1H, J=13 Hz), 4.03–3.96 (m, 1H), 3.90 (dd, 1H, J=9.8 Hz), 3.85 (s, 3H), 3.64 (s, 3H), 3.46 (quartet, 1H, J=9 Hz), 2.54–2.38 (m, 2H), 2.25–2.14 (m, 1H), 2.08–1.96 (m, 1H).

EXAMPLE 114

(1RS,2RS,3RS)-2-(4-Fluorophenyl)-3-((2-methoxy-5-(pyridin-3-yl)phenyl)methylamino)cyclopentanecarboxylic acid methyl ester dihydrochloride Step A:

2-Methoxy-5-(pyridin-3-yl)benzaldehyde

The title compound was prepared by employing the method described in Example 111, Step A with (3-formyl-4-methoxyphenyl)-boronic acid and the commercially available 3-bromopyridine. NMR (400 MHz, CDCl$_3$): δ 10.53 (s, 1H), 8.89 (d, 1H, J=2 Hz), 8.63 (dd, 1H, J=5.1 Hz), 8.10 (dt, 1H, J=8.2 Hz), 8.09 (d, 1H, J=2 Hz), 7.83 (dd, 1H, J=9.2 Hz), 7.56 (dd, 1H, J=8.5 Hz), 7.17 (d, 1H, J=9 Hz), 4.02 (s, 3H). Mass spectrum (NH$_3$/CI): 214 (M+1).

Step B:

(1RS ,2RS ,3RS)-2-(4-Fluorophenyl)-3-((2-methoxy-5-(pyridin-3-yl)phenyl)methylamino)cyclopentanecarboxylic acid methyl ester The title compound was prepared by employing the method described in Example 89, Step A with (1RS,2RS, 3RS)-2-(4-fluorophenyl)-3-azidocyclopentanecarboxylic acid methyl ester (from Example 91, Step D) and the aldehyde from the preceding step. NMR (400 MHz, CD$_3$OD): δ 8.72 (dd, 1H, J=3.1 Hz), 8.45 (dd, 1H, J=5.2 Hz), 8.01 (dt, 1H, J=8.2 Hz), 7.54 (dd, 1H, J=9.2 Hz), 7.48 (dd, 1H, J=8.5 Hz), 7.38 (d, 1H, J=2 Hz), 7.22 (dd, 2H, J=9.5 Hz), 7.07 (dd, 2H, J=9.5 Hz), 6.98 (d, 1H, J=9 Hz), 3.75 (d, 1H, J=13 Hz), 3.58 (s, 3H), 3.55 (s, 3H), 3.55–3.49 (m, 1H), 3.51 (d, 1H, J=13 Hz), 3.45–3.37 (m, 1H), 3.26 (td, 1H, J=6.2 Hz), 2.36–2.26 (m, 1H), 2.10–2.00 (m, 1H), 1.98–1.88 (m, 2H). Mass spectrum (NH$_3$/CI): 435 (M+1).

Step C:

(1RS,2RS,3RS)-2-(4-Fluorophenyl)-3-((2-methoxy-5-(pyridin-3-yl)phenyl)methylamino)cyclopentanecarboxylic acid methyl ester dihydrochloride Exposure of the product from Step B above to 2.2 equivalents of HCl in methanol/ethyl ether followed by evaporation provided the title compound. NMR (400 MHz, CD$_3$OD): δ 9.15 (d, 1H, J=2 Hz), 8.85 (dt, 1H, J=8.2 Hz), 8.80 (d, 1H, J=5 Hz), 8.04 (dd, 1H, J=8.5 Hz), 7.92 (dd, 1H, J=9.2 Hz), 7.82 (d, 1H, J=2 Hz), 7.43 (dd, 2H, J=9.5 Hz), 7.26 (d, 1H, J=9 Hz), 7.21 (t, 2H, J=9 Hz), 4.30 (d, 1H, J=13 Hz), 4.14 (d, 1H, J=13 Hz), 3.99–3.92 (m, 1H), 3.90 (dd, 1H, J=9.8 Hz), 3.80 (s, 3H), 3.63 (s, 3H), 3.42 (quartet, 1H, J=8 Hz), 2.52–2.38 (m, 2H), 2.22–2.12 (m, 1H), 2.07–1.96 (m, 1H).

EXAMPLE 115

(1RS ,2RS ,3RS)-2-(4-Fluorophenyl)-3-((2-methoxy-5-(pyridin-4-yl)phenyl)methylamino)cyclopentanecarboxylic acid methyl ester dihydrochloride Step A:

(1RS,2RS ,3RS)-2-(4-Fluorophenyl)-3-((2-methoxy-5-(pyridin-4-yl)phenyl)methylamino)cyclopentanecarboxylic acid methyl ester The title compound was prepared by employing the method described in Example 91, Step D with (1RS,2RS, 3RS)-2-(4-fluorophenyl)-3-azidocyclopentanecarboxylic acid methyl ester (from Ex. 89, Step A) and the known 2-bromo-4-(pyridin-4-yl)benzaldehyde (P. J. Ward, et al., J. Med. Chem. 1995, 38, 4985–92). NMR (400 MHz, CD$_3$OD): δ 8.52 (dd, 2H, J=6.2 Hz), 7.67 (dd, 1H, J=9.2 Hz), 7.63 (dd, 2H, J=6.2 Hz), 7.48 (d, 1H, J=2 Hz), 7.22 (dd, 2H, J=9.5 Hz), 7.06 (t, 2H, J=9 Hz), 6.98 (d, 1H, J=9 Hz), 3.76 (d, 1H, J=13 Hz), 3.59 (s, 3H), 3.57 (s, 3H), 3.55–3.36 (m, 2H), 3.51 (d, 1H, J=13 Hz), 3.25 (td, 1H, J=6.2 Hz), 2.36–2.26 (m, 1H), 2.09–2.00 (m, 1H), 1.99–1.88 (m, 2H). Mass spectrum (NH$_3$/CI): 435 (M+1).

Step B:

(1RS,2RS,3RS)-2-(4-Fluorophenyl)-3-((2-methoxy-5-(pyridin-4-yl)phenyl)methylamino)cyclopentanecarboxylic acid methyl ester dihydrochloride Exposure of the product from Step A above to 2.5 equivalents of HCl in methanol/ethyl ether followed by evaporation provided the title compound. NMR (400 MHz, CD$_3$OD): δ 8.83 (d, 2H, J=7 Hz), 8.36(d, 2H, J=7 Hz), 8.14(dd, 1H, J=9.2 Hz), 8.03(d, 1H, J=2 Hz), 7.43 (dd, 2H, J=9.5 Hz), 7.30 (d, 1H, J=9 Hz), 7.21 (t, 2H, J=9 Hz), 4.31 (d, 1H, J=13 Hz), 4.16 (d, 1H, J=13 Hz), 4.00–3.94 (m, 1H), 3.90 (dd, 1H, J=9.8 Hz), 3.85 (s, 3H), 3.63 (s, 3H), 3.46–3.38 (m, 1H), 2.52–2.38 (m, 2H), 2.22–2.12 (m, 1H), 2.08–1.96 (m, 1H).

EXAMPLE 116

(1RS,2RS,3RS)-3-((5-(3,5-Dimethylisoxazol-4-yl)-2-methoxyphenyl)-methylamino)-2-(4-fluorophenyl) cyclopentane-carboxylic acid methyl ester hydrochloride Step A:

(1RS,2RS,3RS)-3-((5-(3,5-Dimethylisoxazol-4-yl)-2-methoxyphenyl)methylamino)-2-(4-fluorophenyl)-cyclopentanecarboxylic acid methyl ester The title compound was prepared by employing the method described in Example 91, Step D with (1RS,2RS,3RS)-2-(4-fluorophenyl)-3-azidocyclopentanecarboxylic acid methyl ester (from Example 89, Step A) and the known 5-(3,5-dimethylisoxazol-4-yl)-2-methoxybenzaldehyde (P. J. Ward, et al., J. Med. Chem. 1995, 38, 4985–92).

NMR (400 MHz, CD$_3$OD): δ 7.22 (dd, 2H, J=9.5 Hz), 7.18 (dd, 1H, J=9.2 Hz), 7.07 (t, 2H, J=9 Hz), 7.01 (d, 1H, J=2 Hz), 6.94 (d, 1H, J=9 Hz), 3.72 (d, 1H, J=13 Hz), 3.58 (s, 3H), 3.54 (s, 3H), 3.53–3.36 (m, 2H), 3.48 (d, 1H, J=13 Hz), 3.24 (td, 1H, J=6.2 Hz), 2.34 (s, 3H), 2.33–226 (m, 1H), 2.19 (s, 3H), 2.10–2.00 (m, 1H), 1.98–1.87 (m, 2H). Mass spectrum (NH$_3$/CI): 453(M+1).

Step B:

(1RS,2RS,3RS)-3-((5-(3,5-Dimethylisoxazol-4-yl)-2-methoxyphenyl)methylamino)-2-(4-fluorophenyl)-cyclopentanecarboxylic acid methyl ester hydrochloride Exposure of the product from Step A above to 1.0 equivalent of HCl in methanol/ethyl ether followed by evaporation provided the title compound. NMR (400 MHz, CD$_3$OD): δ 7.43–7.37 (m, 3H), 7.26–7.19 (m, 3H), 7.14 (d, 1H, J=9 Hz), 4.25 (d, 1H, J=13 Hz), 4.10 (d, 1H, J=13 Hz), 3.95–3.85 (m, 2H), 3.74 (s, 3H), 3.63 (s, 3H), 3.37 (quartet, 1H, J=9 Hz), 2.48–2.38 (m, 2H), 2.36 (s, 3H), 2.20 (s, 3H), 2.16–1.96 (m, 2H).

EXAMPLE 117

Methyl 3-(S,R)-((2-chloro-7-methyl-quinolin-3-yl) methylamino)-2-(S,R) (4-fluorophenyl) cyclopentane-1-(S,R)-carboxylate (Racemic 2,3-cis isomer)

The title compound was prepared by coupling 2-chloro-3-formyl-7-methylquinoline to methyl 3(S,R)-azido-2(R,S)-(4-fluorophenyl)-1-(S,R)-cyclopentanecarboxylate by the procedure described below. All solvents were anhydrous and all the reactions were performed under nitrogen. A 5 mL round bottomed flask fitted with a Teflon magnetic stirrer bar, 3 angstrom powdered molecular sieve (Linde) and a rubber septum was flame dried under nitrogen. Methyl 3(S,R)-azido-2(R,S)-(4-fluorophenyl)-1-(S,R)-cyclopentane-carboxylate (prepared as described in Example 89, Step A) (37 mg, 0.14 mmol) in 800 microliters of dry THF was added to the flask via syringe. Trimethylphosphine (165 microliters in THF (1M), 0.165 mmol) was added via syringe to the flask and the mixture stirred briefly at 50° C. for 10 minutes then at 25° for 1 hour. Then 2-chloro-3-formyl-7-methylquinoline (27 mg, 0.14 mmol) in 200 microliters of dry THF was added in one portion to the flask and the mixture stirred at 25° for 1 h. The solvent was subsequently removed under reduced pressure and 1 mL of dry methanol was added to the reaction mixture, followed by powdered sodium cyanoborohydride (23 mg, 0.36 mmol), then glacial acetic acid (21 microliters, 36 mmol). The reaction mixture was stirred until no starting material was seen by TLC (2 hours) (98/2 CH$_2$Cl$_2$/MeOH). The solvent was removed under reduced pressure and the residue chromatographed with CH$_2$Cl$_2$/MeOH (98/2). Recovered 43 mg of an oil. Mass spec: 428 (M+1). NMR (CDCl$_3$, 400 Mhz): δ 1.8–2.0 (m, 2H), 2.0–2.1 (m, 1H), 2.3–2.4 (m, 1H), 2.52 (s, 3H), 3.3–3.4 (m, 1H), 3.4–3.5 (m, 1H) 3.5–3.58 (m, 1H), 3.60 (s, 3H), 3.65–3.73 (m, 1H), 3.8–3.9 (m, 1H), 6.98 (t, 2H, J=9 Hz), 7.22 (m, 2H), 7.35 (d, 1H, J=9 Hz), 7.61 (d, 1H, J=9 Hz), 7.72 (s, 1H).

EXAMPLE 118

Methyl 3-(S,R)-((3-methoxy-quinolin-2-yl) methylamino)-2-(S,R)-(4-fluorophenyl) cyclopentane-1-(S,R)-carboxylate (Racemic 2,3-cis isomer)

The title compound was prepared by coupling-3-methoxy-quinolin-2-carboxaldehyde to methyl 3(S,R)-azido-2(R,S)-(4-fluorophenyl)-1-(S,R)-cyclopentanecarboxylate by the procedure described in Example 117. Mass spec: 409 (M+1). NMR (CDCl$_3$, 400 Mhz): δ 1.8–2.0 (m, 3H), 2.3–2.4 (m, 1H), 3.2–3.25 (m, 1H), 3.4–3.65 (m, 3H) 3.59 (s, 3H), 3.79 (s over m, 3H+1H), 7.0 (t, 2H, J=9 Hz), 7.17 (dd, 2H, J=7 Hz, J=3 Hz), 7.34 (t, 1H, J=8 Hz), 7.56 (t, 1H, J=8 Hz), 7.62 (s, 1H), 7.64 (s, 1H), 7.77 (d, 1H, J=8 Hz).

EXAMPLE 119

Methyl 3-(S,R)-((3-bromo-benzofuran-7-yl-) methylamino)-2-(S,R)-(4-fluorophenyl) cyclopentane-1-(S,R)-carboxylate (Racemic 2,3-cis isomer)

The title compound was prepared by coupling 5-bromo-benzofuran-7-carboxaldehyde to methyl 3(S,R)-azido-2(R, S)-(4-fluorophenyl)-1-(S,R)-cyclopentanecarboxylate by the procedure described in Example 117. 5-Bromobenzofuran-7-carboxaldehyde was synthesized by the method described in PCT Publication No. WO 95/06645. Mass spec: 446 (M+1). NMR (CDCl$_3$, 400 Mz): δ 1.8–2.0 (m, 3H), 2.25–2.35 (m, 1H), 3.2–3.25 (m, 1H), 3.35–3.42 (m, 1H), 3.45–3.52 (m, 1H), 3.59 (s, 3H), 3.70 (d, 1H, J=15 Hz), 3.90 (d, 1H, J=15 Hz), 6.64 (d, 1H, J=2 Hz), 7.0 (t, 2H, J=9 Hz), 7.07 (bs, 1H), 7.11 (dd, 2H, J=7 Hz, J=3 Hz), 7.40 (d, 1H, J=2 Hz), 7.55 (d, 1H, J=2 Hz).

EXAMPLE 120

Methyl 3-(S,R)-((4,6-dichloropyridin-2-yl) methylamino)-2-(S,R)-(4-fluorophenyl) cyclopentane-1-(S,R)-carboxylate (Racemic 2,3-cis isomer)

The title compound was prepared by coupling 2-formyl-4,6-dichloropyridine to methyl 3(S,R)-azido-2(R,S)-(4- fluorophenyl)-1-(S,R)-cyclopentanecarboxylate by the procedure described in Example 117. 4,6-dichloropyridine-2-carboxaldehyde was prepared by diisobutylaluminum hydride reduction of 2-carbomethoxy-4,6-dichloropyridine which in turn was obtained from chelidamic acid by the procedure of D. G. Markees in *J. Org. Chem.*, (23), p. 1030 (1958).

2-Formyl-4,6-dichloropyridine

To a solution of 2-carbomethoxy-4,6-dichloropyridine (206 mg, 1 mmol) in 4 mL of dry toluene at −78° in a 25 mL round bottomed flask fitted with a stirrer bar and rubber septum, prepared by the procedure of D. G. Markees (vide supra) was slowly added 1.33 mL of 1.5M DIBAL (2 equivalents) in toluene. The mixture was stirred at −78° for 45 minutes, then at −50° for 30 minutes. The mixture was quenched with saturated ammonium chloride. After the effervescence ceased, the mixture was poured into 10 mL of water and extracted with 2×20 mL of methylene chloride. The organic layer was dried over anhydrous $MgSO_4$, filtered and the solvent volume reduced. The residue was purifed by flash chromatography (85/15 hexane/ethyl acetate). Recovered 75 mg of product. NMR ($CDCl_3$ 200 Mhz): δ 7.59 (d, 1H, J=2 Hz), 7.87 (d, 1H, J=2 Hz), 9.97 (s, 1H).

Methyl 3-(S,R)-((4,6-dichloropyridin-2-yl)methylamino)-2-(S,R)-(4-fluorophenyl)cyclopentane-1-(S,R)-carboxylate (Racemic 2,3-cis isomer). Mass spec: 398 (M+1). NMR ($CDCl_3$, 400 Mhz): δ 1.4–1.5 (m, 1H), 1.7–1.8 (m, 1H), 1.9–2.1 (m, 2H), 3.25–3.30 (m, 1H), 3.3–3.42 (m, 1H), 3.45–3.55 (m, 2H), 3.60 (s over m, 3H+1H), 6.64 (d, 1H, J=2 Hz), 7.0–7.05 (m, 3H), 7.16 (s, 1H), 7.2–7.25 (m, 2H).

EXAMPLE 121

Methyl 3-(S,R)-((3-chloro-5-trifluoromethylpyridine-2-yl)methylamino)-2-(S,R)-(4-fluorophenyl)cyclopentane-1-(S,R)-carboxylate (Racemic 2,3-cis isomer)

The title compound was prepared by coupling 3-chloro-5-trifluoromethylpyridine-2-carboxaldehyde (Maybridge Chemical) to methyl 3(S,R)-azido-2(R,S)-(4-fluorophenyl)-1-(S,R)-cyclopentane-carboxylate by the procedure described in Example 117.

Mass spec: 432 (M+1). NMR ($CDCl_3$, 400 Mz): δ 1.85–2.0 (m, 3H), 2.0–2.1 (m, 1H), 3.27–3.33 (m, 1H), 3.33–3.45 (m, 1H), 3.50–3.55 (m, 1H), 3.60 (s, 3H), 3.67 (d, 1H, J=16 Hz), 3.90 (d, 1H, J=16 Hz), 6.95–7.03 (m, 2H), 7.0–7.05 (m, 3H), 7.2–7.25 (m, 2H), 7.78 (d, 1H, J=1.5 Hz), 8.56 (s, 1H).

EXAMPLE 122

Methyl 3-(S,R)-((5-methoxymethoxy-2,3-dihydrobenzofuran-6-yl)methylamino)-2-(S,R)-(4-fluorophenyl)cyclopentane-1-(S,R)-carboxylate (Racemic 2,3-cis isomer)

The title compound was prepared by coupling 6-formyl-5-methoxymethoxy-2,3-dihydrobenzofuran (Sigma-Aldrich Library of Rare Chemicals) to methyl 3(S,R)-azido-2(R,S)-(4-fluorophenyl)-1-(S,R)-cyclopentanecarboxylate by the procedure described in Example 117.

Mass spec: 446 (M+1). NMR ($CDCl_3$, 400 Mz): δ 1.8–2.0 (m, 3H), 2.25–2.35 (m, 1H), 3.05–3.15 (m, 2H), 3.2–3.25 (m, 1H), 3.27 (s, 3H), 3.3–3.5 (m, 3H), 3.58 (s over m, 3H+1H), 4.45–4.55 (m, 2H), 5.75–5.85 (m, 2H), 6.67 (s, 1H), 6.87, (s, 1H), 6.9–7.0 (m, 2H), 7.15–7.2 (m, 2H).

EXAMPLE 123

Methyl 3-(S,R)-((2-methoxy-5-(5-trifluoromethyl-tetrazol-1-yl)-3-pyridine)methylamino)-2-(S,R)-(4-fluorophenyl)cyclopentane-1-(S,R)-carboxylate (Racemic 2,3-cis isomer)

The title compound was prepared by coupling 2-methoxy-3-formyl-5-(5-trifluoromethyl-tetrazol-1-yl)pyridine to methyl 3(S,R)-azido-2(R,S)-(4-fluorophenyl)-1-(S,R)-cyclopentanecarboxylate by the procedure described in Example 117. The synthesis of 2-methoxy-3-formyl-5-(5-trifluoromethyltetrazol-1-yl)pyridine is described below.

Step A:

2-Hydroxy-3-carboxy-5-nitropyridine

The nitration of 2-hydroxy-3-carboxypyridine was performed as taught by Winn et al J. Med. Chem, (36) 2676–2688 (1993). In a 250 mL round bottom flask fitted with a stirrer bar and cooling bath was added 150 mL of concentrated sulfuric acid and 17 g of starting material. Then 10 ml of concentrated nitric acid (67%) was added dropwise to the solution over a period of 20 minutes, keeping the reaction temperature at <8° C. The reaction mixture was warmed to room temperature and stirred overnight. The next day the reaction was heated to 70° C. for 90 minutes. The reaction mixture was cooled to 25° C. and poured the reaction mixture into 1 liter of ice/water. The product, which precipitated out of solution, was recrystallized from ethanol. Recovered 18 g of product. Yield=65%.

Step B:

2-Methoxy-3-carbomethoxy-5-nitropyridine

2-Hydroxy-3-carboxy-5-nitropyridine was converted to 2-chloro-3-chlorocarbonyl-5-nitropyridine in situ and converted to the title compound by reaction with anhydrous methanol according to the procedure of A. Monge et al J. Het. Chem. (29), 1545 (1992). In a 500 mL was added starting material (10.2 g, 54 mmol) in 200 mL of chlorobenzene. Phosphorous oxychloride (20 g, 131 mmol) was added and heated to reflux for 2 hours. The solvent was removed under reduced pressure and residual $POCl_3$ was azeotroped off with 2×50 mL of toluene. Methanol (20 mL) was added to the mixture and the solution stirred at 25° C. for 1 hour, then refluxed overnight. Within 1 hour, all of the intermediate went into solution. There was considerable evolution of HCl. The methanol was stripped and the product neutralized with aqueous saturated sodium bicarbonate. The mixture was extracted with methylene chloride, the organic layer dried over $MgSO_4$, filtered and the solvent removed under reduced pressure. Recovered 5.3 g of crude product. Two spots were observed by TLC (90/10 hexane/ethyl acetate); the higher Rf material (1.6 g) was 2-chloro-3-carbomethoxy-5-nitropyridine, the lower Rf product was the desired 2-methoxy-3-carbomethoxy-5-nitropyridine 850 mg (9% yield).

Step C:

2-Methoxy-3-carbomethoxy-5-aminopyridine

2-Methoxy-3-carbomethoxy-5-nitropyridine (850 mg, 4 mmol) was added to a medium pressure Parr shaker bottle (250 mL) containing 100 mg of 20% Pearlman's catalyst (palladium hydroxide/carbon) and 50 mL of methanol. The bottle was pressurized to 50 psi of hydrogen and shaken for 2 hours. By TLC, no starting material was observed (98/2 $CH_2Cl_2$/MeOH). The catalyst was filtered off, the methanol was removed under reduced pressure and the product used in the next step without further purification. Recovered 680 mg of product (95% yield).

Step D:

2-Methoxy-3-carbomethoxy-5-trifluoroacetamidopyridine

In a 25 mL round bottom flask fitted with a stirrer bar and rubber septum was added 2-methoxy-3-carbomethoxy-5-aminopyridine (520 mg, 2.9 mmol) and 15 mL of $CH_2Cl_2$. The mixture was cooled to 4° C., then added diisopropylethyl amine (1.26 mL , 7.3 mmol). The mixture was stirred vigorously while slowly adding trifluoroacetic anhydride (520 mg, 3.2 mmol) via syringe. After completing the addition, the solution was warmed to 25° C. and stirred for 1 hour. TLC showed no starting material. The solvent was removed under reduced pressure, the residue dissoved in 50 mL of ether and washed successively with 1.0M HCl, 5% sodium bicarbonate then saturated brine solution. The ether layer was dried over MgSO$_4$, filtered and the solvent removed under reduced pressure. Purification by flash chromatography (60/40 hexane/ethyl acetate) afforded 650 mg of product (81% yield).

Step E:

2-Methoxy-3-carbomethoxy-5-(5-trifluoromethyl-1-tetrazole)pyridine

In a 25 mL round bottom flask fitted with a stirrer bar and rubber septum was added 2-methoxy-3-carbomethoxy-5-trifluoroacetamidopyridine (540 mg, 1.9 mmol), triphenylphosphine (520 mg, 2.0 mmol) and 8 mL of CCl$_4$. The solution was refluxed under nitrogen until no starting material was seen by TLC (80/20 hexane/ethyl acetate). The reaction was incomplete so another 520 mg of triphenyl phosphine was added. Total reflux time was 72 hours. The solvent was removed under reduced pressure and relaced with 2 mL of DMF. Sodium azide (130 mg, 2 mmol) was added to the solution and the mixture heated at 60° C. for 2 hours. By TLC, (80/20 hexane/ethyl acetate) all of the iminochloride was consumed. The DMF was removed under high vacuum at 90° C., and the residue was dissolved in CH$_2$Cl$_2$. The organic layer was washed successively with water, 5% sodium bicarbonate and saturated brine. The organic layer was dried over MgSO$_4$, filtered and the solvent removed under reduced pressure. Purification by flash chromatography (80/20 hexane/ethyl acetate) afforded 550 mg of product (95% yield).

Step F:

2-Methoxy-3-formyl-5-(5-trifluoromethyl-tetrazol-1-yl) pyridine

To a 10 mL round bottomed flask fitted with a stirrer bar and rubber septum was added 2-methoxy-3-carbomethoxy-5-(5-trifluoromethyl-tetrazol-1-yl)pyridine (500 mg, 1.66 mmol) in 5 mL of dry toluene. The flask was cooled to −78° C. and DIBAL (1.5M, 2.1 mL, 3.3 mmol) was added slowly so the temperature remained below −50° C. After 2 hr between −78° C. and −45° C., starting material was consumed. Then the reaction mixture was decanted cold into 10 mL of saturated aqueous ammonium chloride. The solution with extracted with 2×20 mL of methylene chloride, the organic layer was dried over MgSO$_4$, filtered and the solvent removed under reduced pressure. Purification by flash chromatography (70/30 hexane/ethyl acetate) gave 220 mg of the alcohol as the overreduced product (44% yield). The alcohol was subjected to TPAP oxidation by adding it (150 mg, 0.54 mmol) in a flask with a stirring bar containing 2 mL of methylene chloride and 100 mg of powdered dried 3 angstrom sieve. The flask was cooled to 0° C. and TPAP (10 mg, 0.05 mmol) and 4-methylmorpholine N-oxide (95 mg, 0.81 mmol), were added together. The flask was warmed to 25° C. and the mixture stirred for 1 hour. The solvent was removed under reduced pressure and the residue placed directly on a silica gel flash column and eluted with (85/15 hexane/ethyl acetate). Recovered 65 mg of desired aldehyde (40% yield). Methyl 3-(S,R)-((2-methoxy-5-(5-trifluoromethyl-1-tetrazol-1-yl)pyridin-3-yl)methylamino)-2-(S,R)-(4-fluorophenyl)cyclopentane-1-(S,R)-carboxylate (Racemic 2,3-cis isomer). Mass spec: 568 (M+1). NMR (CDCl$_3$, 400 Mz): δ 1.75–1.8(m, 1H), 1.9–2.05 (m, 2H), 2.25–2.35 (m, 1H), 3.2–3.25 (m, 1H), 3.3–3.4 (m, 2H), 3.45–3.55 (m, 2H), 3.59 (s over m, 3H+1H), 3.86 (s, 3H), 6.9–7.0 (m, 2H), 7.15–7.2 (m, 2H), 7.48 (d, 1H, J=2 Hz), 8.12 (d, 1H, J=2 Hz).

EXAMPLE 124

Methyl 3-(S,)-(5-(5-trifluoromethyl-1-tetrazol-1-yl)-(7-benzofuran)-methylamino)-2-(S,)-(4-fluorophenyl)cyclopentane-1-(S,)-carboxylate, hydrochloride (chiral product)

The title compound was prepared by coupling 5-(5-trifluoromethyl-1-tetrazol-1-yl)-benzofuran-7-carboxaldehyde methyl with 3(S,R)-azido-2(R,S)-(4-fluorophenyl)-1-(S,R)-cyclopentane-carboxylate by the procedure described in Example 117. The 5-(5-trifluoromethyl-1-tetrazol-1-yl)-benzofuran-7-carboxaldehyde was prepared by the method described in PCT Pub. WO 95/06645. Mass spec: 504 (M+1). NMR (CDCl$_3$, 400 Mz) (free base): δ 1.65–1.7 (m, 1H), 1.8–1.9 (m, 1H), 1.9–2.05 (m, 2H), 2.25–2.35 (m, 1H), 3.25–3.3 (m, 1H), 3.35–3.42 (m, 1H), 3.45–3.52 (m, 1H), 3.59 (s, 3H), 3.83 (d, 1H, J=15 Hz), 4.0 (d, 1H, J=15 Hz), 6.84 (d, 1H, J=2 Hz), 6.93 (t, 2H, J=9 Hz), 7.15 (m, 3H), 7.55 (d, 1H, J=2 Hz), 7.64 (d, 1H, J=2 Hz).

EXAMPLE 125

Methyl 3-(SR)-[(3-methoxy-benzo[b]-thiophen-2-yl)-methylamino]-2-(SR)-(4-fluorophenyl)-cyclopentane-1-(SR)-carboxylate (Racemic 2,3-cis isomer)

To a solution of methyl 3-(SR)-azido-2-(SR)-(4-fluorophenyl)-cyclopentane-1-(SR)-carboxylate (150 mg, 0.570 mmol; from Example 89, Step A) in dry tetrahydrofuran (4 mL) were added powdered 4A molecular sieves (300 mg) and trimethylphosphine (1M solution in THF, 0.673 mL, 0.673 mmol). The reaction mixture was stirred for one hour at room temperature under nitrogen. 3-Methoxybenzo[b]thiophene-2-carboxaldehyde [A. Ricci et al., J. Chem. Soc. (C), 779 (1967)] (127 mg, 0.661 mmol) was then added, and the mixture stirred an additional hour at room temperature. THF was then removed under vacuum with the aid of a warm water bath. The residue was taken up in methanol (5 mL), and glacial acetic acid (90 μL, 1.50 mmol) and sodium cyanoborohydride (94 mg, 1.50 mmol) were added. The reaction mixture was stirred overnight at room temperature, then diluted with methanol (25 mL) and filtered through a pad of Celite. The filtrate was evaporated, and the residue was purified by flash chromatography eluting with 4% isopropanol in hexane to obtain 73 mg of the title compound. 400 MHz $^1$H NMR (CD$_3$OD): d 1.89 (m, 2H), 2.08 (m, 1H), 2.29 (m, 1H), 3.59 (s, 3H), 3.76 (AB q, 2H), 3.78 (s, 3H), 7.04 (t, 2H), 7.27–7.35 (m, 4H), 7.65 (d, 1H), 7.70 (d, 1H). Mass spec (NH$_3$/CI): 414 (M+1).

EXAMPLE 126

Methyl 3-(SR)-{[4-methoxy-2-(4-pyridyl)-thiazol-5-yl]-methylamino}-2-(SR)-(4-fluorophenyl)-cyclopentane-1-(SR)-carboxylate (Racemic 2,3-cis isomer)

Step A:

Ethyl 4-hydroxy-2-(4-pyridyl)-thiazole-5-carboxylate

The title compound was prepared according to the procedure described in F. Duro, Gazz. Chim. Ital., 93, 215 (1963) for ethyl 4-hydroxy-2-phenylthiazole-5-carboxylate.

Step B:

Ethyl 4-methoxy-2-(4-pyridyl)-thiazole-5-carboxylate

To a mixture of ethyl 4-hydroxy-2-(4-pyridyl)-thiazole-5-carboxylate (0.5 gm, 2.0 mmol) in 30% methanol in benzene (30 mL) was added (trimethylsilyl)diazomethane (2.0M solution in hexanes) (1.0 mL, 2.0 mmol). After stirring for 30 minutes at room temperature, an additional 1.0 mL of (trimethylsilyl)diazomethane was added. The mixture was stirred overnight at room temperature and evaporated. The title compound was purified by flash chromatography eluting with 20% acetone in hexane; yield 206 mg.

Step C:

5-(Hydroxymethyl)-4-methoxy-2-(4-pyridyl)-thiazole

To a solution of ethyl 4-methoxy-2-(4-pyridyl)-thiazole-5-carboxylate (169 mg, 0.639 mmol) in THF (4 mL) cooled in an ice-bath was added lithium aluminum hydride portionwise (48 mg, 1.26 mmol). After stirring for 15 minutes at ice temperature, excess LAH was destroyed by sequential addition of water (48 µL), 15% aqueous NaOH (48 µL), and water (144 µL). The mixture was diluted with THF, filtered through a pad of Celite, and evaporated. The title compound was purified by flash chromatography eluting with 25% acetone/hexane.

Step D:

4-Methoxy-2-(4-pyridyl)-thiazole-5-carboxaldehyde 5-(Hydroxymethyl)-4-methoxy-2-(4-pyridyl)-thiazole (182 mg, 0.777 mmol) was dissolved in methylene chloride (4 mL) and treated with 4-methylmorpholine-N-oxide (135 mg, 1.15 mmol), powdered 4A molecular sieves (385 mg), and tetrapropylammonium perruthenate (TPAP) (14 mg, 0.040 mmol) overnight at room temperature. The mixture was applied to a column of silica gel and eluted with 25% acetone in hexane to afford 62 mg of title compound.

Step E:

Methyl 3-(SR)-{[4-methoxy-2-(4-pyridyl)-thiazol-5-yl]-methylamino}-2-(SR)-(4-fluorophenyl)-cyclopentane-1-(SR)-carboxylate Following essentially the same procedure as in Example 125, but employing 4-methoxy-2-(4-pyridyl)-thiazole-5-carbox-aldehyde, the title compound was obtained after flash chromatography eluting with 20% acetone in hexane. 400 MHz $^1$H NMR (CDCl$_3$): d 1.93 (m, 2H), 2.08 (br m, 1H), 2.35 (br m, 1H), 3.60 (s, 3H), 3.93 (s, 3H), 7.01 (m, 2H), 7.68 (m, 2H), 8.63 (m, 2H). Mass spec (NH$_3$/CI): 442 (M+1).

EXAMPLE 127

Methyl 3-(SR)-[(3-methoxy-thien-4-yl)-methylamino]-2-(SR)-(4-fluorophenyl)-cyclopentane-1-(SR)-carboxylate (Racemic 2,3-cis isomer)

Step A:

3-Methoxythiophene-4-carboxaldehyde

The title compound was obtained in a similar sequence to Steps C and D of Example 126 (LAH reduction followed by TPAP oxidation) from methyl 3-methoxythiophene-4-carboxylate; purified by flash chromatography eluting with 5% ethyl acetate in hexane.

Step B:

Methyl 3-(SR)-[(3-methoxy-thien-4-yl)-methylamino]-2-(SR)-(4-fluorophenyl)-cyclopentane-1-(SR)-carboxylate Following essentially the same procedure as in Ex. 125, but employing 3-methoxythiophene-4-carboxaldehyde, the title compound was obtained after flash chromatography eluting with 10% acetone in hexane. 400 MHz $^1$H NMR (CD$_3$OD): d 1.80–2.08 (m, 3H), 2.29 (m, 1H), 3.46 (AB q, 2H), 3.50 (s, 3H), 3.59 (s, 3H), 6.29 (d, 1H), 6.99 (d, 1H), 7.08 (m, 2H), 7.21 (m, 2H). Mass spec (NH$_3$/CI): 364 (M+1).

EXAMPLE 128

Methyl 3-(SR)-[(3-methoxy-thien-2-yl)-methylamino]-2-(SR)-(4-fluorophenyl)-cyclopentane-1-(SR)-carboxylate (Racemic 2,3-cis isomer)

To a solution of methyl 3-(SR)-amino-2-(SR)-(4-fluorophenyl)-cyclopentane-1-(SR)-carboxylate (67 mg, 0.282 mmol) and 3-methoxythiophene-2-carboxaldehyde [G. Henrico et al., *Bull. soc. chim. Fr.*, 265 (1976)] (40.3 mg, 0.283 mmol) in dry tetrahydrofuran (3 mL) were added glacial acetic acid (17 µL) and sodium triacetoxyborohydride (88 mg, 0.415 mmol). The reaction mixture was stirred overnight at room temperature under an inert atmosphere. The mixture was then evaporated, and residue was purified by flash chromatography eluting with 15% acetone in hexane to obtain 67 mg of the title compound. 400 MHz $^1$H NMR (CD$_3$OD): d 1.80–1.97 (m, 2H), 2.08 (m, 1H), 2.29 (m, 1H), 3.59 (s, 3H), 3.63 (AB q, 2H), 3.64 (s, 3H), 6.85 (d, 1H), 7.08 (m, 2H), 7.16 (d, 1H), 7.24 (m, 2H). Mass spec (NH$_3$/CI): 364 (M+1).

EXAMPLE 129

Methyl 3-(SR)-{[2-(pyridin-4-yl)-1H-imidazolyl]-methylamino}-2-(SR)-(4-fluorophenyl)-cyclopentane-1-(SR)-carboxylate (Racemic 2,3-cis isomer)

Step A:

2-(pyridin-4-yl)-1H-imidazole-carboxaldehyde

The title compound was obtained in a similar sequence to Steps C and D of Example 126 (LAH reduction followed by TPAP oxidation) from methyl 2-(pyridin-4-yl)-1H-imidazole-carboxylate; purification was effected by silica gel chromatography eluting with 50% acetone in hexane.

Step B:

Methyl 3-(SR)-{[2-(pyridin-4-yl)-1H-imidazol-yl]-methylamino}-2-(SR)-(4-fluorophenyl)-cyclopentane-1-(SR)-carboxylate Following essentially the same procedure as in Example 128, but employing 2-(pyridin-4-yl)-1H-imidazole-carboxaldehyde, the title compound was obtained after flash chromatography eluting with 5% methanol in methylene chloride. 400 MHz $^1$H NMR (CD$_3$OD): d 1.90 (m, 2H), 2.12 (m, 1H), 2.31 (m, 1H), 3.58 (s, 3H), 3.62 (AB q, 2H), 7.04 (m, 3H), 7.28 (m, 2H), 7.77 (m, 2H), 8.59 (m, 2H). Mass spec (NH$_3$/CI): 395 (M+1).

EXAMPLE 130

Methyl 3-(SR)-[(3-methoxy-5-phenyl-thien-2-yl)-methylamino]-2-(SR)-(4-fluorophenyl)-cyclopentane-1-(SR)-carboxylate Hydrochloride (Racemic 2,3-cis isomer)

Step A:

Methyl 3-hydroxy-5-phenyl-2-carboxylate

The title compound was prepared according to the procedure described in H. Fiesselmann and F. Thoma, *Chem. Ber.*, 89, 1907 (1956).

Step B:

Methyl 3-methoxy-5-phenyl-2-carboxylate

To a solution of methyl 3-hydroxy-5-phenyl-2-carboxylate (1.25 gm, 5.34 mmol) in DMF (7 mL) were added powdered potassium carbonate (1.03 gm, 7.45 mmol) and iodomethane (0.5 mL, 8.03 mmol). The reaction mixture was stirred overnight at room temperature. The mixture was partitioned between diethyl ether and water. The ether layer was washed with saturated brine solution, dried (Na$_2$SO$_4$), and evaporated. The title compound was obtained after flash chromatography eluting with 25% diethyl ether in hexane.

Step C:

3-Methoxy-5-phenyl-thiophene-2-carboxaldehyde

The title compound was obtained in a similar sequence to Steps C and D of Example 126 (LAH reduction followed by TPAP oxidation) from methyl 3-methoxy-5-phenyl-2-carboxylate; purification was effected by flash chromatography eluting with 20% ethyl acetate in hexane.

Step D:

Methyl 3-(SR)-[(3-methoxy-5-phenyl-thien-2-yl)-methylamino]-2-(SR)-(4-fluorophenyl)-cyclopentane-1-(SR)-carboxylate Hydrochloride Following essentially the same procedure as in Example 128, but employing 3-methoxy-5-phenyl-thiophene-2-carboxaldehyde, the title compound was obtained after flash chromatography eluting with 3% isopropanol in hexane. The hydrochloride salt was obtained by treating an ether solution of the amine with 1M HCl in diethyl ether. 400 MHz $^1$H NMR (CD$_3$OD): d 1.82–1.97 (m, 2H), 2.10 (m, 1H), 2.30 (m, 1H), 3.60 (s, 3H), 3.71 (s, 3H), 7.09 (m, 2H), 7.19 (s, 1H), 7.28 (m, 3H), 7.36 (t, 2H), 7.55 (d, 2H).

EXAMPLE 131

Methyl 3-(SR)-{[(5-(4-trifluoromethylphenyl)-1,2,4-oxadiazol-3-yl]-methylamino}-2-(SR)-(4-fluorophenyl)-cyclopentane-1-(SR)-carboxylate
(Racemic 2,3-cis isomer)

To a solution of methyl 3-(SR)-amino-2-(SR)-(4-fluorophenyl)-cyclopentane-1-(SR)-carboxylate (62.8 mg, 0.265 mmol) and 3-(chloromethyl)-5-(4-trifluoromethylphenyl)-1,2,4-oxadiazole (69.5 mg, 0.265 mmol) in acetonitrile (2 mL) was added N,N-diisopropylethylamine (100 μL, 0.574 mmol). The reaction mixture was stirred for 24 hours at 70° C. under an inert atmosphere. The cooled mixture was evaporated, and the residue was purified by flash chromatography eluting with 10% acetone/hexane to obtain 72 mg of the title compound. 400 MHz $^1$H NMR (CD$_3$OD): d 1.90 (m, 2H), 2.08 (m, 1H), 2.31 (m, 1H), 3.60 (s, 3H), 3.70 (AB q, 2H), 7.04 (m, 2H), 7.30 (m, 2H), 7.90 (m, 2H), 8.23 (m, 2H). Mass spec (NH$_3$/CI): 464 (M+1).

EXAMPLE 132

Methyl 3-(SR)-[(5-phenyl-imidazo-[5,1-b]-thiazol-7-yl)-methylamino]-2-(SR)-(4-fluorophenyl)-cyclopentane-1-(SR)-carboxylate (Racemic 2,3-cis isomer)

Step A:

5-Phenylimidazo-[5,1-b]-thiazole-7-carboxaldehyde

Phosphorus oxychloride (0.6 mL, 6.44 mmol) was added to DMF (2.5 mL) over 5 minutes with cooling in an ice-bath. 5-Phenylimidazo-[5,1-b]-thiazole (500 mg, 2.5 mmol) was added, and the mixture was kept overnight at room temperature. The thick solid that had formed was slurried in methylene chloride and stirred for 30 minutes with 10% aqueous sodium carbonate solution. The organic layer was separated, washed with saturated brine solution and evaporated. The title compound was obtained after flash chromatography eluting with 20% acetone in hexane.

Step B:

Methyl 3-(SR)-[(5-phenyl-imidazo-[5,1-b]-thiazol-7-yl)-methylamino]-2-(SR)-(4-fluorophenyl)-cyclopentane-1-(SR)-carboxylate Following essentially the same procedure as in Example 128, but employing 5-phenylimidazo-[5,1-b]-thiazole-7-carboxaldehyde, the title compound was obtained after flash chromatography eluting with 15% acetone in hexane. 400 MHz $^1$H NMR (CD$_3$OD): d 1.93 (m, 2H), 2.16 (m, 1H), 2.32 (m, 1H), 3.60 (s, 3H), 3.69 (AB q, 2H), 7.05 (m, 2H), 7.17 (d, 1H), 7.32 (m, 2H), 7.40 (t, 1H), 7.50 (t, 2H), 7.71 (d, 2H), 7.92 (d, 1H). Mass spec (NH$_3$/CI): 450 (M+1).

EXAMPLE 133

Methyl 3-(SR)-[(6-methoxy-2-methyl-benzothiazol-7-yl)-methylamino]-2-(SR)-(4-fluorophenyl)-cyclopentane-1-(SR)-carboxylate Hydrochloride
(Racemic 2,3-cis isomer)

Step A:

6-Hydroxy-2-methyl-benzothiazole

A mixture of 6-methoxy-2-methyl-benzothiazole (2.5 gm, 0.014 mol) in 30% HBr in acetic acid (15 mL) was stirred for 2 days at 70° C. After cooling, the solid was filtered, washed with ether, and dried in vacuo. The solid was taken up in water (20 mL) and neutralized with saturated NaHCO$_3$ solution. The resulting solid was filtered, washed with water, and dried in vacuo at 40° C.; yield 1.2 gm.

Step B:

6-Hydroxy-2-methyl-benzothiazole-7-carboxaldehyde

To a 3-necked flask equipped with a thermometer and an addition funnel were added 6-hydroxy-2-methyl-benzothiazole (1.0 gm, 6.05 mmol) and hexamethylenetetramine (3.4 gm, 24.3 mmol). After cooling in an ice-bath, trifluoroacetic acid (10 mL) was added dropwise with stirring while maintaining the temperature below 60° C. The reaction mixture was stirred overnight at 70°–75° C., cooled, and evaporated. The residue was taken up in ethyl acetate and neutralized with saturated NaHCO$_3$ solution. The organic layer was washed with saturated brine solution and dried (Na$_2$SO$_4$). The solution was filtered, and the filtrate evaporated. The residue was triturated with a mixture of methylene chloride/methanol and filtered. The filtrate was evaporated, and the residue dissolved in a small volume of methylene chloride and chromatographed on a column of silica gel that was eluted with 25% acetone in hexane affording pure title compound.

Step C:

6-Methoxy-2-methyl-benzothiazole-7-carboxaldehyde

6-Hydroxy-2-methyl-benzothiazole-7-carboxaldehyde (75 mg, 0.362 mmol) was taken up in 30% methanol in benzene (7 mL) and treated with (trimethylsilyl)diazomethane (2.0M solution in hexanes) (0.5 mL, 1.0 mmol) for 2 hours at room temperature. The mixture was evaporated, and the title compound was purified by flash chromatography eluting with 25–30% ethyl acetate in hexane.

Step D:

Methyl 3-(SR)-[(6-methoxy-2-methyl-benzothiazol-7-yl)-methylamino]-2-(SR)-(4-fluorophenyl)-cyclopentane-1-(SR)-carboxylate Hydrochloride Following the procedure as in Example 128, but employing 6-methoxy-2-methyl-benzothiazole-7-carboxaldehyde, an intermediate imine was obtained which was converted into the title compound by treatment of a methanolic solution with glacial acetic acid and sodium cyanoborohydride and subsequent flash chromatography eluting with 5% isopropanol in hexane. The hydrochloride salt was obtained by treating an ether solution of the amine with 1M HCl in diethyl ether.

400 MHz $^1$H NMR (CD$_3$OD): d 1.90–2.10 (m, 3H), 2.30 (m, 1H), 2.75 (s, 3H), 3.19 (m, 1H), 3.59 (s, 3H), 3.63 (s, 3H), 3.79 (AB q, 2H), 7.04 (m, 2H), 7.10 (d, 1H), 7.18 (m, 2H), 7.71 (d, 1H). Mass spec (NH$_3$/CI): 429 (M+1).

EXAMPLE 134

Methyl 3-(SR)-[(5-methoxy-1H-indol-4-yl)-methylamino]-2-(SR)-(4-fluorophenyl)-cyclopentane-1-(SR)-carboxylate Hydrochloride
(Racemic 2,3-cis isomer)

Following essentially the same procedure as in Example 128, but employing 5-methoxy-1H-indole-4- carboxaldehyde [prepared according to the procedures set forth in L. I. Kruse and M. D. Meyer, *J. Org. Chem.* 49, 4761 (1984)], the title compound was obtained after flash chromatography eluting with 15–25% acetone in hexane. The hydrochloride salt was obtained by treating an ether solution of the amine with 1M HCl in diethyl ether. 400 MHz $^1$H NMR (CD$_3$OD): d 1.90–2.40 (4 m's, 4H), 3.40 (m, 1H), 3.50 (m, 1H), 3.56 (s, 3H), 3.59 (s, 3H), 4.10 (AB q, 2H), 6.32 (d, 1H), 6.82 (d, 1H), 7.10 (m, 2H), 7.20 (m, 2H), 7.27 (d, 1H), 7.32 (d, 1H). Mass spec (NH$_3$/CI): 397 (M+1).

EXAMPLE 135

Methyl 3-(SR)-[(5-bromo-2-isopropoxy-phenyl)-methylamino]-2-(SR)-(4-fluorophenyl)-cyclopentane-1-(SR)-carboxylate Hydrochloride (Racemic 2,3-cis isomer)

Step A:
5-Bromo-2-isopropoxy-benzaldehyde

To a solution of 5-bromosalicylaldehyde (5.0 gm, 0.025 mol) in DMF (40 mL) were added powdered potassium carbonate (5.15 gm, 0.037 mol) and 2-iodopropane (3.5 mL, 0.035 mol) dropwise with stirring. The mixture was stirred overnight at room temperature, partitioned between diethyl ether and water. The aqueous was extracted with ether, and the combined organic layers were washed with water, saturated brine solution, dried (Na$_2$SO$_4$), and evaporated to afford 6.0 gm of pure title compound.

Step B:
Methyl 3-(SR)-[(5-bromo-2-isopropoxy-phenyl)-methylamino]-2-(SR)-(4-fluorophenyl)-cyclopentane-1-(SR)-carboxylate Hydrochloride Following essentially the same procedure as in Example 128, but employing 5-bromo-2-isopropoxy-benzaldehyde, the title compound was obtained after flash chromatography eluting with 10% acetone in hexane. The hydrochloride salt was obtained by treating an ether solution of the amine with 1M HCl in diethyl ether.

400 MHz $^1$H NMR (CD$_3$OD): d 1.00 (d, 3H), 1.07 (d, 3H), 1.91 (m, 2H), 2.07 (m, 1H), 2.29 (m, 1H), 3.22 (m, 1H), 3.51 (AB q, 2H), 3.58 (s, 3H), 4.40 (septet, 1H), 6.78 (d, 1H), 7.04 (m, 2H), 7.21 (m, 3H), 7.30 (dd, 1H). Mass spec (NH$_3$/CI): 464 (M+1).

EXAMPLE 136

Methyl 3-(S)-[(5-cyano-2-isopropoxy-phenyl)-methylamino]-2-(S)-(4-fluorophenyl)-cyclopentane-1-(S)-carboxylate Hydrochloride (Non-racemic 2,3-cis isomer)

Step A:
5-Cyano-2-isopropoxy-benzaldehyde

The title compound was prepared by the treatment of 5-bromo-2-isopropoxy-benzaldehyde (3.5 gm, 0.014 mol) with copper(I) cyanide (2.5 gm, 0.028 mol) in refluxing DMF for 28 hours. The cooled mixture was poured into a mixture of water (100 mL) and ethyl acetate (100 mL). The mixture was filtered through a pad of Celite, the organic layer separated, washed with saturated brine solution, dried (Na2SO$_4$), and evaporated. The title compound was purified by flash chromatography eluting with 15% ethyl acetate in hexane; yield 1.9 gm of a white solid.

Step B:
Methyl 3-(S)-[(5-cyano-2-isopropoxy-phenyl)-methylamino]-2-(S)-(4-fluorophenyl)-cyclopentane-1-(S)-carboxylate Hydrochloride Following essentially the same procedure as in Example 128, but employing methyl 3-(S)-amino-2-(S)-(4-fluorophenyl)-cyclopentane-1-(S)-carboxylate and 5-cyano-2-isopropoxy-benzaldehyde, the title compound was obtained after flash chromatography eluting with 15% acetone in hexane. The hydrochloride salt was obtained by treating an ether solution of the amine with 1M HCl in diethyl ether. 400 MHz $^1$H NMR (CD$_3$OD): d 1.04 (d, 3H), 1.10 (d, 3H), 1.92 (m, 2H), 2.08 (m, 1H), 2.30 (m, 1H), 3.21 (m, 1H), 3.56 (AB q, 2H), 3.58 (s, 3H), 4.55 (septet, 1H), 7.00–7.08 (m, 3H), 7.21 (m, 2H), 7.47 (d, 1H), 7.59 (dd, 1H). Mass spec (NH$_3$/CI): 411 (M+1).

EXAMPLE 137

3-(S)-[(5-Cyano-2-isopropoxy-phenyl)-methylamino]-2-(S)-(4-fluorophenyl)-cyclopentane-1-(S)-carboxamide Hydrochloride (Non-racemic 2, 3-cis isomer)

Following essentially the same procedure as in Example 128, but employing 3-(S)-amino-2-(S)-(4-fluorophenyl)-cyclopentane-1-(S)-carboxamide (prepared by catalytic hydrogenation of 3-(S)-azido- 2(S)-(4-fluorophenyl)-cyclopentane-1-(S)-carboxamide which was prepared essentially as described in Example 93, Step A) and 5-cyano-2-isopropoxy-benzaldehyde, the title compound was obtained after flash chromatography eluting with 4% methanol in methylene chloride. The hydrochloride salt was obtained by treating an ether solution of the amine with 1M HCl in diethyl ether. 400 MHz $^1$H NMR (CD$_3$OD): d 1.08 (d, 3H), 1.12 (d, 3H), 1.91 (m, 2H), 2.11 (m, 1H), 2.27 (m, 1H), 3.62 (AB q, 2H), 4.57 (septet, 1H), 7.01–7.09 (m, 3H), 7.23 (m, 2H), 7.49 (d, 1H), 7.61 (dd, 1H). Mass spec (NH$_3$/CI): 396 (M+1).

EXAMPLE 138

1-(S)-[(5-Cyano-2-isopropoxy-phenyl)-methylamino]-2-(S)-(4-fluorophenyl)-3-(S)-(2-thiazol-2-yl)-cyclopentane Hydrochloride (Non-racemic 2,3-cis isomer)

Following essentially the same procedure as in Example 125, but employing 1-(S)-azido-2-(S)-(4-fluorophenyl)-3-(S)-(2-thiazol-2-yl)-cyclopentane (Example 94, Step A) and 5-cyano-2-isopropoxy-benzaldehyde, the title compound was obtained after flash chrom. eluting with 10–15% acetone in hexane. The hydrochloride salt was obtained by treating an ether solution of the amine with 1M HCl in diethyl ether. 400 MHz $^1$H NMR (CD$_3$OD): d 1.05 (d, 3H), 1.1 1 (d, 3H), 2.00 (m, 2H), 2.22 (m, 1H), 2.51 (m, 1H), 3.59 (dd, 1H), 4.18 (m, 1H), 4.56 (septet, 1H), 7.01 (m, 3H), 7.27 (m, 2H), 7.32 (d, 1H), 7.48 (d, 1H), 7.58 (m, 2H). Mass spec (NH$_3$/CI): 436 (M+1).

EXAMPLE 139

Methyl 3-(S)-[(5-methoxycarbonyl-2-isopropoxy-phenyl)-methylamino]-2-(S)-(4-fluorophenyl)-cyclopentane-1-(S)-carboxylate Hydrochloride (Non-racemic 2,3-cis isomer)

Following essentially the same procedure as in Example 128, but employing methyl 3-(S)-amnino-2-(S)-(4-fluorophenyl)-cyclopentane-1-(S)-carboxylate and 5-methoxycarbonyl- 2-isopropoxy-benzaldehyde, the title compound was obtained after flash chromatography eluting with 5% isopropanol in hexane. The hydrochloride salt was obtained by treating an ether solution of the amine with 1M HCl in diethyl ether. 400 MHz 1H NMR (CD$_3$OD): d 1.06

(d, 3H), 1.11 (d, 3H), 1.97 (m, 2H), 2.11 (m, 1H), 2.32 (m, 1H), 3.58 (s, 3H), 3.63 (AB q, 2H), 3.87 (s, 3H), 4.55 (septet, 1H), 6.98 (d, 1H), 7.07 (m, 2H), 7.21 (m, 2H), 7.78 (d, 1H), 7.91 (dd, 1H). Mass spec (NH$_3$/CI): 444 (M+1).

EXAMPLE 140

Methyl 3-(S)-[(5-aminocarbonyl-2-isopropoxy-phenyl)-methylamino]-2-(S)-(4-fluorophenyl)-cyclopentane-1-(S)-carboxylate Hydrochloride
(Non-racemic 2,3-cis isomer)

Following essentially the same procedure as in Example 128, but employing methyl 3-(S)-amino-2-(S)-(4-fluorophenyl)-cyclopentane-1-(S)-carboxylate and 5-aminocarbonyl-2-isopropoxy-benzaldehyde, the title compound was obtained after flash chromatography eluting with 2% methanol in methylene chloride. The hydrochloride salt was obtained by treating an ether solution of the amine with 1M HCl in diethyl ether. 400 MHz $^1$H NMR (CD$_3$OD): d 1.06 (d, 3H), 1.11 (d, 3H), 1.98 (m, 2H), 2.12 (m, 1H), 2.32 (m, 1H), 3.59 (s, 3H), 4.54 (septet, 1H), 6.95 (d, 1H), 7.07 (m, 2H), 7.21 (m, 2H), 7.69 (d, 1H), 7.80 (dd, 1H). Mass spec (NH$_3$/CI): 429 (M+1).

EXAMPLE 141

Methyl 3-(SR)-{[5-(4-fluorophenyl)-2-isopropoxy-phenyl]-methylamino}-2-(SR)-(4-fluorophenyl)-cyclopentane-1-(SR)-carboxylate Hydrochloride
(Racemic 2,3-cis isomer)
Step A:
2-Isopropoxy-5-(4-fluorophenyl)-benzaldehyde To a solution of 5-bromo-2-isopropoxy-benzaldehyde (504 mg, 2.07 mmol) in 1,2-dimethoxyethane (5 mL) were added tetrakis(triphenylphosphine)palladium(0) (87 mg, 0.075 mmol), 2M aqueous sodium carbonate (2.5 mL), and 4-fluorobenzeneboronic acid (396 mg, 2.83 mmol). The reaction mixture was stirred for 2 hours at reflux temperature, cooled, diluted with ethyl acetate, washed with water, saturated brine solution, dried (Na$_2$SO$_4$), and evaporated. The title compound was purified by flash chromatography eluting with 4% diethyl ether in hexane; yield 347 mg.
Step B:
Methyl 3-(SR)-{[5-(4-fluorophenyl)-2-isopropoxy-phenyl]-methylamino}-2-(SR)-(4-fluorophenyl)-cyclopentane-1-(SR)-carboxylate Hydrochloride Following essentially the same procedure as in Example 128, but employing 2-isopropoxy-5-(4-fluorophenyl)-benzaldehyde, the title compound was obtained after flash chromatography eluting with 20% EtOAc in hexane. The hydrochloride salt was obtained by treating an ether solution of the amine with 1M HCl in diethyl ether. 400 MHz $^1$H NMR (CD$_3$OD): d 1.03 (d, 3H), 1.09 (d, 3H), 1.96 (m, 2H), 2.08 (m, 1H), 2.30 (m, 1H), 3.58 (s, 3H), 4.46 (septet, 1H), 6.91 (d, 1H), 7.03 (m, 2H), 7.12 (m, 2H), 7.21 (m, 2H), 7.30 (d, 1H), 7.41 (dd, 1H), 7.52 (m, 2H). Mass spec (NH$_3$/CI): 480 (M+1).

EXAMPLE 142

Methyl 3-(S)-{[2-isopropoxy-5-(2-methyl-2H-tetrazol-5-yl)-phenyl]-methylamino}-2-(S)-(4-fluorophenyl)-cyclopentane-1-(S)-carboxylate Hydrochloride (Non-racemic 2,3-cis isomer)

Following essentially the same procedure as in Example 128, but employing methyl 3-(S)-amino-2-(S)-(4-fluorophenyl)-cyclopentane-1-(S)-carboxylate and 2-isopropoxy-5-(2-methyl-2H-tetrazol-5-yl)-benzaldehyde [prepared according to the procedures given in PCT International Application WO 95/08549, published 30 Mar. 1995, p. 57, for 2-methoxy-5-(2-methyl-2H-tetrazol-5-yl)-benzaldehyde], the title compound was obtained after flash chromatography eluting with 15% acetone in hexane. The hydrochloride salt was obtained by treating an ether solution of the amine with 1M HCl in diethyl ether.

400 MHz $^1$H NMR (CD$_3$OD): d 1.03 (d, 3H), 1.10 (d, 3H), 1.97 (m, 2H), 2.09 (m, 1H), 2.31 (m, 1H), 3.58 (s, 3H), 3.62 (AB q, 2H), 4.40 (s, 3H), 4.52 (septet, 1H), 6.98–7.07 (m, 3H), 7.21 (m, 2H), 7.81 (d, 1H), 7.94 (dd, 1H). Mass spec (NH$_3$/CI): 468 (M+1).

EXAMPLE 143

Methyl 3-(S)-{[2-isopropoxy-5-(1-methyl-1H-tetrazol-5-yl)-phenyl]-methylamino}-2-(S)-(4-fluorophenyl)-cyclopentane-1-(S)-carboxylate Hydrochloride (Non-racemic 2,3-cis isomer)

Following essentially the same procedure as in Example 128, but employing methyl 3-(S)-amino-2-(S)-(4-fluorophenyl)-cyclopentane-1-(S)-carboxylate and 2-isopropoxy-5-(1-methyl-1H-tetrazol-5-yl)-benzaldehyde [prepared according to the procedures given in PCT International Application WO 95/08549, published 30 Mar. 1995, p. 57, for 2-methoxy-5-(1-methyl-1H-tetrazol-5-yl)-benzaldehyde], the title compound was obtained after flash chromatography eluting with 20% acetone in hexane. The hydrochloride salt was obtained by treating an ether solution of the amine with 1M HCl in diethyl ether.

400 MHz $^1$H NMR (CD$_3$OD): d 1.07 (d, 3H), 1.12 (d, 3H), 1.95 (m, 2H), 2.08 (m, 1H), 2.31 (m, 1H), 3.58 (s, 3H), 3.65 (AB q, 2H), 4.18 (s, 3H), 4.58 (septet, 1H), 7.03 (m, 2H), 7.10 (d, 1H), 7.21 (m, 2H), 7.58 (d, 1H), 7.68 (dd, 1H). Mass spec (NH$_3$/CI): 468 (M+1).

EXAMPLE 144

Methyl 3-(SR)-((2-isopropoxy-5-(tetrazol-1-yl) phenyl)methylamino)-2-(SR)-(4-fluorophenyl) cyclopentane-1-(SR)carboxylate
Step A:
2-Isopropoxy-5-(1-tetrazol-1-yl)-benzaldehyde To a solution of 500 mg (2.63 mmol) 1-hydroxy-4-(1-tetrazol-1-yl)-2-benzaldehyde in 5 mL of DMF was added 545 mg (3.95 mmol) of powdered potassium carbonate and 368 ul (3.68 mmol) of isopropyl iodide. The mixture was stirred at room temperature for 18 h, diluted with water, extracted with ethyl acetate, washed with brine, dried over magnesium sulfate, and evaporated to give the title compound. Mass spec 233 (M+1). NMR (CDCl$_3$): δ 1.37 (d, 6H), 4.39 (m, 1H), 7.55 (d, 1H), 8.13 (d, 1H), 8.15 (d, 1H), 10.10 (s, 1H), 10.40 (s, 1H)
Step B:
Methyl 3-(SR)-((2-isopropoxy-5-(tetrazol-1-yl)phenyl) methylamino)-2-(SR)-(4-fluorophenyl)cyclopentane-1-(SR) -carboxylate To a solution of 150 mg (0.57 mmol) methyl-3-(SR)-azido-2-(SR)-(4-fluorophenyl)cyclopentane-1-(SR)-carboxylate in 4 ml of THF was added 300 mg of 4 Å sieves, 0.67 mL (0.67 mmol) of a 1.0M solution of trimethylphosphine in THF, and stirred at room temperature for 1 h. 154 mg (0.66 mmol) of 2-isopropoxy-5-(tetrazol-1-yl)-benzaldehyde was added and the mixture stirred at room temperature for 1 h. The mixture was evaporated to dryness, 5 mL of methanol, 94 mg (1.50 mmol) of sodium cyanoborohydride, 90 ul (1.50 mmol) of acetic acid were added, and the mixture stirred for 0.5 h. The mixture was filtered through celite, and concentrated to dryness, purified by flash silica gel chromatography using 50% ethyl acetate/hexane to give 195 mg of the title compound; mass spec 454 (M+1). NMR (CDCl$_3$): δ 1.15 (m, 6H), 3.58 (s, 3H), 4.47(m, 1H), 6.88 (d, 1H), 6.98 (t, 2H), 7.20 (m, 2H), 7.40 (s, 1H), 7.45 (d, 1H), 8.85 (s, 1H)

EXAMPLE 145

3-(SR)-((2-isopropoxy-5-(tetrazol-1-yl)phenyl) methylamino)-2-(SR)-(4-fluorophenyl)cyclopentane-1-(SR)-tert-butyl-carboxamide Step A:

2-(4-fluorophenyl)-3-azido-cyclopentane-1-(SR)-tert-butylcarboxamide

To a solution of 172 mg (0.69 mmol) 3-(SR)-azido-2-(SR)-(4-fluorophenyl)cyclopentane-1-(SR)-carboxylic acid in 2.5 mL of methylene chloride at 0° were added 78 ul (0.90 mmol) of oxalyl chloride and 10 ul of DMF, stirred for 1 h, and concentrated. The mixture was taken up in 3 mL of methylene chloride, added 363 ul (5.0 mmol) of tert-butylamine and stirred at room temperature for 1 h. The mixture was treated with 1.5 mL of 2N hydrochloric acid, extracted with ether, washed with sodium bicarbonate, brine, dried over magnesium sulfate, concentrated in vacuo, and purified by flash silica gel chromatography eluting with (1:3) ethyl acetate/hexane to give 186 mg of the title compound. NMR (CDCl$_3$): δ 1.15 (s, 9H), 1.95 (m, 1H), 2.12 (m, 3H), 2.77 (m, 1H), 3.35 (m, 1H), 4.10 (m, 1H), 4.96 (b, 1H), 7.03 (t, 2H), 7.29 (m, 2H)

Step B:

3-(SR)-amino-2-(SR)-(4-fluorophenyl)cyclopentane-1-(SR)-tert-butylcarboxamide

A mixture of 166 mg (0.55 mmol) 3-(SR)-azido-2-(SR)-(4-fluorophenyl)cyclopentane-1-(SR)-tert-butylcarboxamide in 3 mL of methanol and 30 mg of 10% Pd/C was hydrogenated at atmospheric pressure for 1 h. The reaction was filtered free of catalyst and evaporated to dryness to be used in the next step.

Step C:

3-(SR)-((2-isopropoxy-5-(tetrazol-1-yl)phenyl) methylamino)-2-(SR)-(4-fluorophenyl)cyclopentane-1-(SR) -tert-butyl-carboxamide To a solution of 150 mg (0.54 mmol) 3-(SR)-amino-2-(SR)-(4-fluorophenyl) cyclopentane-1-(SR)-tert-butylcarboxamide in 4 mL of THF was added 125 mg (0.54 mmol) 2-isopropoxy-5-(tetrazol-1-yl)-2-benzaldehyde, 31 ul (0.54 nunol) acetic acid, 172 mg (0.81 mmol) sodium triacetoxyborohydride, and the mixture stirred at room temperature for 18 h and evaporated in vacuo. The residue was purified by flash chromatography, eluting with 30% acetone/hexane to give 166 mg of the title compound. mass spec 495 (M+1). NMR (CD$_3$OD): δ 1.07 (d, 3H), 1.13 (d, 3H), 1.20 (s, 9H), 4.55 (m, 1H), 7.05 (m, 2H), 7.23 (m, 2H), 7.60 (m, 2H), 7.67 (m, 1H), 9.62 (s, 1H)

EXAMPLE 146

Methyl-3-(SR)-((2-tert-butyloxy-5-(1-tetrazolyl) phenyl)methylamino)-2-(SR)-(4-fluorophenyl) cyclopentane-1-(SR)carboxylate Step A:

1-tert-butyoxy-4-(1-tertrazolyl)-2-benzaldehyde

A solution of 653 mg (3.43 imnol) tetrazol-1-yl-salicylaldehyde in 2.3 mL N,N-dimethylformamide-di-tert-butyl acetal was heated at 70° for 4 h, and partitioned between water and ethyl acetate. Washed organics with water, brine, dried over magnesium sulfate, and evaporated in vacuo. The residue was purified by silica gel flash chromatography eluding 0.5% methanol/methylene chloride to give 136 mg of the title compound. NMR (CDCl$_3$): δ 1.53 (s, 9H), 7.36 (d, 1H), 7.93 (m, 1H), 8.05 (s, 1H), 9.00 (s, 1H), 10.43 (s, 1H)

Step B:

Methyl 3-(SR)-((2-tert-butyloxy-5-(tetrazol-1-yl)phenyl) methylamino)-2-(SR)-(4-fluorophenyl) cyclopentane-1-(SR)carboxylate The title compound was prepared in a similar fashion as Example 144, Step B, but substituting 2-tert-butyloxy-5-(tetrazol-1-yl)-benzaldehyde to give the title compound which was purified by silica gel flash chromatography eluting with 50% ethyl acetate/hexane to give 206 mg of the title compound; mass spec 468 (M+1) NMR (CD$_3$OD): δ 1.27 (s, 9H), 3.56 (s, 3H), 7.05 (t, 2H), 7.24 (m, 3H), 7.63 (m, 2H), 9.62 (s, 1H)

EXAMPLE 147

Methyl 3-(SR)-((2-isopropoxy-5-(5-trifluoromethyltetrazol-1-yl) phenyl)methylamino)-2-(SR)-(4-fluorophenyl)cyclopentane-1-(SR) carboxylate Step A:

2-Isopropoxy-5-(trifluoromethyltetrazol-1-yl)-benzaldehyde

The above compound was prepared in a similar fashion as Example 144, Step A, but substituting 2-isoproproxy-5-(5-trifluoromethyltetrazol-1-yl)-benzaldehyde to give after purification by silica gel flash chromatography, eluting with 10% acetone/hexane, 428 mg of the title compound; mass spec 301 (M+1). NMR (CD$_3$OD): δ 1.48 (d, 6H), 4.80 (m, 1H), 7.18 (d, 1H), 7.60 (m, 1H), 7.93 (d, 1H), 10.47 (s, 1H)

Step B:

Methyl 3-(SR)-((2-isopropoxy-5-(5-trifluoromethyl-tetrazol-1-yl)phenyl)methylamino)-2-(SR)-(4-fluorophenyl) cyclopentane-1-(SR)carboxylate The above was synthesized in a similar fashion as Example 144, Step B, using the above aldehyde to give after purification by flash chromatography, eluting with 10% ethyl acetatelhexane, 95 mg of the title compound; mass spec 522 (M+1). NMR (CD$_3$OD): δ 1.08 (d, 3H), 1.17 (d, 3H), 3.57 (s, 3H), 4.57 (m, 1H), 7.03 (t, 2H), 7.10 (d, 1H), 7.23 (m, 2H), 7.36 (d, 1H), 7.45 (m, 1H)

EXAMPLE 148

3-(SR)-((2-Isopropoxy-5-(5-trifluoromethyltetrazol-1-yl)phenyl)methylamino)-2-(SR)-(4-fluorophenyl) cyclopentane-1-(SR)carboxamide The title compound was synthesized in a similar fashion as Example 144, Step B, using the aldehyde from Example 147, to give after purification by silica gel flash chromatography, eluting with 3% methanol/methylene chloride, 114 mg of the title compound; mass spec 507 (M+1). NMR (CD$_3$OD): δ 1.10 (d, 3H), 1.15 (d, 3H), 3.51 (m, 3H), 3.75 (d, 1H), 4.56 (m, 3H), 7.00 (t, 2H), 7.10 (d, 1H), 7.23 (m, 2H), 7.37 (s, 1H), 7.45 (d, 1H)

EXAMPLE 149

Methyl 3-(SR)-((2-cyclobutyloxy-5-(1-tetrazolyl) phenyl)methylamino)-2-(SR)-(4-fluorophenyl) cyclopentane-1-(SR)carboxylate The title compound was prepared in a similar fashion as Example 144, Step B, substituting 2-cyclobutyloxy-5-

(tetrazol-1-yl)- 2-benzaldehyde to give after purification by flash chromatography, eluting with 20% acetone/hexane, 32 mg of the title compound; mass spec 466 (M+1). NMR (CD$_3$OD): δ 1.73 (b, 2H), 2.00 (b, 2H), 2.34 (b, 2H), 3.57 (s, 3H), 4.57 (m, 1H), 6.90 (d, 1H), 7.07 (t, 2H), 7.25 (m, 2H), 7.63 (m, 2H), 9.62 (s, 1H)

EXAMPLE 150

Methyl 3-(SR)-((2-methylsulfanyl)phenyl)methylamino)-2-(SR)-(4-fluorophenyl)cyclopentane-1-(SR)carboxylate Step A:

Methyl-2-(methylthio)benzoate

To a solution of 160 mg (2.97 mmol) of sodium methoxide in 10 mL of methanol was added at 0°, 0.4 mL (2.97 mmol) of methyl thiosalicylate, 0.37 mL (5.97 mmol) of iodomethane and stirred at room temperature for 1 h. The reaction mixture was concentrated in vacuo, taken up in ethyl acetate, washed with water, brine, dried over sodium sulfate, and concentrated in vacuo to give 2.10 g of the title compound.

NMR (CDCl$_3$): δ 2.44 (s, 3H), 3.90 (s, 3H), 7.14 (t, 1H), 7.27 (s, 1H), 7.45(m, 1H), 7.97 (d, 1H).

Step B:

2-(Methylthio)benzylalcohol

To a solution of 514 mg (2.82 mmol) of methyl-2-methylthiobenzoate in 10 mL of THF was added 107 mg (2.82 mmol) of lithium aluminum hydride at 0°, warmed to room temperature and stirred for 0.5 h. A mixture of 0.11 mL of 15% sodium hydroxide was added at 0° followed by 0.33 mL water, filtered, washed with water, and extracted with ethyl acetate, dried over sodium sulfate, and concentrated to give 402 mg of the title compound. NMR (CDCl$_3$): δ 2.48 (s, 3H), 4.75 (s, 2H), 7.17 (m, 1H), 7.27 (m, 2H), 7.36 (d, 1H).

Step C:

2-(Methylthio)benzylbromide

To a solution of 400 mg (2.59 mmol) of 2-methylthiobenzylalcohol in 8 mL of methanol was added 1.42 g (3.37 mmol) of triphenylphosphine dibromide and stirred at room temperature for 18 h. The mixture was concentrated and purified by silica gel flash chromatography, eluting with 2% ethyl acetate/hexane to give 289 mg of the title compound. NMR (CDCl$_3$): δ 2.50 (s, 3H), 4.63 (s, 2H), 7.13 (m, 1H), 7.27 (m, 2H), 7.34 (d, 1).

Step D:

Methyl-3-(SR)-((2-methylsulfanyl)phenyl)methylamino)-2-(SR)-(4-fluorophenyl)cyclopentane-1-(SR)carboxylate To a solution of 50 mg (0.21 mmol) of methyl-3-(SR)-amino-2-(SR)-(4-fluorophenyl) cyclopentane-1-(SR) carboxylate in 2.0 mL of acetonitrile was added 55 mg (0.25 mmol) of 2-(methylthio)-benzylbromide, 48 ul (0.27 mmol) of diisopropylethylamine, and the mixture stirred at room temperature for 2.5 h and 50° for 0.5 h. The mixture was concentrated in vacuo and purified by flash chromatography, eluting with 5% methanol/methylene chloride to give 46 mg of the title compound; mass spec 374 (M+1). NMR (CD$_3$OD): δ 2.26 (s, 3H), 3.57 (s, 3H), 7.03 (m 4H), 7.20 (m, 4H).

EXAMPLE 151

Methyl 3-(SR)-((2-methylsulfonyl)phenyl)methylamino)-2-(SR)-(4-fluorophenyl)cyclopentane-1-(SR)carboxylate Step A:

2-(Methylsulfonyl)benzylbromide

To a solution of 124 mg (0.57 mmol) of 2-(methylthio)-benzylbromide in 8.0 mL of methanol was added a solution of 702 mg of oxone in 7.0 mL of water. The solution was stirred for 4.5 h, concentrated in vacuo and purified by silica gel flash chromatography, eluting with 10% ethyl acetate/hexane to give 105 mg of the title compound. mass spec 249(M+). NMR (CDCl$_3$): δ 3.25 (s, 3H), 5.07 (s, 2H), 7.50 (m, 1H), 7.60 (m, 2H), 8.05 (d, 1H).

Step B:

Methyl-3-(SR)-((2-methylsulfonyl)phenyl)methylamino)-2-(SR)-(4-fluorophenyl)cyclopentane-1-(SR)carboxylate The title compound was prepared as previously described in Example 150, Step D, substituting the sulfone from Step A, and purified by flash chromatography, eluting with 20% acetone/hexane to give 23 mg of the title compound; mass spec 406 (M+1). NMR (CD$_3$OD): δ 1.93 (m, 2H), 2.09 (m, 1H), 2.28 (m, 1H), 3.05 (s, 3H), 3.60 (s, 3H), 3.68 (d, 1H), 4.09 (d, 1H), 7.00 (t, 2H), 7.22 (m, 2H), 7.34 (d, 1H), 7.48 (t, 1H), 7.59 (t, 1H), 7.93 (d, 1H).

EXAMPLE 152

Methyl 3-(SR)-((2-methylsulfinyl)phenyl)methylamino)-2-(SR)-(4-fluorophenyl)cyclopentane-1-(SR)carboxylate The title compound was prepared by treating the compound of Example 150 with Oxone in aqueous methanol at room temperature to give after purification by silica gel flash chromatography, eluting with 1% methanol/methylene chloride, 9.0 mg of the title compound; mass spec 390 (M+1). NMR (CD$_3$OD): δ 2.52 (s, 3H), 2.73 (s, 3H), 3.60 (s, 3H), 7.05 (m, 2H), 7.28 (m, 3H), 7.43 (m, 1H), 7.51 (t, 1H), 7.88 (m, 1H).

EXAMPLE 153

3-(SR)-((2-Isopropoxy-5-(tetrazol-1-yl)phenyl)methylamino)-2-(SR)-(4-fluorophenyl)cyclopentane-1-(SR)carboxamide To a solution of 50 mg (0.23 mmol) of 3-(SR)-amino-2-(SR)-(4-fluorophenyl)cyclopentane-1-(SR)-carboxamide in 2.0 mL of THF was added 52 mg (0.23 mmol) of 2-isopropyl-5-(1-tetrazol-1-yl)-2-benzaldehyde, 20 ul (0.34 mmol) acetic acid, and 72 mg (0.34 mmol) of sodium triacetoxyborohydride. The mixture was stirred at room temperature for 72 h, concentrated in vacuo, taken up in methylene chloride, and concentrated in vacuo. The residue was purified by silica gel flash chromatography, eluting with 5% methanol/methylene chloride to give 67 mg of the title compound; mass spec 439 (M+1)

NMR (CD$_3$OD): δ 1.07 (d, 3H), 1.15 (d, 3H), 4.56 (m, 1H), 7.06 (m, 3H), 7.25 (m, 2H), 7.61 (d, 1H), 7.69 (d, 1H), 9.62 (s, 1H).

EXAMPLE 154

Methyl 3-(S)-((2-cyclopropylmethyloxy-5-(tetrazol-1-yl)phenyl)methylamino)-2-(S)-(4-fluorophenyl)cyclopentane-1-(S)carboxylate hydrochloride The title compound was synthesized in a similar fashion as Example 153, substituting 2-cyclopropylmethyloxy-5-

(tetrazol-1-yl)-benzaldehyde and purified by silica gel flash chromatography, eluting with 15% isopropyl alcohol/hexane to give 109 mg which was converted to the hydrochloride salt by treatment with 1.0M solution of hydrogen chloride in ether, to give the title compound; mass spec 466 (M+1)

NMR (CD$_3$OD): δ 0.22 (m, 2H), 0.53 (d, 2H), 0.90 (m, 1H), 3.58 (s, 3H), 3.69 (m, 2H), 3.82 (d, 1H), 7.03 (m, 3H), 7.19 (m, 2H), 7.57 (d, 1H) 7.67 (m, 1H), 9.61 (s, 1H).

EXAMPLE 155

Methyl 3-(S)-((2-methylsulfanyl-5-(5-trifluoromethyltetrazol-1-yl)phenyl)methylamino)-2-(S)-(4-fluorophenyl)cyclopentane-1-(S)carboxylate hydrochloride The title compound was prepared in a similar fashion as Example 153, substituting 2-methylsulfanyl-5-(5-trifluoromethyl-tetrazol-1-yl)-benzaldehyde and purified by silica gel flash chromatogaphy, eluding 2% isopropyl alcohol/hexane to give 28 mg of the title compound; mass spec 510 (M+1), NMR (CD$_3$OD): δ 2.59 (s, 3H), 3.65 (s, 3H), 3.93 (t, 1H), 4.03 (t, 1H), 4.20 (d, 1H), 4.35 (d, 1H), 7.18 (t, 1H), 7.42 (m, 2H), 7.59 (d, 1H) 7.65 (d, 1H), 7.70 (d, 1H).

EXAMPLE 156

Methyl 3-(S)-((2-methylsulfoxyl-5-(5-trifluoromethyltetrazol-1-yl)phenyl)methylamino)-2-(S)-(4-fluorophenyl)cyclopentane-1-(S)carboxylate The title compound was prepared by treating the compound of Example 155 with Oxone in aqueous methanol at room temperature, and purified by silica gel chromatoraphy, eluting with 1% methanol-methylene chloride to give 12 mg of the title compound. mass spec 526 (M+1). NMR (CD$_3$OD): δ 2.61 (s, 3H), 2.80 (s, 3H), 3.60 (s, 3H), 3.77 (d, 1H), 3.87 (d, 1H), 7.00 (q, 3H), 7.30 (m, 3H), 7.45 (d, 1H), 7.60 (d, 1H) 7.77 (m, 2H), 7.93 (m, 1H), 8.16 (t, 2H), 8.33 (d, 1H).

EXAMPLE 157

Methyl 3-(S)-((2-methylsulfanyl-5-(thiophene-3-carbonylamino)phenyl)-methylamino)-2-(S)-(4-fluorophenyl)-cyclopentane-1-(S)carboxylate hydrochloride The title compound was synthesized in a similar fashion as Example 144, Step B, substituting 2-methylsulfanyl-5-(thiophene-3-carbonylamino)-benzaldehyde and purified by silica gel flash chromatography, eluting with 3% methanol/methylene chloride to give 81 mg of the title compound. mass spec 499 (M+1). NMR (CD$_3$OD): δ 2.25 (s, 3H), 3.60 (s, 3H), 3.74 (d, 1H), 5.50 (s, 2H), 7.02 (t, 2H), 7.20 (m, 3H), 7.47 (m, 1H), 7.52 (t, 1H), 7.60 (m, 2H) 8.20 (t, 1H).

EXAMPLE 158

1S-(1'R-(3,5-Bistrifluoromethyl)phenyl)ethoxy)-2S-phenyl-3R-hydroxymethyl cyclohexane and 1S-(1'S-methyl-(3,5-bistrifluoromethyl)benzyloxy)-2S-phenyl-3R-hydroxymethyl cyclohexane Step A:

1S-Phenyl-2R-(carboxy-2'S-benzyloxazolidinone)-cyclohex-5-ene

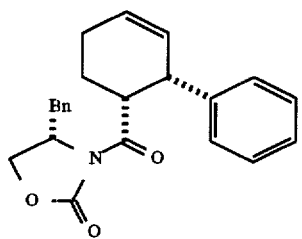

To a solution of the acryloyloxazolidinone (7.60 g, 32.8 mmol) in CH$_2$Cl$_2$ (175 mL) at −50° C. was added freshly distilled 1-phenyl-1,3-butadiene (16.9 g, 130 mmol). The reaction was cooled to −70° C. whereupon a solution of diethylaluminum chloride (24.0 mL, 1.8M in PhMe, 43.0 mmol, 1.4 equiv) was added. The mixture was stirred for 5 min and then added to a stirred solution of 1M aq. HCl (500 mL). After the bubbling subsided the aqueous was extracted with CH$_2$Cl$_2$ (3×300 mL). The combined organic extracts were washed with brine (1×300 mL), dried (Na$_2$SO$_4$) and concentrated in vacuo yielding a white semisolid. The residue was triturated with hexanes (−250 mL) and the solid collected by vacuum filtration with cold hexane washes affording 12.5 g (99%) of the Diels-Alder adduct as a white solid.

$^1$H NMR (CDCl$_3$, 500 MHz) δ 7.10–7.46 (m, 10H), 5.95–6.03 (m, 1H), 5.75–5.81 (m, 1H), 4.48–4.56 (m, 1H), 4.26 (br. s, 1H), 4.13 (d, 2H, J=5.2 Hz), 4.06 (ddd, 1H, J=11.9, 6.4, 2.9 Hz), 2.92 (dd, 1H, J=13.0, 2.9 Hz), 2.29–2.39 (m, 2H), 2.06–2.25 (m, 2H), 1.75–1.83 (m, 1H) ppm.

Step B:

1S-Phenyl-2R-carboxycyclohex-5-ene

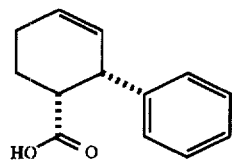

To a solution of the oxazolidinone (12.5 g, 34.6 mmol) in THF (500 mL) and H$_2$O(170 mL) at 0° C. was added 30% H$_2$O$_2$ (31.4 mL, 277 mmoL), followed by LiOH·H$_2$O (2.90 g, 69.2 mmol). The mixture was allowed to warm to room temp. and stirred for 20 h, whereupon the mixture was quenched by addition of Na$_2$S$_2$O$_3$ (8.9 equiv, 39.0 g, 308 mmol) and H$_2$O (210 mL) at 0° C., followed by addition of 0.5N aq. NaHCO$_3$ (350 mL). The THF was removed in vacuo, the mixture diluted with H$_2$O (500 mL) and then extracted with CH$_2$Cl$_2$ (3×500 mL). The combined organic extracts were washed with brine, dried (Na$_2$SO$_4$) and concentrated in vacuo yielding the oxazolidone auxiliary. The aqueous layer was then acidified with 2N aq. HCl to pH=1. The aqueous layer was then extracted with EtOAc (3×500 mL). The combined organic extracts were washed with brine, dried (Na$_2$SO$_4$) and concentrated in vacuo yielding the carboxylic acid (7.0 g, 99%) as a colorless oil. $^1$H NMR (CDCl$_3$, 500 MHz) δ 7.15–7.40 (m, 5H), 5.93–6.07 (m, 1H), 5.75–5.86 (m, 1H), 3.89 (br. s, 1H), 2.96 (dd, 1H, J=15.4, 5.8 Hz), 2.26–2.35 (m, 1H), 2.13–2.23 (m, 1H), 1.75–1.88 (m, 2H) ppm.

Step C:

163

4R-Iodo-8S-phenyl-7-oxo-6-oxabicyclo[3.2.1]octane

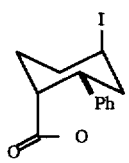

To a vigorously stirred biphasic mixture of the acid (6.50 g, 32.1 mmol) in CH₂Cl₂ (250 mL) and sat. aq. NaHCO₃ (250 mL) at 0° C. was added I₂ (10.5 g, 41.5 mmol). The mixture was stirred 15 min at 0° C. then 30 min at room temp, whereupon it was quenched by the addition of excess 0.25M Na₂S₂O₃. The mixture was diluted with sat. aq. NaHCO₃ (100 mL) and H₂O (200 mL) and extracted with CH₂Cl₂ (3×300 mL). The combined organic extracts were washed with brine, dried (Na₂SO₄) and concentrated in vacuo yielding the iodolactone (8.6 g, 82%) as a yellow solid which was used directly in the next step.

¹H NMR (CDCl₃, 500 MHz) δ 23—7.41 (m, 5H), 4.86 (d, 1H, J=4.1 z), 4.69 (t, 1H, J=4.5 Hz), 4.20 (s, 1H), 2.94 (br. d, 1H, J=4.3 Hz), 2.45–2.55 (m, 1H), 2.01–2.26 (m, 3H) ppm.

Step D:

8S-Phenyl-7-oxo-6-oxabicyclo[3.2.1]octane

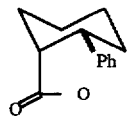

To a solution of the iodolactone (8.0 g, 24.4 mmol) in PhH (500 mL) was added nBu₃SnH (10.6 g, 36.6 mmol) and AIBN (100 mg, 0.61 mmol). The reaction mixture was heated to reflux for 2 h, and then left standing at room temp overnight. The reaction mixture was concentrated in vacuo. The residue was purified by column chromatography (150 g silica gel 60, 60 mm diam. column, 0–40% EtOAc/hexanes) to afford the bicyclic lactone (5.20 g, 100%) as a colorless oil. ¹H NMR (CDCl₃, 500 MHz) δ 7.21–7.43 (m, 5H), 4.93 (d, 1H, J=4.5 Hz), 3.12 (s, 1H), 2.86 (br. d, 1H, J=4.1 Hz), 2.10–2.26 (m, 2H), 1.78–1.96 (m, 4H) ppm.

Step E:

1S-Hydroxy-2S-phenyl-3R-hydroxymethylcyclohexane

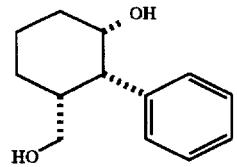

To a solution of the lactone (5.1 g, 24.4 mmol) in Et₂O (220 mL) at 0° C. was added LiAlH₄ (2.77 g, 73.2 mmol). The reaction mixture was maintained at 0° C. for 1 h whereupon it was quenched by sequential addition of H₂O (2.8 mL), 15% aq. NaOH (2.8 mL) and H₂O (8.4 mL). The mixture was stirred for 30 min, then had added to it sat. aq. Rochelle's salts (200 mL) and vigorously stirred 1 h. The mixture was then extracted with EtOAc (3×200 mL) and the combined organic extracts were washed with brine, dried (Na₂SO₄), and concentrated in vacuo to yield the diol (4.8 g, 96%) as a colorless oil, which was used directly in the next step. ¹H NMR (CDCl3, 500 MHz) δ 7.20–7.51 (m, 5H), 4.02–4.10 (m, 1H), 3.43 (dd, 1H, J=10.8, 5.5 Hz), 3.36 (dd,

164

1H, J=11.0, 6.2 Hz), 3.27 (t, 1H, J=4.9 Hz), 2.39 (br. s, 2H), 1.96–2.12 (m, 2H), 1.65–1.83 (m, 4H), 1.45–1.58 (m, 1H) ppm.

Step F:

1S-Hydroxy-2S-phenyl-3R-t-butyl-dimethylsilyloxymethylcyclohexane

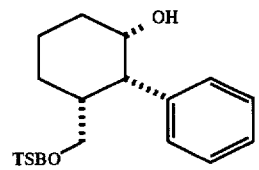

To a solution of the diol (4.80 g, 23.3. mmol) in CH₂Cl₂ (50 mL) at room temp was added iPr₂NEt (3.0 g, 23.3 mmol), and TBSOTf (3.5 g, 23.3 mmol). The mixture was stirred 18 h at room temp and an additional 0.1 equivs of iPr₂NEt and TBSOTf were added. After 2 h the mixture was concentrated in vacuo and the residue was purifed by column chromatography (150 g silica gel 60, 60 mm diam. column, 10–25% EtOAc/hexanes) to afford the monosilylated alcohol (7.45 g, 99%) as a colorless oil. ¹H NMR (CDCl₃, 500 MHz) δ 7.20–7.56 (m, 5H), 3.97–4.08 (m, 1H), 3.40 (dd, 1H, J=10.1, 5.3 Hz), 3.34 (dd, 1H, J=10.0, 5.9 Hz), 3.29 (t, 1H, J=4.8 Hz), 2.04–2.10 (m, 1H), 1.94–2.03 (m, 1H), 1.78–1.85 (m, 1H), 1.65–1.77 (m, 3H), 1.48–1.55 (m, 1H), 0.89 (s, 9H), −0.029 (s, 3H), −0.042 (s, 3H) ppm.

Step G:

1S(3,5-Bis(trifluoromethyl)-benzoyloxy-2S-phenyl-3R-t-butyl-dimethylsilyloxymethylcyclohexane

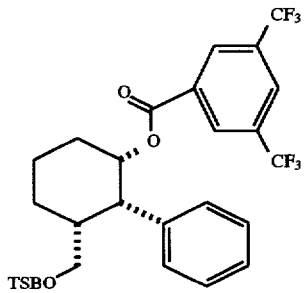

A solution of the alcohol (5.30 g, 16.5 mmol), 3,5-bis-trifluoromethylbenzoyl chloride (6.91 g, 24.8 mmol), DMAP (1.51 g, 12.4 mmol), and Et₃N (5.01 g, 49.6 mmol) in CH₂Cl₂ (200 mL) at 0° C. was stirred for 30 min, then at room temp for 3 h. The reaction was quenched by addition of sat. aq. NaHCO₃ (100 mL), diluted with H₂O (50 mL) and extracted with CH₂Cl₂ (3×150 mL). The combined organic extracts were washed with brine, dried (Na₂SO₄), and concentrated in vacuo to yield the crude ester as an oil. The residue was purifed by column chromatography (160 g silica gel 60, 60 mm diam. column, 2.5–5.0% EtOAc/hexanes) to afford the ester (8.70 g, 100%) as a colorless oil. ¹H NMR (CDCl₃, 500 MHz) δ 8.05 (s, 2H), 7.97 (s, 1H), 7.25–7.40 (m, 5H), 5.35–5.44 (m, 1H), 3.62 (t, 1H, J=5.5 Hz), 3.42 (dd, 1H, J=9.9, 6.7 Hz), 3.34 (dd, 1H, J=9.8, 8.0 Hz), 2.17–2.25 (m, 1H), 1.92–2.13 (m, 3H), 1.60–1.78 (m, 3H), 0.85 (s, 9H), −0.10 (s, 3H), −0.14 (s, 3H) ppm.

Step H:

1S-(1'R-(3,5-Bistrifluoromethyl)phenyl)ethoxy)-2S-phenyl-3R-t-butyl-dimethylsilyloxymethylcyclohexane

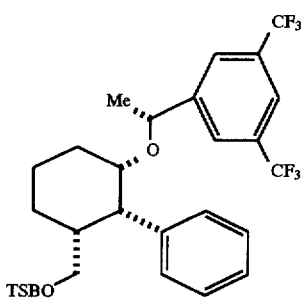

To a solution of the benzoate (626 mg, 1.12 mmol) in THF (14 mL) was added freshly prepared Cp$_2$TiMe$_2$ (6.7 mL, 1M in PhMe, 6.7 mmol). The flask was wrapped with tin foil and heated in the dark to 80° C. for 18 h. The reaction was cooled to room temp and concentrated in vacuo. The residue was passed thru neutral alumina (40 g 100% hexanes-2.5% EtOAc/hexanes) and the desired fractions concentrated in vacuo affording the crude enol as an orange semisolid. The enol was then taken up in 2:1 EtOAc/MeOH (24 mL) and treated with 10% Pd/C (300 mg), shaken on the Parr apparatus at 45 psi for 1.5 h. The reaction mixture was concentrated and the residue was purifed by column chromatography (30 g silica gel 60, 35 mm diam. column, 2.5–5.0% EtOAc/hexanes) to afford the ether (586 mg, 93%) as a colorless oil as a mixture of methyl diastereomers (~3.5:1).

$^1$H NMR (CDCl$_3$, 500 MHz) δ 7.72 (s, 1H), 7.59 (s, 2H), 7.15–7.32 (m, 5H), 4.71 (q, 1H, J=6.4 Hz), 3.67–3.75 (m, 1H), 3.36 (dd, 1H, J=9.9, 7.6 Hz), 3.16–3.30 (m, 2H), 1.89–2.10 (m, 3H), 1.78–1.87 (m, 1H), 1.44–1.64 (m, 3H), 1.41 (d, 3H, J=6.4 Hz), 0.84 (s, 9H), –0.097 (s, 3H), –0.105 (s, 3H) ppm.

Step I:

1S-(1'R-(3,5-bistrifluoromethyl)phenyl)ethoxy)-2S-phenyl-3R-hydroxymethyl cyclohexane and 1S-(1'S-methyl-(3,5-bistrifluoromethyl)benzyloxy)-2S-phenyl-3R-hydroxymethyl cyclohexane

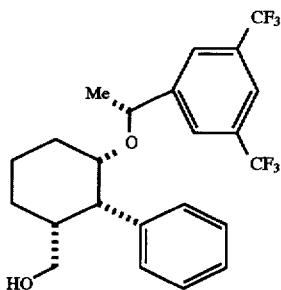

The mixture of methyl diastereomeric ethers (565 mg, 1.01 mmol) was taken up in 5:86:9 48% aq. HF:CH$_3$CN:H$_2$O (12 mL) and stirred at room temp for 1.5 h. The reaction mixture was diluted with H$_2$O(100 mL) and extracted with EtOAc (3×100 mL). The combined organic extracts were washed with brine, dried (Na$_2$SO$_4$), and concentrated in vacuo. The residue was purifed by column chromatography (14 g silica gel 60, 24 mm diam. column, 15–40% EtOAc/hexanes) to afford the alcohols; Diast A (94 mg, 21%) and Diast B (326 mg, 72%) as colorless oils. Diastereomer A; $^1$H NMR (CDCl$_3$, 500 MHz) δ 7.72 (s, 1H), 7.59 (s, 2H), 7.20–7.37 (m, 5H), 4.75 (q, 1H, J=6.4 Hz), 3.72–3.79 (m, 1H), 3.53 (dd, 1H, J=11.0, 6.0 Hz), 3.39 (dd, 1H, J=11.0, 6.2 Hz), 3.22 (t, 1H, J=4.7 Hz), 1.96–2.18 (m, 3H), 1.82–1.94 (m, 1H), 1.70–1.81 (m, 2H), 1.48–1.66 (m, 2H), 1.47 (d, 3H, J=6.4 Hz) ppm. Diastereomer B; $^1$H NMR (CDCl$_3$, 500 MHz) δ 7.78 (s, 1H), 7.75 (s, 2H), 7.25–7.50 (m, 5H), 4.76 (q, 1H, J=6.4 Hz), 3.59–3.67 (m, 1H), 3.51–3.58 (m, 1H), 3.43–3.50 (m, 1H), 3.32–3.42 (m, 1H), 1.82–2.07 (m, 3H), 1.50–1.72 (m, 1H), 1.32–1.43 (m, 2H), 1.22 (d, 3H, J=6.4 Hz) ppm.

EXAMPLE 159

1S-((1'R-(3,5-Bistrifluoromethyl)phenyl)ethoxy)-2S-phenyl-3S-N-methylamino cyclohexane Step A:

1S-(1'R-(3,5-Bistrifluoromethyl)phenyl)ethoxy)-2S-phenylcyclohexane-3R-carboxaldehyde

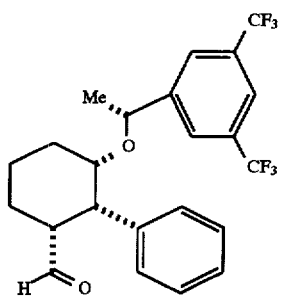

To a solution of oxalyl chloride (124 mg, 0.98 mmol) in CH$_2$Cl$_2$ (4 mL) at –70° C. was added DMSO (153 mg, 1.96 mmol) and the mixtuire stirred 20 min. Then a solution of the alcohol (175 mg, 0.39 mmol) in CH$_2$Cl$_2$ (1 mL) was added at –70° C. and the resultant mixture stirred 1 h, whereupon Et$_3$N (0.54 mL, 3.92 mmol) was added and the mixture allowed to warm to room temp and stirred 1 h. The reaction mixture was diluted with H$_2$O (50 mL) and extracted with CH$_2$Cl$_2$ (3×40 mL). The combined organic extracts were washed with brine, dried (Na$_2$SO$_4$), and concentrated in vacuo. The residue was purifed by column chromatography (13 g silica gel 60, 24 mm diam. column, 5–15% EtOAc/hexanes) to afford the aldehyde (126 mg, 73%) as a colorless oil. $^1$H NMR (CDCl$_3$, 500 MHz) δ 9.91 (s, 1H), 7.79 (s, 1H), 7.69 (s, 2H), 7.20–7.38 (m, 5H), 4.70 (q, 1H, J=6.4 Hz), 3.96 (t, 1H, J=2.0 Hz), 3.20 (dd, 1H, J=4.8, 1.6 Hz), 2.77–2.83 (m, 1H), 2.41–2.50 (m, 1H), 2.19–2.27 (m, 1H), 1.78–1.90 (m, 1H), 1.47–1.70 (m, 3H), 1.45 (d, 3H, J=6.4 Hz) ppm.

Step B:

1S-(1'R-(3,5-Bistrifluoromethyl)phenyl)ethoxy)-2S-phenylcyclohexane-3S-carboxaldehyde

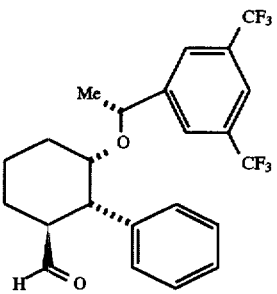

The aldehyde was taken up in MeOH (5 mL) and treated with NaOMe (0.5 mL of 0.32M in MeOH) at room temp for 2 h. The reaction mixture was quenched with H$_2$O (50 mL) and extracted with EtOAc (3×30 mL). The combined organic extracts were washed with brine, dried (Na₂SO₄), and concentrated in vacuo to afford the epimerized aldehyde (122 mg, 99%) as a colorless oil. ¹H NMR (CDCl₃, 500 MHz) δ 9.44 (d, 1H, J=3.0 Hz), 7.64 (s, 1H), 7.13–7.30 (m, 7H), 4.40 (q, 1H, J=6.4 Hz), 3.55 (d, 1H, J=2.3 Hz), 3.28–3.38 (m, 1H), 2.87 (dd, 1H, J=12.1, 2.3 Hz), 2.18 (bd, 1H, J=14.1 Hz), 2.03 (dd, 1H, J=12.7, 3.1 Hz), 1.80–1.92 (m, 1H), 1.70–1.78 (m, 1H), 1.38–1.50 (m, 2H), 1.38 (d, 3H, J=6.4 Hz) ppm.

Step C:

1S-1'R-(3,5-Bistrifluoromethyl)phenyl)ethoxy)-2S-phenylcyclohexane-3S-carboxylic acid

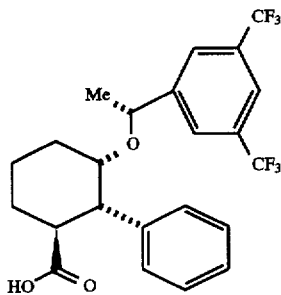

To a solution of the aldehyde (1.05 g, 2.36 mmol) in THF (17 mL) at 0° C. was added sulfamic acid (3.6 mL, 1M aq.), NaH₂PO₄ (1.3 mL, 2.7M aq.), and NaClO₂ (3.6 mL, 1M aq.). The reaction mixture was allowed to warm to room temp and stirred for 18 h. The reaction mixture was then quenched by addition of H₂O (50 mL), and extracted with CH₂Cl₂ (3×30 mL). The combined organic extracts were washed with brine, dried (Na₂SO₄), and concentrated in vacuo to afford the carboxylic acid (1.15 g, 99%) as a colorless oil, used directly in the next step. ¹H NMR (CDCl₃, 500 MHz) δ 7.63 (s, 1H), 7.09–7.30 (m, 7H), 4.34 (q, 1H, J=6.4 Hz), 3.70–3.80 (m, 1H), 3.49 (bs, 1H), 3.30 (td, 1H, J=12.1, 3.6 Hz), 2.87 (dd, 1H, J=12.1, 2.3 Hz), 2.13 (bd, 2H, J=12.8 Hz), 1.75–1.90 (m, 1H), 1.40–1.70 (m, 2H), 1.35 (d, 3H, J=6.4 Hz) ppm.

Step D:

1S-1'R-(3,5-Bistrifluoromethyl)phenyl)ethoxy)-2S-phenyl-3S-aminobenzoyl cyclohexane

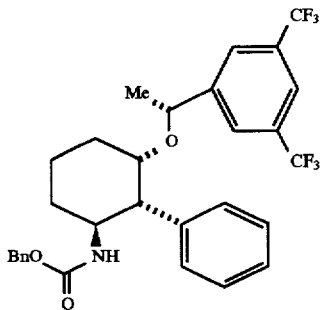

To a solution of the carboxylic acid (114 mg, 0.248 mmol) in CH₂Cl₂ (2.5 mL) at 0° C. was added oxalyl chloride (0.5 mL) followed by DMF (2 drops). The reaction mixture was stirred at room temp for 1 h, whereupon it was concentrated in vacuo from CH₂Cl₂ (3×). The residue was taken up in acetone (3 mL) and had added to it a solution of NaN₃ (80 mg, 1.34 mmol) in H₂O (3 mL). After stirring at room temp for 2 h, the reaction mixture was diluted with H₂O(25 mL) and extracted with benzene (3×30 mL). The combined organic extracts were washed with brine, dried (Na₂SO₄), and concentrated in vacuo to ~5 mL. Benzene (5 mL) was added followed by excess benzyl alcohol (2 mL), diisopropylethyl amine (0.087 mL, 0.50 mmol), and catalytic DMAP (~5 mg). The reaction mixture was heated to 80° C. under argon for 18 h. The cooled reaction mixture was concentrated in vacuo and the residue was purified by radial chromatography (2 mm plate size, 10–25% EtOAc/hexanes, 2 ml/min flow) and afforded 110 mg (95%) of the CBZ protected amine as a colorless glass. ¹H NMR (CDCl₃, 500 MHz) δ 7.62 (s, 1H), 7.10–7.38 (m, 12H), 5.0 (bs, 2H), 4.32–4.48 (m, 3H), 3.55 (s, 1 2.56 (bd, 1H, J=11.4 Hz), 2.34 (bd, 1H, J=10.9 Hz), 2.12 (bd, 1H, J=13.2 Hz), 1.84–1.96 (m, 1H), 1.58–1.72 (m, 1H), 1.38 (d, 3H, J=6.4 Hz), 1.26–1.42 (m, 1H) ppm.

Step E:

1S-(1'R-(3,5-Bistrifluoromethyl)phenyl)ethoxy)-2S-phenyl-3S-N-methylamino cyclohexane

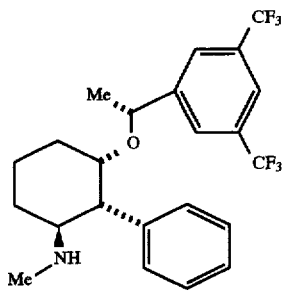

(i) To a solution of the CBZ-amine (140 mg, 0.248 mmol) in DMF (3 mL) at 0° C. was added NaH (22.0 mg, 0.928 mmol). The ice bath was removed and after stirring 15 min MeI (264 mg, 1.86 mmol) was added and the resultant mixture was stiorred at room temp. for 16 h. An additional amount of NaH (6.0 mg) and MeI (30 μL) were added and the mixture stirred an additonal 6 h to complete the reaction. The reaction mixture was quenched by addition of H₂O (50 mL). The organics were extracted with EtOAc (3×30 mL) and the combined organic extracts were washed with H₂O (3×20 mL), brine (1×20 ml), dried (Na₂SO₄), and concentrated in vacuo. The residue was purifed by column chromatography (13 g silica gel 60, 24 mm diam. column, 10% acetone/hexanes) to afford the methylamide (139 mg, 97%) as a colorless oil. The ¹H NMR showed a very complex mixture of conformational rotamers. (ii) The CBZ amine (110 mg, 0.190 mmol) was treated with Pd/C (220 mg) and H₂ (50 psi) in EtOAc (11 mL) on the Parr shaker apparatus for 4.5 h. The reaction mixture was filtered through celite with EtOAc washing, and concentrated in vacuo to afford the amine (75 mg, 89%) as a colorless oil. ¹H NMR (CDCl₃, 500 MHz) δ 7.63 (s, 1H), 7.07–7.42 (m, 7H), 4.38 (q, 1H, J=6.4 Hz), 3.48 (d, 1H, J=1.8 Hz), 3.20 (dt, 1H, J=11.0, 4.1 Hz), 2.56 (dd, 1H, J=11.3, 2.6 Hz), 2.32 (s, 3H), 2.26 (dd, 1H, J=12.6, 2.8 Hz), 2.11 (d, 1H, J=12.9 Hz), 1.77–1.90 (m, 1H), 1.62–1.73 (m, 1H), 1.38 (d, 1H, J=6.4 Hz), 1.32–1.47 (m, 1H), 1.15–1.36 (m, 2H) ppm. ESIMS/CI m/z calcd. for C₂₃H₂₅N₁O₁F₆ 445.45; found 446.2 (100%), 447.2 (30%).

EXAMPLE 160

1S-(1'R-(3,5-Bistrifluoromethyl)phenyl)ethoxy)-2S-phenyl-3S-(N-N-(aminocarbonylmethyl)-N-(methyl)amino)-cyclohexane

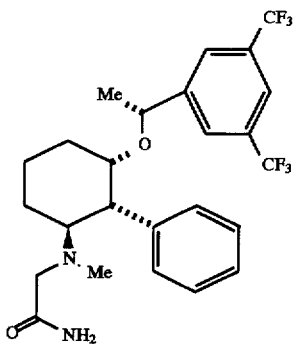

To a solution of the amine (11.0 mg, 0.025 mmol) in CH$_3$CN (1 mL) at room temp was added diisopropylethyl amine (4.8 mg, 0.037 mmol) and iodoacetamide (5.0 mg, 0.027 mmol). The reaction mixture was heated to 50° C. under Ar for 4 h whereupon it was cooled to room temp and quenched by addition of sat. aq. NaHCO$_3$ (10 mL). The mixture was extracted with EtOAc (3×10 mL) and the combined organic extracts were washed with brine, dried (Na$_2$SO$_4$), and concentrated in vacuo. The residue was purifed by column chromatography (1.8 g silica gel 60, 8 mm diam. column, 2.5–8.0% MeOH/CH$_2$Cl$_2$) to afford the acetamide (10.2 mg, 81%) as a colorless solid. ESIMS/CI m/z calcd. for C$_{25}$H$_{28}$N$_2$O$_2$F$_6$ 502.50; found 503.2 (18%), 485.2 (20%), 474.2 (16%), 446.2 (100%).

EXAMPLE 161

1S-(1'R-(3,5-Bistrifluoromethyl)phenyl)ethoxy)-2S-phenyl-3S-(N-methyl-N-(5-oxo-1,2,4-triazol-2-yl)methylamino))-cyclohexane

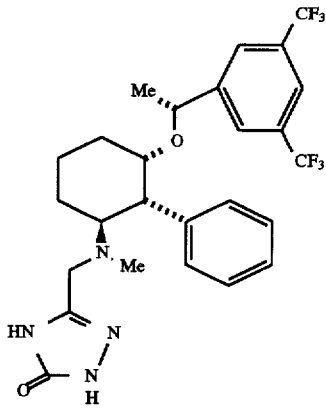

To a solution of the amine (25.0 mg, 0.056 mmol) in CH$_3$CN (2 mL) at room temp was added diisopropylethyl amine (14.5 mg, 0.112 mmol) and hydrazino ester (14.0 mg, 0.084 mmol). The reaction mixture was stirred at room temp under Ar for 2 h whereupon it was cooled to room temp and quenched by addition of sat. aq. NaHCO$_3$ (10 mL). The mixture was extracted with EtOAc (3×10 mL) and the combined organic extracts were washed with brine, dried (Na$_2$SO$_4$), and concentrated in vacuo. The residue was purifed by column chromatography (6 g silica gel 60, 24 mm diam. column, 2.5–8.0% MeOH/CH$_2$Cl$_2$) to afford the hydrazino ester which was used directly in the next step. The ester was taken up in xylenes (2 mL) and heated to 145° C. for 2 h. The reaction mixture was cooled and concentrated in vacuo to afford the triazolinone (24.0 mg, 79%) as a tan solid. ESIMS/CI m/z calcd. for C$_{28}$H$_{28}$N$_4$O$_2$F$_6$ 542.53; found 543.2 (100%), 544.2 (25%).

EXAMPLE 162

1S-(1'R-(3,5-Bistrifluoromethyl)phenyl)ethoxy)-2S-phenyl-3S-(N-methyl-N-(5-(1,2,4-triazolylmethyl)amino))-cyclohexane

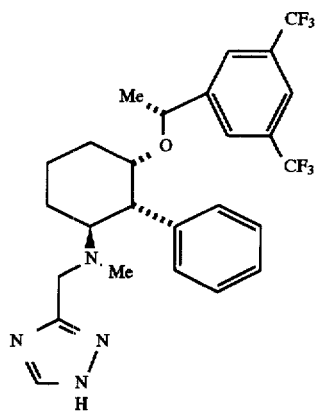

To a solution of the amine (25.0 mg, 0.056 mmol) in CH$_3$CN (2 mL) at room temp was added diisopropylethyl amine (14.5 mg, 0.112 mmol) and hydrazinoaldehyde (14.5 mg, 0.084 mmol). The reaction mixture was stirred at room temp under Ar for 2 h whereupon it was cooled to room temp and quenched by addition of sat. aq. NaHCO$_3$ (10 mL). The mixture was extracted with EtOAc (3×10 mL) and the combined organic extracts were washed with brine, dried (Na$_2$SO$_4$), and concentrated in vacuo. The residue was purifed by column chromatography (6 g silica gel 60, 24 mm diam. column, 2.5–8.0% MeOH/CH$_2$Cl$_2$) to afford the hydrazinoaldehyde which was used directly in the next step. The aldehyde was taken up in xylenes (2 mL) and heated to 145° C. for 5 h. The reaction mixture was cooled and concentrated in vacuo to afford the triazolinone (21.0 mg, 71%) as a pale yellow solid. ESIMS/CI m/z calcd. for C$_{26}$H$_{28}$N$_4$O$_1$F$_6$ 526.53; found 527.3 (50%), 528.3 (15%), 447.2 (30%), 446.2 (100%).

EXAMPLE 163

1S-(1'R-(3,5-bistrifluoromethyl)phenyl)ethoxy)-2S-phenyl-3S-aminocyclohexane

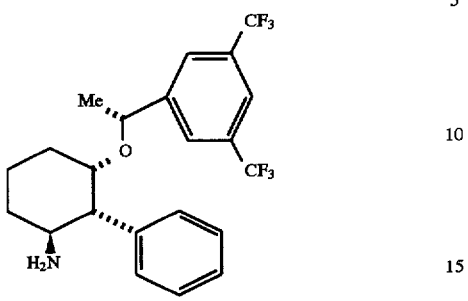

The CBZ amine (100 mg, 0.177 mmol) was treated with Pd/C (30 mg) and H₂ (50 psi) in EtOH (8 mL) on the Parr shaker apparatus for 30 min. The reaction mixture was filtered through celite with EtOAc washing, and concentrated in vacuo. The residue was purifed by column chromatography (11 g silica gel 60, 24 mm diam. column, 5–8% MeOH/CH₂Cl₂) to afford the amine (64 mg, 84%) as a colorless oil. ¹H NMR (CDCl₃, 500 MHz) δ 7.63 (s, 1H), 7.20–7.41 (m, 7H), 4.39 (q, 1H, J=6.4 Hz), 3.58 (dt, 1H, J=11.0, 4.1 Hz), 3.49 (d, 1H, J=2.1 Hz), 2.40 (dd, 1H, J=11.0, 2.5 Hz), 2.05–2.15 (m, 2H), 1.62–1.92 (m, 4H), 1.40–1.46 (m, 1H), 1.38 (d, 3H, J=6.5 Hz), 1.23–1.33 (m, 1H) ppm.

EXAMPLE 164

1S-1'R-(3,5-Bistrifluoromethyl)phenyl)ethoxy)-2S-phenyl-3S-(amino-aminocarbonyl methyl aminocyclohexane

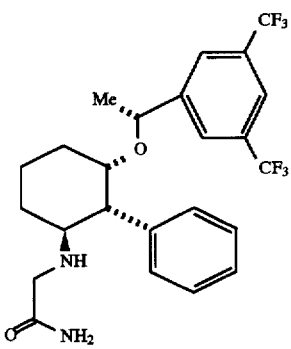

To a solution of the amine (15.0 mg, 0.035 mmol) in CH₃CN (1 mL) at room temp was added diisopropylethyl amine (6.7 mg, 0.052 mmol) and iodoacetamide (7.0 mg, 0.039 mmol). The reaction mixture was heated to 50° C. under Ar for 3 h whereupon it was cooled to room temp and quenched by addition of sat. aq. NaHCO₃ (10 mL). The mixture was extracted with EtOAc (3×10 mL) and the combined organic extracts were washed with brine, dried (Na₂SO₄), and concentrated in vacuo. The residue was purifed by column chromatography (1.5 g silica gel 60, 14 mm diam. column, 2.5–8.0% MeOH/CH₂Cl₂) to afford the amide (12.2 mg, 71%) as a colorless solid.

¹H NMR (CDCl₃, 500 MHz) δ 7.63 (s, 1H), 7.19–7.35 (m, 7H), 6.88 (bs, 1H), 5.30 (bs, 1H), 4.42 (q, 1H, J=6.4 Hz), 3.50 (d, 1H, J=2.1 Hz), 3.32 (dt, 1H, J=11.2, 3.9 Hz), 3.17 (ABX, 2H, J=17.4 Hz), 2.48 (dd, 1H, J=11.2, 2.5 Hz), 2.21 (dd, 1H, J=12.6, 2.8 Hz), 2.11 (bd, 1H, J=14.2 Hz), 1.75–1.88 (m, 1H), 1.65–1.72 (m, 1H), 1.45–1.60 (m, 1H), 1.39 (d, 3H, J=6.5 Hz), 1.07–1.20 (m, 1H) ppm.

EXAMPLE 165

1S-1'R-(3,5-Bistrifluoromethyl)phenyl)ethoxy)-2S-phenyl-3S-(N-(2-pyrrolidinone-5-(S)-yl-methyl)) aminocyclohexane

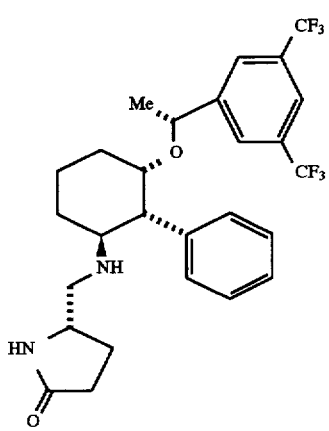

To a solution of the amine (36.0 mg, 0.083 mmol) in CH₃CN (0.5 mL) at room temp was added diisopropylethyl amine (21.0 mg, 0.167 mmol) and 5-methylbromopyrolidinone (30.0 mg, 0.167 mmol). The reaction mixture was heated to 100° C. in a sealed tube for 24 h whereupon it was cooled to room temp and concentrated in vacuo. The residue was purified by radial chromatography (1 mm plate thickness, 2 mls/min, 2.5–8.0% MeOH/CH₂Cl₂) to afford the pyrrolidinone adduct (25.0 mg, 57%) as a colorless solid. ¹H NMR (CDCl₃, 500 MHz) δ 7.63 (s, 1H), 7.16–7.36 (m, 7H), 5.69 (br s, 1H), 4.38 (q, 1H, J=6.4 Hz), 3.43–3.58 (m, 2H), 3.26 (dt, 1H, J=10.9, 3.9 Hz), 2.63 (dd, 1H, J=11.9, 4.1 Hz), 2.46–2.54 (m, 2H), 2.26 (t, 2H, J=8.1 Hz), 2.17–2.22 (m, 1H), 2.04–2.15 (m, 2H), 1.74–1.85 (m, 1H), 1.64–1.70 (m, 1H), 1.50–1.60 (m, 1H), 1.36–1.44 (m, 1H), 1.38 (d, 3H, J=6.4 Hz), 1.15 (ddd, 1H, J=24.1, 13.2, 3.7 Hz) ppm.

EXAMPLE 166

1S-(N-2-Methoxy-5-(1,2,3,4-tetrazol-1-yl)) benzylamino-2S-phenyl-3S-hydroxymethylcyclohexane and 1R-(N-2-Methoxy-5-(1,2,3,4-tetrazol-1-yl))benzylamino-2S-phenyl-3S-hydroxymethylcyclohexane Step A:

1-Oxo-2R-phenyl-3S-t-butyldimethylsilyloxymethylcyclohexane

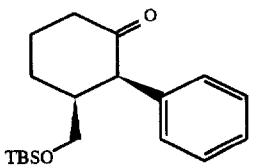

To a solution of the alcohol (12.4 g, 38.7 mmol) in CH₂Cl₂ (500 mL) was added pyridine (14.1 mL, 174 mmol) and Dess-Martin periodinane reagent (24.6 g, 58.1 mmol) at room temp. After 3 h the reaction mixture was quenched by addition of sat. aq. NaHCO$_3$ (200 mL), diluted with H$_2$O (300 mL) and extracted with EtOAc (3×300 mL). The combined organic extracts were washed with brine, dried (Na$_2$SO$_4$), and concentrated in vacuo to yield the ketone (12.3 g, 100%) as a colorless glass, which was used directly in the next step.

$^1$H NMR (CDCl$_3$, 500 MHz) δ 7.20–7.41 (m, 5H), 3.83 (d, 1H, J=5.8 Hz), 3.44–3.53 (m, 2H), 2.60 (dt, 1H, J=15.1, 6.2 Hz), 2.41–2.50 (m, 1H), 2.33–2.39 (m, 1H), 2.20–2.30 (m, 1H), 1.89–2.08 (m, 3H), 0.89 (s, 9H), −0.011 (s, 3H), −0.039 (s, 3H) ppm.

Step B:

1-Oxo-2S-phenyl-3S-t-butyldimethylsilyloxymethylcyclohexane

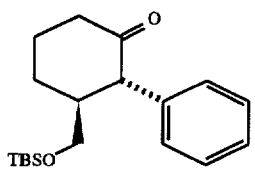

To a solution of the ketone (12.3 g, 38.0 mmol) in MeOH (330 mL) at room temp was added 1M NaOMe (110 mL) and the mixture stirred for 16h. The reaction mixture was diluted with H$_2$O (500 mL) and concentrated to remove the MeOH. The aqueous was then extracted with EtOAc (3×300 mL), the combined organic extracts were washed with brine, dried (Na$_2$SO$_4$), and concentrated in vacuo. The residue was purified by column chromatography (150 g silica gel 60, 60 mm diam. column, 5–25% EtOAc/hexanes) to afford the epimerized ketone (11.6 g, 94%) as a colorless glass. $^1$H NMR (CDCl$_3$, 500 MHz) δ 7.25–7.38 (m, 3H), 7.06–7.15 (m, 2H), 3.62 (d, 1H, J=11.9 Hz), 3.37 (dd, 1H, J=9.8, 2.3 Hz), 3.18 (dd, 1H, J=9.9, 4.8 Hz), 2.52–2.58 (m, 1H), 2.46 (dt, 1H, J=13.3, 6.0 Hz), 2.09–2.24 (m, 2H), 1.98–2.07 (m, 1H), 1.78–1.97 (m, 2H), 0.090 (s, 9H), −0.047 (s, 3H), −0.080 (s, 3H) ppm.

Step C:

1R-Hydroxy-2S-phenyl-3S-t-butyl-dimethylsilyloxymethylcyclohexane

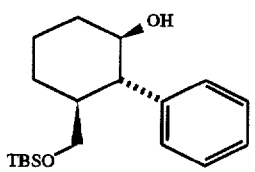

To a solution of the ketone (11.6 g, 36.3 mmol) in THF (250 mL) at −85° C. under Ar was added 1M LiAlH$_4$ (54.5 mL, 54.5 mmol). After stirring 1.5 h at −85° C. the reaction was quenched by addition of sat. Rochelle's salts (100 mL), allowed to warm to room temp. and diluted with H$_2$O (200 mL), and CH$_2$Cl$_2$ (300 mL). This mixture was vigorously stirred for 30 min and extracted with CH$_2$Cl$_2$ (3×200 mL). The combined organic extracts were washed with brine, dried (Na$_2$SO$_4$), and concentrated in vacuo to afford the alcohol (11.6 g, 100%) as a ~6:1 ratio of the C-1 diastereomers, used directly in the next step. Major diastereomer: $^1$H NMR (CDCl$_3$, 500 MHz) δ 7.20–7.41 (m, 5H), 3.72 (dt, 1H, J=10.2, 4.2 Hz), 3.26 (dd, 1H, J=9.9, 2.5 Hz), 3.11 (dd, 1H, J=9.8, 6.2 Hz), 2.38 (t, 1H, J=10.6 Hz), 2.29–2.37 (m, 1H), 1.84–1.94 (m, 2H), 1.67–1.75 (m, 1H), 1.26–1.60 (m, 4H), 0.86 (s, 9H), −0.086 (s, 3H), −0.11 (s, 3H) ppm.

Step D:

1S-Azido-2S-phenyl-3S-t-butyl-dimethylsilyloxymethylcyclohexane

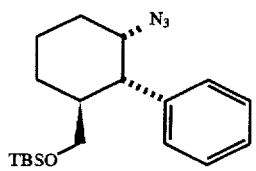

To a solution of the alcohol (1.00 g, 3.12 mmol), PPh$_3$ (2.29 g, 8.74 mmol), imidazole (531 mg, 7.80 mmol), and Zn(N$_3$)$_2$pyr$_2$ (2.16 g, 7.02 mmol), in PhMe (60 mL) at room temp under N$_2$ was added slowly via syringe DEAD (1.52 g, 8.74 mmol). The reaction mixture was stirred 1 h forming an orange solution and gummy residue. The mixture was filtered through Celite with EtOAc (300 mL) and Et$_2$O (300 mL). The organic filtrate was washed with 1M HCl, sat. aq. NaHCO$_3$, brine, and dried (Na$_2$SO$_4$) and concentrated in vacuo. The residue was purified by column chromatography (50 g silica gel 60, 60 mm diam. column, 0–5% EtOAc/hexanes) to afford the azido adduct (871 mg, 81%) as a colorless glass, and unreacted cis 1-hydroxy-2-phenyl adduct (43 mg, 4.3%). $^1$H NMR (CDCl$_3$, 500 MHz) δ 7.20–7.41 (m, 5H), 3.83 (s, 1H), 3.35 (dd, 1H, J=9.8, 2.5 Hz), 3.20 (dd, 1H, J=9.9, 5.8 Hz), 2.68 (dd, 1H, J=11.6, 2.7 Hz), 2.12–2.22 (m, 1H), 2.04–2.11 (m, 1H), 1.88–2.00 (m, 1H), 1.64–1.81 (m, 3H), 1.36–1.52 (m, 1H), 0.84 (s, 9H), −0.115 (s, 3H), −0.187 (s, 3H) ppm.

Step E:

1S-Amino-2S-phenyl-3S-t-butyl-dimethylsilyloxymethylcyclohexane

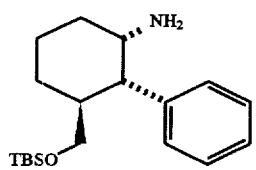

The azide (3.00 g, 8.68 mmol) was treated with Pd/C (3 g) and H$_2$ (50 psi) in MeOH (250 mL) on the Parr shaker apparatus for 3 h. The reaction mixture was filtered through celite with MeOH washing, and concentrated in vacuo. The residue was purifed by column chromatography (30 g silica gel 60, 45 mm diam. column, 5–8% MeOH/CH$_2$Cl$_2$) to afford the amine (2.49 g, 90%) as a colorless oil.

$^1$H NMR (CDCl$_3$, 500 MHz) δ 7.18–7.40 (m, 5H), 3.45 (dd, 1H, J=9.9, 2.8 Hz), 3.23 (dd, 1H, J=9.8, 6.6 Hz), 3.100 (bd, 1H, J=3.0 Hz), 2.65 (dd, 1H, J=11.9, 3.2 Hz), 2.16–2.26 (m, 1H), 1.94–2.10 (m, 1H), 1.40–1.92 (m, 4H), 1.20–1.39 (m, 1H), 1.06 (bs, 2H), 0.85 (s, 9H), −0.097 (s, 3H), −0–162 (s, 3H) ppm.

Step F:

1S-N-2-methoxy-5-(1,2,3,4-tetrazol-1-yl))benzylamino-2S-phenyl-3 S-t-butyldimethylsilyloxymethylcyclohexane

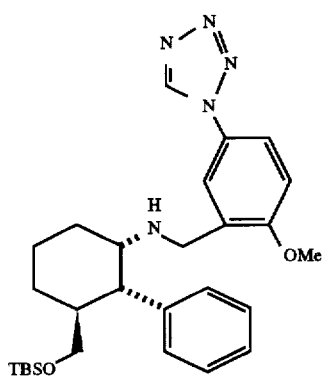

A solution of the amines (600 mg, 1.88 mmol; >20:1 cis:trans), HOAc (228 mg, 3.99 mmol), 3A mol sieves (2.4 g), and the appropriate aldehyde (427 mg, 2.09 mmol) in MeOH (27 mL) was stirred at room temp under $N_2$ for 4 h. NaCNBH$_3$ (358 mg, 5.69 mmol) was added and the mixture stirred at room temp for 16 h, whereupon it was filtered through Celite with MeOH washes, and the filtrate concentrated in vacuo. The residue was partitioned between $H_2O$/sat. aq. NaHCO$_3$ (150 mL) and EtOAc (150 mL), followed by extraction with EtOAc (3×150 mL). The combined organic extracts were washed with brine, dried (Na$_2$SO$_4$), and concentrated in vacuo. The residue was purifed by column chromatography (45 g silica gel 60, 45 mm diam. column, 40–80% EtOAc/hexanes) to afford the 1,2-cis benzylamine (553 mg, 58%) as a colorless glass. In addition a small amount (30 mg) of the 1,2-trans adduct is isolated. 1,2-C is adduct; $^1$H NMR (CDCl$_3$, 500 MHz) 8.70 (s, 1H), 7.45 (dd, 1H, J=8.7, 2.5 Hz), 7.10–7.31 (m, 6H), 6.82 (d, 1H, J=8.7 Hz), 3.75 (d, 1H, J=14.8 Hz), 3.62 (s, 3H), 3.57 (d, 1H, J=15.0 Hz), 3.42 (dd, 1H, J=9.8, 2.5 Hz), 3.22 (dd, 1H, J=9.8, 6.1 Hz), 2.68–2.78 (m, 2H), 2.25–2.35 (m, 1H), 1.97–2.09 (m, 2H), 1.60–1.88 (m, 2H), 1.53–1.60 (m, 1H), 1.27–1.48 (m, 2H), 0.81 (s, 9H), −0.132 (s, 3H), −0.213 (s, 3H) ppm; $^{13}$C NMR (CDCl$_3$, 125 Mhz) d 158.5, 142.5, 140.8, 128.9, 128.2, 126.5, 126.3, 122.1, 121.1, 115.1, 110.6, 65.9, 56.7, 55.6, 49.5, 45.4, 36.1, 30.0, 29.0, 25.9, 19.4, 18.3, −5.53, −5.67 ppm. 1,2-Trans adduct; $^1$H NMR (CDCl$_3$, 500 MHz) 8.83 (s, 1H), 7.51 (dd, 1H, J=8.7, 2.5 Hz), 7.10–7.32 (m, 6H), 6.84 (d, 1H, J=8.7 Hz), 3.77 (d, 1H, J=13.9 Hz), 3.64 (d, 1H, J=13.9 Hz), 3.56 (s, 3H), 3.18 (dd, 1H, J=9.6, 2.3 Hz), 3.03 (dd, 1H, J=9.8, 5.8 Hz), 2.59 (dt, 1H, J=10.5, 3.6 Hz), 2.40 (t, 1H, J=10.7 Hz), 2.20–2.23 (m, 1H), 1.83–1.94 (m, 2H), 1.58–1.68 (m, 1H), 1.18–1.43 (m, 3H), 0.83 (s, 9H), −0.12 (s, 3H), −0.14 (s, 3H) ppm.

Step G:

1S-N-2-methoxy-5-(1,2,3,4-tetrazol-1-yl))benzylamino-2S-phenyl-3S-hydroxymethylcyclohexane

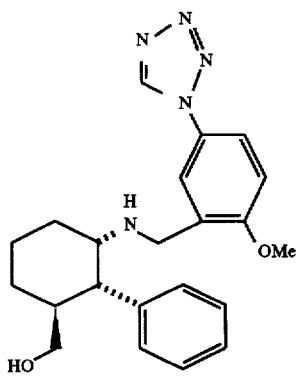

The cis-1,2-silyl ether (28 mg, 0.055 mmol) had added to it a solution mixture (2 mL) containing THF/pyridine/95% HF-pyridine complex 5:1:0.5 at room temperature. After stirring for 3 h the reaction mixture was quenched by addition of $H_2O$ (20 mL) and sat. NaHCO$_3$ (20 mL). The mixture was extracted with EtOAc (3×25 mL) and the combined organic extracts were washed with brine, dried (Na$_2$SO$_4$), and concentrated in vacuo to afford the 3-hydroxymethyl adduct (25 mg, 100%) as a colorless oil. $^1$H NMR (CDCl$_3$, 500 MHz) δ 8.71 (s, 1H), 7.45 (dd, 1H, J=8.7, 2.5 Hz), 7.14–7.31 (m, 6H), 6.83 (d, 1H, J=8.7 Hz), 3.76 (d, 1H, J=14.9 Hz), 3.62 (s, 3H), 3.57 (d, 1H, J=14.8 Hz), 3.50 (dd, 1H, J=11.0, 3.0 Hz), 3.30 (dd, 1H, J=11.0, 6.5 Hz), 2.75 (bd, 1H, J=2.8 Hz), 2.69 (dd, 1H, J=11.9, 3.2 Hz), 2.32–2.41 (m, 1H), 2.02–2.09 (m, 2H), 1.78–1.90 (m, 1H), 1.55–1.66 (m, 2H), 1.40–1.50 (m, 1H), 1.33 (ddd, 2H, J=25.4, 13.1, 3.9 Hz) ppm.

Step H:

1R-(N-2-Methoxy-5-(1,2,3,4-tetrazol-1-yl))benzylamino-2S-phenyl-3S-hydroxymethylcyclohexane

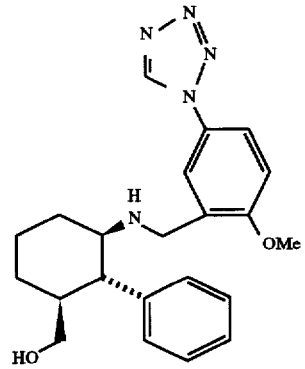

The cis-1,2-silyl ether (26 mg, 0.053 mmol) had added to it a solution mixture (2 mL) containing THF/pyridine/95% HF-pyridine complex 5:1:0.5 at room temperature. After stirring for 2.5 h the reaction mixture was quenched by addition of $H_2O$ (20 mL) and sat. NaHCO$_3$ (20 mL). The mixture was extracted with EtOAc (3×25 mL) and the combined organic extracts were washed with brine, dried (Na$_2$SO$_4$), and concentrated in vacuo to afford the 3-hydroxymethyl adduct (20 mg, 98%) as a colorless oil. ESIMS/CI m/z calcd. for $C_{22}H_{27}N_5O_2$ 393.22; found 394.2 (100%), 279.1 (40%), 207.1 (70%), 188.1 (35%), 120.1 (45%).

EXAMPLE 167

1S-(N-2-Methoxy-5-(5-trifluoromethyl-1,2,3,4-tetrazol-1-yl))benzylamino-2S-phenyl-3S-hydroxymethylcyclohexane Step A:

1S-N-2-methoxy-5-(5-trifluoromethyl-1,2,3,4-tetrazol-1-yl))benzylamino-2S-phenyl-3S-t-butyldimethyl-silyloxymethylcyclohexane

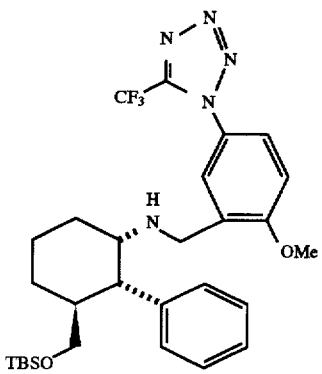

A solution of the amine (725 mg, 2.27 mmol), HOAc (245 mg, 4.09 mmol), 3A mol sieves (3.0 g), and the aldehyde (802 mg, 2.94 mmol) in MeOH (30 mL) was stirred at room temp under $N_2$ for 4 h. NaCNBH$_3$ (428 mg, 6.81 mmol) was added and the mixture stirred at room temp for 16 h, whereupon it was filtered thru Celite with MeOH washes, and the filtrate concentrated in vacuo. The residue was partitioned between $H_2O$/sat aq. NaHCO$_3$ (200 mL) and EtOAc (200 mL), followed by extraction with EtOAc (3×200 mL). The combined organic extracts were washed with brine, dried (Na$_2$SO$_4$), and concentrated in vacuo. The residue was purifed by column chromatography (50 g silica gel 60, 45 mm diam. column, 15–50% EtOAc/hexanes) to afford the benzylamine (760 mg, 66%) as a colorless glass. $^1$H NMR (CDCl$_3$, 500 MHz) δ 6.97–7.32 (m, 7H), 6.82 (d, 1H, J=8.7 Hz), 3.76 (d, 1H, J=15.5 Hz), 3.68 (s, 3H), 3.57 (d, 1H, J=16.1 Hz), 3.43 (dd, 1H, J=9.8, 2.3 Hz), 3.18–3.26 (m, 1H), 2.65–2.74 (m, 2H), 2.23–2.32 (m, 1H), 1.97–2.13 (m, 2H), 1.72–1.81 (m, 1H), 1.52–1.63 (m, 1H), 1.25–1.45 (m, 3H), 0.81 (s, 9H), –0.130 (s, 3H), –0.210 (s, 3H) ppm.

Step B:

1S-(N-2-Methoxy-5-(5-trifluoromethyl-1,2,3,4-tetrazol-1-yl))benzylamino-2S-phenyl-3S-hydroxymethylcyclohexane

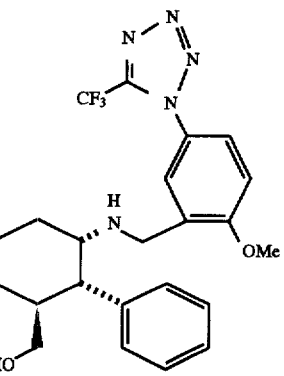

The silyl ether (32 mg, 0.054 mmol) had added to it a solution mixture (3 mL) containing THF/pyridine/95% HF-pyridine complex 5:1:0.5 at room temperature. After stirring for 2 h the reaction mixture was quenched by addition of $H_2O$ (30 mL) and sat. NaHCO$_3$ (30 mL). The mixture was extracted with EtOAc (3×40 mL) and the combined organic extracts were washed with brine, dried (Na$_2$SO$_4$), and concentrated in vacuo to afford the 3-hydroxymethyl adduct (25 mg, 99%) as a colorless oil. $^1$H NMR (CDCl$_3$, 500 MHz) δ 7.02–7.37 (m, 6H), 6.80–6.86 (m, 2H), 3.79 (d, 1H, J=15.3 Hz), 3.67 (s, 3H), 3.57 (d, 1H, J=15.5 Hz), 3.50 (dd, 1H, J=10.8, 2.7 Hz), 3.31 (dd, 1H, J=10.8, 6.4 Hz), 2.62–2.75 (m, 2H), 2.30–2.41 (m, 1H), 1.97–2.10 (m, 2H), 1.75–1.88 (m, 1H), 1.52–1.70 (m, 1H), 1.39–1.48 (m, 1H), 1.33 (ddd, 2H, J=25.4, 13.1, 3.7 Hz) ppm.

EXAMPLE 168

1S-(N-2-Methoxy-5-(1,2,3,4-tetrazol-1-yl)) benzylamino-2S -phenylcyclohexane-3S-carboxylic acid and t-Butyl-1S-(N-2-methoxy-5-(1,2,3,4-tetrazol-1-yl))benzylamino-2S-phenylcyclohexane-3S-carboxamide Step A:

1S-[(N-Benzyloxycarbonyl)-(N-2-methoxy-5-(1,2,3,4-tetrazol-1-yl))]benzylamino-2S-phenyl-3S-hydroxymethylcyclohexane

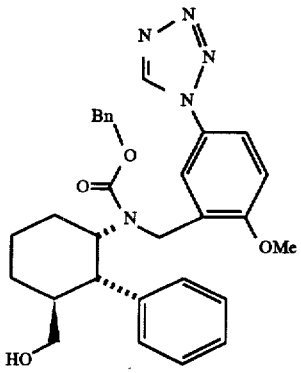

A solution of the amine (350 mg, 0.689 mmol), diisopropylethylamine (276 mg, 2.07 mmol) and benzoyl chloride (175 mg, 1.03 mmol) in $CH_2Cl_2$ (6 mL) was stirred at room temp for 19 h, whereupon it was quenched by addition of $H_2O$ (25 mL), and extracted with EtOAc (3×30 mL). The combined organic extracts were washed with brine, dried ($Na_2SO_4$), and concentrated in vacuo to afford a mixture of the N-CBZ-3-t-butyldimethylsiloxymethyl and N-CBZ-3-hydroxymethyl adducts as an oil which were used directly in the following procedure. ESIMS/CI m/z calcd. for $C_{36}H_{47}N_5O_4Si_1$ 641.34; found 642.3 (38%), 528.1 (100%), 391.2 (39%), 279.1 (41%), 258.1 (70%), 222.1 (40%). The mixture was taken up in THF (4 mL) and was treated with a solution containing pyridine (1.0 mL), THF (5 mL) and 95% HF-pyridine complex (0.5 g). After stirring for 3 h the reaction mixture was quenched by addition of $H_2O$ (50 mL) and sat. $NaHCO_3$ (50 mL). The mixture was extracted with EtOAc (3×30 mL) and the combined organic extracts were washed with brine, dried ($Na_2SO_4$), and concentrated in vacuo to afford the N-CBZ-3-hydroxymethyl adduct (363 mg, 100%) as a colorless oil. The $^1H$ NMR showed a very complex mixture of conformational rotamers.

Step B:

1S-[(N-Benzyloxycarbonyl)-(N-2-methoxy-5-(1,2,3,4-tetrazol-1-yl))]benzylamino-2S-phenylcyclohexane-3S-carboxylic acid

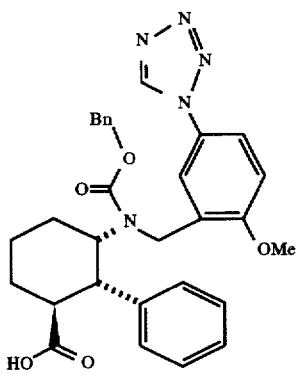

To a solution of oxalyl chloride (233 mg, 1.84 mmol) in $CH_2Cl_2$ (7 mL) at –70° C. was added DMSO (286 mg, 3.67 mmol) and the mixture stirred 20 min. Then a solution of the alcohol (363 mg, 0.689 mmol) in $CH_2Cl_2$ (3 mL) was added at –70° C. and the resultant mixture stirred 1 h, whereupon $Et_3N$ (1.02 mL, 7.35 mmol) was added and the mixture allowed to warm to room temp and stirred 1 h. The reaction mixture was diluted with $H_2O$ (125 mL) and extracted with $CH_2Cl_2$ (3×75 mL). The combined organic extracts were washed with brine, dried ($Na_2SO_4$), and concentrated in vacuo to afford the aldehyde (~360 mg) which was used directly below. The 3-carboxaldehyde (360 mg) was taken up in THF (8 mL) cooled to 0° C. and treated with 2.7M aqueous sulfamic acid (0.50 mL, 1.32 mmol), 1M aqueous $NaH_2PO_4$ (1.32 mL, 1.32 mmol) and finally 1M aqueous $NaClO_2$ (1.32 mL, 1.32 mmol). The mixture was allowed to warm to room temperature and stirred 16 h. The reaction mixture was diluted with $H_2O$ (25 mL) extracted with $CH_2Cl_2$ (3×75 mL). The combined organic extracts were washed with brine, dried ($Na_2SO_4$), and concentrated in vacuo. The residue was purifed by column chromatography (21 g silica gel 60, 24 mm diam. column, 2.5–8.0% MeOH/$CH_2Cl_2$) to afford the carboxylic acid (228 mg, 61% overall yield from alcohol) as a white solid. $^1H$ NMR ($CDCl_3$, 500 MHz) δ 9.00 (s, 1H), 7.00–7.60 (m, 13H), 6.88 (d, 1H, J=9.0 Hz), 5.33 (d, 1H, J=11.9 Hz), 5.07 (bs, 1H), 4.97 (d, 1H, J=12.1 Hz), 4.61 (bs, 1H), 4.37 (s, 1H), 4.09 (d, 1H, J=18.5 Hz), 3.79 (s, 3H), 3.40 (d, 1H, J=18.6 Hz), 3.12 (s, 1H), 2.05–2.30 (m, 2H), 1.61–1.80 (m, 2H), 1.44–1.54 (m, 1H) ppm. FTIR 3100, 2950, 1694, 1504, 1462, 1415, 1251, 1212, 1126, 1091, 910, 733, 701 cm$^{-1}$.

Step C:

1S-N-2-methoxy-5-(1,2,3,4-tetrazol-1-yl))benzylamino-2S-phenylcyclohexane-3S-carboxylic acid

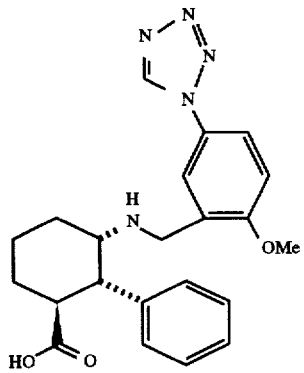

To a solution of the N-CBZ carboxylate (16 mg, 0.030 mmol) in MeOH (2 mL) at room temp was added ammonium formate (37 mg, 0.590 mmol) and 10% Pd/C (25 mg) and the mixture stirred vigorously for 1 h. The reaction mixture was filtered through Celite with MeOH washes and then concentrated in vacuo. The residue was taken up in $CHCl_3$ (2 mL) and passed through a nylon sep-pak with $CHCl_3$ washes and then concentrated affording the deprotected amine as a colorless glass (11.5 mg, 94%). ESIMS/CI m/z calcd. for $C_{22}H_{25}N_5O_3$ 407.20; found 408.2 (20%), 279.1 (19%), 258.1 (30%), 239.1 (35%), 191.1 (60%), 137.1 (40%), 120.1 (100%).

Step D:

(N-(t-Butyl)-1S-(N-2-methoxy-5-(1,2,3,4-tetrazol-1-yl))benzylamino-2S-phenylcyclohexane-3S-carboxamide

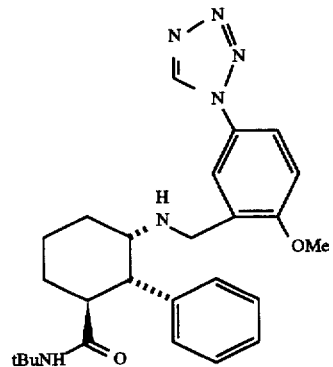

To a solution of the acid (20.0 mg, 0.037 mmol) in $CH_2Cl_2$ (2 mL) at room temp was added excess oxalyl chloride (0.5 mL), followed by a catalytic amount of DMF (1 drop). The reaction mixture was stirred 1 h whereupon it was concentrated and then redissolved in $CH_2Cl_2$ and reconcentrated (3×5 mL). The residue was taken up in $CH_2Cl_2$ (2 mL) and had added to it t-butylamine (8.1 mg, 0.111 mmol) at room temp. After stirring 1 h, the reaction was diluted with $H_2O$ (50 mL) and extracted with $CH_2Cl_2$ (3×25 mL). The combined organic extracts were washed with brine, dried ($Na_2SO_4$), and concentrated in vacuo to afford the amide (23 mg) which was used directly below. To a solution of the N-CBZ carboxamide (23 mg, 0.037 mmol) in MeOH (3 mL) at room temp was added ammonium formate (46 mg, 0.740 mmol) and 10% Pd/C (25 mg) and the mixture stirred vigorously for 2 h. The reaction mixture was filtered through Celite with MeOH washes and then concentrated in vacuo.

The residue was taken up in EtOAc (4 mL) and passed through a nylon sep-pak with EtOAc washes and then concentrated affording the t-butylamide as a colorless glass (16.0 mg, 94%). $^1$H NMR (CDCl$_3$, 500 MHz) δ 8.89 (s, 1H), 7.55 (dd, 1H, J=8.7, 2.5 Hz), 7.38 (d, 1H, J=2.3 Hz), 7.19–7.33 (m, 6H), 6.85 (d, 1H, J=14.1 Hz), 5.59 (s, 1H), 3.97 (d, 1H, J=14.1 Hz), 3.66 (d, 1H, J=14.4 Hz), 3.51 (s, 3H), 3.18 (dd, 1H, J=11.8, 3.2 Hz), 3.08 (dt, 1H, J=11.5, 3.2 Hz), 2.97 (d, 1H, J=2.7 Hz), 1.98–2.16 (m, 2H), 1.80–1.92 (m, 1H), 1.60–1.74 (m, 2H), 1.27–1.42 (m, 1H), 1.08 (s, 9H) ppm. ESIMS/CI m/z calcd. for C$_{26}$H$_{34}$N$_6$O$_2$ 462.60; found 463.2 (95%), 391.2 (90%), 279.1 (40%), 275.2 (100%), 258.1 (78%).

EXAMPLE 169

1S-N-2-Methoxy-5-(1,2,3,4-tetrazol-1-yl))benzylamino-2S-phenyl-3R-hydroxymethylcyclohexaneand 1R-(N-2-methoxy-5-(1,2,3,4-tetrazol-1-yl))benzylamino-2S-phenyl-3R-hydroxymethylcyclohexane Step A:
1 - O x o - 2 S - p h e n y l - 3 R - t - butyldimethylsilyoxymethylcyclohexane

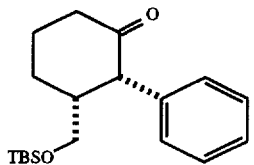

To a solution of the alcohol (115 mg, 0.36 mmol) in CH$_2$Cl$_2$ (10 mL) was added pyridine (261 µL, 3.24 mmol) and Dess-Martin periodinane reagent (456 mg, 1.08 mmol) at room temp. After 18 h the reaction mixture was quenched by addition of sat. aq. NaHCO$_3$ (20 mL), diluted with H$_2$O (30 mL) and extracted with EtOAc (3×30 mL). The combined organic extracts were washed with brine, dried (Na$_2$SO$_4$), and concentrated in vacuo. The residue was purifed by column chromatography (16 g silica gel 60, 30 mm diam. column, 5–15% EtOAc/hexanes) to afford the ketone (109 mg, 96%) as a colorless solid.

$^1$H NMR (CDCl$_3$, 500 MHz) δ 7.20–7.41 (m, 5H), 3.83 (d, 1H, J=5.8 Hz), 3.44–3.53 (m, 2H), 2.60 (dt, 1H, J=15.1, 6.2 Hz), 2.41–2.50 (m, 1H), 2.33–2.39 (m, 1H), 2.20–2.30 (m, 1H), 1.89–2.08 (m, 3H), 0.88 (s, 9H), −0.015 (s, 3H), −0.042 (s, 3H) ppm.

Step B:
1 - R S - A m i n o - 2 S - p h e n y l - 3 R - t - butyldimethylsilyoxymethylcyclohexane

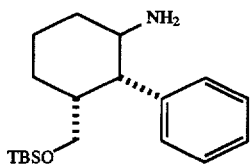

To a solution of the ketone (100 mg, 0.314 mmol) in iPrOH (8 mL) at room temp was added NH$_4$OAc (242 mg, 3.14 mmol), NaCNBH$_3$ (20 mg, 0.314 mmol) and crushed 3 Å molecular sieves (100 mg). The reaction mixture was stirred 18 h, whereupon it was filtered through celite with MeOH washes (150 mL), concentrated in vacuo and the residue partitioned between 1N NaOH (100 mL) and CH$_2$Cl$_2$ (50 mL). The mixture was extracted with CH$_2$Cl$_2$ (3×50 mL). The combined organic extracts were washed with brine, dried (Na$_2$SO$_4$), and concentrated in vacuo. The residue was purifed by column chromatography (11 g silica gel 60, 24 mm diam. column, 5–8% MeOH/CH$_2$Cl$_2$) to afford the amines (75 mg, 74%) as a colorless glass as a mixture of diastereomers.

Step C:
1S -(N-2-Methoxy-5-(1,2,3,4-tetrazol-1-yl))benzylamino-2S-phenyl-3R-t-butyldimethylsilyloxymethylcyclohexane and 1R-(N-2-Methoxy-5-(1,2,3,4-tetrazol-1-yl))benzyl-amino-2S-phenyl-3R-t-butyldimethylsilyloxymethyl-cyclohexane

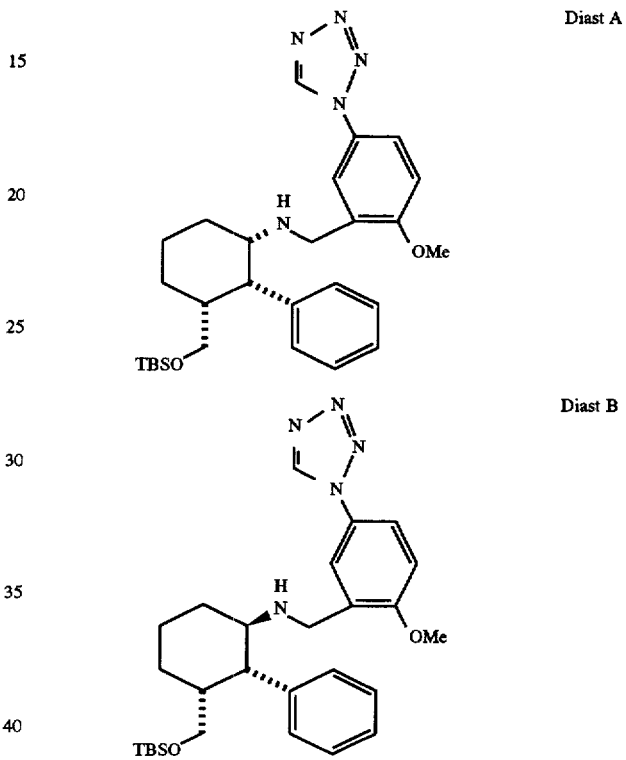

A solution of the amines (72.0 mg, 0.225 mmol), HOAc (20.0 mg, 0.34 mmol), 3 Å mol sieves (300 mg), and the aldehyde (51.0 mg, 0.248 mmol) in MeOH (3 mL) was stirred at room temp under N$_2$ for 45 min. NaCNBH$_3$ (43.0 mg, 0.68 mmol) was added and the mixture stirred at room temp for 3 h, whereupon it was filtered thru Celite with MeOH washes, and the filtrate concentrated in vacuo. The residue was partitioned between H$_2$O/sat. aq. NaHCO$_3$ (200 mL) and EtOAc (200 mL), followed by extraction with EtOAc (3×200 mL). The combined organic extracts were washed with brine, dried (Na$_2$SO$_4$), and concentrated in vacuo. The residue was purifed by radial chromatography (1 mm plate, silica gel 60, 50–100% EtOAc/hexanes) to afford the minor benzyl amine Diast A (22 mg, 19%) as a colorless glass in addition to the major amine, Diast B (62 mg, 55%) as a colorless glass. Diast A; $^1$H NMR (CDCl$_3$, 500 MHz) δ 8.71 (s, 1H), 7.46 (dd, 1H, J=8.7, 2.3 Hz), 7.12–7.30 (m, 7H), 6.83 (d, 1H, J=8.7 Hz), 3.72–3.83 (m, 1H), 3.61 (s, 3H), 3.55–3.60 (m, 1H), 3.43 (dd, 1H, J=9.6, 2.3 Hz), 3.23 (dd, 1H, J=9.7, 6.2 Hz), 2.69–2.80 (m, 2H), 2.27–2.39 (m, 1H), 1.97–2.10 (m, 2H), 1.65–1.90 (m, 2H), 1.55–1.62 (m, 1H), 1.39–1.49 (m, 1H), 1.23–1.39 (m, 2H), 0.81 (s, 9H), −0.13 (s, 3H), −0.22 (s, 3H) ppm. Diast B; $^1$H NMR (CDCl$_3$, 500 MHz) δ 8.82 (s, 1H), 7.50 (dd, 1H, J=8.7, 2.7 Hz), 7.06–7.30 (m, 7H), 6.84 (d, 1H, J=8.7 Hz), 3.76 (d, 1H, J=13.9 Hz), 3.64 (d, 1H, J=14.2 Hz), 3.56 (s, 3H), 3.17 (dd, 1H, J=9.9, 2.8 Hz), 3.03 (dd, 1H, J=9.8, 5.9 Hz), 2.58 (dt, 1H, J=10.5, 3.7 Hz), 2.39 (t, 1H, J=10.9 Hz), 2.20–2.30 (m, 1H), 1.85–1.92 (m, 2H), 1.58–1.68 (m, 1H), 1.15–1.47 (m, 5H), 0.83 (s, 9H), −0.12 (s, 3H), −0.14 (s, 3H) ppm.

Step D:

1S-N-2-Methoxy-5-(1,2,3,4-tetrazol-1-yl))benzylamino-2S-phenyl-3R-hydroxymethylcyclohexane

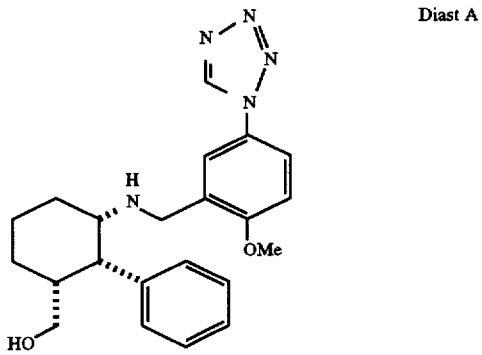

Diast A

The silyl ether minor diastereomer (21.0 mg, 0.042 mmol) was taken up in 5:86:9 48% aq. HF:CH$_3$CN:H$_2$O (2 mL) and stirred at room temp for 3 h. The reaction mixture was diluted with H$_2$O(10 mL), and 1N NaOH (to ph=8) and extracted with EtOAc (3×25 mL). The combined organic extracts were washed with brine, dried (Na$_2$SO$_4$), and concentrated in vacuo affording the alcohol (13.3 mg, 83%) as a colorless solid. $^1$H NMR (CDCl$_3$, 500 MHz) δ 8.72 (s, 1H), 7.46 (dd, 1H, J=8.7, 2.7 Hz), 7.16–7.32 (m, 7H), 6.84 (d, 1H, J=8.7 Hz), 3.79 (d, 1H, J=14.9 Hz), 3.62 (s, 3H), 3.58 (d, 1H, J=14.8 Hz), 3.51 (dd, 1H, J=10.7, 2.7 Hz), 3.32 (dd, 1H, J=11.0, 6.4 Hz), 2.77 (d, 1H, J=2.8 Hz), 2.71 (dd, 1H, J=12.1, 3.2 Hz), 2.35–2.46 (m, 1H), 2.02–2.21 (m, 2H), 1.80–1.90 (m, 1H), 1.59–1.65 (m, 1H), 1.43–1.52 (m, 1H), 1.26–1.40 (m, 2H) ppm.

Step E:

1R-(N-2-Methoxy-5-(1,2,3,4-tetrazol-1-yl))benzylamino-2S-phenyl-3R-hydroxymethylcyclohexane

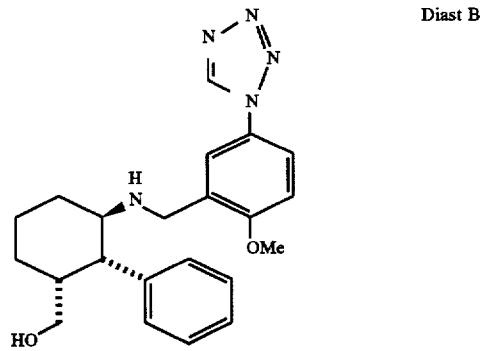

Diast B

The silyl ether major diastereomer (54.0 mg, 0.107 mmol) was taken up in 5:86:9 48% aq. HF:CH$_3$CN:H$_2$O (4 mL) and stirred at room temp for 3 h. The reaction mixture was diluted with H$_2$O(25 mL), and 1N NaOH (to ph=8) and extracted with EtOAc (3×50 mL). The combined organic extracts were washed with brine, dried (Na$_2$SO$_4$), and concentrated in vacuo affording the alcohol (32.0 mg, 78%) as a colorless solid. $^1$H NMR (CDCl$_3$, 500 MHz) δ 8.83 (s, 1H), 7.51 (dd, 1H, J=8.7, 2.7 Hz), 7.10–7.32 (m, 7H), 6.85 (d, 1H, J=8.8 Hz), 3.77 (d, 1H, J=14.2 Hz), 3.64 (d, 1H, J=14.2 Hz), 3.57 (s, 3H), 3.28 (dd, 1H, J=10.7, 3.4 Hz), 3.14 (dd, 1H, J=10.7, 6.2 Hz), 2.61 (dt, 1H, J=10.5, 3.6 Hz), 2.32 (t, 1H, J=11.0 Hz), 2.24–2.30 (m, 1H), 1.88–2.01 (m, 2H), 1.52–1.83 (m, 2H), 1.48–1.50 (m, 1H), 1.30–1.42 (m, 2H) ppm.

EXAMPLE 170

1R-(N-2-Methoxy-5-(tetrazol-1-yl))benzylamino-2S-phenyl-3S-methylamino-cyclohexane Step A:

1S-t-Butyldimethylsilyloxy-2S-phenyl-3R-t-butyldimethylsilyloxymethylcyclohexane

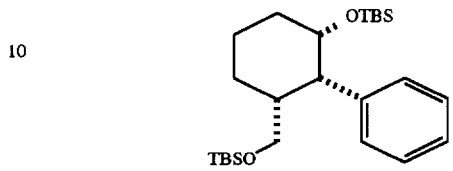

To a solution of the diol (450 mg, 2.18. mmol) in CH$_2$Cl$_2$ (16 mL) at 0° C. was added Et$_3$N (1.10 g, 10.9 mmol), and TBSOTf (1.72 g, 6.54 mmol). The mixture was stirred 2 h at 0° C., whereupon it was quenched by addition of H$_2$O and sat. aq. NaHCO$_3$, and extracted with EtOAc (3×50 mL). The combined organic extracts were washed with brine, dried (Na$_2$SO$_4$), and concentrated in vacuo. The residue was purifed by column chromatography (35 g silica gel 60, 34 mm diam. column, 0–5% EtOAc/hexanes) to afford the bis-silylated diether (801 mg, 85%) as a colorless oil used directly in the next step.

Step B:

1S-t-Butyldimethylsilyloxy-2S-phenyl-3R-hydroxycyclohexane

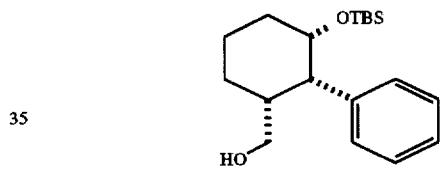

The diether (790 mg, 1.82 mmol) was taken up in THF (25 mL) and had added to it a solution containing pyridine (5.0 mL), THF (20 mL) and 95% HF-pyridine complex (2.5 g). After stirring for 3 h the reaction mixture was quenched by addition of H$_2$O (150 mL) and sat. NaHCO$_3$ (100 mL). The mixture was extracted with EtOAc (3×100 mL) and the combined organic extracts were washed with brine, dried (Na$_2$SO$_4$), and concentrated in vacuo to afford the monoprotected 1-silylether-3-alcohol (575 mg, 100%) as a colorless oil. $^1$H NMR (CDCl$_3$, 500 MHz) δ 7.20–7.43 (m, 5H), 4.10–4.16 (m, 1H), 3.60–3.69 (m, 1H), 3.45–3.53 (m, 1H), 3.11 (t, 1H, J=4.60 Hz), 2.30 (bs, 1H), 1.98–2.10 (m, 2H), 1.78–1.94 (m, 2H), 1.58–1.70 (m, 2H), 1.46–1.54 (m, 1H), 0.86 (s, 9H), 0.057 (s, 3H), 0.007 (s, 3H).

Step C:

1S-t-Butyl-dimethylsilyloxy-2S-phenylcyclohexane-3R-carboxaldehyde

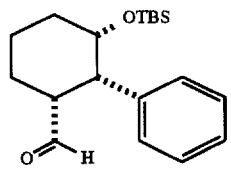

The alcohol (575 mg, 1.79 mmol) was treated under standard Swern oxidation reaction conditions to afford, after column chromatography (40 g silica gel 60, 34 mm column, 5–10% EtOAc/hexanes), the aldehyde (520 mg, 91%) as a colorless oil.

¹H NMR (CDCl₃, 500 MHz) δ 9.87 (s, 1H), 7.22–7.48 (m, 5H), 4.52 (t, 1H, J=1.9 Hz), 3.20 (d, 1H, J=4.1 Hz), 2.76 (dd, 1H, J=8.2, 4.5 Hz), 2.40 (dd, 1H, J=13.7, 2.3 Hz), 1.83–1.96 (m, 2H), 1.55–1.68 (m, 2H), 1.42–1.50 (m, 1H), 0.86 (s, 9H), 0.072 (s, 3H), 0.00 (s, 3H).

Step D:

1S-t-Butyl-dimethylsilyloxy-2S-phenylcyclohexane-3S-carboxaldehyde

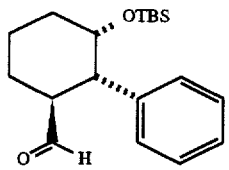

To a solution of the aldehyde (515 mg, 1.62 mmol) in MeOH (25.0 mL) at room temp was added 0.5M NaOMe (25.0 mL) and the mixture stirred for 2h. The reaction mixture was diluted with H₂O (500 mL) and concentrated to remove the MeOH. The aqueous was then extracted with EtOAc (3×150 mL), the combined organic extracts were washed with brine, dried (Na₂SO₄), and concentrated in vacuo to afford the epimerized aldehyde (440 mg, 86%) as a colorless glass.

¹H NMR (CDCl₃, 500 MHz) δ 9.47 (d, 1H, J=3.5 Hz), 7.18–7.40 (m, 5H), 3.99 (d, 1H, J=2.3 Hz), 3.20–3.35 (m, 1H), 2.88 (dd, 1H, J=12.2, 2.1 Hz), 1.83–2.00 (m, 3H), 1.58–1.70 (m, 2H), 1.35–1.47 (m, 1H), 0.84 (s, 9H), –0.188 (s, 3H), –0.616 (s, 3H).

Step E:

1S-t-Butyl-dimethylsilyloxy-2S-phenylcyclohexane-3S-carboxylic acid

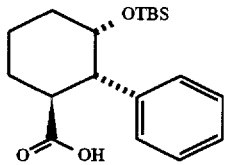

The aldehyde (440 mg, 1.38 mmol) was treated under oxidation conditions as per Example 168, Step B to afford, after column chromatography (35 g silica gel 60, 34 mm column, 2.5–8% MeOH/CH₂Cl₂), the carboxylic acid (460 mg, 100%) as a colorless solid. ¹H NMR (CDCl₃, 500 MHz) δ 7.15–7.30 (m, 5H), 3.94 (s, 1H), 3.72–3.80 (m, 1H), 3.26 (dt, 1H, J=11.9, 3.4 Hz), 2.89 (dd, 1H, J=11.9, 2.0 Hz), 2.08–2.26 (m, 1H), 1.80–1.02 (m, 2H), 1.50–1.62 (m, 2H), 0.80 (s, 9H), –0.226 (s, 3H), –0.660 (s, 3H).

Step F:

1S-t-Butyldimethylsilyloxy-2S-phenyl-3S-aminobenzoyl cyclohexane

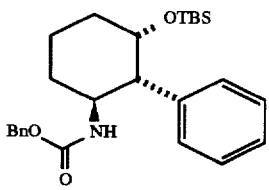

To a solution of the carboxylic acid (450 mg, 1.34 mmol) in CH₂Cl₂ (10 ml) at 0° C. was added oxalyl chloride (2.0 mL) followed by DMF (5 drops). The reaction mixture was stirred at room temp for 1 h, whereupon it was concentrated in vacuo from CH₂Cl₂ (3×). The residue was taken up in acetone (12 mL) and had added to it a solution of NaN₃ (437 mg, 6.72 mmol) in H₂O (12 mL). After stirring at room temp for 2.5 h, the reaction mixture was concentrated and the residue was diluted with H₂O (25 mL) and extracted with benzene (3×40 mL). The combined organic extracts were washed with brine, dried (Na₂SO₄), and concentrated in vacuo to ~5 mL. Benzene (70 mL) was added followed by excess benzyl alcohol (8 mL), diisopropylethyl amine (0.468 mL, 2.68 mmol), and catalytic DMAP (~8 mg). The reaction mixture was heated to 80° C. under argon for 18 h. The cooled reaction mixture was concentrated in vacuo and the residue was purified by column chromatography (35 g silica gel 60, 34 mm column, 10–25% EtOAc/hexanes), and afforded 523 mg (89%) of the CBZ protected amine as a colorless glass. ¹H NMR (CDCl₃, 500 MHz) δ 7.10–7.50 (m, 10H), 4.95–5.10 (m, 2H), 4.35–4.53 (m, 2H), 4.03 (s, 1H), 2.60 (d, 1H, J=11.0 Hz), 2.25–2.40 (m, 1H), 1.90–2.02 (m, 1H), 1.83 (d, 1H, J=12.6 Hz), 1.50–1.63 (m, 2H), 1.32–1.43 (m, 1H), 0.85 (s, 9H), –0.202 (s, 3H), –0.608 (s, 3H) ppm.

Step G:

1S-t-Butyldimethylsilyloxy-2S-phenyl-3S-N-methylaminobenzoyl cyclohexane

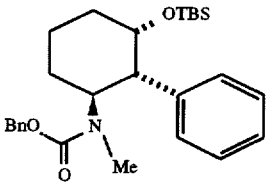

To a solution of the CBZ-amine (520 mg, 1.18 mmol) in DMF (15 mL) at 0° C. was added NaH (57 mg, 2.36 mmol). The ice bath was removed and after stirring 15 min MeI (669 mg, 4.72 mmol) was added and the resultant mixture was stiorred at room temp. for 16 h. An additional amount of NaH (20 mg) and MeI (100 μL) were added and the mixture stirred an additional 6 h to complete the reaction. The reaction mixture was quenched by addition of H₂O (200 mL). The organics were extracted with EtOAc (3×100 mL) and the combined organic extracts were washed with H₂O (3×100 mL), brine (1×100 ml), dried (Na₂SO₄), and concentrated in vacuo. The residue was purifed by column chromatography (30 g silica gel 60, 34 mm diam. column, 5–15% EtOAc/hexanes) to afford the methylamide (461 mg, 86%) as a colorless oil. The ¹H NMR showed a complex mixture of conformational rotamers. ¹H NMR (CDCl₃, 500 MHz) δ 7.05–7.50 (m, 10H), 5.33 (d, 0.5H, J=12.1 Hz), 5.08 (s, 1H), 5.03 (d, 1H, J=12.4 Hz), 4.85–4.93 (m, 0.5H), 4.04 (s, 0.5H), 3.98 (s, 0.5H), 2.65–2.78 (m, 1H), 2.54 (s, 3H), 1.90–2.04 (m, 1H), 1.75–1.89 (m, 2H), 1.46–1.66 (m, 3H), 0.84 (s, 4.5H), 0.81 (s, 4.5H), –0.23 (s, 3H), –0.62 (s, 1.5H), –0.70 (s, 1.5H) ppm.

Step H:

1S Hydroxy-2S-phenyl-3S-N-methylaminobenzoyl cyclohexane

187

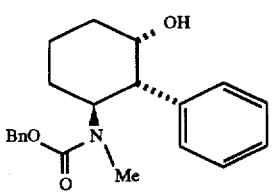

The silyl ether was deprotected under the standard aqueous HF conditions as per Example 158, Step I to afford, after column chromatography (13 g silica gel 60, 24 mm diam. column, 15–40% EtOAc/hexanes), the alcohol (280 mg, 82%) as a colorless glass. The $^1$H NMR showed a complex mixture of conformational rotamers. $^1$H NMR (CDCl$_3$, 500 MHz) δ 7.10–7.50 (m, 10H), 5.28 (d, 0.5H, J=12.2 Hz), 5.00–5.15 (m, 2H), 4.82–4.90 (m, 0.5H), 4.04 (s, 0.5H), 4.00 (s, 0.5H), 2.78–2.98 (m, 1H), 2.59 (s, 3H), 1.80–2.01 (m, 3H), 1.40–1.78 (m, 4H) ppm. FTIR 3452, 2934, 1692, 1452, 1405, 1315, 1144, 699 cm$^{-1}$.

Step I:

1-Oxo-2S-phenyl-3S-N-methylaminobenzoyl cyclohexane

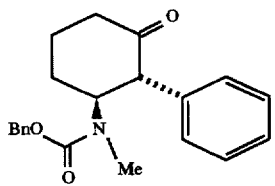

The alcohol (270 mg, 0.795 mmol) was oxidized using Dess-Martin periodinane reagent as in Example 169, Step A to afford the ketone (260 mg, 81%) which was used directly in the next step. The $^1$H NMR showed a complex mix of conformational rotamers. $^1$H NMR (CDCl$_3$, 500 MHz) δ 6.98–7.46 (m, 10H), 4.97–5.07 (m, 2H), 4.50 (bs, 1H), 3.90–4.02 (m, 0.67H), 3.72–3.80 (m, 0.33H), 2.76 (s, 1H), 2.67 (s, 2H), 2.52–2.60 (m, 1H), 2.38–2.50 (m, 1H), 2.03–2.26 (m, 3H), 1.72–1.83 (m, 1H) ppm. FTIR 3031, 2944, 1704, 1453, 1326, 1146, 699 cm$^{-1}$.

Step J:

1R,1S-Amino-2R-phenyl-3S-N-methylaminobenzoyl cyclohexane

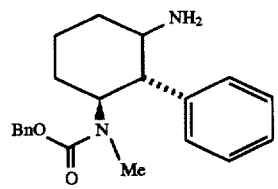

The ketone was reductively aminated as per Example 169, Step B to afford after column chromatography (9.5 g silica gel 60, 24 mm diam. column, 2.5–8% MeOH/CH$_2$Cl$_2$), the amines (48 mg, 75%) as a 1:3 mixture of diastereomers (cis:trans) as colorless glasses. Cis minor diast A: $^1$H NMR (CDCl$_3$, 500 MHz) δ 7.00–7.60 (m, 10H), 4.80–5.36 (m, 3H), 4.20–4.58 (m, 1H), 3.26–3.36 (m, 1H), 2.80–3.04 (m, 1H), 2.60–2.77 (m, 1H), 2.56 (s, 3H), 1.05–2.00 (m, 6H) ppm. Trans major diast B: $^1$H NMR (CDCl$_3$, 500 MHz) δ 7.00–7.43 (m, 10H), 4.85–5.03 (m, 2H), 4.50–4.60 (m, 0.5H), 4.28–4.40 (m, 0.5H), 2.85–3.01 (m, 1.5H), 2.71 (s, 1H), 2.66 (s, 2H), 2.38–2.46 (m, 0.5H), 1.50–2.04 (m, 6H), 1.20–1.38 (m, 2H) ppm. FTIR 3363, 2931, 2858, 1694, 1454, 1313, 1151 cm$^{-1}$.

188

Step K:

1 R-(N-2-methoxy-5-(tetrazol-1-yl))benzylamino-2S-phenyl-3S-methylamino-cyclohexane

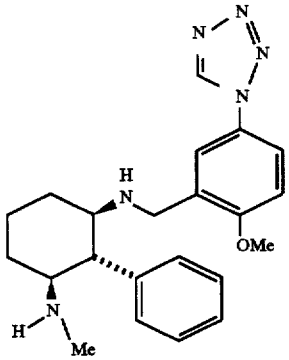

The 1,2-trans amine (24.0 mg, 0.071 mmol) was reductively aminated as per Example 169, Step C with the substituted benzaldehyde to afford, after chromatography, the benzylamine (31 mg, 83%) as a complex mixture of rotational conformers. The adduct was deprotected by treatment of the CBZ amine (31.0 mg, 0.059 mmol) in CH$_3$CN (2.0 mL) at 0° C. with TMSI (30.0 mg, 0.152 mmol) for 30 min. The reaction mixture was quenched by addition of 1M HCl (8 mL), diluted with H$_2$O (10 mL) and extracted with Et$_2$O (2×15 mL). The aqueous layer was then made basic (ph>13) by addition of 1N NaOH. It was then extracted with EtOAc (3×20 mL). The combined organic extracts were washed with brine, dried (Na$_2$SO$_4$) and concentrated in vacuo to afford the methylamine (14.4 mg, 62%) as a colorless glass. $^1$H NMR (CDCl$_3$, 500 MHz) δ 8.83 (s, 1H), 7.49 (dd, 1H, J=8.7, 2.7 Hz), 7.15–7.32 (m, 6H), 6.84 (d, 1H, J=8.7 Hz), 3.75 (d, 1H, J=14.0 Hz), 3.62 (d, 1H, J=14.0 Hz), 3.56 (s, 3H), 2.59 (dt, 1H, J=10.5, 3.9 Hz), 2.53 (dt, 1H, J=10.8, 3.9 Hz), 2.39 (t, 1H, J=10.3 Hz), 2.40–2.47 (m, 1H), 2.19 (s, 3H), 2.10–2.18 (m, 1H), 1.75–1.92 (m, 2H), 1.35–1.45 (m, 1H), 1.20–1.32 (m, 3H) ppm.

EXAMPLE 171

1S-N-2-Methoxy-5-(1,2,3,4-tetrazol-1-yl)) benzylamino-2S-phenyl-3S-methylamino-cyclohexane

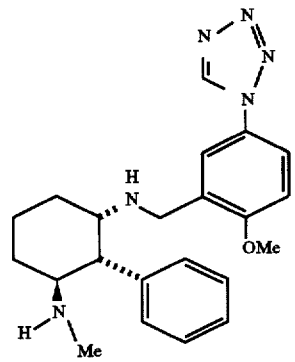

Step A:

The 1,2-cis amine (10.0 mg, 0.071 mmol) was reductively aminated as per Example 169, Step C with the substituted benzaldehyde to afford, after chromatography, the benzylamine (10.1 mg, 64%) as a complex mixture of rotational conformers.

Step B:

The adduct was deprotected by treatment of the CBZ amine (7.20 mg, 0.014 mmol) as described above in Example 170, Step K to afford the methylamine (2.4 mg, 44%) as a colorless glass.

¹H NMR (CDCl₃, 500 MHz) δ 8.82 (s, 1H), 7.47 (dd, 1H, J=8.7, 2.7 Hz), 7.10–7.40 (m, 6H), 6.84 (d, 1H, J=8.7 Hz), 3.73 (d, 1H, J=14.7 Hz), 3.55–3.62 (m, 1H), 3.59 (s, 3H), 3.50 (d, 1H, J=14.5 Hz), 2.86–3.10 (m, 2H), 2.45 (s, 3H), 1.95–2.10 (m, 2H), 1.80–1.90 (m, 2H), 1.50–1.73 (m, 3H), 1.10–1.40 (m, 2H) ppm.

EXAMPLE 172

1(S)-α-methyl(3,5-bis(trifluoromethyl)phenyl)methoxy-2(S)-phenyl-3(S)-L-prolineamide-1-yl-methylcyclohexane Step A:

1(S)-α-Methyl(3,5-bis(trifluoromethyl)phenyl)methoxy-2(S)-phenyl-3(S)-bromomethyl cyclohexane

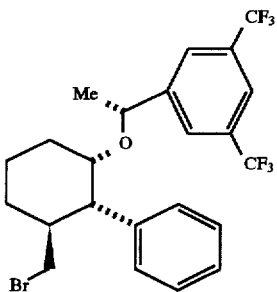

To a solution of the alcohol (1(S)-α-methyl(3,5-bis(trifluoromethyl)phenyl)methoxy-2(R)phenyl-3(S)-hydroxymethyl cyclohexane, 50 mg, 0.11 mmol from Example 163) in CH₂Cl₂ was added PPh₃ (57 mg, 0.17 mmol) and CBr₄ (87 mg, 0.33 mmol). After stirring at room temperature for 24 hrs. the solution was diluted with pentane, filtered through celite, washed with pentane (3×) and concentrated in vacuo. The yellow residue was purifed by column chromatography (15 g silica gel 60, 24 mm diam. column, 10–15% EtOAc/hexanes) to afford the bromide (41 mg, 74%). ¹H NMR (CDCl₃, 500 MHz) δ 7.22–7.71 (m, 8H), 4.42 (q, 1H, J=6.4 Hz), 3.44 (s, 1H), 3.34 (d, 1H, J=10.0 Hz), 3.12 (dd, 1H, J=4.8, 10.5 Hz), 2.55 (s, 2H), 2.13 (d, 1H, J=13.0), 2.05 (d, 1H, J=12 Hz), 1.84–1.89 (m, 1H), 1.42–1.43 (m, 2H), 1.39 (d, 4H, J=6.5 Hz).

Step B:

1(S)-α-Methyl(3,5-bis(trifluoromethyl)phenyl)methoxy-2(S)-phenyl-3(S)-L-proline amide-1-yl-methylcyclohexane

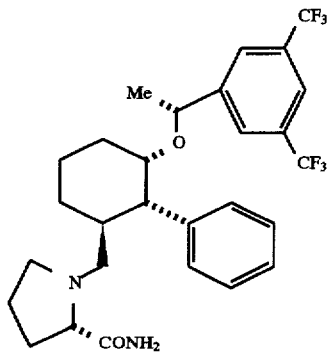

To a solution of the bromide (40 mg, 0.079 mmol) from example 1 in CH₃CN was added diisopropylethylamine (42 mg, 0.32 mmol) and L-prolineamide (28 mg, 0.24 mmol). The reaction was heated to 90° C. and stirred for 7 days. The reaction was then cooled, diluted with water, extracted with EtOAc, washed (brine), dried (Na₂SO₄), filtered and concentrated to yield a light yellow residue. The yellow residue was purified by column chromatography (10 g silica gel 60, 24 mm diam. column, 5–8% MeOH/CH₂Cl₂) to afford the proline amide (28 mg, 66%). ¹H NMR (CDCl₃, 500 MHz) δ 7.61 (s, 1H), 7.19–7.22 (m, 7H), 6.43 (bs, 1H), 5.07 (bs, 1H), 4.40 (q, 1H, J=6.3 Hz), 3.38 (s, 1H), 3.16–3.22 (m, 1H), 2.81 (dd, 1H, J=4.6, 10.1 Hz), 2.49 (dd, 1H, J=4.5, 12.5 Hz), 2.36–2.46 (m, 1H), 2.31 (dd, 1H, J=2.1, 11.7 Hz), 2.17–2.24 (m, 1H), 1.97–2.14 (m, 4H), 1.58–1.85 (m, 5H) 1.38 (d, 3H, J=6.4 Hz) 1.33 (m, 1H) 1.13 (m, 1H). ESI mass spec/CI, C₂₈H₃₂N₂O₂F₆ calcd for 542.2, found 543.3 (15%), 496.2 (100%).

EXAMPLE 173

1(S)-N-(2-Methoxy-5-(1-tetrazolyl))-benzylamino-2(S)-phenyl-3(S)-carboxymethyl cyclohexane

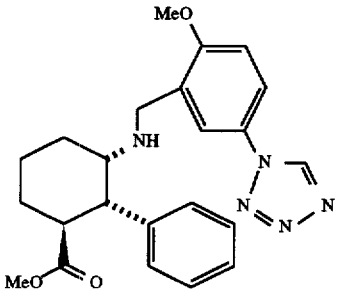

Step A:

To a solution of the N-CBZ acid (14 mg, 0.026 mmol) in Et₂O (1 mL) at room temperature was added diazomethane until a yellow color persisted. The reaction was stirred 30 minutes and then purged with nitrogen. The reaction was concentrated in vacuo to afford the N-CBZ methyl ester which was used directly in the next step.

Step B:

The N-CBZ 3-methyl ester was dissolved in MeOH(1 mL) and treated with 10% Pd/C (14 mg), ammonium formate (33 mg, 0.52 mmol) and stirred at room temperature for 12 hours. The reaction mixture was filtered through celite, washed with MeOH and EtOAc (3×25 mL), and concentrated in vacuo to yield a white solid. The white solid was purified by preparatory thin layer chromatography (Uniplate Silica Gel GF, 20×20 cm, 500 microns) to afford the methyl ester (3.0 mg, 30% yield). ¹H NMR (CDCl₃, 500 MHz) δ 8.77 (s, 1H), 7.46 (d, 1H, J=8.3 Hz), 7.18–7.28 (m, 6H), 6.83 (d, 1H, J=8.9 Hz), 3.73 (d, 1H J=14.4 Hz), 3.58 (s, 3H), 3.52–3.55 (m, 1H), 3.48 (s, 3H), 3.36–3.40 (m, 1H) 3.15 (dd, 1H, J=10.0 Hz), 2.86 (s, 1H), 2.20–2.18 (m, 2H), 1.80–1.85 (m, 1H), 1.42–1.68 (m, 4H).

EXAMPLE 174

1(S)-N-(2-Methoxy-5-(trifluoromethyl-1,2,3,4-tetrazol-1-yl))benzyl-2(S)-phenyl-3(S)-(pyrrolidin-1-yl-methyl)cyclohexane Step A:

1(S)-N-benzyloxycarbonyl-N-(2-methoxy-5-(trifluoromethyl-1,2,3,4-tetrazol-1-yl))-2(S)-phenyl-3(S)-bromomethyl cyclohexane

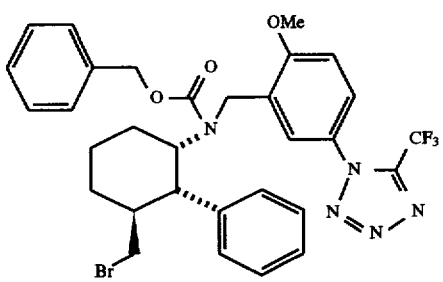

To a solution of the N-CBZ alcohol (100 mg, 0.17 mmol) in CH₂Cl₂ was added PPh₃ (68 mg, 0.26 mmol) and CBr₄ (86 mg, 0.26 mmol). After stirring at room temperature for 2 hrs, the solution was diluted with pentane, filtered through celite, washed with pentane (3×) and concentrated in vacuo. The residue was purified by column chromatography (5 g silica gel 60, 18 mm diam. column, 10–25% EtOAc/hexanes) to afford the bromide (78 mg, 70%). ¹H NMR as a mixture of rotamers (CDCl₃, 500 MHz) δ 7.19–7.44 (m, 10H), 6.92–7.18 (m, 10H), 4.98–5.10 (m, 2H), 4.74–4.70 (m, 0.5H), 4.38–4.45 (m, 0.5H), 4.46–4.58 (m, 2H), 4.08–4.14 (m, 1H), 3.74–3.96 (m, 4H), 3.16–3.56 (m, 3H), 2.61 (s, 0.5H), 2.45 (s, 0.5H), 2.10–2.19 (m, 4H) ppm.

Step B:

1(S)-N-(2-methoxy-5-(trifluoromethyl-1,2,3,4-tetrazol-1-yl))benzyl-2(S)-phenyl-3(S)-pyrrolidin-1-yl-methyl cyclohexane

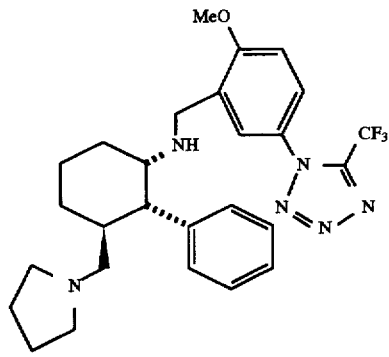

To a solution of the N-CBZ bromide (50 mg, 0.076 mmol) in CH₃CN (2 mL) was added pyrrolidine (27 mg, 0.38 mmol). The reaction was heated to 90° C. and stirred for 3 days. The reaction was then cooled and concentrated in vacuo to yield brown oil which was used directly in the next step. The N-CBZ 3-methyl pyrrolidine was dissolved in MeOH (2 mL) and treated with 10% Pd/C (21 mg), and shaken at 50 PSI under hydrogen for 3 hours. The reaction mixture was filtered through celite, washed with MeOH (3×25 mL), and concentrated in vacuo to yield a white solid. The white solid was purified by column chromatography (4 g silica gel 60, 5–8% MeOH/CH₂Cl₂) to afford the pyrrolidine (21 mg, 44%).

¹H NMR (CDCl₃, 500 MHz) δ 7.12–7.21 (m, 5H), 7.0–7.05 (m, 1H), 6.82 (d, 1H, J=8.7 Hz), 6.76 (d, 1H, J=2.1 Hz), 3.77 (d, 1H, J=15.6 Hz), 3.68 (s, 3H), 3.56 (d, 1H, J=15.8 Hz), 2.66 (d, 1H, J=2.8 Hz), 2.48–2.57 (m, 3H), 2.31–2.42 (m, 3H), 2.21–2.26 (m, 1H), 2.13–2.16 (m, 1H), 2.02 (d, 1H, J=13.1 Hz) 1.66–1.88 (m, 4H), 1.54–1.60 (m, 1H), 1.39–1.47 (m, 1H) 1.18–1.35 (m, 4H) ppm. ESI mass spec/CI, C₂₇H₃₃N₆O₁F₃ calcd for 514.2, found 515.2 (100%), 238.1 (55%).

EXAMPLE 175

1(S)-N-(2-Methoxy-5-(trifluoromethyl-1,2,3,4-tetrazol-1-yl))benzyl-2(S)-phenyl-3(S)-methoxymethylcyclohexane Step A:

1(S)-Azido-2(S)-phenyl-3(S)-hydroxymethyl cyclohexane

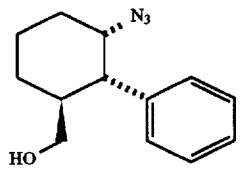

The silyl ether (1(S)-azido-2(S)-phenyl-3(S)-t-butyldimethylsilyloxymethyl cyclohexane) (351 mg, 1.02 mmol) had added to it a solution mixture (10 mL) containing 48% HF/CH₃CN/H₂O 5:86:9 at room temperature. After stirring for 3 hours the reaction mixture was quenched by addition of H₂O (20 mL) and sat. NaHCO₃ solution (20 mL). The mixture was extracted with EtOAc (3×100 mL) and the combined organic extracts were washed with brine, dried (Na₂SO₄), and concentrated in vacuo to afford the 3-hydroxymethyl adduct (210 mg, 89%) as a colorless oil. ¹H NMR (CDCl₃, 500 MHz) δ 7.20–7.34 (m, 5H), 3.38 (dd, 1H, J=2.7, 11 Hz), 3.21 (dd, 1H, J=6.2, 10.8 Hz) 2.78 (s, 1H), 2.63 (dd, 1H, J=2.3, 11.7 Hz) 2.16–2.25 (m, 1H), 2.01 (d, 1H, J=10.8 Hz), 1.97 (d, 1H, J=12.6Hz), 1.66–1.82 (m, 3H), 1.25–1.36 (m, 1H) ppm.

Step B:

1(S)-Azido-2(S)-phenyl-3(S)-methoxymethyl cyclohexane

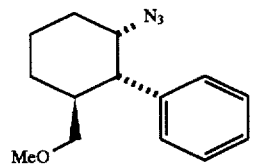

To a vigorously stirred solution of the alcohol (1(S)-azido-2(S)-phenyl-3(S)-hydroxymethyl cyclohexane) (50 mg, 0.22 mmol) and Fluoroboric acid (20 mg, 0.22 mmol) in CH₂Cl₂ (2 mL) at 0° C. was added TMSCHN₂ (25 mg, 0.22 mmol). The stirring was continued at 0° C. and three additional portions of TMSCHN₂ (12 mg, 0.5 mmol; 6 mg, 0.25 mmol; 6 mg, 0.25 mmol) were added at 20 minute intervals. The reaction was stirred for an additional 1 hour and diluted with water. The mixture was extracted with CH₂Cl₂ (3×100 mL) and the combined organic extracts were washed with brine, dried (Na₂SO₄), and concentrated in vacuo. The residue was purified by column chromatography (5 g silica gel 60, 18 mm diam. column, 5–25% EtOAc/hexanes) to afford the 3-methoxymethyl adduct (50 mg, 93%) as a colorless oil. ¹H NMR (CDCl₃, 500 MHz) δ 7.23–7.38 (m, 5H), 3.87 (s, 1H), 3.13–3.21 (m, 4H), 2.94–2.97 (m, 1H), 2.67 (dd, 1H, J=2.3, 11.7 Hz) 2.27–2.33 (m, 1H), 2.03–2.17 (m, 2H), 1.69–1.79 (m, 3H), 1.30–1.40 (m, 1H) ppm.

Step C:

1(S)-N-(2-Methoxy-5-(trifluoromethyl-1,2,3,4-tetrazol-1-yl))benzyl-2(S)-phenyl-3(S)-methoxymethylcyclohexane

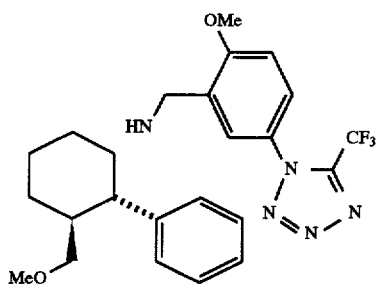

The azide (1(S)-azido-2(S)-phenyl-3(S)-methoxymethylcyclohexane) (35 mg, 0.14 mmol) was dissolved in MeOH(2 mL) and treated with 10% Pd/C (35 mg), and shaken at 50 PSI under hydrogen for 5 hours. The reaction mixture was filtered thru celite, washed with MeOH (3×25 mL), and concentrated in vacuo to yield a yellow oil (31 mg, 99%) which was used directly below. A solution of the amine (31 mg, 0.14 mmol), HOAc (18 mg, 0.30 mmol), 3A mol sieves (125 mg), and the aldehyde [2-methoxy 5-(5-trifluoromethyl-1,2,3,4-tetrzol-1-yl)benzaldehyde] (7.0 mg, 0.16 mmol) in MeOH (2 mL) was stirred at room temp under N for 4 h. NaCNBH$_3$ (26 mg, 0.42 mmol) was added and the mixture stirred at room temp for 16 h, whereupon it was filtered through Celite with MeOH washes, and the filtrate concentrated in vacuo. The residue was partitioned between H$_2$O/sat. aq. NaHCO$_3$ (50 mL) and EtOAc (50 mL), followed by extraction with EtOAc (3×50 mL). The combined organic extracts were washed with brine, dried (Na$_2$SO$_4$), and concentrated in vacuo. The residue was purified by column chromatography (2 g silica gel 60, 18 mm diam. column, 1–5% MeOH/CH$_2$Cl$_2$) to afford the benzylamine (19 mg, 29%) as a colorless oil. $^1$H NMR (CDCl$_3$, 500 MHz) δ 7.16–7.27 (m, 5H), 7.03–7.06 (m, 1H), 6.81–6.83 (m, 2H), 3.76 (d, 1H, J=15.4 Hz), 3.67 (s, 3H), 3.56 (d, 1H, J=15.8 Hz), 3.22 (d, 1H, J=9.4 Hz), 3.15 (s, 3H), 2.96 (t, 1H, J=8.25 Hz), 2.64–2.69 (m, 2H), 2.40–2.42 (m, 1H), 2.00–2.09 (m, 2H), 1.74–1.79 (m, 2H), 1.55 (d, 1H, J=13.1 Hz), 1.43 (t, 1H, J=13.4 Hz), 1.25–1.27 (m, 1H) ppm. ESI mass spec/Cl. C$_{24}$H$_{28}$N$_5$O$_2$F$_3$ calcd for 475.2, found 476.1 (100%), 220.1 (65%).

EXAMPLE 176

1(R)-N-(2-Methoxy-5-(1-tetrazolyl))-benzylamino-2 (R)-phenyl-3(R)-hydroxymethyl cyclohexane

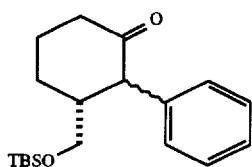

Step A:
2(R,S)-Phenyl-3(R)-t-butyldimethylsilyloxymethyl cyclohexanone

To a solution of the alcohol (1(S)-hydroxy-2(S)-phenyl-3(R)-t-butyldimethylsilyloxy methyl cyclohexane) (5.1 g, 16 mmol) in CH$_2$Cl$_2$ (250 mL) at room temperature was added pyridine (11.4 g, 144 mmol) and Dess Martin reagent (16.2 g, 38.2 mmol). The reaction was stirred for 5 hours and then diluted with water (100 mL) and sat. aq. NaHCO$_3$ (100 mL) solution. The mixture was extracted with EtOAc (3×200 mL) and the combined organic extracts were washed with brine, dried (Na$_2$SO$_4$), and concentrated in vacuo. The residue was purified by column chromatography (150 g silica gel 60, 100 mm diam. column, 10–15% EtOAc/hexanes) to afford a mixture of diastereomers (4.33 g, 87%) as a colorless oil. $^1$H NMR (CDCl$_3$, 500 MHz) δ 7.26–7.37 (m, 4H), 7.10 (d, 1H, J=7.8 Hz), 3.84 (d, 1H, J=5.9 Hz), 3.62 (d, 1H, J=11.7 Hz), 3.47–3.49 (m, 2H), 3.37 (dd, 1H, J=2.3, 7.6 Hz), 3.18 (dd, 1H, J=4.7, 5.3 Hz), 2.53–2.66 (m, 2H), 2.45–2.49 (m, 1H), 2.34–2.40 (m, 1H), 1.80–2.30 (m, 14H), 0.89 (s, 9H), 0.88 (s, 9H), −0.01 (s, 3H), −0.04 (s, 3H), −0.044 (s, 3H), −0.08 (s, 3H).

Step B:

1(R)-Benzylamino-2(R)-phenyl-3(R)-t-butyldimethylsilyloxymethyl cyclohexane

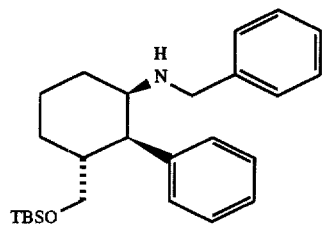

To a solution of the ketone (2(R,S)-phenyl-3(R)-t-butyldimethylsilyloxymethyl cyclohexanone) (1.0 g, 3.14 mmol) in benzene (25 mL) was added benzylamine (841 mg, 7.85 mmol). The reaction was heated to 80° C. and H$_2$O was azeotroped off for a period of 3 hours. The reaction was allowed to cool to room temperature and transferred via syringe to a 50 mL oven dried round bottom flask. The reaction was concentrated in vacuo. To the yellow residue dissolved in 13 mLs of THF and cooled to 0° C. was added lithium triethylborohydride (18.8 mL 1M THF solution, 18.8 mmol). The reaction was stirred at 0° C. for 12 hours and then quenched with the slow addition of water (10 mL) at 0° C. The mixture was extracted with EtOAc (3×100 mL) and the combined organic extracts were washed with brine, dried (Na$_2$SO$_4$), and concentrated in vacuo. The residue was purified by column chromatography (100 g silica gel 60, 40 mm diam. column, 15–25% EtOAc/hexanes) to afford the benzylamine (375 mg, 29%) as a yellow oil. $^1$H NMR (CDCl$_3$, 500 MHz) δ 7.18–7.41 (m, 9H), 6.99 (d, 1H, J=7.5 Hz), 3.85 (s, 2H), 3.70 (d, 1H, J=13.7 Hz), 3.49 (dd, 1H, J=2.1, 7.7 Hz) 3.37 (d, 1H, J=13.8 Hz), 3.27 (dd, 1H, J=2.5, 6.7 Hz), 2.84 (d, 1H, J=3.0 Hz), 2.72 (dd, 1H, J=3.1, 8.7 Hz), 2.34–2.42 (m, 1H), 2.02–2.10 (m, 1H), 1.80–1.91 (m, 1H), 1.54–1.61 (m, 1H), 1.44–1.52 (m, 1H), 1.30–1.40 (m, 1H), 0.86 (s, 9H), −0.08 (s, 3H), −0.15 (s, 3H).

Step C:

1(R)-Amino-2(R)-phenyl-3(R)-t-butyldimethylsilyloxymethylcyclohexane

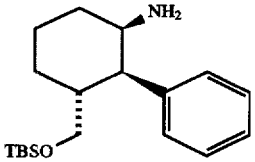

To a solution of the cyclohexylbenzylamine (100 mg, 0.24 mmol) from step B in 1:1 EtOAc/MeOH (5 mL) was added 10% Pd/C (100 mg), ammonium formate (303 mg, 4.8 mmol) and acetic acid (209 mg, 3.5 mmol). The mixture was stirred at room temperature for 5 days, filtered thru celite, washed with methanol and concentrated in vacuo. The residue was purified by column chromatography (20 g silica gel 60, 20 mm diam. column, 2.5–8% MeOH/CH$_2$Cl$_2$) to afford a yellow oil (25 mg, 33%). $^1$H NMR (CDCl$_3$, 500 MHz) δ 7.19–7.34 (m, 5H), 3.44 (dd, 1H, J=2.5, 7.3 Hz), 3.25 (dd, 1H, J=3.7, 6.2 Hz), 3.10 (bs, 1H), 2.70 (dd, 1H, J=2.8, 9.1 Hz), 2.22–2.30 (m, 3H), 1.99–2.03 (m, 1H), 1.92 (d, 1H, J=11.7 Hz), 1.61–1.78 (m, 3H), 1.29–1.38 (m, 1H), 0.83 (s, 9H), −0.11 (s, 3H), −0.18 (s, 3H) ppm.

Step D:

1(R)-N-(2-Methoxy-5-(1-tetrazolyl))-benzylamino-2(R)-phenyl-3(R)-hydroxymethyl cyclohexane

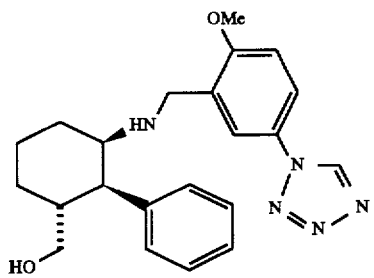

A solution of the amine (25 mg, 0.08 mmol) from example 11, HOAc (10 mg, 0.17 mmol), 3A mol sieves (100 mg), and the aldehyde [2 methoxy-5-(1-tetrazolyl)benzaldehyde] (17 mg, 0.09 mmol) in MeOH (2 mL) was stirred at room temp under N$_2$ for 7 h. NaCNBH$_3$ (15 mg, 0.24 mmol) was added and the mixture stirred at room temp for 16 h, whereupon it was filtered thru Celite with MeOH washes, and the filtrate concentrated in vacuo. The residue was partitioned between H$_2$O/sat. aq. NaHCO$_3$ (50 mL) and EtOAc (50 mL), followed by extraction with EtOAc (3×50 mL). The combined organic extracts were washed with brine, dried (NaSO$_4$), and concentrated in vacuo to yield a light yellow oil which was used directly below. The oil was dissolved in solution (2 mL) containing 48% HF/CH$_3$CN/H$_2$O, 5:86:9 at room temperature. After stirring for 12 hrs, the reaction mixture was quenched by addition of H$_2$O (10 mL) and sat. NaHCO$_3$ solution (10 mL). The mixture was extracted with EtOAc (3×100 mL) and the combined organic extracts were washed with brine, dried (Na$_2$SO$_4$), and concentrated in vacuo to afford a yellow residue. The residue was purified by preparative thin layer chromatography (Uniplate Silica Gel GF, 20×20 cm, 500 microns) to afford the title compound (5.0 mg, 16% yield). ESI mass spec/CI, C$_{22}$H$_{27}$N$_5$O$_2$ calcd for 393.5, found 394.2 (40%), 206.1 (95%), 186.1 (100%).

EXAMPLE 177

1(S)-N-(2-Methoxy-5-(trifluoromethyl-1,2,3,4-tetrazol-1-yl))benzyl-2(S)-phenyl-3(S)-imidazole cyclohexane Step A:

1(S)-Azido-2(S)-phenyl-3(S)-imidazole cyclohexane

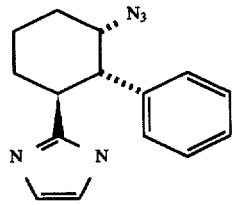

To a solution of oxalyl chloride (152 mg, 1.2 mmol) in CH$_2$Cl$_2$ (3 mL) at −70° C. was added DMSO (188 mg, 2.4 mmol) and the mixture stirred 15 min. Then a solution of the alcohol (1(S)-azido-2(S)-phenyl-3(S)-hydroxymethyl cyclohexane) (110 mg, 0.48 mmol) in CH$_2$Cl$_2$ (1 mL) was added at −70° C. and the resultant mixture stirred 1 h, whereupon Et$_3$N (486 mg, 4.8 mmol) was added and the mixture allowed to warn to room temp and stirred 45 minutes. The reaction mixture was diluted with H$_2$O (50 mL) and extracted with CH$_2$Cl$_2$ (3×40 mL). The combined organic extracts were washed with brine, dried (Na$_2$SO$_4$), and concentrated in vacuo to yield a yellow oil which was used directly below. The yellow oil was dissolved in MeOH (2 mL), cooled to 0° C. and treated with glyoxal trimer powder. The mixture was stirred for 15 minutes and treated with a solution of ammonia (345 uL 2M soln in MeOH, 0.69 mmol), allowed to warm to room temperature and stirred for 12 hours. The reaction mixture was diluted with water (100 mL), extracted with EtOAc (3×50 mL) and the combined organic extracts were washed with brine, dried (Na$_2$SO$_4$), and concentrated in vacuo. The residue was purified by column chromatography (3 g silica gel 60, 10 mm diam. column, 2–8% MeOH/ CH$_2$Cl$_2$) to afford the imidazole (57 mg, 50%) as a colorless oil. $^1$H NMR (CDCl$_3$, 500 MHz) δ 7.22–7.25 (m, 2H), 7.11–7.16 (m, 2H), 7.05–7.09 (m, 1H), 6.66–6.68 (m, 2H), 4.94 (s, 1H), 3.93 (d,1H, J=2.7 Hz), 3.55 (ddd,1H, J=3.6, 8.3, 15.5 Hz), 3.27–3.31 (m, 1H), 2.07–2.12 (m, 1H), 1.67–1.98 (m, 5H) ppm.

Step B:

1(S)-Amino-2(S)-phenyl-3(S)-imidazole cyclohexane

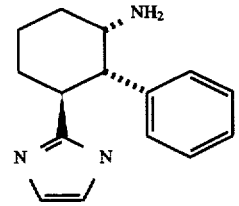

The azide, (1(S)-azido-2(S)-phenyl-3(S)-imidazole cyclohexane) (57 mg, 0.21 mmol) was dissolved in MeOH (2 mL) and treated with 10% Pd/C (50 mg), and shaken at 50 PSI under hydrogen for 4.5 hours. The reaction mixture was filtered through celite, washed with MeOH (3×25 mL), and concentrated in vacuo. The residue was purified by column chromatography (6 g silica gel 60, 20 mm diam. column, 5–8% MeOH/CH$_2$Cl$_2$) to afford the amine (25 mg, 50%) as a colorless oil.

$^1$H NMR (CDCl$_3$, 500 MHz) δ 7.22–7.28 (m, 4H), 7.12–7.20 (m, 1H), 6.70 (s, 2H), 4.58 (bs, 2H), 3.83 (ddd, 1H, J=3.6, 12.1, 15.3 Hz), 3.30–3.37 (m, 2H), 2.18 (d, 1H, J=9.8 Hz), 1.66–1.96 (m, 5H) ppm.

Step C:

1(S)-N-(2-Methoxy-5-(trifluoromethyl-tetrazol-1-yl)) benzyl-2(S)-phenyl-3(S)-imidazole cyclohexane

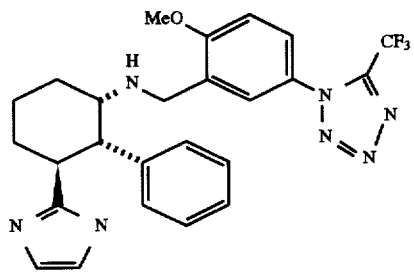

A solution of the amine (25 mg, 0.08 mmol) from Step B, HOAc (10 mg, 0.17 mmol), 3A mol sieves (100 mg), and the aldehyde [2-methoxy 5-(5-trifluoromethyl-1,2,3,4-tetrazol-1-yl) benzaldehyde] (17 mg, 0.09 mmol) in MeOH (2 mL) was stirred at room temp under N₂ for 7 h. NaCNBH₃ (15 mg, 0.24 mmol) was added and the mixture stirred at room temp for 16 h, whereupon it was filtered through Celite with MeOH washes, and the filtrate concentrated in vacuo. The residue was partitioned between H₂O/sat. aq. NaHCO₃ (50 mL) and EtOAc (50 mL), followed by extraction with EtOAc (3×50 mL). The combined organic extracts were washed with brine, dried (Na₂SO₄), and concentrated in vacuo. The residue was purified by column chromatography (2 g silica gel 60, 20 mm diam. column, 5% MeOH/CH₂Cl₂) to afford the title compound (31 mg, 63%) as a colorless oil. ¹H NMR (CDCl₃, 500 MHz) δ 7.22 (dd, 1H, J=2.5, 9.7 Hz), 7.07–7.13 (m, 4H), 6.97–7.09 (m, 1H), 6.87 (d, 1H, J=6.4 Hz), 6.83 (d, 1H, J=8.7 Hz), 6.74 (s, 2H) 3.83 (dt, 1H, J=3.5, 12.4 Hz), 3.74 (d, 1H, J=15.4 Hz), 3.63 (s, 3H), 3.54 (d, 1H, J=15.3 Hz), 3.35 (dd, 1H, J=2.7, 12.1 Hz), 2.90 (d, 1H, J=2.5 Hz), 2.19 (d, 1H, J=11.4 Hz), 2.09 (d, 1H, J=13.5 Hz), 1.92–2.05 (m, 1H), 1.71–1.81 (m, 1H), 1.57–1.64 (m, 2H) ppm. ESI mass spec/CI. C₂₅H₂₆N₇O₁F₃ calcd for 497.2, found 499.1 (20%), 498.1 (30%), 225.1 (100%).

EXAMPLE 177

1(S)-N-(2-Methoxy-5-(1-tetrazolyl))-benzylamino-2(S)-phenyl-3(S)-ethyl cyclohexane

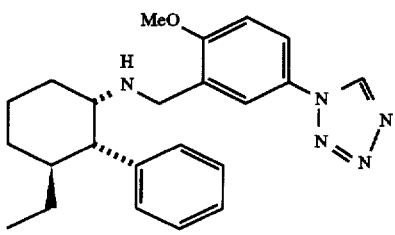

To a solution of methyltriphenylphosphoniumbromide (170 mg, 0.48 mmol) in THF (2 mL) at −70° C. was added nBuLi (440 uL 2.5M soln. in hexane, 1.1 mmol). The reaction mixture was allowed to warm to room temperature over a 1 hour period. The reaction mixture was then recooled to −70° C. and treated with a solution of the aldehyde (100 mg, 0.19 mmol, from Example 168, Step B) in THF (1 mL). The ice bath was removed and the reaction mixture was allowed to warm to room temperature and stirred for 2.5 hours. The reaction was quenched with a saturated solution of NH₄Cl, diluted with water, and extracted with EtOAc (3×50 mL). The combined organic extracts were washed with brine, dried (Na₂SO₄), and concentrated in vacuo to yield a brown oil which was used directly as described in the next paragraph. The oil was dissolved in MeOH (5 mL) and treated with 10% Pd/C (100 mg) and shaken at 50 PSI under hydrogen for 6 hours. The reaction mixture was filtered through celite, washed with MeOH (3×25 mL) and concentrated in vacuo. The residue was purified by column chromatography (2 g silica gel 60, 10 mm diam. column, 2.5–5% MeOH/CH₂Cl₂) to afford the title compound (10 mg, 13%) as an oil. ¹H NMR (CDCl₃, 500 MHz) δ 8.71 (s, 1H), 7.44–7.46 (m, 1H), 7.25–7.28 (m, 2H), 7.16–7.18 (m, 3H), 7.12 (s, 1H), 6.82 (d, 1H, J=8.7 Hz), 3.76 (d, 1H, J=14.9 Hz), 3.62 (s, 3H), 3.56 (d, 1H, J=15.1 Hz), 2.72 (s, 1H), 2.55 (dd, 1H, J=2.7, 11.6 Hz), 2.05–2.06 (m, 4H), 1.78–1.81 (m, 1H), 1.57 (d, 1H, J=13.3 Hz), 1.28–1.47 (m, 3H), 1.03–1.06 (m, 1H), 0.85–0.91 (m, 1H), 0.79 (t, 3H, J=7.3 Hz) ppm. ESI mass spec/CI. C₂₃H₂₉N₅O₁ calc 391.2, found 392.1 (100%), 364.3 (30%)

EXAMPLE 178

1(S)-N-(2-Methoxy-5-(1-tetrazolyl))-benzylamino-2(S)-phenylcyclohexane

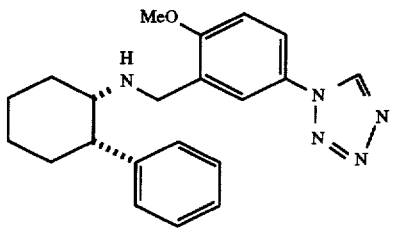

To a solution of the azide (100 mg, 0.50 mmol) from Example 180, Step A in THF (4 mL) at room temperature was added 4A mol sieves (200 mg). The reaction flask was flushed with N₂ and then treated with Me₃P (600 uL 1M solution in THF, 0.6 mmol), and stirred for 1 hour. The aldehyde [2 methoxy-5-(1-tetrazolyl)benzaldehyde] was then added and the reaction flask was flushed with N₂ once more and stirred at room temperature for 1 hour. The reaction mixture was concentrated to a volume of 2 mL and charged with MeOH (2 mL), NaCNBH₄ (94 mg, 1.5 mmole), HOAc (60 mg, 1.0 mmol) and stirred at room temperature for 1 hour. The reaction was filtered thru Celite with MeOH washes, and the filtrate concentrated in vacuo. The residue was partitioned between H₂O/sat. aq. NaHCO₃ (50 mL) and EtOAc (50 mL), followed by extraction with EtOAc (3×50 mL). The combined organic extracts were washed with brine, dried (Na₂SO₄), and concentrated in vacuo. The residue was purified by column chromatography (20 g silica gel 60, 25 mm diam. column, 40–80% EtOAc/hexanes) to afford the title compound (97 mg, 54%) as a colorless oil. 1H NMR (CDCl₃, 500 MHz) δ 8.74 (s, 1H), 7.45–7.48 (m, 1H), 7.23–7.26 (m, 2H), 7.14–7.18 (m, 4H), 6.82 (d, 1H, J=8.7 Hz), 3.74 (d, 1H, J=14.9 Hz), 3.59 (s, 3H), 3.57 (d, 1H, J=15.1 Hz), 2.89 (s, 1H), 2.84 (d, 1H, J=12.8 Hz), 2.04–2.10 (m, 2H), 1.91 (d, 1H, J=13.1 Hz), 1.64–1.74 (m, 2H), 1.39–1.52 (m, 3H), ppm.

EXAMPLE 179

1(S)-N-(2-Methoxy-5-(trifluoromethyl-tetrazol-1-yl))benzyl-2(S)-phenyl-3(S)-pyrrole cyclohexane Step A:

1(S)-Azido-2(S)-phenyl-3(S)-bromomethylcyclohexane

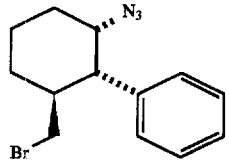

To a solution of the alcohol (1(S)-azido-2(S)-phenyl-3(S)-hydroxymethyl cyclohexane, 140 mg, 0.60 mmol) in CH₂Cl₂ was added PPh₃ (236 mg, 0.90 mmol) and CBr₄ (300 mg, 0.90 mmol). After stirring at room temperature for 2 hrs. the solution was diluted with pentane, filtered through celite, washed with pentane (3×) and concentrated in vacuo. The yellow residue was purified by column chromatography (10 g silica gel 60, 20 mm diam. column, 5–10% EtOAc/hexanes) to afford the bromide (203 mg, 99%). ¹H NMR (CDCl₃, 500 MHz) δ 7.27–7.40 (m, 5H), 3.85 (s, 1H), 3.34 (dd, 1H, J=2.3, 10.1 Hz), 3.14 (dd, 1H, J=5.7, 10.0 Hz), 2.73

(dd, 1H, J=2.5, 11.5 Hz), 2.34–2.39 (m, 1H), 2.11–2.12 (m, 1H), 1.99–2.09 (m, 1H), 1.70–1.85 (m, 2H), 1.44–1.55 (m, 2H) ppm.

Step B:

1(S)-Azido-2(S)-phenyl-3(S)-pyrrol-1-yl methylcyclohexane

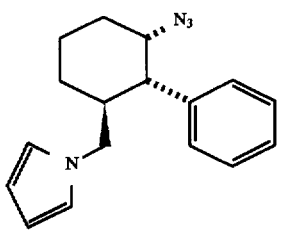

To a solution of the bromide (1(S)-azido-2(S)-phenyl-3(S)-bromomethyl cyclohexane, 203 mg, 0.69 mmol) in $CH_2Cl_2$ (2 mL) at 0° C. was added pyrrole (74 mg, 1.10 mmol), ammonium bromide (354 mg, 1.10 mmol) and 1 mL of a 50% aq. NaOH solution. The reaction mixture was then heated to a gentle reflux. After 20 hours the reaction was cooled, diluted with $H_2O$ (10 mL) and extracted with $CH_2Cl_2$ (3×50 mL). The combined organic extracts were washed with 1N HCl (1×50 mL), brine, dried ($Na_2SO_4$), and concentrated in vacuo. The residue was purified by column chromatography (20 g silica gel 60, 20 mm diam. column, 10–15% acetone/hexanes) to afford the pyrrole (60 mg, 31%).

$^1$H NMR (CDCl$_3$, 500 MHz) δ 7.33–7.46 (m, 5H), 6.51–6.52 (m, 2H), 6.14–6.16 (m, 2H), 3.85 (s, 1H), 3.82 (dd, 1H, J=3.2, 13.8 Hz), 3.48 (dd, 1H, J=8.0, 14.2 Hz), 2.49–2.59 (m, 2H), 2.09–2.11 (m, 1H), 1.66–1.81 (m, 3H), 1.15–1.17 (m, 1H) ppm.

Step C:

1(S)-Amino-2(S)-phenyl-3(S)-pyrrol-1-yl methyl cyclohexane

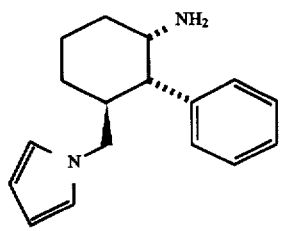

The azide (30 mg, 0.11 mmol) from Step B was dissolved in MeOH (2 mL) and treated with 10% Pd/C (15 mg), and shaken at 30 PSI under hydrogen for 30 minutes. The reaction mixture was filtered thru Celite, washed with MeOH (3×25 mL), and concentrated in vacuo. The residue was purified by column chromatography (2 g silica gel 60, 10 mm diam. column, 2.5–5% MeOH/CH$_2$Cl$_2$) to afford the amino pyrrole (10 mg, 36%). $^1$H NMR (CDCl$_3$, 500 MHz) δ 7.21–7.42 (m, 5H), 6.50 (d, 2H, J=1.8 Hz), 6.11 (d, 2H, J=1.9 Hz), 3.86 (d, 1H, J=13.9 Hz), 3.46–3.50 (m, 1H), 3.17 (s, 1H), 2.56 (bs, 2H), 1.55–1.85 (m, 8H) ppm.

Step D:

1(S)-N-(2-Methoxy-5-(trifluoromethyl-tetrazol-1-yl))benzyl-2(S)-phenyl-3(S)-pyrrol-1-yl methyl cyclohexane

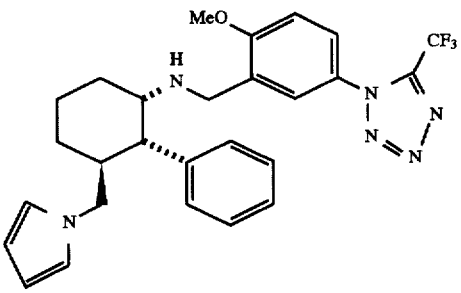

A solution of the amine (10 mg, 0.04 mmol) from Step C, HOAc (5 mg, 0.08 mmol), 3A mol sieves (50 mg), and the aldehyde [2-methoxy 5-(5-trifluoromethyl-1,2,3,4-tetrzol-1-yl)benzaldehyde] (12 mg, 0.04 mmol) in MeOH (2 mL) was stirred at room temperature under N$_2$ for 7 h. NaCNBH$_3$ (8 mg, 0.12 mmol) was added and the mixture stirred at room temp for 16 h, whereupon it was filtered thru Celite with MeOH washes, and the filtrate concentrated in vacuo. The residue was partitioned between H$_2$O/sat. aq. NaHCO$_3$ (50 mL) and EtOAc (50 mL), followed by extraction with EtOAc (3×50 mL). The combined organic extracts were washed with brine, dried (Na$_2$SO$_4$), and concentrated in vacuo. The residue was purified by column chromatography (2 g silica gel 60, 20 mm diam. column, 2.5–5% MeOH/CH$_2$Cl$_2$) to afford the title compound (11.5mg, 58%) as a colorless oil. $^1$H NMR (CDCl$_3$, 500 MHz) δ 7.21–7.27 (m, 5H), 7.09–7.12 (m, 1H), 6.82 (d, 2H, J=7.1 Hz), 6.47 (s, 2H), 6.09 (s, 2H), 3.85 (d, 1H, J=13.7 Hz), 3.75 (d, 1H, J=15.5 Hz), 3.66 (s, 3H), 3.53 (d, 1H, J=15.6 Hz), 3.42–3.46 (m, 1H), 2.70 (s, 1H), 2.57 (s, 2H), 1.99 (d, 1H, J=13.9 Hz), 1.71–1.77 (m, 1H), 1.11–1.53 (m, 5H) ppm. ESI mass spec/CI, C$_{27}$H$_{29}$N$_6$O$_1$F$_3$ calcd for 510.2, found 511.3 (100%).

EXAMPLE 180

1(S)-N-(2-Methoxy-5-(trifluoromethyl-1,2,3,4-tetrazol-1-yl))benzyl-2(S)-phenyl

Step A:

1(S)-Azido-2(S)-phenyl cyclohexane

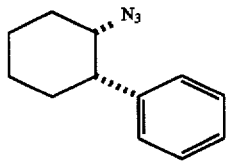

To a solution of the commercially available trans-1-hydroxy-2-phenylcyclohexanol (1.10 g, 6.24 mmol), PPh$_3$ (4.58 g, 17.5 mmol), imidazole (1.06 g, 15.6 mmol), and Zn(N$_3$)$_2$pyr$_2$ (4.31 g, 14.0 mmol), in PhMe (80 mL) at room temp under N$_2$ was added slowly via syringe DEAD (3.05 g, 17.5 mmol). The reaction mixture was stirred 1 h forming an orange solution and gummy residue. The mixture was filtered through Celite with EtOAc (300 mL) and Et$_2$O (300 mL). The organic filtrate was washed with 1M HCl, sat. aq. NaHCO$_3$, brine, and dried (Na$_2$SO$_4$) and concentrated in vacuo. The residue was purified by column chromatography (55 g silica gel 60, 45 mm diam. column, 0–5% EtOAc/hexanes) to afford the azido adduct (570 mg, 45%) as a colorless glass. $^1$H NMR (CDCl$_3$, 500 MHz) δ $^1$H NMR (CDCl$_3$, 500 MHz) δ 7.26–7.37 (m, 5H), 3.97 (d, 1H, J=2.5 Hz), 2.80 (dt, 1H, J=3.0, 12.6 Hz), 2.09–2.13 (m, 1H), 2.02

(ddd, 1H, J=3.7, 13.1, 25.9 Hz), 1.92 (dd, 1H, J=1.4 Hz), 1.71–1.80 (m, 2H), 1.61–1.66 (m, 2H), 1.39–1.47 (m, 1H) ppm.

Step B:

1(S)-N-(2-methoxy-5-(trifluoromethyl-1,2,3,4-tetrazol-1-yl))benzyl-2(S)-phenylcyclohexane

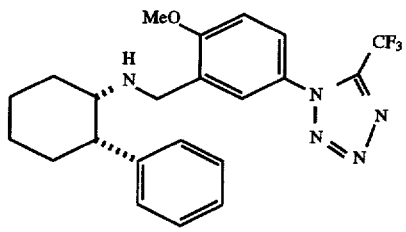

To a solution of the azide (150 mg, 0.75 mmol) from Step A in THF (8 mL) at room temperature was added 4A mol sieves (300 mg). The reaction flask was flushed with $N_2$ and then treated with $Me_3P$ (890 uL 1M solution in THF, 0.89 mmol), and stirred for 1 hour. The aldehyde [2-methoxy 5-(5-trifluoromethyl-1,2,3,4-tetrzol-1-yl)benzaldehyde] was then added and the reaction flask was flushed with $N_2$ once more and stirred at room temperature for 1 hour. The reaction mixture was concentrated to a volume of 2 mL and charged with MeOH (8 mL). $NaCNBH_4$ (140 mg, 2.24 mmole), HOAc (89 mg, 1.49 mmol) and stirred at room temperature for 1 hour. The reaction was filtered thru Celite with MeOH washes, and the filtrate concentrated in vacuo. The residue was partitioned between $H_2O$/sat. aq. $NaHCO_3$ (50 mL) and EtOAc (50 mL), followed by extraction with EtOAc (3×50 mL). The combined organic extracts were washed with brine, dried ($Na_2SO_4$), and concentrated in vacuo. The residue was purified by column chromatography (30 g silica gel 60, 25 mm diam. column, 10–40% EtOAc/hexanes) to afford the title compound (231 mg, 72%) as a colorless oil. $^1H$ NMR ($CDCl_3$, 500 MHz) δ 7.28 (d, 1H, J=1.4 Hz), 7.22 (dd, 1H, J=2.5, 7.6 Hz), 7.13–7.19 (m, 3H), 7.04–7.07 (m, 1H), 6.92 (d, 2H, J=2.3 Hz), 6.81 (d, 1H, J=8.7 Hz), 3.78 (d, 1H, J=15.3 Hz), 3.64 (s, 3H), 3.54 (d, 1H, J=15.3 Hz), 2.82–2.85 (m, 2H), 2.01–2.10 (m, 2H), 1.91 (d, 1H, J=13.1 Hz), 1.64–1.73 (m, 2H), 1.38–1.52 (m, 3H), ppm.

EXAMPLE 181

1S-[(N-Benzyloxycarbonyl)-(N-2-methoxy-5-(5-trifluoromethyl-1-tetrazol-1-yl))]benzylamino-2S-phenyl-3S-(2-hydroxyethyl)-cyclohexane Step A:

1S-[(N-Benzyloxycarbonyl)-(N-2-methoxy-5-(5-trifluoromethyl-1,2,3,4-tetrazol-1-yl))]benzylamino-2S-phenyl-3S -hydroxymethylcyclohexane

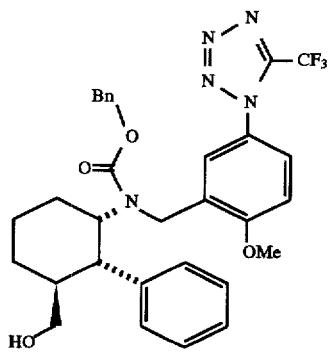

A solution of the amine (340 mg, 0.591 mmol), from Step A Example 167, diisopropylethylamine (129 mg, 0.998 mmol) and benzoyl chloride (126 mg, 0.740 mmol) in $CH_2Cl_2$ (12 mL) was stirred at room temp for 19 h, whereupon it was quenched by addition of $H_2O$ (35 mL), and extracted with EtOAc (3×30 mL). The combined organic extracts were washed with brine, dried ($Na_2SO_4$), and concentrated in vacuo to afford a mixture of the N-CBZ-3-t-butyldimethylsiloxymethyl and N-CBZ-3-hydroxymethyl adducts as an oil which were used directly in the next step. ESIMS/CI m/z calcd. for $C_{37}H_{46}N_5O_4F_3Si_1$ 709.33; found 710.2 (97%), 576.2 (100%), 391.2 (20%), 279.1 (16%), 258.0 (26%).

Step B:

The mixture was taken up in THF (6 mL) and had added to it a solution containing pyridine (2.0 mL), THF (10 mL) and 95% HF-pyridine complex (1.0 g). After stirring for 3 h the reaction mixture was quenched by addition of $H_2O$ (150 mL) and sat. $NaHCO_3$ (100 mL). The mixture was extracted with EtOAc (3×75 mL) and the combined organic extracts were washed with brine, dried ($Na_2SO_4$), and concentrated in vacuo. The residue was purifed by column chromatography (30 g silica gel 60, 24 mm diam. column, 40–80% EtOAc/hexanes) to afford the benzylamine (336 mg, 96%) as a colorless glass. The $^1H$ NMR showed a very complex mixture of conformational rotamers. ESIMS/CI m/z calcd. for $C_{31}H_{32}N_5O_4F_3$ 595.24; found 596.1 (100%), 568.1 (18%), 279.1 (20%), 258.1 (25%).

Step C:

1S-[(N-Benzyloxycarbonyl)-(N-2-methoxy-5-(5-trifluoro-methyl-1,2,3,4-tetrazol-1-yl))]benzylamino-2S-phenyl-3S-(2-hydroxyethyl)-cyclohexane

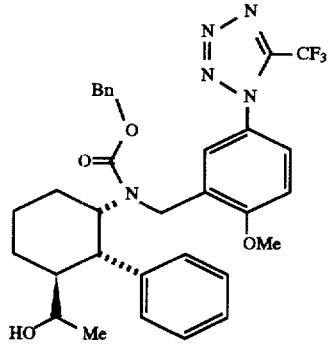

To a solution of oxalyl chloride (364 mg, 2.87 mmol) in $CH_2Cl_2$ (12 mL) at –70° C. was added DMSO (450 mg, 5.76 mmol) and the mixture stirred 20 min. Then a solution of the alcohol (570 mg, 0.960 mmol), in $CH_2Cl_2$ (4 mL) was added at –70° C. and the resultant mixture stirred 1 h, whereupon Et₃N (1.59 mL, 11.5 mmol) was added and the mixture allowed to warm to room temp and stirred 1 h. The reaction mixture was diluted with H₂O (200 mL) and extracted with CH₂Cl₂ (3×150 mL). The combined organic extracts were washed with brine, dried (Na₂SO₄), and concentrated in vacuo to afford the aldehyde (~585 mg) which was used directly as described in the next paragraph.

The aldehyde (300 mg, 0.505 mmol) was taken up in THF (10 mL) and cooled to 0° C., whereupon MeMgBr (3M in Et₂O, 0.35 mL, 1.04 mmol) was added and the mixture stirred 3 h. The reaction was quenched by addition of sat. aqueous NH₄Cl (25 mL), diluted with H₂O (75 mL) and extracted with CH₂Cl₂ (3×50 mL). The combined organic extracts were washed with brine, dried (Na₂SO₄), and concentrated in vacuo. The residue was purifed by column chromatography (35 g silica gel 60, 30 mm diam. column, 25–50% EtOAc/hexanes) to afford the alcohols (286 mg, 93%) as a mixture of rotamers and diastereomers.

Step D:

To a solution of the 1-CBZ protected amino-3-(2-hydroxyethyl) diastereomers from Step C above (140 mg, 0.230 mmol) in MeOH (12 mL) at room temp was added ammonium formate (289 mg, 4.60 mmol) and 10% Pd/C (150 mg) and the mixture stirred vigorously for 1 h. The reaction mixture was filtered through Celite with MeOH washes and then concentrated in vacuo. The residue was purified by radial chromatography (2 mm plate thickness, 4 mls/min flow, 1–5% MeOH/CH₂Cl₂) to afford the separated methyl diastereomers. A (38 mg) and B (55 mg), in an overall yield of 85% as colorless oils. Diastereomer A: ¹H NMR (CDCl₃, 500 MHz) δ 7.00–7.39 (m, 7H), 6.83 (d, 1H, J=8.7 Hz), 3.68–3.92 (m, 2H), 3.67 (s, 3H), 3.57 (d, 1H, J=15.3 Hz), 2.91 (d, 1H, J=12.1 Hz), 2.73 (s, 1H), 2.09–2.20 (m, 1H), 2.01 (d, 1H, J=14.2 Hz), 1.70–1.92 (m, 2H), 1.28–1.50 (m, 2H), 1.13 (d, 3H, J=6.5 Hz) ppm. Diastereomer B: ¹H NMR (CDCl₃, 500 Mhz) d 7.00–7.27 (m, 7H), 6.82 (d, 1H, J=8.9 Hz), 3.74–3.85 (m, 2H), 3.69 (s, 3H), 3.57 (d, 1H, J=15.8 Hz), 2.67 (d, 1H, J=3.0 Hz), 2.45–2.56 (m, 2H), 1.97–2.09 (m, 2H), 1.70–1.83 (m, 1H), 1.59–1.68 (m, 1H), 1.39–1.47 (m, 1H), 1.15–1.34 (m, 1H), 0.91 (d, 3H, J=6.4 Hz) ppm.

EXAMPLE 182

1S-1'R-(3,5-Bistrifluoromethyl)phenyl)ethoxy)-2S-phenyl-3S-hydroxymethyl cyclohexane

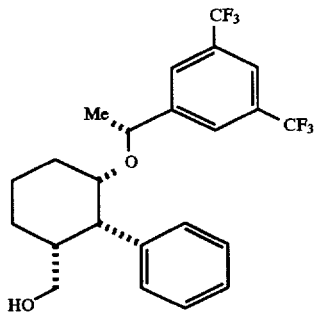

A solution of the aldehyde (44.0 mg, 0.034 mmol) from Step B Example 159, and CH₂Cl₂ (2.0 mL) at −70° C. under Argon was treated with DIBAL-H (75 µL, 0.075 mmol). After 1 h the reaction mixture was quenched by addition of MeOH (0.5 mL), followed by sat. aq. Rochelle salts (5 mL), diluted with H₂O (10 mL), and CH₂Cl₂ (20 mL), and stirred vigorously for 1 h at room temp. The mixture was extracted with CH₂Cl₂ (3×25 mL) and the combined organic extracts were washed with brine, dried (Na₂SO₄) and concentrated in vacuo to afford the alcohol (15.0 mg, 100%) as a colorless glass. ¹H NMR (CDCl₃, 500 MHz) δ 7.63 (s, 1H), 7.29 (s, 2H), 7.15–7.28 (m, 5H), 4.42 (q, 1H, J=6.4 Hz), 3.40–3.49 (m, 2H), 3.28 (dd, 1H, J=10.9, 5.9 Hz), 2.51 (dd, 1H, J=11.9, 2.3 Hz), 2.40–2.47 (m, 1H), 2.10–2.16 (m, 1H), 2.00–2.07 (m, 1H), 1.80–1.92 (m, 1H), 1.65–1.72 (m, 1H), 1.40 (d, 3H, J=6.4 Hz), 1.25–1.46 (m, 3H) ppm.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

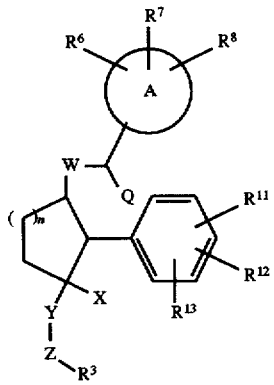

or a pharmaceutically acceptable salt thereof, wherein:

the circle A:

is selected from the group consisting of:
(A) phenyl,
(B) benzofuranyl,
(C) benzothiophenyl,
(D) benzothiazoyl,
(E) indolyl,
(F) imidazolyl,
(G) oxadiazolyl,
(H) pyridyl,
(I) pyrimidyl,
(J) quinolinyl, (K) thiazolyl,
(L) thienyl,
(M) thiophenyl, and
(N) dihydrobenzofuranyl;

Q is selected from the group consisting of:
(1) hydrogen, and
(2) $C_{1-6}$ alkyl;

W is selected from the group consisting of:
(1) —O—,
(2) —NH—,
(3) —N($C_{1-6}$ alkyl)—,
(4) —NH—CO—, and
(3) —N($C_{1-6}$ alkyl)—CO—,
wherein if W is —NHCO— or —N($C_{1-6}$ alkyl)—CO—, then optionally Q and the carbon atom to which it is attached are absent;

X is selected from the group consisting of:
(1) hydrogen, and
(2) $C_{1-6}$ alkyl;

Y is selected from the group consisting of:
(1) a single bond,
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo, wherein halo is fluoro, chloro, bromo or iodo,
(h) —$NR^9R^{10}$, wherein $R^9$ and $R^{10}$ are independently selected from:
(I) hydrogen,
(II) $C_{1-6}$ alkyl,
(III) phenyl,
(IV) ($C_{1-6}$ alkyl)-phenyl,
(V) ($C_{1-6}$ alkyl)-hydroxy, and
(VI) ($C_{1-6}$ alkyl)-($C_{1-4}$ alkoxy),
(i) —$NR^9$—$COR^{10}$, wherein $R^9$ and $R^{10}$ are as defined above,
(j) —$NR^9$—$CO_2R^{10}$, wherein $R^9$ and $R^{10}$ are as defined above,
(k) —CO—$NR^9R^{10}$, wherein $R^9$ and $R^{10}$ are as defined above,
(l) —$COR^9$, wherein $R^9$ is as defined above, and
(m) —$CO_2R^9$, wherein $R^9$ is as defined above;

Z is selected from the group consisting of:
(1) —$NR^{15}$—, wherein $R^{15}$ is selected from the group consisting of:
(a) hydrogen;
(b) $C_{1-6}$ alkyl, unsubstituted or substituted with one or more of the substituents selected from:
(i) hydroxy,
(ii) oxo,
(iii) $C_{1-6}$ alkoxy,
(iv) phenyl-$C_{1-3}$ alkoxy,
(v) phenyl,
(vi) —CN,
(vii) halo,
(viii) —$NR^9R^{10}$,
(ix) —$NR^9$—$COR^{10}$,
(x) —$NR^9$—$CO_2R^{10}$,
(xi) —CO—$NR^9R^{10}$,
(xii) —$COR^9$,
(xiii) —$CO_2R^9$;

(c) phenyl, unsubstituted or substituted with one or more of the substituents selected from:
(i) hydroxy,
(ii) $C_{1-6}$ alkoxy,
(iii) $C_{1-6}$ alkyl,
(iv) $C_{2-5}$ alkenyl,
(v) halo,
(vi) —CN,
(vii) —$NO_2$,
(viii) —$CF_3$,
(ix) —$(CH_2)_m$—$NR^9R^{10}$, wherein m is 0, 1 or 2,
(x) —$NR^9$—$COR^{10}$,
(xi) —$NR^9$—$CO_2R^{10}$,
(xii) —CO—$NR^9R^{10}$,
(xiii) —$CO_2$—$NR^9R^{10}$,
(xiv) —$COR^9$,
(xv) —$CO_2R^9$,
(2) —CO—$NR^{15}$—,
(3) —$NR^{15}$—CO—,
(4) —$SO_2$—$NR^{15}$—,
(5) —$NR^{15}$—$SO_2$—,
(6) —$SO_2$—,
(7) —CO—O—$R^{15}$,
(8) —O—CO—$R^{15}$,
(9) —CO—$R^{15}$,
(10) —$CH_2$—$OR^{15}$;

or if $R^3$ is other than hydrogen, then Z is optionally absent;

or if X is other than hydrogen, then $R^{15}$ and X may be joined together to form a 3- to 7-membered heterocyclic ring containing a group selected from: —$NR^3$—, —CO—$NR^3$—, —$NR^3$—CO—, —$SO_2$—$NR^3$—, —$NR^3$—$SO_2$—, —$SO_2$—, —CO—O—, —O—CO—, —O—, and —CO—, and wherein the heterocyclic ring is optionally substituted with one or more of the substitutents selected from:
(i) hydroxy,
(ii) oxo,
(iii) $C_{1-6}$ alkoxy,
(iv) phenyl-$C_{1-3}$ alkoxy,
(v) phenyl,
(vi) —CN,
(vii) halo,
(viii) —$NR^9R^{10}$,
(ix) —$NR^9$—$COR^{10}$,
(x) —$NR^9$—$CO_2R^{10}$,
(xi) —CO—$NR^9R^{10}$,
(xii) —$COR^9$,
(xiii) —$CO_2R^9$;

$R^3$ is selected from the group consisting of:
(1) hydrogen,
(2) —$R^5$, and
(3) $C_{1-6}$ alkyl substituted with —$R^5$, and if Z is —CO—O—$R^{15}$, —O—CO-$R^{15}$, —CO—$R^{15}$, or —$CH_2$—$OR^{15}$, then $R^3$ is absent;

$R^5$ is selected from the group consisting of:
(1) hydroxy,
(2) $C_{1-6}$ alkoxy,
(3) phenyl-$C_{1-3}$ alkoxy,
(4) phenyl,
(5) —CN,
(6) halo,
(7) —$NR^9R^{10}$,
(8) —$NR^9$—$COR^{10}$,
(9) —$NR^9$—$CO_2R^{10}$,
(10) —CO—$NR^9R^{10}$,

(11) —COR$^9$,
(12) —CO$_2$R$^9$;
(13) heterocycle, wherein the heterocycle is selected from the group consisting of:
(A) benzimidazolyl,
(B) benzofuranyl,
(C) benzothiophenyl,
(D) benzoxazolyl,
(E) furanyl,
(F) imidazolyl,
(G) indolyl,
(H) isooxazolyl,
(I) isothiazolyl,
(J) oxadiazolyl,
(K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl,
(U) thienyl,
(V) triazolyl,
(W) azetidinyl,
(X) 1,4-dioxanyl,
(Y) hexahydroazepinyl,
(Z) piperazinyl,
(AA) piperidinyl,
(AB) pyrrolidinyl,
(AC) morpholinyl,
(AD) thiomorpholinyl,
(AE) dihydrobenzimidazolyl,
(AF) dihydrobenzofuranyl,
(AG) dihydrobenzothiophenyl,
(AH) dihydrobenzoxazolyl,
(AI) dihydrofuranyl
(AJ) dihydroimidazolyl,
(AK) dihydroindolyl,
(AL) dihydroisooxazolyl,
(AM) dihydroisothiazolyl,
(AN) dihydrooxadiazolyl,
(AO) dihydrooxazolyl,
(AP) dihydropyrazinyl,
(AQ) dihydropyrazolyl,
(AR) dihydropyridinyl,
(AS) dihydropyrimidinyl,
(AT) dihydropyrrolyl,
(AU) dihydroquinolinyl,
(AV) dihydrotetrazolyl,
(AW) dihydrothiadiazolyl,
(AX) dihydrothiazolyl,
(AY) dihydrothienyl,
(AZ) dihydrotriazolyl,
(BA) dihydroazetidinyl,
(BB) dihydro-1,4-dioxanyl,
(BC) tetrahydrofuranyl, and
(BD) tetrahydrothienyl,
and wherein the heterocycle is unsubstituted or substituted with one or more substituent(s) selected from:
(i) C$_{1-6}$ alkyl, unsubstituted or substituted with halo, —CF$_3$, —OCH$_3$, or phenyl,
(ii) C$_{1-6}$ alkoxy,
(iii) oxo,
(iv) hydroxy,
(v) thioxo,
(vi) —SR$^9$,
(vii) halo,
(viii) cyano,
(ix) phenyl,
(x) trifluoromethyl,
(xi) —(CH$_2$)$_m$—NR$^9$R$^{10}$,
(xii) —NR$^9$COR$^{10}$,
(xiii) —CONR$^9$R$^{10}$,
(xiv) —CO$_2$R$^9$, and
(xv) —(CH$_2$)$_m$—OR$^9$,
(14) —CO-heterocycle, wherein heterocycle is as defined above;

R$^6$, R$^7$ and R$^8$ are independently selected from the group consisting of:
(1) hydrogen,
(2) C$_{1-6}$ alkoxy,
(3) halo,
(4) C$_{1-6}$ alkyl, unsubstituted or substituted with one or more of the substituents selected from:
(a) hydroxy,
(b) oxo,
(c) C$_{1-6}$ alkoxy,
(d) phenyl-C$_{1-3}$ alkoxy,
(e) phenyl,
(f) —CN,
(g) halo,
(h) —NR$^9$R$^{10}$,
(i) —NR$^9$—COR$^{10}$,
(j) —NR$^9$—CO$_2$R$^{10}$,
(k) —CO—NR$^9$R$^{10}$,
(l) —COR$^9$,
(m) —CO$_2$R$^9$,
(n) heterocycle, wherein heterocycle is as defined above,
(5) hydroxy,
(6) —CN,
(7) —CF$_3$,
(8) —NO$_2$,
(9) —SR$^{14}$, wherein R$^{14}$ is hydrogen or C$_{1-6}$alkyl,
(10) —SOR$^{14}$,
(11) —SO$_2$R$^{14}$,
(12) —NR$^9$—COR$^{10}$,
(13) —CO—NR$^9$—COR$^{10}$,
(14) —NR$^9$R$^{10}$,
(15) —NR$^9$—CO$_2$R$^{10}$,
(16) —COR$^9$,
(17) —CO$_2$R$^9$,
(18) heterocycle, wherein heterocycle is as defined above,
(19) —(C$_{1-6}$alkyl)-heterocycle, wherein heterocycle is as defined above,
(20) —N(heterocycle)—SO$_2$R$^{14}$, wherein heterocycle is as defined above;

R$^{11}$, R$^{12}$ and R$^{13}$ are independently selected from:
(1) hydrogen,
(2) C$_{1-6}$ alkyl, unsubstituted or substituted with one or more of the substituents selected from:
(a) hydroxy,
(b) oxo,
(c) C$_{1-6}$ alkoxy,
(d) phenyl-C$_{1-3}$ alkoxy,
(e) phenyl,
(f) —CN,
(g) halo,
(h) —NR$^9$R$^{10}$, (i) —NR$^9$—COR$^{10}$,
(j) —NR$^9$—CO$_2$R$^{10}$,
(k) —CO—NR$^9$R$^{10}$,
(l) —COR$^9$,
(m) —CO$_2$R$^9$;
(3) halo,
(4) —CN,
(5) —CF$_3$,
(6) —NO$_2$,
(7) hydroxy,
(8) C$_{1-6}$alkoxy,
(9) —COR$^9$,
(10) —CO$_2$R$^9$; and n is an integer selected from 1, 2 or 3;

with the proviso that if A is phenyl and W is —O—, —NH— or —N(C$_{1-6}$ alkyl)—, then at least one of the following four conditions must be met:
(1) Q is other than hydrogen
(2) Y is a single bond,
(3) X is other than hydrogen, or
(4) at least one of R$^6$, R$^7$ and R$^8$ is heterocycle —(C$_{1-6}$alkyl)-heterocycle or —N(heterocycle)—SO$_2$R$^{14}$ wherein heterocycle and R$^{14}$ are as defined above.

2. The compound of claim 1 wherein A is selected from the group consisting of:
(A) phenyl,
(B) benzofuranyl,
(C) benzothiazoyl,
(D) indolyl,
(E) imidazolyl,
(F) oxadiazolyl,
(G) pyridyl,
(H) quinolinyl,
(I) thiazolyl,
(J) thienyl, and
(K) dihydrobenzofuranyl.

3. The compound of claim 1 wherein A is phenyl.
4. The compound of claim 1 wherein n is 1 or 2.
5. The compound of claim 1 wherein n is 1.
6. The compound of claim 1 wherein W is —NH— or —N(Cl$_{1-6}$ alkyl)—, and Q is other than hydrogen.
7. The compound of claim 1 wherein W is —NH— or —N(C$_{1-6}$ alkyl)—, and Y is a single bond.
8. The compound of claim 1 wherein W is —NH— or —N(C$_{1-6}$ alkyl)—, and X is other than hydrogen.
9. The compound of claim 1 wherein W is —NH— or —N(C$_{1-6}$ alkyl)—, and at least one of R$^6$, R$^7$ and R$^8$ is heterocycle, —(C$_{1-6}$alkyl)-heterocycle, or —N(heterocycle)—SO$_2$R$^{14}$, wherein heterocycle and R$^{14}$ are as defined in claim 1.
10. The compound of claim 1 wherein W is —NH— and Q and the carbon atom to which it is attached are absent.
11. The compound of claim 1 or a pharmaceutically acceptable salt thereof, wherein:

A is selected from the group consisting of:
(A) phenyl,
(B) benzofuranyl,
(C) benzothiazoyl,
(D) indolyl,
(E) imidazolyl,
(F) oxadiazolyl,
(G) pyridyl,
(H) quinolinyl,
(I) thiazolyl,
(J) thienyl, and
(K) dihydrobenzofuranyl;

Q is selected from the group consisting of:
(1) hydrogen, and
(2) —CH$_3$;

W is selected from the group consisting of:
(1) —O—,
(2) —NH—, and
(3) —N(CH$_3$)—;

X is hydrogen;

Y is selected from the group consisting of:
(1) a single bond, and
(2) —CH$_2$;

Z is selected from the group consisting of:
(1) —NR$^{15}$—, wherein R$^{15}$ is selected from the group consisting of: hydrogen, —CH$_3$, and —CH$_2$CH$_2$OCH$_3$,
(2) —CO—NR$^{15}$—,
(3) —NR$^{15}$—CO—,
(4) —SO$_2$—NR$^{15}$—, and
(5) —NR$^{15}$—SO$_2$—,
or Z is optionally absent;

R$^3$ is selected from the group consisting of:
(1) —R$^5$, and
(2) C$_{1-6}$ alkyl substituted with —R$^5$;

R$^5$ is selected from the group consisting of:
(1) —NR$^9$R$^{10}$, wherein R$^9$ and R$^{10}$ are independently selected from:
(a) hydrogen,
(b) C$_{1-6}$ alkyl,
(c) (C$_{1-6}$ alkyl)-hydroxy, and
(d) (C$_{1-6}$ alkyl)—(C$_{1-4}$ alkoxy),
(2) —CO—NR$^9$R$^{10}$,
(3) —NR$^9$—COR$^{10}$,
(4) heterocycle, wherein the heterocycle is selected from the group consisting of:
(A) imidazolyl,
(B) triazolyl,
(C) tetrazolyl,
(D) pyridyl,
(E) piperazinyl,
(F) piperidinyl,
(G) pyrrolidinyl,
(H) morpholinyl,
and wherein the heterocycle is unsubstituted or substituted with one or more substituent(s) selected from:
(i) C$_{1-6}$ alkyl, unsubstituted or substituted with halo, —CF$_3$, —OCH$_3$, or phenyl,
(ii) C$_{1-6}$ alkoxy,
(iii) oxo, and
(iv) hydroxy,
(5) —CO-heterocycle, wherein heterocycle is as defined above;

R$^6$, R$^7$ and R$^8$ are independently selected from the group consisting of:
(1) hydrogen,
(2) —CF$_3$,
(3) C$_{1-6}$alkoxy, and
(4) 1-, 2- or 5-tetrazolyl, wherein the tetrazolyl is unsubstituted or substituted with a substitutent selected from the group consisting of:
(a) C$_{1-6}$ alkyl,
(b) -cyclopropyl,
(c) CH$_2$-cyclopropyl,
(d) —S—C$_{1-4}$alkyl, (e) —SO—$C_{1-4}$alkyl,
(f) —$SO_2$—$C_{1-4}$alkyl,
(g) phenyl,
(h) —$NR^9R^{10}$,
(i) —$CH_2$—CO—$CF_3$, and
(j) —$CF_3$;

$R^{11}$, $R^{12}$ and $R^{13}$ are independently selected from:
(1) hydrogen, and
(2) fluoro;

n is 1 or 2;

with the proviso that if W is —O—, —NH— or —N($CH_3$)—, then at least one of the following conditions must be met:
(1) Q is —$CH_3$,
(2) Y is a single bond, and/or
(3) at least one of $R^6$, $R^7$ and $R^8$ is heterocycle, —($C_{1-6}$alkyl)-heterocycle, or —N(heterocycle)—$SO_2R^{14}$, wherein heterocycle and $R^{14}$ are as defined above.

12. The compound of claim 1 wherein Q is selected from the group consisting of:
(1) hydrogen, and
(2) methyl.

13. The compound of claim 1 wherein Y is selected from the group consisting of:
(1) a single bond, and
(2) —$CH_2$—.

14. The compound of claim 1 wherein Z is selected from the group consisting of:
(1) —$NR^{15}$—, wherein $R^{15}$ is selected from the group consisting of: hydrogen, —$CH_3$, and —$CH_2CH_2OCH_3$,
(2) —CO—$NR^{15}$—,
(3) —$NR^{15}$—CO—,
(4) —$SO_2$—$NR^{15}$—, and
(5) —$NR^{15}$—$SO_2$—,
or if $R^3$ is other than hydrogen, then Z is optionally absent.

15. The compound of claim 1 wherein $R^3$ is selected from the group consisting of:
(1) —$R^5$, and
(2) $C_{1-6}$ alkyl substituted with —$R^5$,
or if Z is —CO—O—$R^{15}$, —O—CO—$R^{15}$, —CO—$R^{15}$, or —$CH_2$—$OR^{15}$, then $R^3$ is absent.

16. The compound of claim 15 wherein if $R^3$ is —$R^5$ or $C_{1-6}$ alkyl substituted with —$R^5$, then $R^5$ is selected from the group consisting of:
(1) —$NR^9R^{10}$, wherein $R^9$ and $R^{10}$ are independently selected from:
(a) hydrogen,
(b) $C_{1-6}$ alkyl,
(c) ($C_{1-6}$ alkyl)-hydroxy, and
(d) ($C_{1-6}$ alkyl)—($C_{1-4}$ alkoxy),
(2) —CO—$NR^9R^{10}$, wherein $R^9$ and $R^{10}$ are as defined immediately above,
(3) —$NR^9$—$COR^{10}$, wherein $R^9$ and $R^{10}$ are as defined immediately above,
(4) heterocycle, wherein the heterocycle is selected from the group consisting of:
(A) imidazolyl,
(B) triazolyl,
(C) tetrazolyl,
(D) pyridyl,
(E) piperazinyl,
(F) piperidinyl,
(G) pyrrolidinyl,
(H) morpholinyl,
and wherein the heterocycle is unsubstituted or substituted with one or more substituent(s) selected from:
(i) $C_{1-6}$ alkyl, unsubstituted or substituted with halo, —$CF_3$, —$OCH_3$, or phenyl,
(ii) $C_{1-6}$ alkoxy,
(iii) oxo, and
(iv) hydroxy,
(5) —CO-heterocycle, wherein heterocycle is as defined above.

17. The compound of claim 1 wherein W is —NH— or —N($C_{1-6}$ alkyl)—, Q is hydrogen, X is hydrogen, Y is a single bond, and one of $R^6$, $R^7$ and $R^8$ is heterocycle, —($C_{1-6}$alkyl)-heterocycle, or —N(heterocycle)—$SO_2R^{14}$, wherein heterocycle and $R^{14}$ are as defined above, and another of $R^6$, $R^7$ and $R^8$ is —$OCH_3$.

18. The compound of claim 1 wherein $R^6$, $R^7$ and $R^8$ are independently selected from the group consisting of:
(1) hydrogen,
(2) —$CF_3$,
(3) $C_{1-4}$alkoxy, and
(4) heterocycle, wherein the heterocycle is selected from the group consisting of:
(A) tetrazolyl,
(B) imidazolyl,
(C) triazolyl,
(D) pyridyl,
and wherein the heterocycle is unsubstituted or substituted with one or more substituent(s) selected from:
(i) $C_{1-4}$ alkyl,
(ii) -cyclopropyl, and
(iii) —$CF_3$.

19. The compound of claim 1 wherein the ring A bearing $R^6$, $R^7$ and $R^8$ is selected from:
3,5-bis(trifluormethyl)phenyl,
2-methoxy-5-tetrazol-1-yl-phenyl,
2-methoxy-5-(5-methyl-tetrazol-1-yl)-phenyl,
2-methoxy-5-(5-ethyl-tetrazol-1-yl)-phenyl,
2-methoxy-5-(5-propyl-tetrazol-1-yl)-phenyl,
2-methoxy-5-(5-trifluoromethyl-tetrazol-1-yl)-phenyl,
2-methoxy-5-(5-cyclopropyl-tetrazol-1-yl)-phenyl, and
2-methoxy-5-(5-methylsulfanyl-tetrazol-1-yl)-phenyl.

20. The compound of claim 1 wherein $R^{11}$, $R^{12}$ and $R^{13}$ are independently selected from:
(1) hydrogen, and
(2) fluoro.

21. The compound of claim 1 wherein the phenyl ring bearing $R^{11}$, $R^{12}$ and $R^{13}$ is unsubstituted phenyl or is parafluorophenyl.

22. A compound which is selected from the group consisting of:
1-(S)-(1-(R)-(3,5-bis(trifluoromethyl)phenyl)ethoxy)-2-(S)-(4-fluorophenyl)-3-(R)-(2-methoxyethylamino) cyclopentane;
1-(S)-(1-(R)-(3,5-bis(trifluoromethyl)phenyl)ethoxy)-2-(S)-(4-fluorophenyl)-3-(R)-(N-(aminocarbonylmethyl)-N-(2-methoxyethyl)-amino)cyclopentane;
methyl 3-(S)-((2-methoxy-5-(1-tetrazolyl)phenyl) methylamino)-2-(S)-(4-fluorophenyl)cyclopentane-1-(S)-carboxylate;
1-(S)-((2-methoxy-5-(1-tetrazolyl)phenyl) methylamino)-2-(S)-(4-fluorophenyl)-3-(S)-(aminocarbonyl) cyclopentane;

1-(S)-((2-methoxy-5-(1-tetrazolyl)phenyl)methylamino)-2-(S)-(4-fluorophenyl)-3-(S)-(dimethylaminocarbonyl)cyclopentane;

1-(S)-((2-methoxy-5-(1-tetrazolyl)phenyl)methylamino)-2-(S)-(4-fluorophenyl)-3-(S)-(morpholin-4-ylcarbonyl)cyclopentane;

1-(S)-((2-methoxy-5-(1-tetrazolyl)phenyl)methylamino)-2-(S)-(4-fluorophenyl)-3-(S)-(t-butylaminocarbonyl)cyclopentane;

1-(S)-((2-methoxy-5-(1-tetrazolyl)phenyl)methylamino)-2-(S)-(4-fluorophenyl)-3-(S)-(aminocarbonylmethylamino)cyclopentane;

1-(S)-((2-methoxy-5-(1-tetrazolyl)phenyl)methylamino)-2-(S)-(4-fluorophenyl)-3-(S)-(methoxycarbonylamino)cyclopentane;

1-(S)-((2-methoxy-5-(1-tetrazolyl)phenyl)methylamino)-2-(S)-($^4$-fluorophenyl)-3-(S)-(dimethylaminocarbonylamino)cyclopentane;

1-(S)-((2-methoxy-5-(1-tetrazolyl)phenyl)methylamino)-2-(S)-(4-fluorophenyl)-3-(S)-(methylaminocarbonylamino)cyclopentane;

1-(S)-((2-methoxy-5-(1-tetrazolyl)phenyl)methylamino)-2-(S)-(4-fluorophenyl)-3-(S)-(ethylsulfonylamino)cyclopentane;

1-(S)-((2-methoxy-5-(1-tetrazolyl)phenyl)methylamino)-2-(S)-($^4$-fluorophenyl)-3-(S)-(pyrrolidin-1-ylmethyl)cyclopentane;

1-(S)-((2-methoxy-5-(5-trifluoromethyltetrazol-1-yl)phenyl)methylamino)-2-(S)-(4-fluorophenyl)-3-(S)-(pyrrolidin-1-ylmethyl)cyclopentane;

1-(S)-((2-methoxy-5-(1-tetrazolyl)phenyl)methylamino)-2-(S)-(4-fluorophenyl)-3-(S)-(1,2,3-triazol-1-ylmethyl)cyclopentane;

1-(S)-((2-methoxy-5-(5-trifluoromethyltetrazol-1-yl)phenyl)methylamino)-2-(S)-(4-fluorophenyl)-3-(S)-(2-methyl-5-tetrazol-5-ylmethyl)cyclopentane;

methyl 3-(SR)-(2-methoxy-5-((5-trifluoromethyl)tetrazol-1-yl)phenyl)methylamino-2-(SR)-(4-fluorophenyl)-cyclopentane-1-(SR)-carboxylate;

N-((2-methoxy-5-trifluoromethoxy)phenylmethyl)-3-(SR)-(5-methyl-1,3,4-oxadiazol-2-yl)-2-(SR)-(4-fluorophenyl)cyclopentan-1-(SR)-amine;

methyl 3-(S)-{[2-isopropoxy-5-(1-methyl-1H-tetrazol-5-yl)-phenyl]-methylamino}-2-(S)-(4-fluorophenyl)-cyclopentane-1-(S)-carboxylate;

3-(SR)-((2-isopropoxy-5-(5-trifluoromethyltetrazol-1-yl)phenyl)methylamino)-2-(SR)-(4-fluorophenyl)cyclopentane-1-(SR)carboxamide;

methyl 3-(SR)-((2-cyclobutyloxy-5-(1-tetrazolyl)phenyl)methyl-amino)-2-(SR)-(4-fluorophenyl)cyclopentane-1-(SR)carboxylate;

3-(SR)-((2-isopropoxy-5-(tetrazol-1-yl)phenyl)methylamino)-2-(SR)-(4-fluorophenyl)cyclopentane-1-(SR) carboxamide;

1S-(1'S-methyl-(3,5-bistrifluoromethyl)benzyloxy)-2S-phenyl-3R-hydroxymethyl cyclohexane;

1S-((1'R-(3,5-bistrifluoromethyl)phenyl)ethoxy)-2S-phenyl-3S-(N-methyl-N-(5-oxo-1,2,4-triazol-2-yl)methylamino))-cyclohexane;

1S-((1'R-(3,5-bistrifluoromethyl)phenyl)ethoxy)-2S-phenyl-3S-(N-methyl-N-(5-(1,2,4-triazolylmethyl)amino))-cyclohexane;

1S-((1'R-(3,5-bistrifluoromethyl)phenyl)ethoxy)-2S-phenyl-3S-aminocyclohexane;

1S-(1'R-(3,5-bistrifluoromethyl)phenyl)ethoxy)-2S-phenyl-3S-(amino-aminocarbonyl methyl aminocyclohexane;

1S-(1'R-(3,5-bistrifluoromethyl)phenyl)ethoxy)-2S-phenyl-3S-(N-(2-pyrrolidinone-5-(S)-yl-methyl))aminocyclohexane;

1S-(N-2-methoxy-5-(5-trifluoromethyl-1,2,3,4-tetrazol-1-yl))benzylamino-2S-phenyl-3S-hydroxymethylcyclohexane;

1S-(N-2-methoxy-5-(1,2,3,4-tetrazol-1-yl))benzylamino-2S-phenyl-3S-methylamino-cyclohexane;

1(S)-N-(2-methoxy-5-(trifluoromethyl-1,2,3,4-tetrazol-1-yl))benzyl-2(S)-phenyl-3 (S)-(pyrrolidin-1-yl-methyl)cyclohexane;

1(S)-N-(2-methoxy-5-(trifluoromethyl-1,2,3,4-tetrazol-1-yl))benzyl-2(S)-phenyl-3(S)-methoxymethylcyclohexane;

1(S)-N-(2-methoxy-5-(1-tetrazolyl))-benzylamino-2(S)-phenylcyclohexane;

1(S)-N-(2-methoxy-5-(trifluoromethyl-1,2,3,4-tetrazol-1-yl))benzyl-2(S)-phenylcyclohexane;

1S- [(N-benzyloxycarbonyl)-(N-2-methoxy-5-(5-trifluoro-methyl-1,2,3,4-tetrazol-1-yl))]benzylamino-2S-phenyl-3S-(2-hydroxyethyl)-cyclohexane;

or pharmaceutically acceptable salts and individual diasteromers thereof.

23. A compound which is selected from the group consisting:

3-(S)-(2-methoxy-5-((5-trifluoromethyl)tetrazol-1-yl)phenyl)-methylamino-2-(S)-(4-fluorophenyl)cyclopentane-1-(S)-(N-t-butyl)carboxamide;

3-(SR)-(2-methoxy-5-((5-trifluoromethyl)tetrazol-1-yl)phenyl)methylamino-2-(SR)-(4-fluorophenyl)-cyclopentane-1-(SR)-(N-t-butyl)carboxamide;

1-(S)-((2-isopropoxy-5-(5-trifluoromethyltetrazol-1-yl)phenyl)methylamino)-2-(S)-(4-fluorophenyl)-3-(S)-(pyrrolidin-1-ylmethyl)cyclopentane;

1-(S)-((2-methoxy-5-(5-trifluoromethyltetrazol-1-yl)phenyl)methylamino)-2-(S)-(4-fluorophenyl)-3-(S)-(2-(S)-(aminocarbonyl)pyrrolidin-1-ylmethyl)cyclopentane;

1-(S)-((2-methoxy-5-(5-trifluoromethyltetrazol-1-yl)phenyl)methylamino)-2-(S)-(4-fluorophenyl)-3-(S)-(1-methyl-5-tetrazol-5-ylmethyl)-cyclopentane;

N-(2-methoxy-5-((5-trifluoromethyl)tetrazol-1-yl)phenyl)methyl)-3-(SR)-(imidazol-2-yl)-2-(SR)-(4-fluorophenyl)cyclopentan-1-(SR)-amine;

N-(2-methoxy-5-((5-trifluoromethyl)tetrazol-1-yl)phenyl)methyl)-3-(SR)-((1-methyl)imidazol-2-yl)-2-(SR)-(4-fluorophenyl)cyclopentan-1-(SR)-amine;

N-(2-methoxy-5-((5-trifluoromethyl)tetrazol-1-yl)phenyl)methyl)-3-(SR)-(thiazol-2-yl)-2-(SR)-(4-fluorophenyl)cyclopentan-1-(SR)-amine;

N-(2-methoxy-5-((5-trifluoromethyl)tetrazol1-yl)phenyl)methyl)-3-(S)-(thiazol-2-yl)-2-(S)-(4-fluorophenyl)cyclopentan-1-(S)-amine;

N-(2-methoxy-5-((5-trifluoromethyl)tetrazol-1-yl)phenyl)methyl)-3-(SR)-(isoxazol-3-yl)-2-(SR)-(4-fluorophenyl)cyclopentan-1-(SR)-amine;

N-(2-methoxy-5-((5-trifluoromethyl)tetrazol-1-yl)phenyl)methyl)-3-(S)-(5-methyl-1,3,4-oxadiazol-2-yl)-2-(S)-(4-fluorophenyl)cyclopentan-1-(S)-amine;

N-(2-methoxy-5-((5-trifluoromethyl)tetrazol-1-yl)phenyl)methyl)-3-(SR)-(tetrazol-1-yl)-2-(RS)-(4-fluorophenyl)cyclopentan-1-(SR)-amine;

N-(2-methoxy-5-((5-trifluoromethyl)tetrazol-1-yl)phenyl)methyl)-3-(SR)-(1,2,4-triazol-4-yl)-2-(SR)-(4-fluorophenyl)cyclopentan-1-(SR)-amine;

(1RS,2RS,3RS)-3-((5-(3,5-dimethylisoxazol-4-yl)-2-methoxyphenyl)methylamino)-2-(4-fluorophenyl) cyclopentane-carboxylic acid methyl ester;

methyl 3-(S,R)-((2-methoxy-5-(5-trifluoromethyl-tetrazol-1-yl)-3-pyridine)methylamino)-2-(S,R)-(4-fluorophenyl)cyclopentane-1-(S,R)-carboxylate;

methyl 3-(S,)-(5-(5-trifluoromethyl-1-tetrazol-1-yl)-(7-benzofuran)methylamino)-2-(S,)-(4-fluorophenyl)cyclopentane-1-(S,)-carboxylate;

methyl 3-(S)-[(5-cyano-2-isopropoxy-phenyl)-methylamino]-2-(S)-(4-fluorophenyl)-cyclopentane-1-(S)-carboxylate;

1-(S)- [(5-cyano-2-isopropoxy-phenyl)-methylamino]-2-(S)-(4-fluorophenyl)-3-(S)-(2-thiazol-2-yl)-cyclopentane;

methyl 3-(SR)-((2-isopropoxy-5-(tetrazol-1-yl)phenyl) methylamino)-2-(SR)-(4-fluorophenyl)cyclopentane-1-(SR)carboxylate;

3-(SR)-((2-isopropoxy-5-(tetrazol-1-yl)phenyl) methylamino)-2-(SR)-(4-fluorophenyl)cyclopentane-1-(SR)-tert-butyl-carboxamide;

methyl 3-(SR)-((2-isopropoxy-5-(5-trifluoromethyltetrazol-1-yl)phenyl) methylamino)-2-(SR)-(4-fluorophenyl)cyclopentane-1-(SR) carboxylate;

methyl 3-(S)-((2-methylsulfanyl-5-(5-trifluoromethyltetrazol-1-yl)phenyl)methylamino)-2-(S)-(4-fluorophenyl)cyclopentane-1-(S) carboxylate;

1(S)-N-(2-methoxy-5-(1-tetrazolyl))-benzylamino-2(S)-phenyl-3(S)-carboxymethyl cyclohexane;

1(S)-N-(2-methoxy-5-(trifluoromethyl-1,2,3,4-tetrazol-1-yl))benzyl-2(S)-phenyl-3(S)-imidazole cyclohexane; and 1(S)-N-(2-methoxy-5-(1-tetrazolyl))-benzylamino-2(S)-phenyl-3(S)-ethyl cyclohexane;

or pharmaceutically acceptable salts and individual diasteromers thereof.

24. A pharmaceutical composition comprising a pharmaceutically acceptable carrier and an effective amount of the compound of claim 1.

25. A method for antagonizing the effect of substance P at its receptor site or for the blockade of neurokinin-1 receptors in a mammal which comprises the administration to the mammal of the compound of claim 1 in an amount that is effective for antagonizing the effect of substance P at its receptor site in the mammal.

26. A method for antagonizing the effect of neurokinin A at its receptor site or for the blockade of neurokinin-2 receptors in a mammal which comprises the administration to the mammal of the compound of claim 1 in an amount that is effective for antagonizing the effect of neurokinin A at its receptor site in the mammal.

27. A method of treating or preventing pain or nociception attributable to or associated with migraine in a mammal in need thereof which comprises the administration to the mammmal of an effective amount of the compound of claim 1.

28. A method of treating a condition selected from the group consisting of: diabetic neuropathy; peripheral neuropathy; AIDS related neuropathy; chemotherapy-induced neuropathy; and neuralgia, in a mammal in need thereof which comprises the administration to the mammal of an effective amount of the compound of claim 1.

29. A method for the treatment of cystic fibrosis in a mammal in need thereof which comprises the administration to the mammal of an effective amount of the compound of claim 1.

30. A method for the treatment or prevention of emesis in a mammal in need thereof which comprises the administration to the mammal of an effective amount of the compound of claim 1.

* * * * *